US009051342B2

(12) United States Patent
Almstead et al.

(10) Patent No.: US 9,051,342 B2
(45) Date of Patent: Jun. 9, 2015

(54) PYRAZOLE OR TRIAZOLE COMPOUNDS AND THEIR USE FOR THE MANUFACTURE OF A MEDICAMENT FOR TREATING SOMATIC MUTATION RELATED DISEASES

(75) Inventors: Neil Almstead, Princeton, NJ (US); Gary M. Karp, Princeton Junction, NJ (US); Richard Wilde, Somerville, NJ (US); Ellen Welch, Califon, NJ (US); Jeffrey A. Campbell, Bethlehem, PA (US); Hongyu Ren, Dayton, NJ (US); Guangming Chen, Bridgewater, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 1154 days.

(21) Appl. No.: 11/577,177

(22) PCT Filed: Oct. 13, 2005

(86) PCT No.: PCT/US2005/036761
§ 371 (c)(1),
(2), (4) Date: May 2, 2008

(87) PCT Pub. No.: WO2006/044502
PCT Pub. Date: Apr. 27, 2006

(65) Prior Publication Data
US 2008/0280869 A1    Nov. 13, 2008

Related U.S. Application Data

(60) Provisional application No. 60/617,633, filed on Oct. 13, 2004, provisional application No. 60/617,634, filed on Oct. 13, 2004, provisional application No. 60/617,655, filed on Oct. 13, 2004, provisional application No. 60/617,670, filed on Oct. 13, 2004, provisional application No. 60/617,653, filed on Oct. 13, 2004, provisional application No. 60/624,170, filed on Nov. 3, 2004.

(51) Int. Cl.
| | | |
|---|---|---|
| *A61K 31/397* | (2006.01) | |
| *A61K 31/41* | (2006.01) | |
| *A61K 31/415* | (2006.01) | |
| *C07F 9/653* | (2006.01) | |
| *C07D 231/12* | (2006.01) | |
| *C07D 233/64* | (2006.01) | |
| *C07D 249/08* | (2006.01) | |
| *C07D 261/08* | (2006.01) | |
| *C07D 263/32* | (2006.01) | |
| *C07D 271/06* | (2006.01) | |
| *C07D 277/30* | (2006.01) | |
| *C07D 285/12* | (2006.01) | |
| *C07D 307/68* | (2006.01) | |
| *C07D 333/24* | (2006.01) | |
| *C07D 413/12* | (2006.01) | |

(52) U.S. Cl.
CPC .......... *C07F 9/65306* (2013.01); *C07D 231/12* (2013.01); *C07D 233/64* (2013.01); *C07D 249/08* (2013.01); *C07D 261/08* (2013.01); *C07D 263/32* (2013.01); *C07D 271/06* (2013.01); *C07D 277/30* (2013.01); *C07D 285/12* (2013.01); *C07D 307/68* (2013.01); *C07D 333/24* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 3,642,813 A | 2/1972 | Kirchmayr et al. | |
| 3,803,162 A | 4/1974 | Aebli et al. | |
| 3,932,430 A | 1/1976 | Habeck et al. | |
| 4,038,285 A * | 7/1977 | Johnson | 548/343.5 |
| 4,546,113 A * | 10/1985 | Glazer | 514/636 |
| 5,260,451 A | 11/1993 | Dannhardt et al. | |
| 5,436,252 A | 7/1995 | Sorensen et al. | |
| 5,466,823 A | 11/1995 | Talley et al. | |
| 5,756,530 A | 5/1998 | Lee et al. | |
| 6,255,327 B1 | 7/2001 | Brenner et al. | |
| 7,226,930 B2 | 6/2007 | Hopper et al. | |
| 2004/0058918 A1 | 3/2004 | Dominguez et al. | |
| 2004/0259904 A1 | 12/2004 | Tong et al. | |
| 2005/0009834 A1 | 1/2005 | Itoh et al. | |
| 2005/0261177 A1 | 11/2005 | Toda et al. | |

FOREIGN PATENT DOCUMENTS

| | | | | |
|---|---|---|---|---|
| CA | 2 322 195 A1 | 10/1999 | | |
| CA | 2322195 | * 10/1999 | ........... | C07D 249/08 |
| EP | 1 023 063 B1 | 9/2003 | | |
| EP | 1 386 915 A1 | 2/2004 | | |
| EP | 0 838 453 B1 | 4/2005 | | |
| EP | 2 284 154 A1 | 2/2011 | | |
| GB | 1 263 940 | 2/1972 | | |

(Continued)

OTHER PUBLICATIONS

STN Search Report containing Accession No. 1977:552219 (1977).*
Vollhardt et al (Organic Chemistry, 4th Edition, p. 817, 2002).*
Gibson (Pharmaceutical preformulation and formulation: a practical guide from candidate drug selection to commercial dosage form, p. 28, 2001).*
STN Search Report (Accession No. 1980:110914) containing Genas et al (Bulletin de la Societe Chimique de Franc 1-2(Part 2):17-25, 1979) summary and compounds.*

(Continued)

*Primary Examiner* — Craig Ricci
(74) *Attorney, Agent, or Firm* — Hoffmann & Baron, LLP

(57) ABSTRACT

The present invention relates to methods, compounds, and compositions for treating or preventing diseases associated with nonsense mutations in an mRNA by administering the compounds or compositions of the present invention. More particularly, the present invention relates to methods, compounds, and compositions for suppressing premature translation termination associated with a nonsense mutation in an mRNA.

4 Claims, 3 Drawing Sheets

(56) References Cited

FOREIGN PATENT DOCUMENTS

| | | | |
|---|---|---|---|
| JP | 58-177977 A | 10/1983 | |
| JP | 2003-26663 A | 1/2003 | |
| JP | 2004-526728 A | 9/2004 | |
| JP | 2006-523719 A | 10/2006 | |
| JP | 2008-510808 A | 4/2008 | |
| WO | WO 98/04135 A1 | 2/1998 | |
| WO | 99/17769 A1 | 4/1999 | |
| WO | 99/54314 A1 | 10/1999 | |
| WO | WO 99/54314 * | 10/1999 | ......... C07D 207/333 |
| WO | 02/068417 A2 | 9/2002 | |
| WO | 02/072621 A2 | 9/2002 | |
| WO | 03/010162 A1 | 2/2003 | |
| WO | 03/027085 A2 | 4/2003 | |
| WO | 03/051315 A2 | 6/2003 | |
| WO | 03/051833 A2 | 6/2003 | |
| WO | 03/059904 A1 | 7/2003 | |
| WO | 03/097609 A1 | 11/2003 | |
| WO | 2004/072050 A1 | 8/2004 | |
| WO | 2004/094411 A1 | 11/2004 | |
| WO | 2006/023462 A1 | 3/2006 | |
| WO | 2007/059356 A2 | 5/2007 | |

OTHER PUBLICATIONS

STN Search Report (Accession No. 1980:43264)—containing summary of Palmberg et al (Helvetica Chimica Acta 62(6):1816-1853, 1979).*
International Search Report for PCT/US2005/036761 mailed May 31, 2006.
Hamilton, Robert W., "The Antiarrhythmic and Antiinflammatory Activity of a Series of Tricyclic Pyrazoles," J. Heterocyclic Chem., 13, 545-553 (1976).
Klingsberg, Erwin, "The 1,2-Dithiolium Cation. A New Pseudoaromatic System. I. Preparation and Properties of 3-Phenyl- and 4-Phenyl-1,2-dithiolium Salts," vol. 83, 2934-2937 (1961).
Kuo, Mack R. et al. "Targeting Tuberculosis and Malaria through Inhibition of Enoyl Reductase," The Journal of Biological Chemistry, vol. 278, No. 23, 20851-20859 (Jun. 6, 2003).
Palmberg, von Roger B. and Siegrist, Adolf Emil, "188. Anil-Synthese, Über die Herstellung von Stilbenyl-Derivaten des Pyrazols," Helvetica Chimica Acta—vol. 62, Fasc. 6 (1979)—Nr. 188, 1816-1853 (with English abstract on p. 1816).
Roppe, Jeffrey et al., "Discovery of Novel Heteroarylazoles That Are Metabotropic Glutamate Subtype 5 Receptor Antagonists with Anxiolytic Activity," Journal of Medicinal Chemistry, 2004, vol. 47, No. 19, 4645-4648.
English translation of Notice of Reasons for Rejection issued for Japanese Patent Application No. 2007-536865, mailed on Feb. 7, 2012.
Communication issued to European Application No. 10 185 133.5, mailed on Feb. 21, 2013.
Communication issued to European Application No. 10 185 139.2, mailed on Feb. 21, 2013.
STN Search Report containing Accession No. 1977:552219 CAPLUS (1977).
STN Search Report (Accession No. 1980:43264)—containing summary of Palmberg et al (Helvetica Chimica Acta 62(6):1816-1853. 1979).
STN Search Report (Accession No. 1980:110914)—containing Genas et al. (Bulletin de la Societe Chimique de France (1979), (1-2, Pt. 2), 17-25.
Vollhardt and Schore, Organic Chemistry, 4th Edition, p. 817, 2002.
Gibson, Mark, Pharmaceutical Preformulation and Formulation: A Practical Guide from Candidate Drug Selection to Commercial Dosage Form, p. 28, 2001.
International Preliminary Report on Patentability for International Application No. PCT/US2005/036761, Date of Issuance of report: Apr. 17, 2007.
Written Opinion of the International Searching Authority for PCT/US2005/036761, dated May 2006.

* cited by examiner

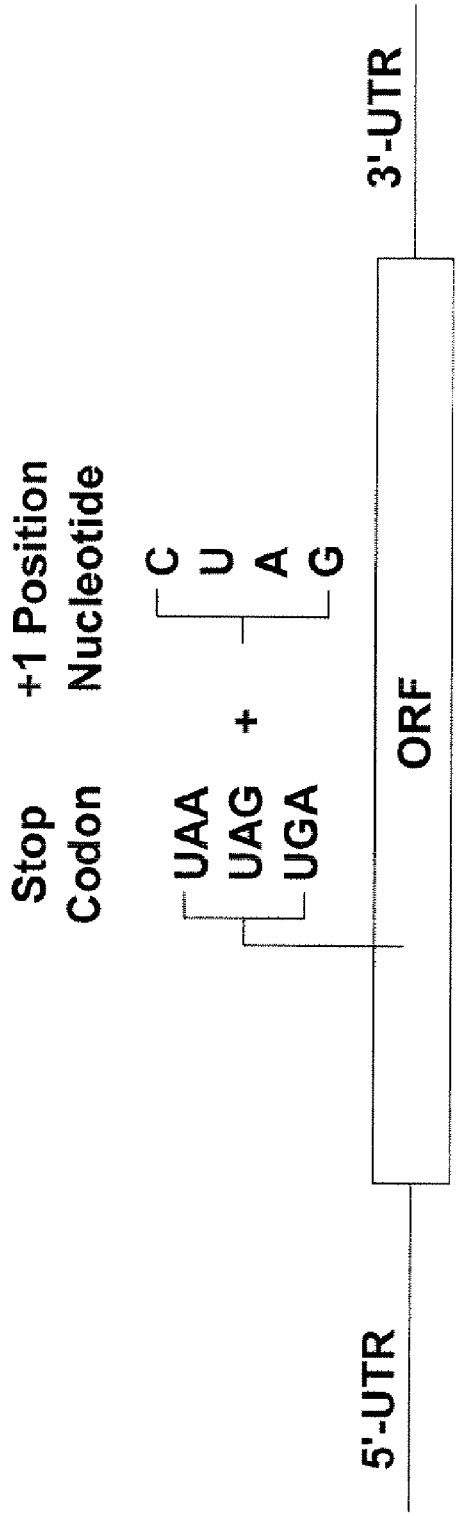
Figure 1: Luminescence Assay

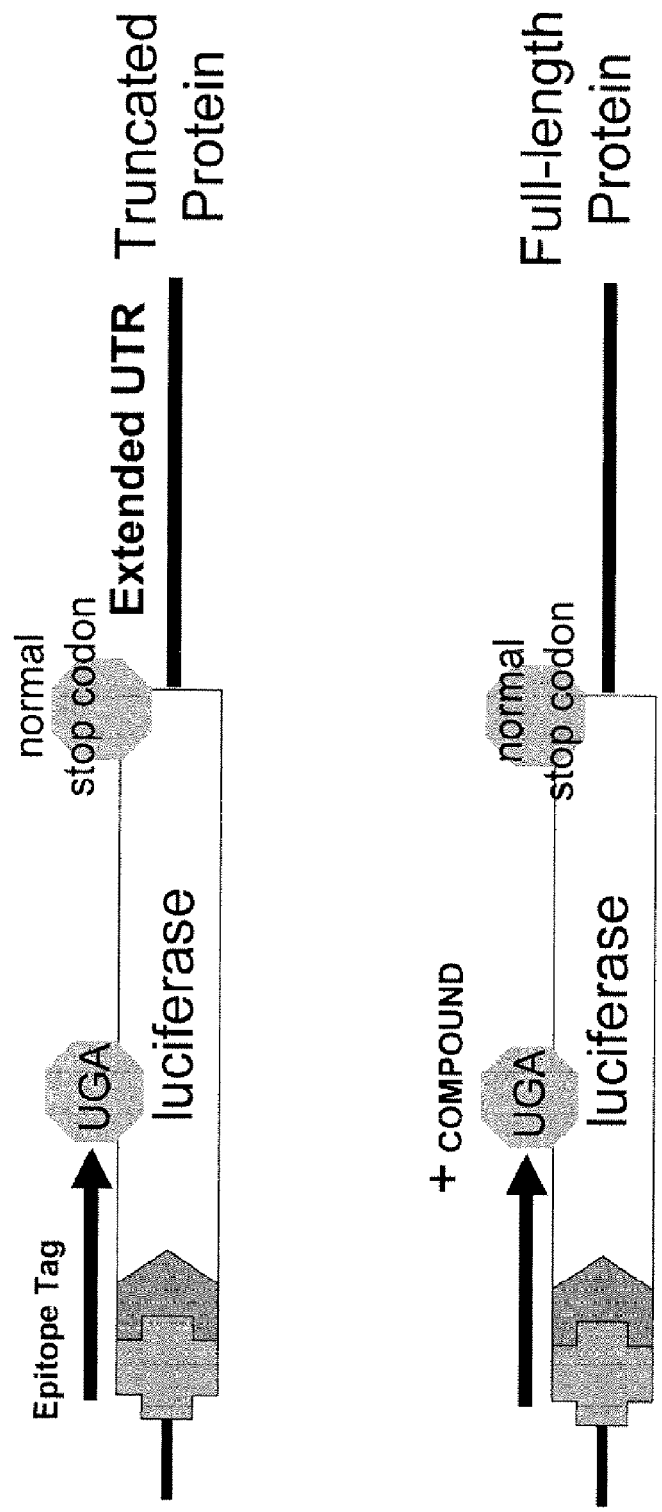

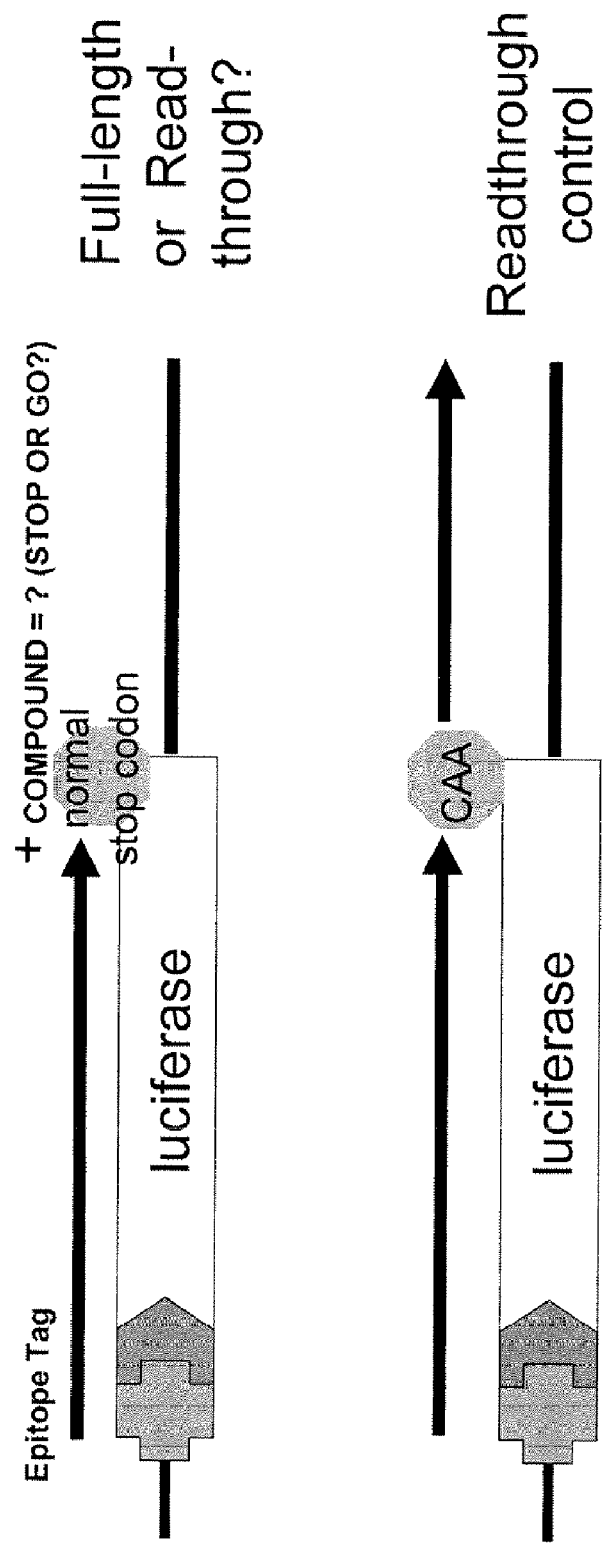
Figure 3: Readthrough Assay

US 9,051,342 B2

PYRAZOLE OR TRIAZOLE COMPOUNDS AND THEIR USE FOR THE MANUFACTURE OF A MEDICAMENT FOR TREATING SOMATIC MUTATION RELATED DISEASES

CROSS-REFERENCE TO RELATED APPLICATIONS

This application is a national phase application under 35 U.S.C. §371 of International Application No. PCT/US2005/036761 filed Oct. 13, 2005, the disclosure of which is hereby incorporated by reference in its entirety, and which claims priority to and the benefit under 35 U.S.C. §119 of U.S. Provisional Application No. 60/617,633, filed Oct. 13, 2004, U.S. Provisional Application No. 60/617,634, filed Oct. 13, 2004, U.S. Provisional Application No. 60/617,655, filed Oct. 13, 2004, U.S. Provisional Application No. 60/617,670, filed Oct. 13, 2004, all of which applications are herein incorporated by reference in their entireties. International Application No. PCT/US2005/036761 also claims priority to and the benefit under 35 U.S.C. §119 of U.S. Provisional Application No. 60/617,653, filed Oct. 13, 2004, and U.S. Provisional Application No. 60/624,170, filed Nov. 3, 2004. U.S. Provisional Application No. 60/624,170, filed Nov. 3, 2004, is herein incorporated by reference in its entirety. The present application also incorporates by reference herein in their entireties International Application No. PCT/US2005/036764, filed on Oct. 13, 2005, International Application No. PCT/US2005/037052, filed Oct. 13, 2005, International Application No. PCT/US2005/036673, filed Oct. 13, 2005, and International Application No. PCT/US2005/036762, filed Oct. 13, 2005.

FIELD OF THE INVENTION

The present invention relates to methods, compounds, and compositions for treating or preventing diseases associated with nonsense mutations in an mRNA by administering the compounds or compositions of the present invention. More particularly, the present invention relates to methods, compounds, and compositions for suppressing premature translation termination associated with a nonsense mutation in an mRNA.

BACKGROUND OF THE INVENTION

Gene expression in cells depends upon the sequential processes of transcription and translation. Together, these processes produce a protein from the nucleotide sequence of its corresponding gene.

Transcription involves the synthesis of mRNA from DNA by RNA polymerase. Transcription begins at a promoter region of the gene and continues until termination is induced, such as by the formation of a stem-loop structure in the nascent RNA or the binding of the rho gene product.

Protein is then produced from mRNA by the process of translation, occurring on the ribosome with the aid of tRNA, tRNA synthetases and various other protein and RNA species. Translation comprises the three phases of initiation, elongation and termination. Translation is initiated by the formation of an initiation complex consisting of protein factors, mRNA, tRNA, cofactors and the ribosomal subunits that recognize signals on the mRNA that direct the translation machinery to begin translation on the mRNA. Once the initiation complex is formed, growth of the polypeptide chain occurs by the repetitive addition of amino acids by the peptidyl transferase activity of the ribosome as well as tRNA and tRNA synthetases. The presence of one of the three termination codons (UAA, UAG, UGA) in the A site of the ribosome signals the polypeptide chain release factors (RFs) to bind and recognize the termination signal. Subsequently, the ester bond between the 3' nucleotide of the tRNA located in the ribosome's P site and the nascent polypeptide chain is hydrolyzed, the completed polypeptide chain is released, and the ribosome subunits are recycled for another round of translation.

Mutations of the DNA sequence in which the number of bases is altered are categorized as insertion or deletion mutations (e.g., frameshift mutations) and can result in major disruptions of the genome. Mutations of the DNA that change one base into another and result in an amino acid substitution are labeled missense mutations. Base substitutions are subdivided into the classes of transitions (one purine to another purine, or one pyrimidine to another pyrimidine) and transversions (a purine to a pyrimidine, or a pyrimidine to a purine).

Transition and transversion mutations can result in a nonsense mutation changing an amino acid codon into one of the three stop codons. These premature stop codons can produce aberrant proteins in cells as a result of premature translation termination. A nonsense mutation in an essential gene can be lethal and can also result in a number of human diseases, such as, cancers, lysosomal storage disorders, the muscular dystrophies, cystic fibrosis and hemophilia, to name a few.

The human p53 gene is the most commonly mutated gene in human cancer (Zambetti, G. P. and Levine, A., *FASEB* 7:855-865 (1993)). Found in both genetic and spontaneous cancers, over 50 different types of human cancers contain p53 mutations and mutations of this gene occur in 50-55% of all human cancers (Hollstein, M., et al., *Nucleic Acids Res.* 22:3551-55 (1994); International Agency for Research on Cancer (IARC) database). Approximately 70% of colorectal cancer, 50% of lung cancer and 40% of breast cancers contain mutant p53 (Koshland, D., *Science* 262:1953 (1993)). Aberrant forms of p53 are associated with poor prognosis, more aggressive tumors, metastasis, and lower 5 year survival rates (Id.). p53's role in the induction of cell growth arrest and/or apoptosis upon DNA damage is believed to be essential for the destruction of mutated cells that would have otherwise gained a growth advantage. In addition, p53 sensitizes rapidly dividing cells to apoptotic signals. Of greater than 15,000 reported mutations in the p53 gene, approximately 7% are nonsense mutations. Accordingly, there is a need for a safe and effective treatment directed to p53 nonsense mutations.

In bacterial and eukaryotic strains with nonsense mutations, suppression of the nonsense mutation can arise as a result of a mutation in one of the tRNA molecules so that the mutant tRNA can recognize the nonsense codon, as a result of mutations in proteins that are involved in the translation process, as a result of mutations in the ribosome (either the ribosomal RNA or ribosomal proteins), or by the addition of compounds known to alter the translation process (for example, cycloheximide or the aminoglycoside antibiotics). The result is that an amino acid will be incorporated into the polypeptide chain, at the site of the nonsense mutation, and translation will not prematurely terminate at the nonsense codon. The inserted amino acid will not necessarily be identical to the original amino acid of the wild-type protein, however, many amino acid substitutions do not have a gross effect on protein structure or function. Thus, a protein produced by the suppression of a nonsense mutation would be likely to possess activity close to that of the wild-type protein. This scenario provides an opportunity to treat diseases associated with nonsense mutations by avoiding premature termination of translation through suppression of the nonsense mutation.

The ability of aminoglycoside antibiotics to promote readthrough of eukaryotic stop codons has attracted interest in these drugs as potential therapeutic agents in human diseases caused by nonsense mutations. One disease for which such a therapeutic strategy may be viable is classical late infantile neuronal ceroid lipofuscinosis (LINCL), a fatal childhood neurodegenerative disease with currently no effective treatment. Premature stop codon mutations in the gene CLN2 encoding the lysosomal tripeptidyl-peptidase 1 (TPP-I) are associated with disease in approximately half of children diagnosed with LINCL. The ability of the aminoglycoside gentamicin to restore TPP-I activity in LINCL cell lines has been examined. In one patient-derived cell line that was compound heterozygous for a commonly seen nonsense mutation (Arg208Stop) and a different rare nonsense mutation, approximately 7% of normal levels of TPP-I were maximally restored with gentamicin treatment. These results suggest that pharmacological suppression of nonsense mutations by aminoglycosides or functionally similar pharmaceuticals may have therapeutic potential in LINCL (Sleat et. al., Eur. J. Ped. Neural. 5:Suppl A 57-62 (2001)).

In cultured cells having premature stop codons in the Cystic Fibrosis Transmembrane Conductance Regulator (CFTR) gene, treatment with aminoglycosides led to the production of full-length CFTR (Bedwell et. al., Nat. Med. 3:1280-1284 (1997); Howard et. al. Nat. Med. 2: 467-469 (1996)). In mouse models for Duchenne muscular dystrophy, gentamicin sulfate was observed to suppress translational termination at premature stop codons resulting in full-length dystrophin (Barton-Davis et. al., J. Clin. Invest. 104:375-381 (1999)). A small increase in the amount of full-length dystrophin provided protection against contraction-induced damage in the mdx mice. The amino acid inserted at the site of the nonsense codon was not determined in these studies.

Accordingly, small molecule therapeutics or prophylactics that suppress premature translation termination by mediating the misreading of the nonsense codon would be useful for the treatment of a number of diseases. The discovery of small molecule drugs, particularly orally bioavailable drugs, can lead to the introduction of a broad spectrum of selective therapeutics or prophylactics to the public which can be used against disease caused by nonsense mutations is just beginning.

Clitocine (6-Amino-5-nitro-4-(β-D-ribo-furanosylamino) pyrimidine) is a naturally occurring exocyclic amino nucleoside that was first isolated from the mushroom *Clitocybe inversa* (Kubo et al., Tet. Lett. 27: 4277 (1986)). The total synthesis of clitocine has also been reported. (Moss et al., J. Med. Chem. 31:786-790 (1988) and Kamikawa et al., J. Chem. Soc. Chem. Commun. 195 (1988)). Clitocine has been reported to possess insecticidal activity and cytostatic activity against leukemia cell lines (Kubo et al., Tet. Lett. 27: 4277 (1986) and Moss et al., J. Med. Chem. 31:786-790 (1988)). However, the use of clitocine as a therapeutic for diseases associated with a nonsense mutation has not been disclosed until now. Nor has anyone reported the development of an analogue or derivative of clitocine that has utility as a therapeutic for cancer or a disease associated with a nonsense mutation.

Thus, there remains a need to develop characterize and optimize lead molecules for the development of novel drugs for treating or preventing diseases associated with nonsense mutations of mRNA. Accordingly, it is an object of the present invention to provide such compounds.

All documents referred to herein are incorporated by reference into the present application as though fully set forth herein.

SUMMARY OF THE INVENTION

In accordance with the present invention, compounds that suppress premature translation termination associated with a nonsense mutation in mRNA have been identified, and methods for their use provided.

In one aspect of the invention, compounds of Formula (1) are provided which are useful for suppressing premature translation termination associated with a nonsense mutation in mRNA, and for treating diseases associated with nonsense mutations in mRNA:

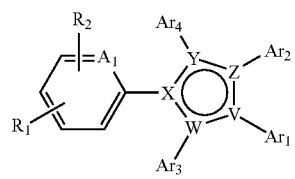

wherein:
 $A_1$ is C, CH or N;
 V and X are independently selected from N or C;
 W is selected from N, C or CH;
 wherein at least one of V, W, or X is N, and wherein if W is N, at least one of V or X is also N;
 Y and Z are independently selected from N, C, C—$R_c$, C=O, C=S, wherein $R_c$ is H, $CH_3$, or $NH_2$; with the proviso that when one of Y or Z is C=O or C=S, the other may also be selected from NH, S, or O;
 $R_1$ is carboxy, cyano, or a carbonyl group which is optionally substituted with a $C_1$-$C_4$ alkoxy group,
 $R_2$ is absent or a nitro;
 $Ar_1$ is a $C_1$ to $C_4$ alkyl which is optionally substituted with an R group; a$C_6$ to $C_{10}$ aryl which is optionally substituted with one, two or three independently selected R groups; a live to ten membered heterocycle which is optionally substituted with one, two or three independently selected R groups; together with $Ar_2$ and the heterocycle to which $Ar_1$ and $Ar_2$ are attached form a ring structure selected from $Ar_{1-2}$; or together with $Ar_3$ and the heterocycle to which $Ar_1$ and $Ar_3$ are attached form a ring structure selected from $Ar_{1-3}$;
 Are is absent or together with $Ar_1$ and the heterocycle to which $Ar_1$ and $Ar_2$ are attached form a ring structure selected from $Ar_{1-2}$;
 $Ar_3$ is absent or together with $Ar_1$ and the heterocycle to which $Ar_1$ and $Ar_3$ are attached form a ring structure selected from $Ar_{1-3}$;
 $Ar_4$ is absent; or is a $C_1$-$C_4$ alkyl, a $C_1$-$C_4$ alkoxy, or a $C_1$-$C_4$ thioalkyl, any of which together with $A_1$ forms a four to seven membered carbocycle or heterocycle;
 R is hydrogen; a —$R_a$ group; or two R groups, where R may also include an oxy group, together with the phenyl or heterocycle to which they are attached form a ring structure selected from RR;
  wherein:
   $Ar_{1-2}$ and $Ar_{1-3}$ are selected from an eleven to fourteen membered hetero-tricycle ring structure optionally substituted with one or more halogens, $C_1$-$C_4$ alkyl groups, $C_1$-$C_4$ haloalkyl groups, $C_1$-$C_4$ alkoxy groups optionally substituted with a halogen or a $C_1$-$C_4$ alkoxy group, $C_1$-$C_4$ haloalkoxy groups, or amino groups optionally substituted with a carbonyl group which is substituted with a $C_1$-$C_4$ alkyl group;

RR is a nine to ten membered bicyclic ring structure optionally substituted with one or more halogens, $C_1$-$C_4$ alkyl groups, $C_1$-$C_4$ haloalkyl groups, $C_1$-$C_4$ alkoxy groups, oxo groups, or $C_1$-$C_4$ haloalkoxy groups;

$R_a$ is selected from the group consisting of: a hydroxy group; a halogen; a $C_1$-$C_4$ alkyl which is optionally substituted with one or more independently selected halogen or hydroxy groups; a $C_1$-$C_4$ alkoxy which is optionally substituted with one or more independently selected halogen or phenyl groups; a $C_4$-$C_8$ cycloalkyl which is optionally substituted with one or more independently selected $C_1$-$C_4$ alkyl groups; an —$R_b$ group; a —O—$R_b$ group; a four to six-membered heterocycle which is optionally substituted with one or more independently selected $C_1$-$C_4$ alkyl, oxo, or —$R_b$ groups; a nine to ten membered heterocycle having two ring structures; a carbonyl which is optionally substituted with a hydroxy, a $C_1$-$C_4$ alkyl, or a $C_1$-$C_4$ alkoxy group; a carbamoyl which is optionally substituted with one or two $C_1$-$C_4$ alkyl groups; a nitro group; a cyano group; a thio which is optionally substituted with a hydroxy, a $C_1$-$C_4$ alkyl, or —$R_b$ group; a sulfonyl which is optionally substituted with a hydroxy, a $C_1$-$C_4$ alkyl, or —$R_b$ group; or an amino which is optionally substituted with one or two independently selected $C_1$-$C_4$ alkyl, sulfonyl, or carbonyl groups, wherein the aminosulfonyl group is optionally substituted with a hydroxy, a $C_1$-$C_4$ alkyl, or —$R_b$ group and wherein the aminocarbonyl group is optionally substituted with a $C_1$-$C_4$ alkyl, a $C_1$-$C_4$ haloalkyl, a benzoxy, or an amino group which is optionally substituted with an —$R_b$ group;

wherein —$R_b$ is a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups;

or a pharmaceutically acceptable salt, hydrate, solvate, clathrate, racemate, stereoisomer, or polymorph of said compound of Formula 1.

In another aspect of the invention, methods are provided for the suppression of premature translation termination associated with a nonsense mutation, and for the prevention or treatment of diseases associated with nonsense mutations of mRNA. Such diseases include, but are not limited to, genetic diseases caused by premature translation termination associated with a nonsense mutation, such as a CNS disease, an inflammatory disease, a neurodegenerative disease, an autoimmune disease, a cardiovascular disease, or a pulmonary disease; more preferably the disease is cancer (or other proliferative diseases), amyloidosis, Alzheimer's disease, atherosclerosis, giantism, dwarfism, hypothyroidism, hyperthyroidism, cystic fibrosis, aging, obesity, Parkinson's disease, Niemann Pick's disease, familial hypercholesterolemia, retinitis pigmentosa, Marfan syndrome, lysosomal storage disorders, the muscular dystrophies, cystic fibrosis, hemophilia, or classical late infantile neuronal ceroid lipofuscinosis (LINCL).

In one embodiment, the invention is directed to methods for suppressing premature translation termination associated with a nonsense mutation in mRNA comprising administering a nonsense-suppressing amount of at least one compound of the invention to a subject in need thereof.

In yet another embodiment, methods for treating cancer, lysosomal storage disorders, a muscular dystrophy, cystic fibrosis, hemophilia, or classical late infantile neuronal ceroid lipofuscinosis are provided comprising administering a therapeutically effective amount of at least one compound of the invention to a subject in need thereof.

These and other aspects of the invention will be more clearly understood with reference to the following preferred embodiments and detailed description.

CERTAIN EMBODIMENTS

1. A method of treating or preventing a disease resulting from a somatic mutation comprising administering to a patient in need thereof an effective amount of a compound of Formula 1:

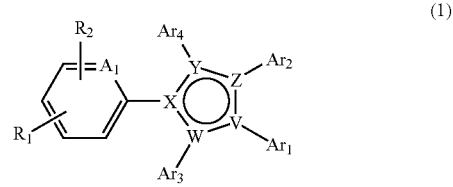

(1)

wherein:

$A_1$ is C, CH or N;

V and X are independently selected from N or C;

W is selected from N, C or CH;

wherein at least one of V, W, or X is N, and wherein if W is N, at least one of V or X is also N;

Y and Z are independently selected from N, C, C—$R_c$, C═O, C═S, wherein $R_c$ is H, $CH_3$, or $NH_2$; with the proviso that when one of Y or Z is C═O or C═S, the other may also be selected from NH, S, or O;

$R_1$ is carboxy, cyano, or a carbonyl group which is optionally substituted with a $C_1$-$C_4$ alkoxy group, $R_2$ is absent or a nitro;

$Ar_1$ is a $C_1$ to $C_4$ alkyl which is optionally substituted with an R group; a $C_6$ to $C_{10}$ aryl which is optionally substituted with one, two or three independently selected R groups; a five to ten membered heterocycle which is optionally substituted with one, two or three independently selected R groups; together with $Ar_2$ and the heterocycle to which $Ar_1$ and $Ar_2$ are attached form a ring structure selected from $Ar_{1-2}$; or together with $Ar_3$ and the heterocycle to which $Ar_1$ and $Ar_3$ are attached form a ring structure selected from $Ar_{1-3}$;

$Ar_2$ is absent or together with $Ar_1$ and the heterocycle to which $Ar_1$ and $Ar_2$ are attached form a ring structure selected from $Ar_{1-2}$ $Ar_3$ is absent or together with $Ar_1$ and the heterocycle to which $Ar_1$ and $Ar_3$ are attached form a ring structure selected from $Ar_{1-3}$;

$Ar_4$ is absent; or is a $C_1$-$C_4$ alkyl, a $C_1$-$C_4$ alkoxy, or a $C_1$-$C_4$ thioalkyl, any of which together with $A_1$ forms a four to seven membered carbocycle or heterocycle;

R is hydrogen; a —$R_a$ group; or two R groups, where R may also include an oxy group, together with the phenyl or heterocycle to which they are attached form a ring structure selected from RR;

wherein:

$Ar_{1-2}$ and $Ar_{1-3}$ are selected from an eleven to fourteen membered hetero-tricycle ring structure optionally substituted with one or more halogens, $C_1$-$C_4$ alkyl groups, $C_1$-$C_4$ haloalkyl groups, $C_1$-$C_4$ alkoxy groups optionally substituted with a halogen or a $C_1$-$C_4$ alkoxy group, $C_1$-$C_4$ haloalkoxy groups, or amino groups optionally substituted with a carbonyl group which is substituted with a $C_1$-$C_4$ alkyl group;

RR is a nine to ten membered bicyclic ring structure optionally substituted with one or more halogens, $C_1$-$C_4$ alkyl groups, $C_1$-$C_4$ haloalkyl groups, $C_1$-$C_4$ alkoxy groups, oxo groups, or $C_1$-$C_4$ haloalkoxy groups;

$R_a$ is selected from the group consisting of: a hydroxy group; a halogen; a $C_1$-$C_4$ alkyl which is optionally substituted with one or more independently selected halogen or hydroxy groups; a $C_1$-$C_4$ alkoxy which is optionally substituted with one or more independently selected halogen or phenyl groups; a $C_4$-$C_8$ cycloalkyl which is optionally substituted with one or more independently selected $C_1$-$C_4$ alkyl groups; an —$R_b$ group; a —O—$R_b$ group; a four to six-membered heterocycle which is optionally substituted with one or more independently selected $C_1$-$C_4$ alkyl, oxo, or —$R_b$ groups; a nine to ten membered heterocycle having two ring structures; a carbonyl which is optionally substituted with a hydroxy, a $C_1$-$C_4$ alkyl, or a $C_1$-$C_4$ alkoxy group; a carbamoyl which is optionally substituted with one or two $C_1$-$C_4$ alkyl groups; a nitro group; a cyano group; a thio which is optionally substituted with a hydroxy, a $C_1$-$C_4$ alkyl, or —$R_b$ group; a sulfonyl which is optionally substituted with a hydroxy, a $C_1$-$C_4$ alkyl, or —$R_b$ group; or an amino which is optionally substituted with one or two independently selected $C_1$-$C_4$ alkyl, sulfonyl, or carbonyl groups, wherein the aminosulfonyl group is optionally substituted with a hydroxy, a $C_1$-$C_4$ alkyl, or —$R_b$ group and wherein the aminocarbonyl group is optionally substituted with a $C_1$-$C_4$ alkyl, a $C_1$-$C_4$ haloalkyl, a benzoxy, or an amino group which is optionally substituted with an —$R_b$ group;

wherein —$R_b$ is a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups;

or a pharmaceutically acceptable salt, hydrate, solvate, clathrate, racemate, stereoisomer, or polymorph of said compound of Formula 1.

2. The method of embodiment 1, wherein the compound, or a pharmaceutically acceptable salt, hydrate, solvate, clathrate polymorph, racemate, stereoisomer, or polymorph thereof, is administered as a composition comprising the compound and a pharmaceutically acceptable carrier or diluent.

3. The method of embodiment 1, wherein the administration is intravenous.

4. The method of embodiment 1, wherein $Ar_{1-2}$ is selected from the following:

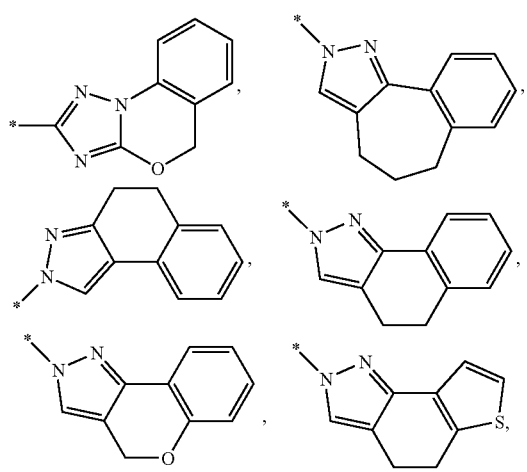

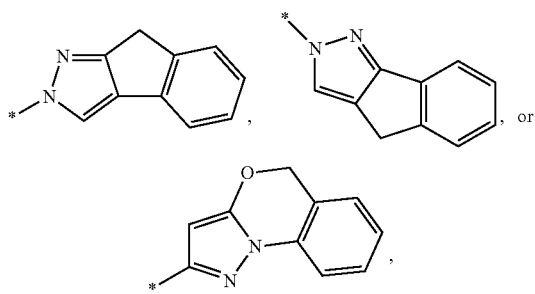

wherein the * indicates the bond of attachment of $Ar_{1-2}$ to the 6-membered ring of Formula 1.

$Ar_{1-3}$ is selected from the following:

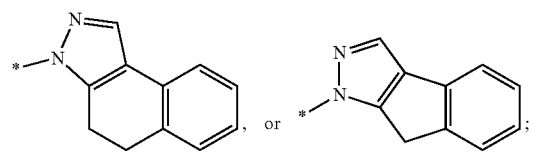 [SMILES: *n1ncc2c1CCc1ccccc1-2 ; *n1ncc2c1Cc1ccccc1-2]

wherein the * indicates the bond of attachment of $Ar_{1-3}$ to the 6-membered ring of Formula 1.

and RR is selected from the following: a quinoline group; a napthyl group; a benzo[1,3]dioxole group; a benzo[1,4]dioxole group; an indolyl group; or a quinoxaline group;

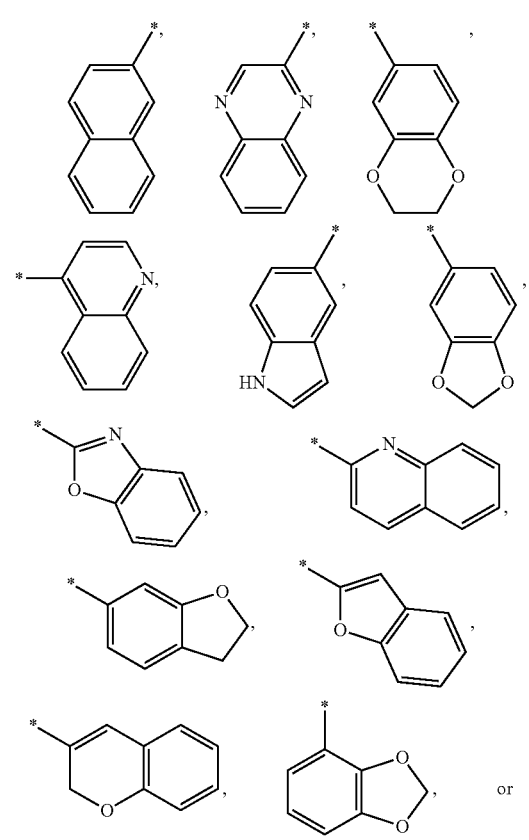

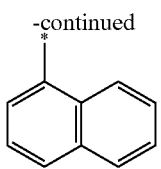

wherein the * indicates the bond of attachment of RR to the 5-membered ring of Formula 1.

5. The method of embodiment 1, wherein the compound of Formula 1 is a compound Formula 1-A:

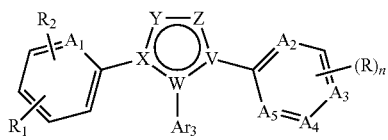

wherein $A_1$, $A_2$, $A_3$, $A_4$, and $A_5$ are independently selected from N, C and CH; $Ar_3$ is absent or hydrogen and n is 0, 1, or 2.

6. The method of embodiment 5, wherein $R_2$ is absent and $A_1$, $A_2$, $A_3$, $A_4$, and $A_5$ are independently selected from C and CH.

7. The method of embodiment 5, wherein $R_1$ is a carboxy group.

8. The method embodiment 1, wherein the compound of Formula 1 is a compound of Formula 1-B:

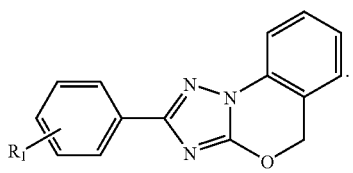

9. The method of embodiment 8, wherein $R_1$ is a carboxy group.

10. The method of embodiment 1, wherein the compound of Formula 1 is a compound of Formula 1-C:

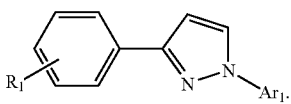

11. The method of embodiment 10, wherein $Ar_1$ is a thienyl group.

12. The method of embodiment 10, wherein $R_1$ is a carboxy group.

13. The method of embodiment 1, wherein the compound of Formula 1 is a compound of Formula 1-D:

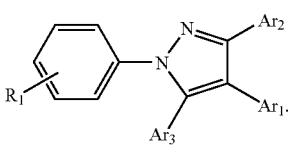

14. The method of embodiment 13, wherein $Ar_2$ is absent.
15. The method of embodiment 13, wherein $Ar_3$ is hydrogen.

16. The method of embodiment 13, wherein $R_1$ is a carboxy group.

17. The method of embodiment 1, wherein the compound of Formula 1 is a compound of Formula 1-E:

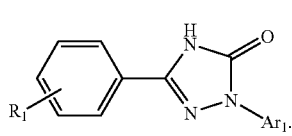

18. The method of embodiment 17, wherein $Ar_1$ is a phenyl group optionally substituted with one or two R groups.
19. The method of embodiment 18, wherein the one or two R groups are independently selected from a $C_1$-$C_4$ alkyl group and a halogen.
20. The method of embodiment 17, wherein $R_1$ is a carboxy group.

21. The method of embodiment 1, wherein the compound of Formula 1 is a compound of Formula 1-F:

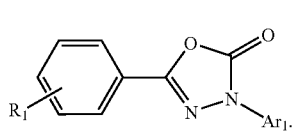

22. The method of embodiment 21, wherein $Ar_1$ is a phenyl group optionally substituted with one or two R groups.
23. The method of embodiment 22, wherein the one or two R groups are independently selected from a $C_1$-$C_4$ alkyl group, a halogen, $C_1$-$C_4$ haloalkyl, and a methanesulfonyl group, or two R groups together form a quinoline group.
24. The method of embodiment 21, wherein $R_1$ is a carboxy group.

25. The method of embodiment 1, wherein the compound of Formula 1 is a compound of Formula 1-G:

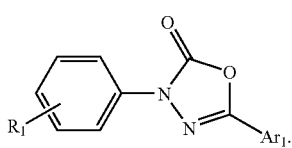

26. The method of embodiment 25, wherein $Ar_1$ is a phenyl group optionally substituted with one or two R groups.
27. The method of embodiment 26, wherein the one or two R groups are independently selected from a $C_1$-$C_4$ alkyl group and a cyano group.
28. The method of embodiment 25, wherein $R_1$ is a carboxy group.

29. The method of embodiment 1, wherein the compound of Formula 1 is a compound of Formula 1-H:

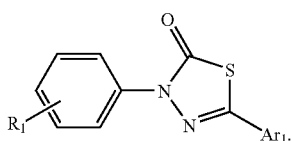

30. The method of embodiment 29, wherein $Ar_1$ is a phenyl group optionally substituted with one or two R groups.

31. The method of embodiment 30, wherein the one or two R groups are $C_1$-$C_4$ alkyl groups.

32. The method of embodiment 29, wherein $R_1$ is a carboxy group.

33. The method of embodiment 1, wherein the compound of Formula 1 is a compound of Formula 1-I:

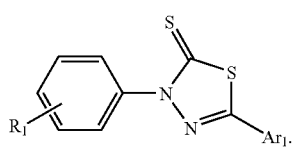

1-I

34. The method of embodiment 33, wherein $Ar_1$ is a phenyl group optionally substituted with one or two R groups.

35. The method of embodiment 34, wherein the one or two R groups are $C_1$-$C_4$ alkyl groups.

36. The method of embodiment 33, wherein $R_1$ is a carboxy group.

37. The method of embodiment 1, wherein the compound of Formula 1 is a compound of Formula 1-J:

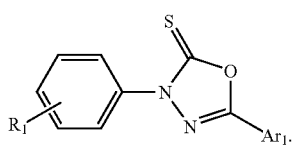

1-J

38. The method of embodiment 37, wherein $Ar_1$ is a phenyl group optionally substituted with one or two R groups.

39. The method of embodiment 38, wherein the one or two R groups are $C_1$-$C_4$ alkyl groups.

40. The method of embodiment 37, wherein $R_1$ is a carboxy group.

41. A method of treating or preventing an autoimmune disease, a blood disease, a collagen disease, diabetes, a neurodegenerative disease, a cardiovascular disease, a pulmonary disease, or an inflammatory disease or central nervous system disease comprising administering to a patient in need thereof an effective amount of a compound of Formula 1, or a pharmaceutically acceptable salt, hydrate, solvate, clathrate, racemate, stereoisomer, or polymorph thereof.

42. The method of embodiment 41, wherein the administration is intravenous.

43. The method of embodiment 41, wherein the autoimmune disease is rheumatoid arthritis or graft versus host disease.

44. The method of embodiment 41, wherein the inflammatory disease is arthritis.

45. The method of embodiment 41, wherein the central nervous system disease is multiple sclerosis, muscular dystrophy, Duchenne muscular dystrophy, Alzheimer's disease, a neurodegenerative disease or Parkinson's disease.

46. The method of embodiment 41, wherein the blood disorder is hemophilia, Von Willebrand disease, or β-thalassemia.

47. The method of embodiment 41, wherein the collagen disease is osteogenesis imperfecta or cirrhosis.

48. A method of treating or preventing familial polycythemia, immunodeficiency, kidney disease, cystic fibrosis, familial hypercholesterolemia, retinitis pigmentosa, amyloidosis, hemophilia, Alzheimer's disease, Tay Sachs disease, Niemann Pick disease, Parkinson's disease, atherosclerosis, giantism, dwarfism, hyperthyroidism, aging, obesity, Duchenne muscular dystrophy or Marfan syndrome comprising administering to a patient in need thereof an effective amount of a compound of Formula 1, or a pharmaceutically acceptable salt, hydrate, solvate, clathrate, racemate, stereoisomer, or polymorph thereof.

49. The method of embodiment 48, wherein the administration is intravenous.

50. A method of treating or preventing cancer in a human comprising administering to a human in need thereof an effective amount of a compound of Formula 1, or a pharmaceutically acceptable salt, hydrate, solvate, clathrate, racemate, stereoisomer, or polymorph thereof.

51. The method of embodiment 50, wherein the administration is intravenous.

52. The method of embodiment 50, wherein the cancer is of the head and neck, eye, skin, mouth, throat, esophagus, chest, bone, blood, lung, colon, sigmoid, rectum, stomach, prostate, breast, ovaries, kidney, liver, pancreas, brain, intestine, heart or adrenals.

53. The method of embodiment 50, wherein the compound, or a pharmaceutically acceptable salt, hydrate, solvate, clathrate or stereoisomer thereof, comprises a pharmaceutically acceptable carrier or diluent.

54. The method of embodiment 50, wherein the cancer is a solid tumor.

55. The method of embodiment 50, wherein the cancer is sarcoma, carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor or multiple myeloma.

56. The method of embodiment 50, wherein the cancer is acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, chronic lymphocytic leukemia, hairy cell leukemia, or multiple myeloma.

57. A method of treating or preventing a disease associated with a mutation of the p53 gene comprising administering to a patient in need thereof an effective amount of a compound of Formula 1, or a pharmaceutically acceptable salt, hydrate, solvate, clathrate, racemate, stereoisomer, or polymorph thereof.

58. The method of embodiment 57, wherein the administration is intravenous.

59. The method of embodiment 57, wherein the disease is sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma or retinoblastoma.

60. A method of inhibiting the growth of a cancer cell comprising contacting the cancer cell with an effective amount of a compound of Formula 1, or a pharmaceutically acceptable salt, hydrate, solvate, clathrate, racemate, stereoisomer, or polymorph thereof.

61. A method for selectively producing a protein in a mammal comprising,
transcribing a gene containing a nonsense mutation in the mammal; and
providing an effective amount of a compound of the present invention to said mammal, wherein said protein is produced from said gene containing a nonsense mutation.

BRIEF DESCRIPTION OF THE DRAWINGS

FIG. 1 provides schematic representations of constructs for luciferase based assays to evaluate the suppression of a nonsense mutation.

FIG. 2 provides schematic representations of the luciferase constructs engineered to harbor one or more epitope tags in the N-terminus of the luciferase protein.

FIG. 3 provides schematic representations of constructs for luciferase based assays to evaluate readthrough efficiency.

DETAILED DESCRIPTION OF THE INVENTION

Premature translation termination can produce aberrant proteins which can be lethal or can cause a number of diseases, including as non-limiting examples, cancers, lysosomal storage disorders, the muscular dystrophies, cystic fibrosis and hemophilia. In accordance with the present invention, compounds that suppress nonsense mutations have been identified, and methods for their use provided.

A. Compounds of the Invention

In one aspect of the invention, compounds of the invention are provided which are useful in suppression of a nonsense mutation. In certain embodiments, the compounds of the invention specifically suppresses a nonsense mutation, while in other embodiments, the compounds of the invention suppress a nonsense mutation as well as treat a disease, including as non-limiting examples, cancers, lysosomal storage disorders, the muscular dystrophies, cystic fibrosis and hemophilia.

Preferred compounds of the present invention useful in the suppression of a nonsense mutation include those of Formula (1) as shown below.

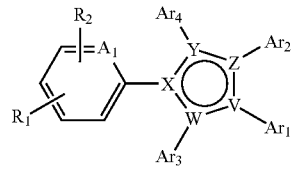

wherein:
$A_1$ is C, CH or N;
V and X are independently selected from N or C;
W is selected from N, C or CH;
wherein at least one of V, W, or X is N, and wherein if W is N, at least one of V or X is also N;
Y and Z are independently selected from N, C, C—$R_c$, C=O, C=S, wherein R, is H, $CH_3$, or $NH_2$; with the proviso that when one of Y or Z is C=O or C=S, the other may also be selected from NH, S, or O;
$R_1$ is carboxy, cyano, or a carbonyl group which is optionally substituted with a $C_1$-$C_4$ alkoxy group,
$R_2$ is absent or a nitro;
$Ar_1$ is a $C_1$ to $C_4$ alkyl which is optionally substituted with an R group; a $C_6$ to $C_{10}$ aryl which is optionally substituted with one, two or three independently selected R groups; a five to ten membered heterocycle which is optionally substituted with one, two or three independently selected R groups; together with $Ar_2$ and the heterocycle to which $Ar_1$ and $Ar_2$ are attached form a ring structure selected from $Ar_{1-2}$; or together with $Ar_3$ and the heterocycle to which $Ar_1$ and $Ar_3$ are attached form a ring structure selected from $Ar_{1-3}$;
$Ar_2$ is absent or together with $Ar_1$ and the heterocycle to which $Ar_1$ and $Ar_2$ are attached form a ring structure selected from $Ar_{1-2}$
$Ar_3$ is absent or together with $Ar_1$ and the heterocycle to which $Ar_1$ and $Ar_3$ are attached form a ring structure selected from $Ar_{1-3}$;
$Ar_4$ is absent; or is a $C_1$-$C_4$ alkyl, a $C_1$-$C_4$ alkoxy, or a $C_1$-$C_4$ thioalkyl, any of which together with $A_1$ forms a four to seven membered carbocycle or heterocycle;
R is hydrogen; a —$R_a$ group; or two R groups, where R may also include an oxy group, together with the phenyl or heterocycle to which they are attached form a ring structure selected from RR;
wherein:
$Ar_{1-2}$ and $Ar_{1-3}$ are selected from an eleven to fourteen membered hetero-tricycle ring structure optionally substituted with one or more halogens, $C_1$-$C_4$ alkyl groups, $C_1$-$C_4$ haloalkyl groups, $C_1$-$C_4$ alkoxy groups optionally substituted with a halogen or a $C_1$-$C_4$ alkoxy group, $C_1$-$C_4$ haloalkoxy groups, or amino groups optionally substituted with a carbonyl group which is substituted with a $C_1$-$C_4$ alkyl group;
RR is a nine to ten membered bicyclic ring structure optionally substituted with one or more halogens, $C_1$-$C_4$ alkyl groups, $C_1$-$C_4$ haloalkyl groups, $C_1$-$C_4$ alkoxy groups, oxo groups, or $C_1$-$C_4$ haloalkoxy groups;
$R_a$ is selected from the group consisting of: a hydroxy group; a halogen; a $C_1$-$C_4$ alkyl which is optionally substituted with one or more independently selected halogen or hydroxy groups; a $C_1$-$C_4$ alkoxy which is optionally substituted with one or more independently selected halogen or phenyl groups; a $C_4$-$C_8$ cycloalkyl which is optionally substituted with one or more independently selected $C_1$-$C_4$ alkyl groups; an —$R_b$ group; a —O—$R_b$ group; a four to six-membered heterocycle which is optionally substituted with one or more independently selected $C_1$-$C_4$ alkyl, oxo, or —$R_b$ groups; a nine to ten membered heterocycle having two ring structures; a carbonyl which is optionally substituted with a hydroxy, a $C_1$-$C_4$ alkyl, or a $C_1$-$C_4$ alkoxy group; a carbamoyl which is optionally substituted with one or two $C_1$-$C_4$ alkyl groups; a nitro group; a cyano group; a thio which is optionally substituted with a hydroxy, a $C_1$-$C_4$ alkyl, or —$R_b$ group; a sulfonyl which is optionally substituted with a hydroxy, a $C_1$-$C_4$ alkyl, or —$R_b$ group; or an amino which is optionally substituted with one or two independently selected $C_1$-$C_4$ alkyl, sulfonyl, or carbonyl groups, wherein the aminosulfonyl group is optionally substituted with a hydroxy, a $C_1$-$C_4$ alkyl, or —$R_b$ group and wherein the aminocarbonyl group is optionally substituted with a $C_1$-$C_4$ alkyl, a $C_1$-$C_4$ haloalkyl, a benzoxy, or an amino group which is optionally substituted with an —$R_b$ group;

wherein —$R_b$ is a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups;

or a pharmaceutically acceptable salt, hydrate, solvate, clathrate, racemate, stereoisomer, or polymorph of said compound of Formula 1.

In a preferred embodiment of Formula 1, $Ar_{1-2}$ is selected from the following, optionally substituted as in Formula 1:

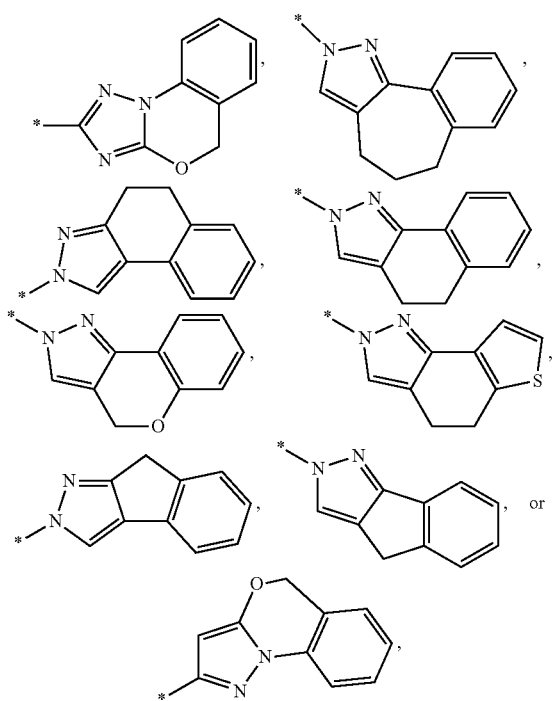

wherein the * indicates the bond of attachment of $Ar_{1-2}$ to the 6-membered ring of Formula 1.

In another preferred embodiment of Formula 1, $Ar_{1-3}$ is selected from the following, optionally substituted as in Formula 1:

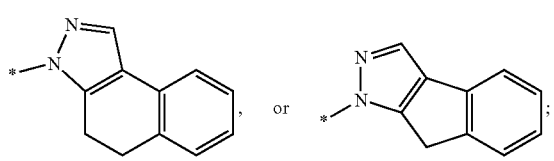 [SMILES: *n1ncc2c1CCc1ccccc1-2 ; *n1ncc2c1Cc1ccccc1-2]

wherein the * indicates the bond of attachment of $Ar_{1-3}$ to the 6-membered ring of Formula 1.

In another preferred embodiment of Formula 1, $Ar_4$-$A_1$ may, together with the $A_1$ and V/W/X/Y/Z containing rings to which $Ar_4$-$A_1$ is joined, form a three, four or five membered fused ring structure. In a preferred embodiment of Formula 1, $Ar_4$-$A_1$, together with the $A_1$ and V/W/X/Y/Z containing rings to which it is joined, form a heterotricycle which may be optionally substituted as described herein.

In yet another preferred embodiment of Formula 1, $Ar_4$-$A_1$, together with the $A_1$ and V/W/X/Y/Z containing rings to which $Ar_4$-$A_1$ is joined, may be selected from:

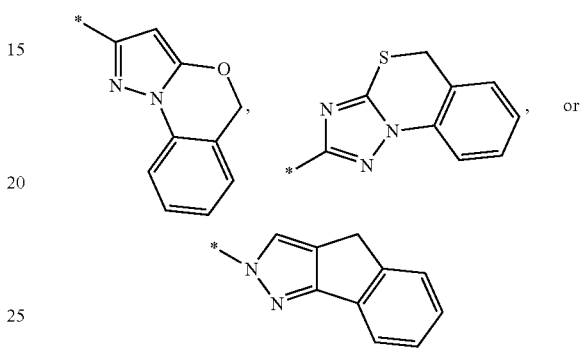

wherein the * indicates the bond of attachment to $Ar_1$ of a tricycle formed between $Ar_4$-$A_1$, the $A_1$ containing ring and the V/W/X/Y/Z containing ring of Formula 1.

In yet another preferred embodiment of Formula 1, RR is selected from the following: a quinoline group; a napthyl group; a benzo[1,3]dioxole group; a benzo[1,4]dioxole group; an indolyl group; or a quinoxaline group;

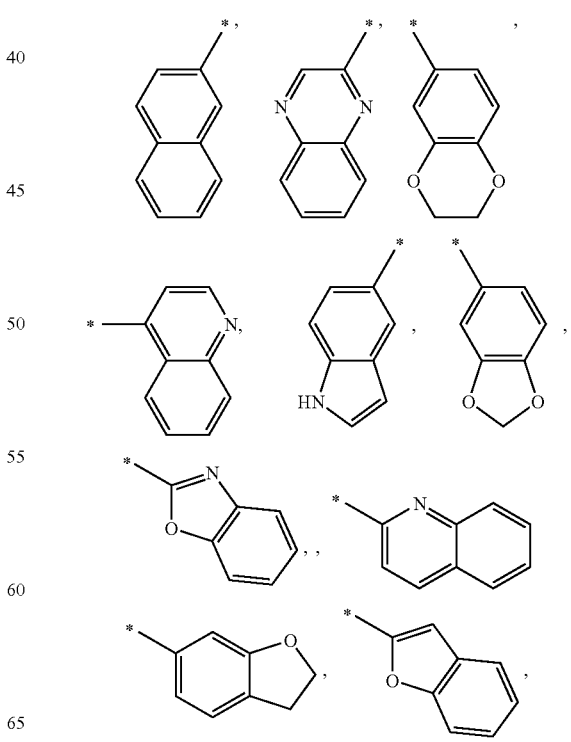

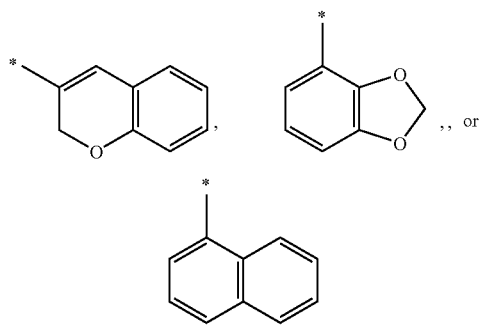
wherein the * indicates the bond of attachment of RR to the 5-membered ring of Formula 1.
In yet another preferred embodiment of Formula 1, $Ar_{1-2}$ may be selected from:
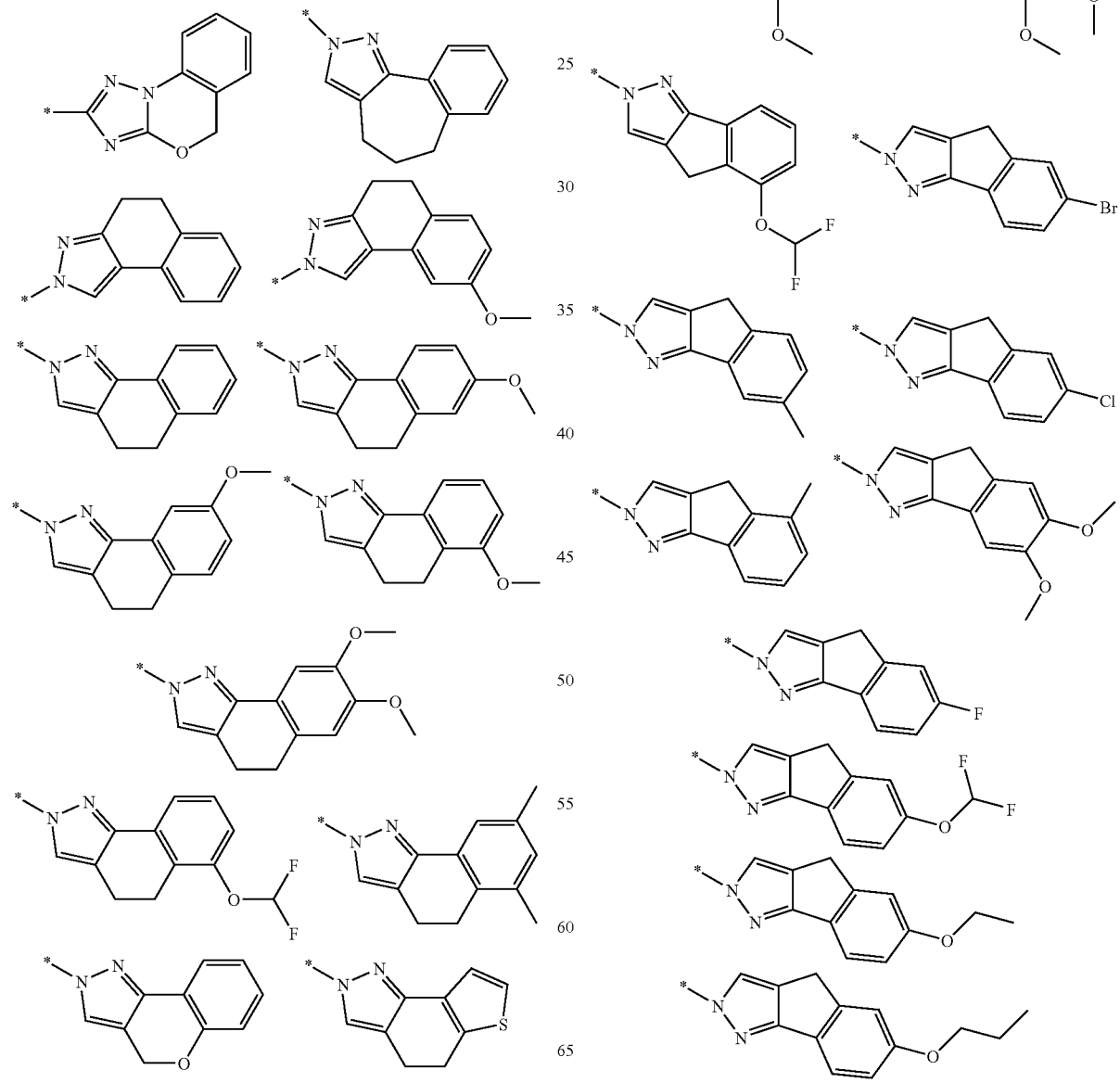

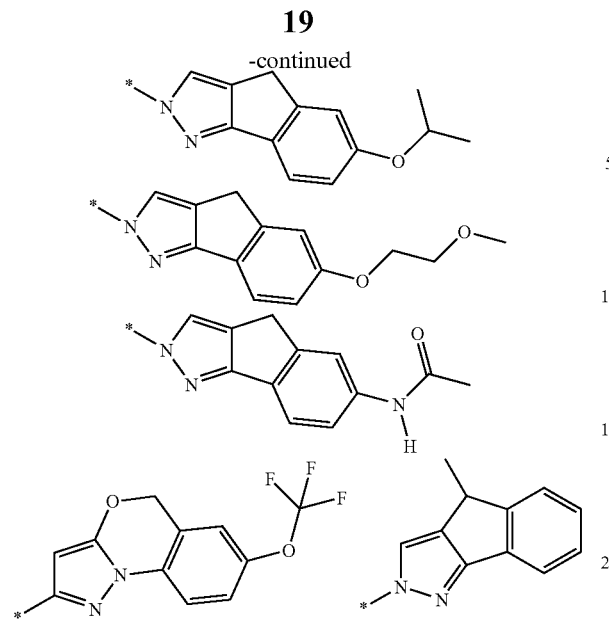

wherein the * indicates the bond of attachment of $Ar_{1-2}$ to the 6-membered ring of Formula 1.

In yet another preferred embodiment of Formula 1, $Ar_{1-3}$ may be selected from:

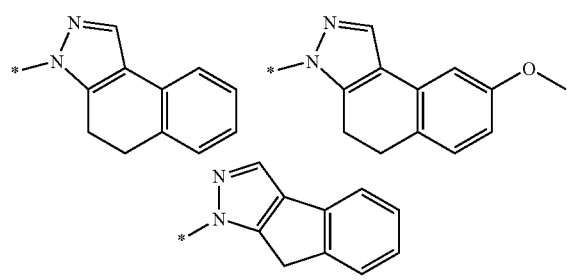

wherein the * indicates the bond of attachment of $Ar_{1-3}$ to the 6-membered ring of Formula 1.

In yet another preferred embodiment of Formula 1, $Ar_4$-$A_1$, together with the $A_1$ and V/W/X/Y/Z containing rings to which $Ar_4$-$A_1$ is joined, may be selected from:

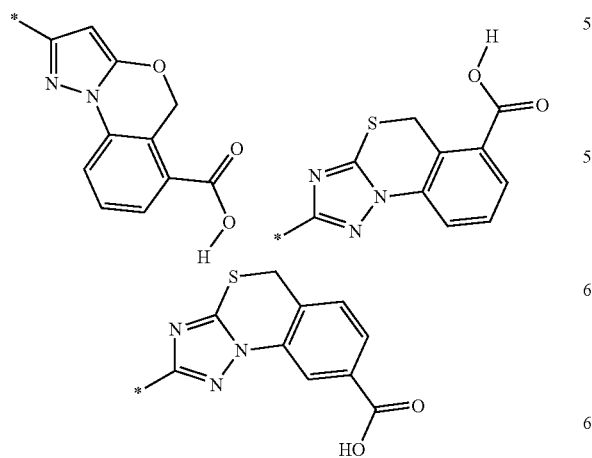

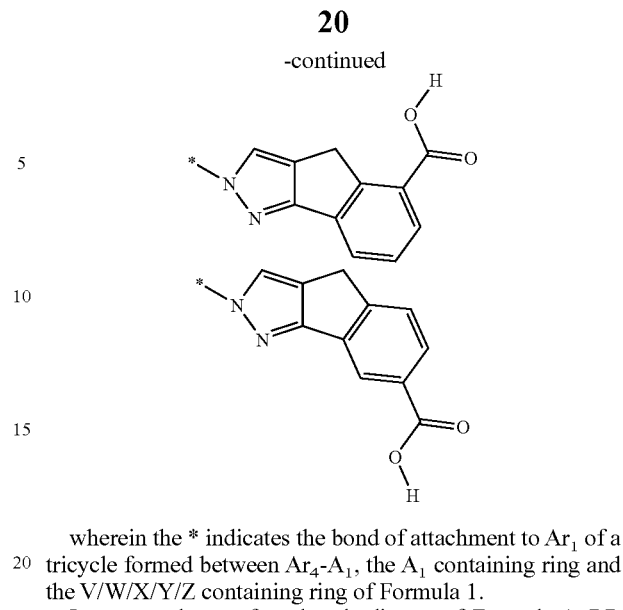

wherein the * indicates the bond of attachment to $Ar_1$ of a tricycle formed between $Ar_4$-$A_1$, the $A_1$ containing ring and the V/W/X/Y/Z containing ring of Formula 1.

In yet another preferred embodiment of Formula 1, RR may be selected from:

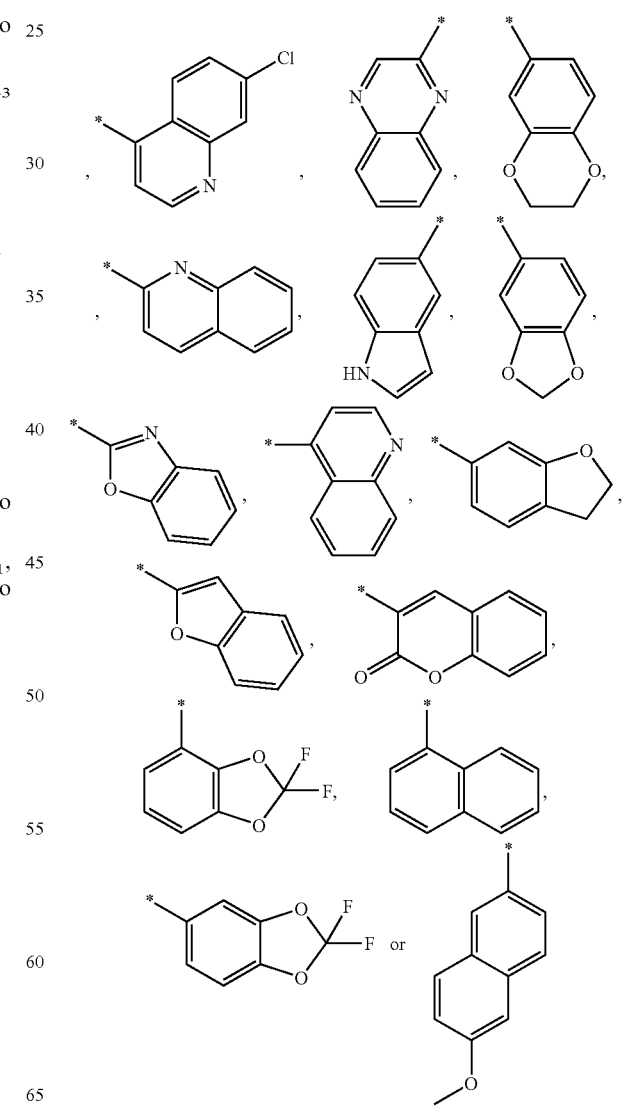

In yet other preferred embodiments of Formula 1, Ar₁ may be selected from:
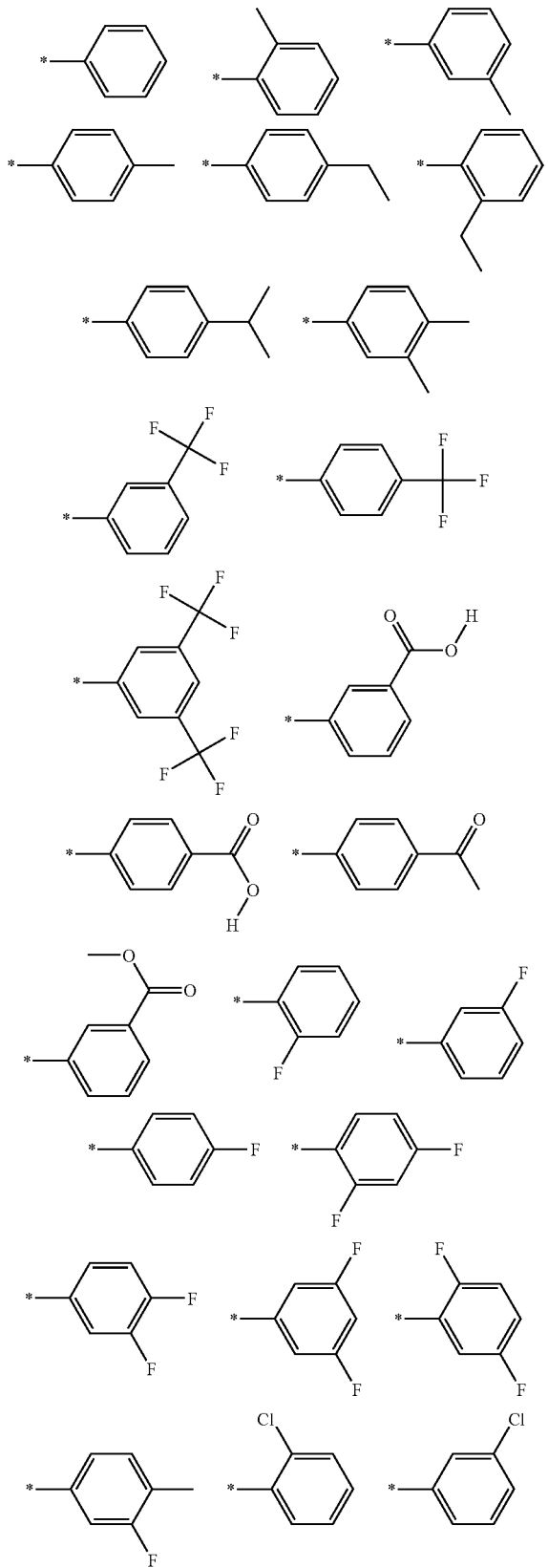
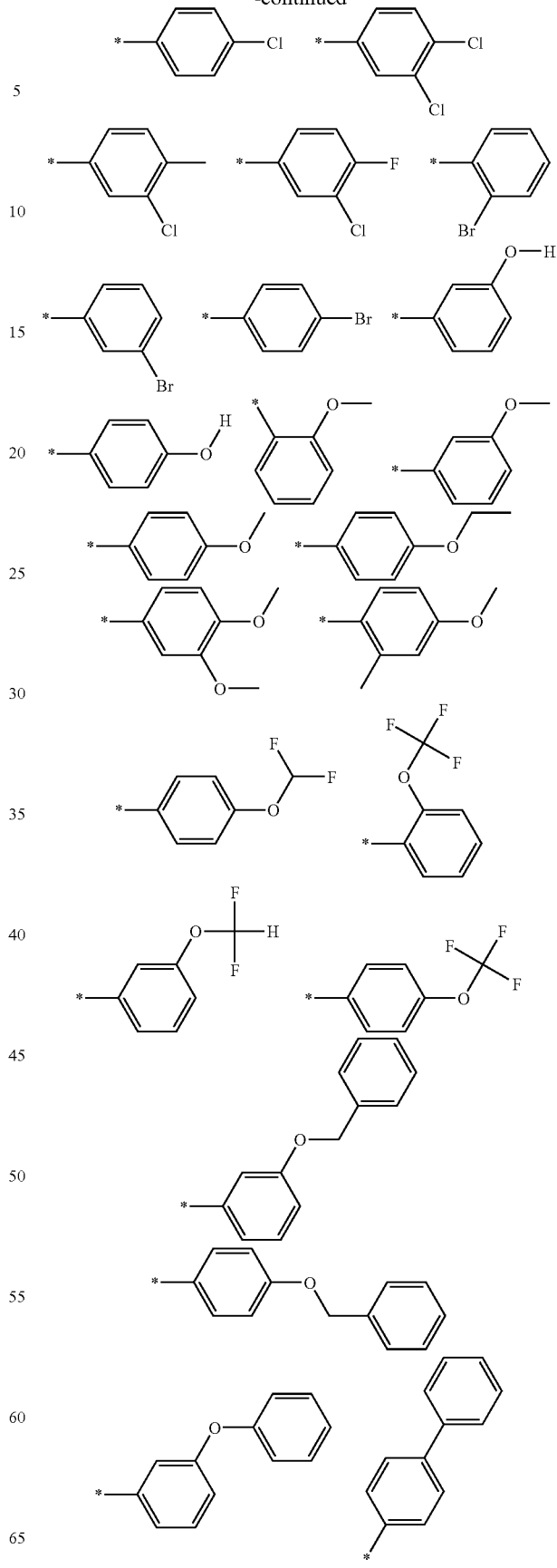

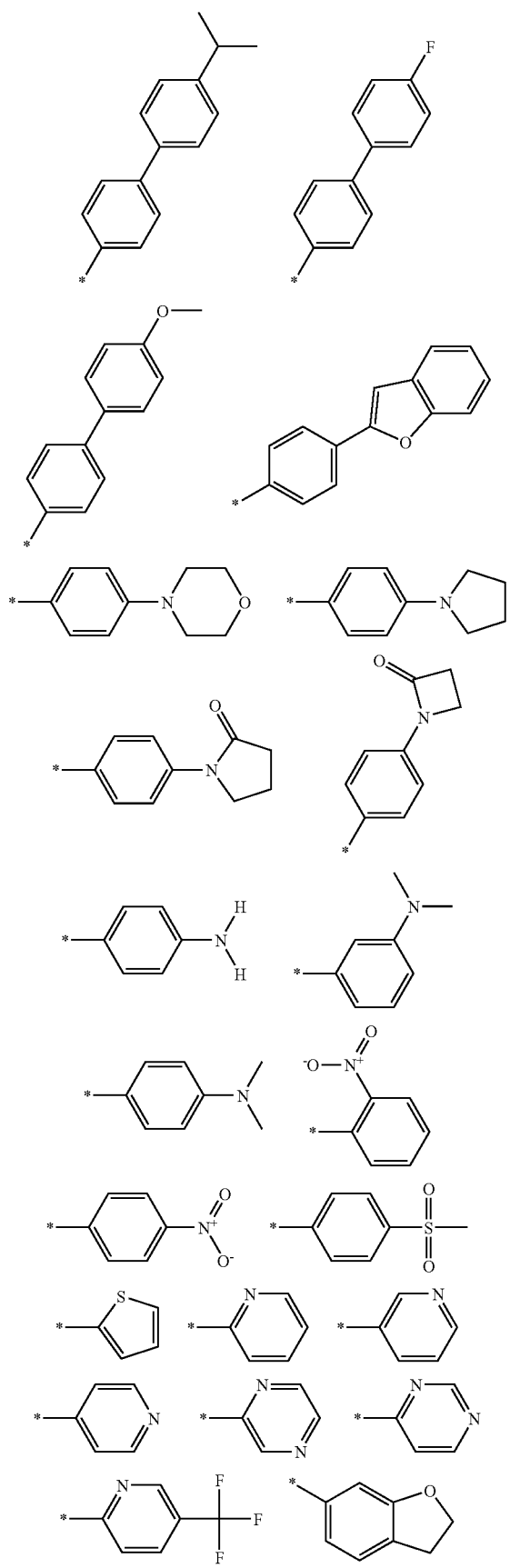
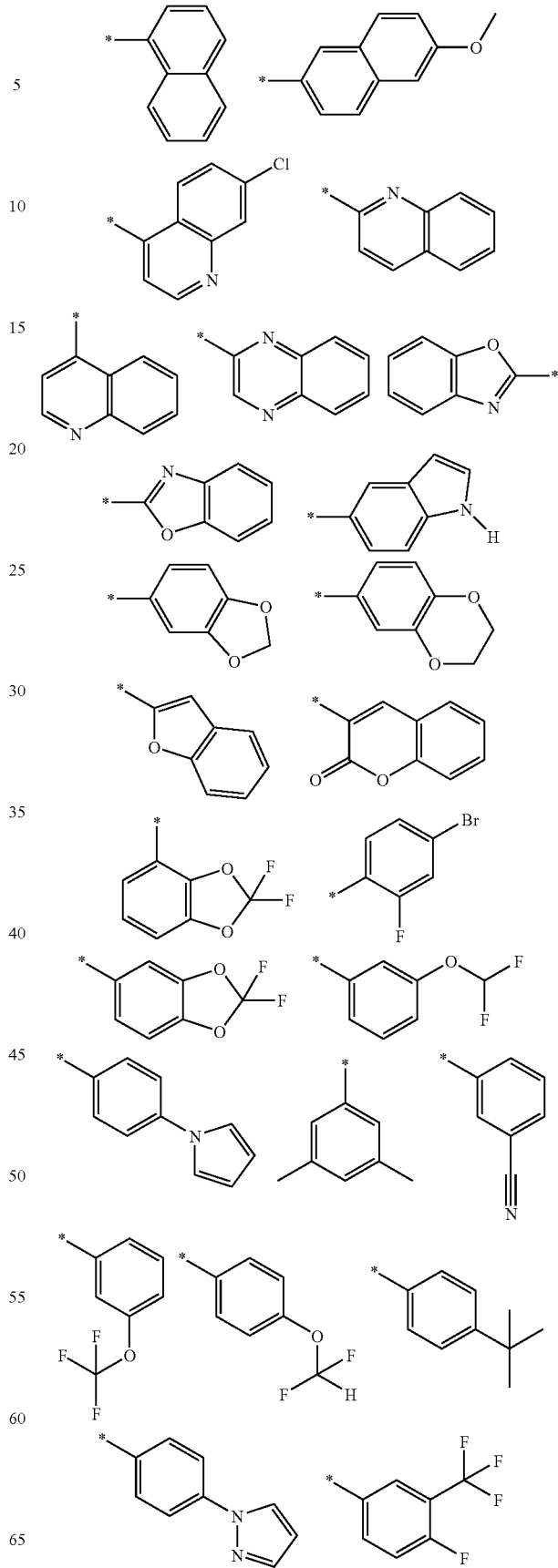

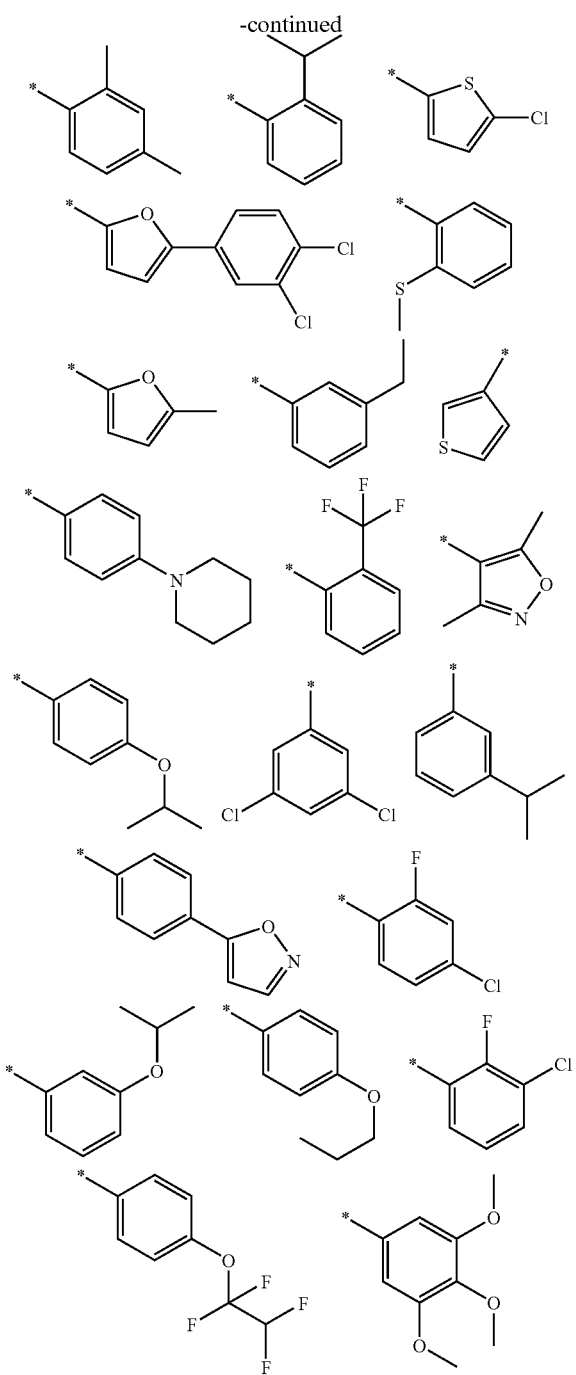

wherein the * indicates the bond of attachment of $Ar_1$ to the 5-membered ring of Formula 1.

As recognized by one of skill in the art, certain compounds of the invention may include at least one chiral center, and as such may exist as racemic mixtures or as enantiomerically pure compositions. As used herein, "enantiomerically pure" refers to compositions consisting substantially of a single isomer, preferably consisting of 90%, 92%, 95%, 98%, 99%, or 100% of a single isomer.

As used herein, the term "alkyl" generally refers to saturated hydrocarbyl radicals of straight, branched or cyclic configuration including methyl, ethyl, n-propyl, isopropyl, n-butyl, isobutyl, sec-butyl, tert-butyl, n-pentyl, n-hexyl, cyclohexyl, n-heptyl, octyl, n-octyl, and the like. In some embodiments, alkyl substituents may be $C_1$ to $C_8$, $C_3$ to $C_8$, $C_1$ to $C_6$, or $C_1$ to $C_4$ alkyl groups. In certain embodiments, the alkyl group may be optionally substituted with one or more halogen or alkoxy groups. For instance, the alkyl group may include one or more halogen substituents to form a haloalkyl, including monohaloalkyl, dihaloalkyl, and trihaloalkyl.

As used herein, "alkenyl" generally refers to linear, branched or cyclic alkene radicals having one or more carbon-carbon double bonds, such as $C_2$ to $C_6$ alkylene groups including 3-propenyl.

As used herein, "aryl" refers to a carbocyclic aromatic ring structure. Included in the scope of aryl groups are aromatic rings having from five to twenty carbon atoms. Aryl ring structures include compounds having one or more ring structures, such as mono-, bi-, or tricyclic compounds. Examples of aryl groups that include phenyl, tolyl, anthracenyl, fluorenyl, indenyl, azulenyl, phenanthrenyl (i.e., phenanthrene), and napthyl (i.e., napthalene) ring structures. In certain embodiments, the aryl group may be optionally substituted.

As used herein, "heterocycle" refers to cyclic ring structures in which one or more atoms in the ring, the heteroatom(s), is an element other than carbon. Heteroatoms are typically O, S or N atoms. Included within the scope of heterocycle, and independently selectable, are O, N, and S heterocycle ring structures. The ring structure may include compounds having one or more ring structures, such as mono-, bi-, or tricyclic compounds, and may be aromatic, i.e., the ring structure may be a heteroaryl. Example of heterocyclo groups include morpholinyl, pyrrolidinonyl, pyrrolidinyl, piperidinyl, pi perazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. In certain embodiments, the heterocycle may optionally be substituted. As used herein, "heteroaryl" refers to cyclic aromatic ring structures in which one or more atoms in the ring, the heteroatom(s), is an element other than carbon. Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, the heteroaryl groups may be selected from heteroaryl groups that contain two or more heteroatoms, three or more heteroatoms, or four or more heteroatoms. Heteroaryl ring structures may be selected from those that contain five or more atoms, six or more atoms, or eight or more atoms. In a preferred embodiment, the heteroaryl including five to ten atoms. Examples of heteroaryl ring structures include: acridine, benzimidazole, benzoxazole, benzodioxole, benzofuran, 1,3-diazine, 1,2-diazine, 1,2-diazole, 1,4-diazanaphthalene, furan, furazan, imidazole, indole, isoxazole, isoquinoline, isothiazole, oxazole, purine, pyridazine, pyrazole, pyridine, pyrazine, pyrimidine, pyrrole, quinoline, quinoxaline, thiazole, thiophene, 1,3,5-triazine, 1,2,4-triazine, 1,2,3-triazine, tetrazole and quinazoline.

As used herein, "alkoxy" generally refers to a group with the structure —O—R. In certain embodiments, R may be an alkyl group, such as a $C_1$ to $C_8$, $C_1$ to $C_6$ alkyl group, or $C_1$ to $C_4$ alkyl group. In certain embodiments, the R group of the alkoxy may optionally be substituted with at least one halogen. For example, the R group of the alkoxy may be a haloalkyl, i.e., haloalkoxy.

Halogen substituents may be independently selected from the halogens such as fluorine, chlorine, bromine, iodine, and astatine.

For the purposes of this invention, where one or more functionalities or substituents are incorporated into a compound of the invention, including preferred embodiments, each functionality or substituent appearing at any location within the disclosed compounds may be independently selected, and as appropriate, independently substituted. Further, where a more generic substituent is set forth for any position in the molecules of the present invention, it is understood that the generic substituent may be replaced with more specific substituents, and the resulting molecules are within the scope of the molecules of the present invention.

With reference to Formula 1, in an embodiment, R is preferably in a meta and/or para position and is preferably a halogen, a $C_1$-$C_4$ alkyl, a $C_1$-$C_4$ haloalkyl, a $C_1$-$C_4$ alkoxy, a $C_1$-$C_4$ haloalkoxy, an amino which is optionally substituted with one or more $C_1$-$C_4$ alkyl groups, an —$R_b$ group, a pyrrolyl group, an imidazolyl group, or two R groups together with the phenyl ring to which they are attached form a benzo[1,3]dioxole or 2,3-dihydro-benzo[1,4]dioxinyl group. Particularly preferred R groups include those shown in the table above.

In a preferred embodiment, compounds of Formula 1 includes those of Formula 1-A:

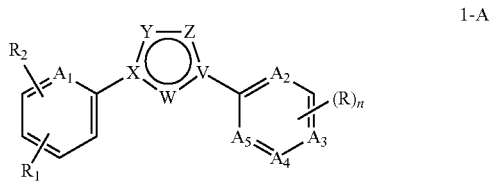

With reference to Formula 1-A, in an embodiment, $A_1$, $A_2$, $A_3$, $A_4$, and $A_5$ are independently selected from N, C and CH, and n is 0, 1, or 2. In a preferred embodiment, $R_2$ is absent and $A_1$, $A_2$, $A_3$, $A_4$, and $A_5$ are independently selected from C and CH. $R_1$ is preferably a carboxy group, and is preferably located in a meta or para position. In a further embodiment of Formula 1-A, R may be independently selected from: hydrogen; a hydroxy group; a $C_1$-$C_4$ alkyl group; a halogen; a $C_1$-$C_4$ haloalkyl group; a $C_1$-$C_4$ alkoxy group; a $C_1$-$C_4$ haloalkoxy group; a phenyloxy group; a benzyloxy group; a $C_6$-$C_8$ aryl which is optionally substituted with one or more independently selected halogens, $C_1$-$C_4$ alkyl groups, and/or $C_1$-$C_4$ alkoxy groups; an amino group which is optionally substituted with one or two independently selected $C_1$-$C_4$ alkyl groups; a cyano group; a —C(O)—$R_d$ group, wherein $R_d$ is a hydroxy group, a $C_1$-$C_4$ alkyl group or a $C_1$-$C_4$ alkoxy group; a methanesulfonyl group; a nitro group; a benzofuranyl group; a pyrrolidinyl group; a pyrrolidinonyl group; a azetidinonyl group; a morpholinyl group; or two R groups together with the phenyl or heterocycle to which they are attached form a ring structure selected from RR.

In a preferred embodiment of Formula 1-A, V, W, and Y are each N, while X is C and Z is C—$R_c$. $R_c$ is preferably hydrogen or a methyl group. In a particularly preferred embodiment, compounds of Formula 1-A include the compounds of Formula 1-A-1 as follows:

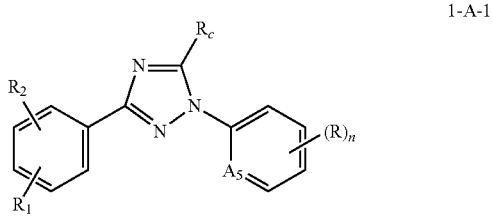

With reference to Formula 1-A-1, in an embodiment, $R_1$ is preferably a carboxy group, and is preferably located in a meta or para position. In an embodiment, $R_2$ is preferably absent. In another embodiment, $R_c$ is preferably hydrogen or a methyl group. In a further embodiment, R is preferably independently selected from: a halogen; a $C_1$-$C_4$ alkyl; a $C_1$-$C_4$ haloalkyl; a $C_1$-$C_4$ alkoxy which is optionally substituted with one or more halogens; a $C_6$-$C_8$ aryl which is optionally substituted with one or more $C_1$-$C_4$ alkyl, $C_1$-$C_4$ haloalkyl, or $C_1$-$C_4$ alkoxy groups; a benzofuryl group; a pyrrolidinyl group; a pyrrolidinonyl group; and/or a azetidinonyl group. Further, n is preferably 0, 1, or 2, and the R groups are preferably located at the meta and/or para positions.

In another preferred embodiment of Formula 1-A, W, X and Z are each N, while V is C and Y is C—$R_c$. $R_c$ is preferably hydrogen or a methyl group. In a particularly preferred embodiment, compounds of Formula 1-A include the compounds of Formula 1-A-2 as follows:

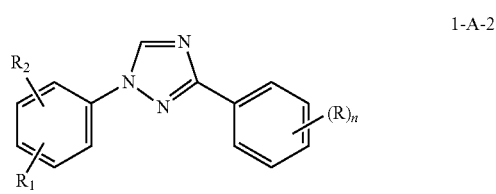

With reference to Formula 1-A-2, $R_1$ is preferably a carboxy group, and is preferably located in a meta or para position. In an embodiment, $R_2$ is preferably absent. In another embodiment, R is preferably independently selected from: a hydroxy, a halogen; a $C_1$-$C_4$ alkoxy; and/or a benzyloxy group. In a further embodiment of Formula 1-A-2, n is preferably 0 or 1, and the R group is preferably located at the meta or para positions.

In another preferred embodiment of Formula 1-A, X, Y and Z are each N, while V is C and W is CH. In a particularly preferred embodiment, compounds of Formula 1-A include the compounds of Formula 1-A-3 as follows:

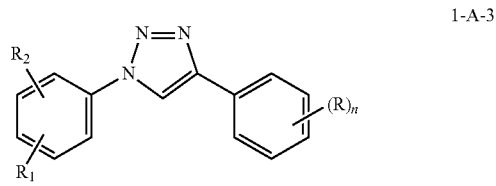

With reference to Formula 1-A-3, in an embodiment, $R_1$ is preferably a carboxy group, and is preferably located in a meta or para position. In an embodiment, $R_2$ is preferably absent. In another embodiment of Formula 1-A-3, R is preferably independently selected from: a halogen; a $C_1$-$C_4$ alkyl; a $C_1$-$C_4$ haloalkyl; a $C_1$-$C_4$ alkoxy which is optionally substituted with one or more halogens; and/or two R groups together with the six membered aryl to which they are attached form a napthyl group which is optionally substituted with one or more $C_1$-$C_4$ alkoxy groups. In a further embodiment, n is preferably 0, 1, or 2, and the R groups are preferably located at the meta and/or para positions.

In another preferred embodiment of Formula 1-A, X and Z are both N, while V is C, W is CH, and Y is C—$R_c$. $R_c$ is preferably hydrogen or an amino group. In a particularly preferred embodiment, compounds of Formula 1-A include the compounds of Formula 1-A-4 as follows:

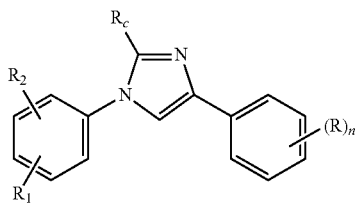

With reference to Formula 1-A-4, in an embodiment, $R_1$ is preferably a carboxy group, and is preferably located in a meta or para position. In an embodiment, $R_2$ is preferably absent. In another embodiment of Formula 1-A-4, $R_c$ is preferably hydrogen or an amino group. In another embodiment, R is preferably independently selected from $C_1$-$C_4$ alkyl groups. In a further embodiment of Formula 1-A-4, n is preferably 0 or 1, and the R group is preferably located at the meta and/or para positions.

In another preferred embodiment of Formula 1-A, V and W are both N, while X is C, and Y and Z are both C—$R_c$. $R_c$ is preferably hydrogen. In a particularly preferred embodiment, compounds of Formula 1-A include the compounds of Formula 1-A-5 as follows:

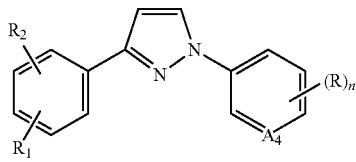

With reference to Formula 1-A-5, in an embodiment, $R_1$ is preferably a carboxy group or cyano, and is preferably located in a meta or para position. In another preferred embodiment of Formula 1-A-5, $R_1$ is preferably a carboxy group and is preferably located in a meta or para position. In an embodiment, $R_2$ is preferably absent. In another embodiment of Formula 1-A-5, R is preferably independently selected from: hydroxy; a halogen; a $C_1$-$C_4$ alkyl; a $C_1$-$C_4$ haloalkyl; a $C_1$-$C_4$ alkoxy which is optionally substituted with one or more halogens; a benzyloxy group; a nitro group; an amino group which is optionally substituted with one or two $C_1$-$C_4$ alkyl groups; and/or two R groups together with the six membered aryl to which they are attached form a benzo[1,3]dioxole group or an indolyl group. In a father embodiment, n is preferably 0, 1, or 2, and the R groups are preferably located at the meta and/or para positions.

In another preferred embodiment of Formula 1-A, V and Y are both N, while X is C, W is CH, and Z is C—$R_c$. In an embodiment, $R_c$ is preferably hydrogen. In a particularly preferred embodiment, compounds of Formula 1-A include the compounds of Formula 1-A-6 as follows:

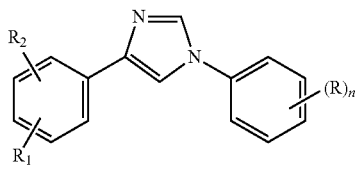

With reference to Formula 1-A-6, in an embodiment, $R_1$ is preferably a carboxy group, and is preferably located in a meta or para position. In another embodiment, $R_2$ is preferably absent. In an embodiment of Formula 1-A-6, R is preferably independently selected from $C_1$-$C_4$ alkyl groups. In a further embodiment, n is preferably 0 or 1, and the R group is preferably located at the meta and/or para positions.

In another preferred embodiment of Formula 1-A, V and Z are both N, while X is C, W is CH, and Y is C—$R_c$. $R_c$ is preferably hydrogen. In a particularly preferred embodiment, compounds of Formula 1-A include the compounds of Formula 1-A-7 as follows:

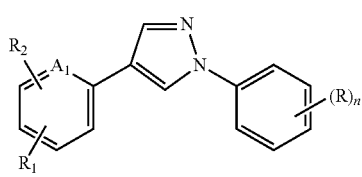

With reference to Formula 1-A-7, in an embodiment, $R_1$ is preferably a carboxy or cyano group, and is preferably located in a meta or para position. In another embodiment, $R_2$ is preferably absent or a nitro group. When $R_2$ is present, it is preferably located in an ortho position. In an embodiment of Formula 1-A-7, R is preferably independently selected from: hydroxy; a halogen; a $C_1$-$C_4$ alkyl; a $C_1$-$C_4$ haloalkyl; a $C_1$-$C_4$ alkoxy which is optionally substituted with one or more halogens; a —C(O)—$OCH_3$ group; and/or two R groups together with the six membered aryl to which they are attached form a benzo[1,3]dioxole group. In a further embodiment of Formula 1-A-7, n is preferably 0, 1, or 2, and the R groups are preferably located at the meta and/or para positions.

In another preferred embodiment of Formula 1-A, W and X are both N, while V is C, and Y and Z are both C—$R_c$. $R_c$ is preferably hydrogen. In a particularly preferred embodiment, compounds of Formula 1-A include the compounds of Formula 1-A-8 as follows:

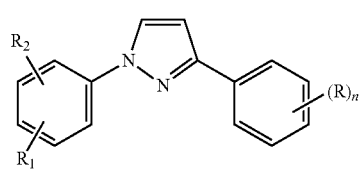

With reference to Formula 1-A-8, in an embodiment, $R_1$ is preferably a carboxy or —C(O)—$OCH_3$ group, and is preferably located in a meta or para position. In another embodiment, $R_2$ is preferably absent. In another embodiment, R is preferably independently selected from: hydroxy; a halogen; a $C_1$-$C_4$ alkyl; a $C_1$-$C_4$ haloalkyl; a $C_1$-$C_4$ alkoxy which is optionally substituted with one or more halogens; a cyano group; and/or a morpholinyl group. In a further embodiment of Formula 1-A-8, n is preferably 0, 1, or 2, and the R groups are preferably located at the meta and/or para positions.

In another preferred embodiment of Formula 1-A, X and Y are both N, while V is C, W is CH and Z is C—$R_c$. $R_c$ is preferably hydrogen. In a particularly preferred embodiment, compounds of Formula 1-A include the compounds of Formula 1-A-9 as follows:

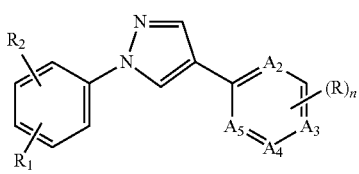

1-A-9

With reference to Formula 1-A-9, in an embodiment, $R_1$ is preferably a carboxy group, and is preferably located in a meta or para position. In another embodiment. $R_2$ is preferably absent. In a further embodiment of Formula 1-A-9, R is preferably independently selected from: hydroxy; a halogen; a $C_1$-$C_4$ alkyl; a $C_1$-$C_4$ haloalkyl; a $C_1$-$C_4$ alkoxy which is optionally substituted with one or more halogens; a phenyloxy group; a nitro group; an amino group which is optionally substituted with one or two $C_1$-$C_4$ alkyl groups; and/or two R groups together with the six membered aryl to which they are attached form a benzo[1,3]dioxole group, a quinoline group, or a quinoxaline group. Further, n is preferably 0, 1, or 2, and the R groups are preferably located at the meta and/or para positions.

In another preferred embodiment of Formula 1-A, V is N, while X is C, W is CH, and Y and Z are both C—$R_c$. $R_c$ is preferably hydrogen. In a particularly preferred embodiment, compounds of Formula 1-A include the compounds of Formula 1-A-10 as follows:

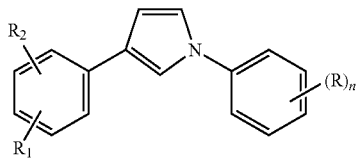

1-A-10

With reference to Formula 1-A-10, $R_1$ is preferably a carboxy group, and is preferably located in a meta or para position. $R_2$ is preferably absent. R is preferably independently selected from: a halogen; a $C_1$-$C_4$ alkyl; a $C_1$-$C_4$ haloalkyl; a $C_1$-$C_4$ alkoxy which is optionally substituted with one or more halogens; a benzyloxy group; and/or two R groups together with the six membered aryl to which they are attached form a benzo[1,4]dioxole group. Further, n is preferably 0, 1, or 2, and the R groups are preferably located at the meta and/or para positions.

In another preferred embodiment of Formula 1-A, X is N, while V is C, W is CH, and Y and Z are both C—$R_c$. $R_c$ is preferably hydrogen. In a particularly preferred embodiment, compounds of Formula 1-A include the compounds of Formula 1-A-11 as follows:

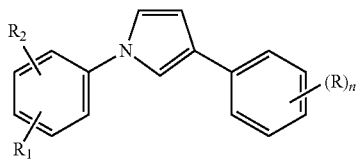

1-A-11

With reference to Formula 1-A-11, $R_1$ is preferably a carboxy group, and is preferably located in a meta or para position. $R_2$ is preferably absent. R is preferably independently selected from $C_1$-$C_4$ alkyl groups. Further, n is preferably 0 or 1, and the R group is preferably located at the meta and/or para positions.

In another preferred embodiment of Formula 1-A, W is N, while X and V are both C, and Y and Z are both C—$R_c$. $R_c$ is preferably hydrogen. In a particularly preferred embodiment, compounds of Formula 1-A include the compounds of Formula 1-A-12 as follows:

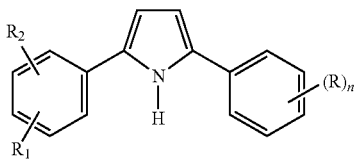

1-A-12

With reference to Formula 1-A-12, $R_1$ is preferably a carboxy group, and is preferably located in a meta or para position. $R_2$ is preferably absent. R is preferably independently selected from $C_1$-$C_4$ alkyl groups. Further, n is preferably 0 or 1, and the R group is preferably located at the meta and/or para positions.

In another preferred embodiment of Formula 1-A, Z is N, while V and X are C, W is CH, and Y is C—$R_c$. $R_c$ is preferably hydrogen. In a particularly preferred embodiment, compounds of Formula 1-A include the compounds of Formula 1-A-13 as follows:

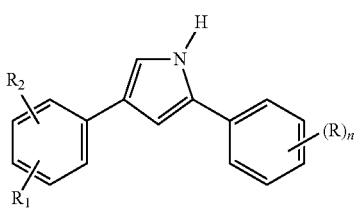

1-A-13

With reference to Formula 1-A-13, $R_1$ is preferably a carboxy group, and is preferably located in a meta or para position. $R_2$ is preferably absent. R is preferably independently selected from $C_1$-$C_4$ alkyl groups. Further, n is preferably 0 or 1, and the R group is preferably located at the meta and/or para positions.

In another preferred embodiment of Formula 1, V, W, and Y are each N, and X and Z are both C. Further, $Ar_1$ and $Ar_2$ together with the heterocycle to which they are attached form a thirteen membered hetero-tricycle ring structure as follows (Formula 1-B):

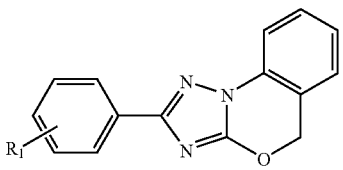

1-B

With reference to Formula 1-B, $R_1$ is preferably carboxy group, and is preferably located in a meta or para position.

In yet another preferred embodiment of Formula 1, V and W are both N, X is C, and Y and Z are each CH (Formula 1-C):

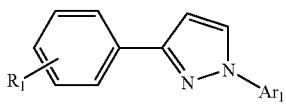
1-C

With reference to Formula 1-C, $R_1$ is preferably a carboxy group, and is preferably located in a meta or para position. Further, $Ar_1$ is preferably a thienyl group.

In yet another preferred embodiment of Formula 1, X and Y are both N, V is C, and W and Z are independently C or CH (Formula 1-D):

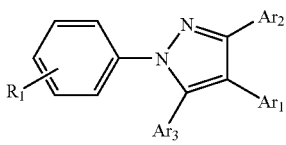
1-D

With reference to Formula 1-D, $R_1$ is preferably a carboxy group, and is preferably located in a meta or para position. Further, $Ar_2$ and/or $Ar_3$ are preferably absent. In another preferred embodiment, $Ar_1$ is preferably a benzooxasole group. In another preferred embodiment of Formula 1-D, $Ar_3$ is absent, and $Ar_1$ and $Ar_2$ together with the five membered ring to which they are attached form an $Ar_{1-2}$ ring structure. In a preferred embodiment of Formula 1-D, $Ar_{1-2}$ is selected from the following, optionally substituted as in Formula 1:

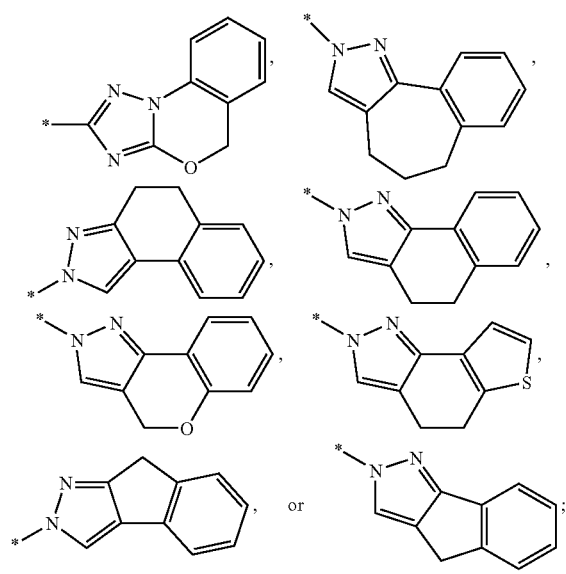

wherein the * indicates the bond of attachment of $Ar_{1-2}$ to the 6-membered ring of Formula 1. In yet another preferred embodiment of Formula 1-D, $Ar_{1-2}$ may be selected from:

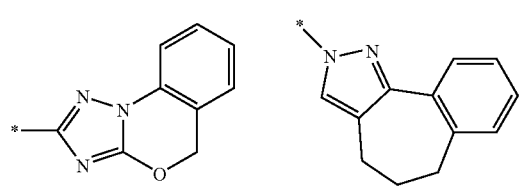

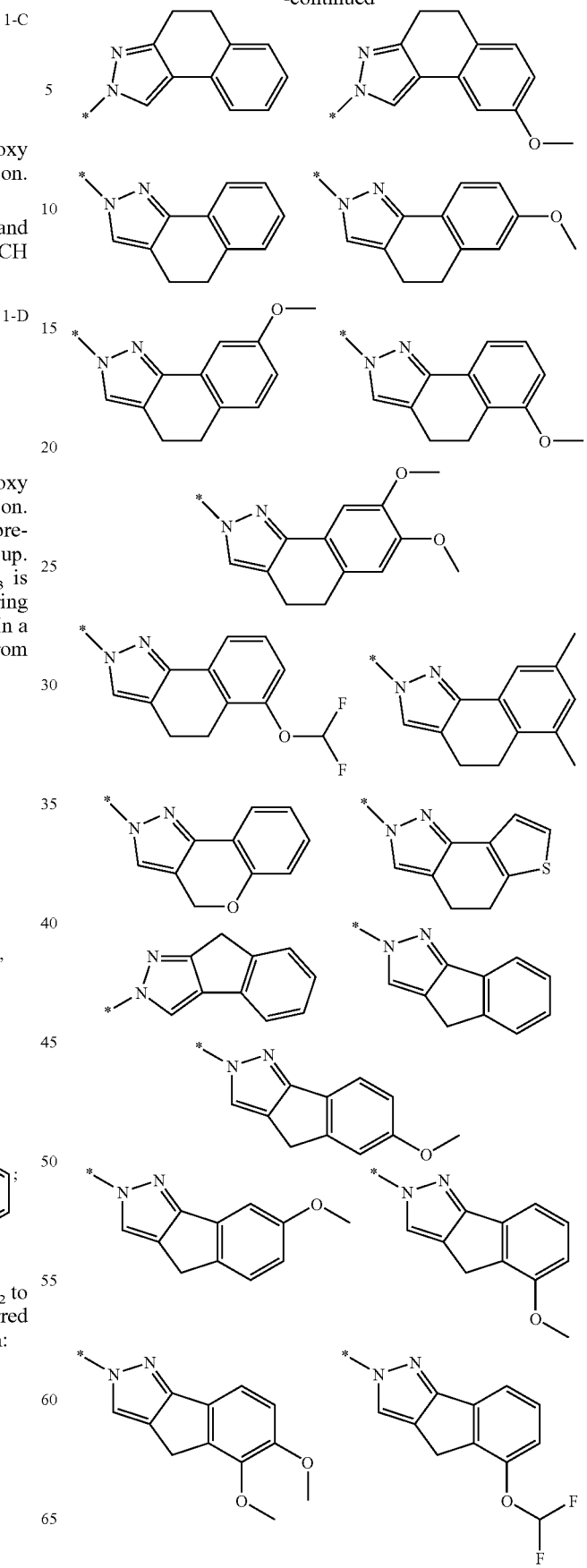

In another preferred embodiment of Formula 1-D, $Ar_2$ is absent, and $Ar_1$ and $Ar_3$ together with the five membered ring to which they are attached form an $Ar_{1-3}$ ring structure. In a preferred embodiment of Formula 1-D, $Ar_{1-3}$ is selected from the following, optionally substituted as in Formula 1:

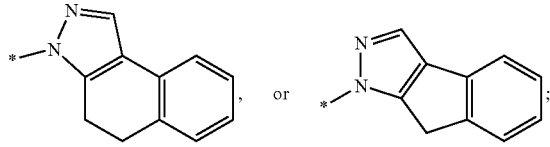 [SMILES: *n1ncc2c1CCc1ccccc1-2 ; *n1ncc2c1Cc1ccccc1-2]

wherein the * indicates the bond of attachment of $Ar_{1-3}$ to the 6-membered ring of Formula 1. In yet another preferred embodiment of Formula 1, $Ar_{1-3}$ may be selected from:

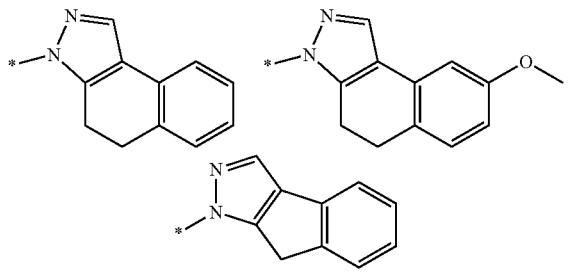

wherein the * indicates the bond of attachment of $Ar_{1-3}$ to the 6-membered ring of Formula 1.

In yet another preferred embodiment of Formula 1, V and W are each N, X is C, Y is NH, and Z is C=O (Formula 1-E):

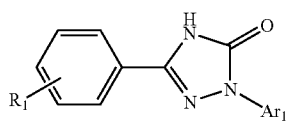

1-E

With reference to Formula 1-E, $R_1$ is preferably a carboxy group, and is preferably located in a meta or para position. Further, $Ar_2$ and/or $Ar_3$ are preferably absent. In another preferred embodiment, $Ar_1$ is preferably a phenyl group optionally substituted with one or two R groups. Further, the one or two R groups are preferably independently selected from a $C_1$-$C_4$ alkyl group and a halogen.

In yet another preferred embodiment of Formula 1, V and W are each N, X is C, Y is O, and Z is C=O (Formula 1-F):

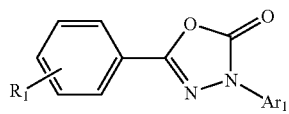

1-F

With reference to Formula 1-F, $R_1$ is preferably a carboxy group, and is preferably located in a meta or para position. Further, $Ar_2$ and/or $Ar_3$ are preferably absent. In another preferred embodiment, $Ar_1$ is preferably a phenyl group optionally substituted with one or two R groups. Further, the one or two R groups are preferably independently selected from a $C_1$-$C_4$ alkyl group, a halogen, $C_1$-$C_4$ haloalkyl, and a methanesulfonyl group, or two R groups together form a quinoline group.

In yet another preferred embodiment of Formula 1, V is C, W and X are each N, Y is C=O and Z is O (Formula 1-G):

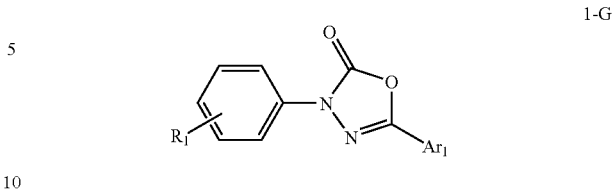

1-G

With reference to Formula 1-G, $R_1$ is preferably a carboxy group, and is preferably located in a meta or para position. Further, $Ar_2$ and/or $Ar_3$ are preferably absent. In another preferred embodiment, $Ar_1$ is preferably a phenyl group optionally substituted with one or two R groups. Further, the one or two R groups are preferably independently selected from a $C_1$-$C_4$ alkyl group and a cyano group.

In yet another preferred embodiment of Formula 1, V is C, W and X are each N, Y is C=O and Z is S (Formula 1-H):

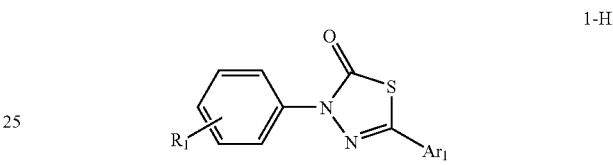

1-H

With reference to Formula 1-H, $R_1$ is preferably a carboxy group, and is preferably located in a meta or para position. Further, $Ar_2$ and/or $Ar_3$ are preferably absent. In another preferred embodiment, $Ar_1$ is preferably a phenyl group optionally substituted with one or two R groups. Further, the one or two R groups are preferably independently selected $C_1$-$C_4$ alkyl groups.

In yet another preferred embodiment of Formula 1, V is C, W and X are each N, Y is C=S and Z is S (Formula 1-I):

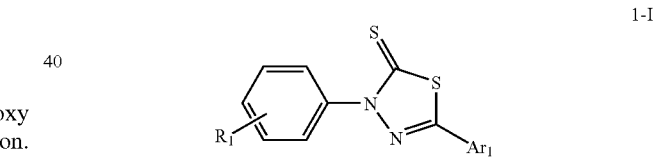

1-I

With reference to Formula 1-I, $R_1$ is preferably a carboxy group, and is preferably located in a meta or para position. Further, $Ar_2$ and/or $Ar_3$ are preferably absent. In another preferred embodiment, $Ar_1$ is preferably a phenyl group optionally substituted with one or two R groups. Further, the one or two R groups are preferably independently selected $C_1$-$C_4$ alkyl groups.

In yet another preferred embodiment of Formula 1, V is C, W and X are each N, Y is C=S and Z is O (Formula 1-J):

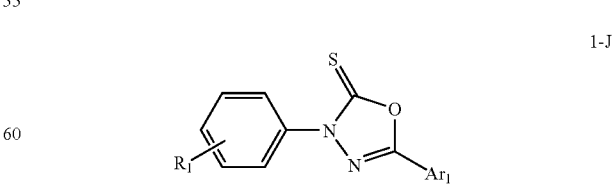

1-J

With reference to Formula 1-J, $R_1$ is preferably a carboxy group, and is preferably located in a meta or para position. Further, $Ar_2$ and/or $Ar_3$ are preferably absent. In another preferred embodiment, $Ar_1$ is preferably a phenyl group optionally substituted with one or two R groups. Further, the one or two R groups are preferably independently selected $C_1$-$C_4$ alkyl groups.

In another preferred embodiment of Formula 1, $Ar_4$ is absent (Formula 1-K):

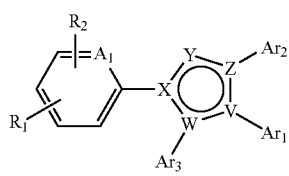

1-K

In an embodiment of Formula 1-K, any substituent patterns as illustrated in Formulas 1-A through 1-J may be preferred.

In an embodiment of Formula 1, $Ar_4$ is a $C_1$-$C_4$ alkyl which together with $A_1$ forms a four to seven membered carbocycle or heterocycle (Formula 1-L).

In a preferred embodiment of Formula 1-L, $Ar_4$ is a $C_1$-$C_4$ alkyl which together with $A_1$ forms a four to seven membered carbocycle. In a preferred embodiment of Formula 1-L, $Ar_4$ is a $C_1$-$C_4$ alkyl which is attached to $A_1$ to form a five to six membered carbocycle. In an embodiment of Formula 1-L, $R_1$ is preferably a carboxy group, and is preferably located in a meta or para position. In a preferred embodiment, $Ar_4$ is a methylene group. In a further preferred embodiment of Formula 1-L, $Ar_2$ and $Ar_3$ are preferably absent. In another preferred embodiment, $Ar_1$ is preferably a phenyl group optionally substituted with one or two R groups. In a further preferred embodiment, $Ar_1$ is a phenyl group optionally substituted with one or more independently selected halogens, $C_1$-$C_4$ alkyl groups, or $C_1$-$C_4$ haloalkoxy groups. In another preferred embodiment, $Ar_1$ is a phenyl group substituted with one or more independently selected halogens, $C_1$-$C_4$ alkyl groups, or $C_1$-$C_4$ haloalkoxy groups. In a further preferred embodiment, $Ar_1$ is a phenyl group substituted with a halogen and a $C_1$-$C_4$ alkyl group. In another preferred embodiment, $Ar_1$ is a phenyl group substituted with a fluorine and a methyl group. In a preferred embodiment, $Ar_1$ is a phenyl group substituted with a $C_1$-$C_4$ haloalkoxy group. In another preferred embodiment, $Ar_1$ is a phenyl group substituted with a trifluromethoxy group.

In an embodiment of Formula 1, $Ar_4$ is a $C_1$-$C_4$ alkoxy which is attached to $A_1$ to form a four to seven membered heterocycle (Formula 1-M).

In a preferred embodiment of Formula 1-M, $Ar_4$ is a $C_1$-$C_4$ alkoxy which is attached to $A_1$ to form a five to six membered heterocycle. In an embodiment of Formula 1-M, $R_1$ is preferably a carboxy group, and is preferably located in a meta or para position. In a preferred embodiment of Formula 1-M, $Ar_4$ is a methoxy group. In a further preferred embodiment of Formula 1-M, $Ar_2$ and $Ar_3$ are preferably absent. In another preferred embodiment, of Formula 1-M, $Ar_1$ is absent. In another preferred embodiment of Formula 1-M, $Ar_1$ is a phenyl group optionally substituted with one or two R groups.

In a further preferred embodiment of Formula 1-M, $Ar_1$ is a phenyl group optionally substituted with one or more independently selected halogens, $C_1$-$C_4$ alkyl groups, or $C_1$-$C_4$ alkoxy, or $C_1$-$C_4$ haloalkyl groups. In a further preferred embodiment of Formula 1-M, $Ar_1$ is a phenyl group substituted with one, two or three independently selected halogens, $C_1$-$C_4$ alkyl groups, $C_1$-$C_4$ alkoxy, or $C_1$-$C_4$ haloalkyl groups. In another preferred embodiment of f Formula 1-M, $Ar_1$ is a phenyl group substituted with one halogen, $C_1$-$C_4$ alkyl, $C_1$-$C_4$ alkoxy, $C_1$-$C_4$ haloalkyl group. In a preferred embodiment of Formula 1-M, $Ar_1$ is a phenyl group substituted with one fluorine, chlorine, methyl, methoxy, or trifluoromethoxy group. In another preferred embodiment of Formula 1-M, $Ar_1$ is a phenyl group substituted with three $C_1$-$C_4$ alkoxy groups. In a further preferred embodiment of Formula 1-M, $Ar_1$ is a phenyl group substituted with three methoxy groups.

In an embodiment of Formula 1, $Ar_4$ is a $C_1$-$C_4$ thioalkyl which is attached to $A_1$ to form a four to seven membered heterocycle (Formula 1-N).

In a preferred embodiment of Formula 1-N, $Ar_4$ is a $C_1$-$C_4$ thioalkyl which is attached to $A_1$ to form a five to six membered heterocycle. In an embodiment of Formula 1-N, $R_1$ is preferably a carboxy group, and is preferably located in a meta or para position. In a preferred embodiment of Formula 1-N, $Ar_4$ is a thiomethyl group. In a further preferred embodiment of Formula 1-N, $Ar_2$ and $Ar_3$ are preferably absent.

In another preferred embodiment of Formula 1-N, $Ar_1$ is a phenyl group optionally substituted with one or more R groups. In another preferred embodiment of Formula 1-N, $Ar_1$ is a phenyl group optionally substituted with one R group. In another preferred embodiment of Formula 1-N, $Ar_1$ is a phenyl group substituted with a $C_1$-$C_4$ alkyl group. In another preferred embodiment of Formula 1-N, $Ar_1$ is a phenyl group substituted with a methyl group.

Preferred compounds of the invention include the compounds in Table X as follows:

TABLE X

Compound

1

2

3

TABLE X-continued
| Compound | |
|---|---|
| 4 | 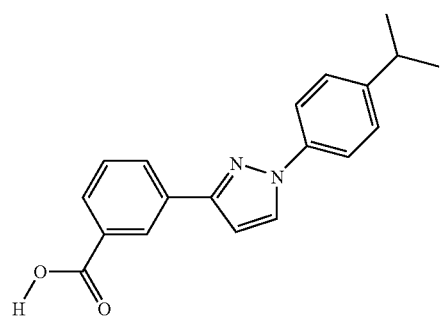 [SMILES: CC(C)c1ccc(-n2ccc(-c3cccc(C(=O)O)c3)n2)cc1] |
| 5 | 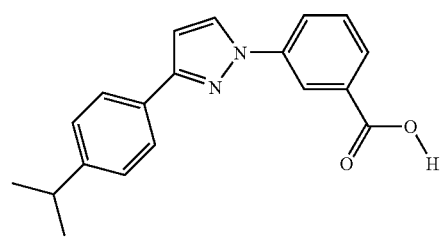 [SMILES: CC(C)c1ccc(-c2ccn(-c3cccc(C(=O)O)c3)n2)cc1] |
| 6 | 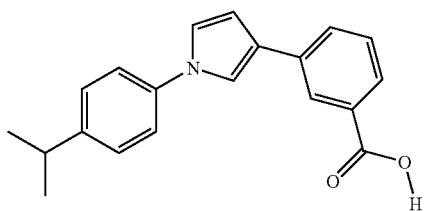 [SMILES: CC(C)c1ccc(-n2ccc(-c3cccc(C(=O)O)c3)c2)cc1] |
| 8 | 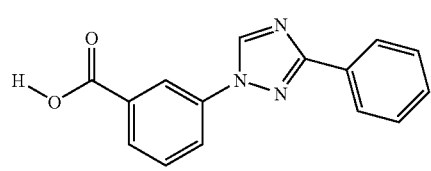 [SMILES: O=C(O)c1cccc(-n2cnc(-c3ccccc3)n2)c1] |
| 9 | 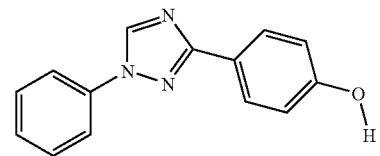 |
| 10 | 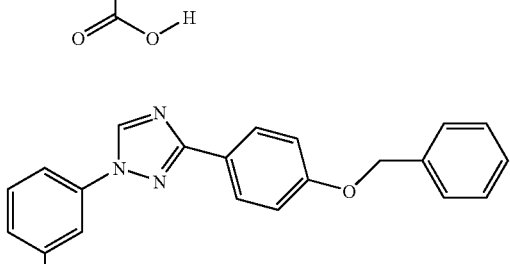 |
| 11 | 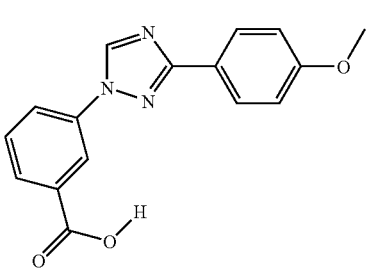 [SMILES: COc1ccc(-c2ncn(-c3cccc(C(=O)O)c3)n2)cc1] |
| 12 | 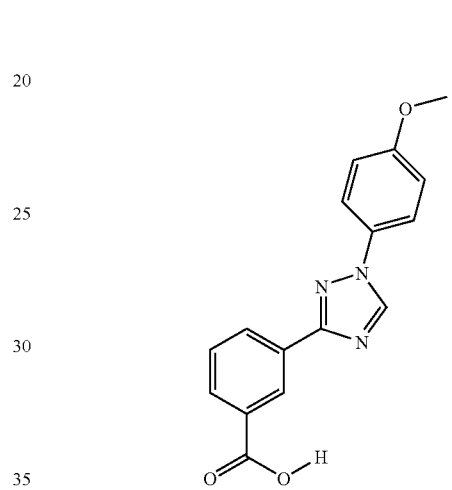 |
| 13 | 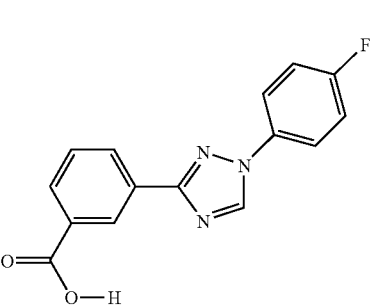 [SMILES: O=C(O)c1cccc(-c2ncn(-c3ccc(F)cc3)n2)c1] |
| 14 | 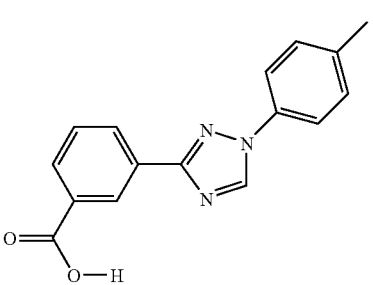 [SMILES: Cc1ccc(-n2cnc(-c3cccc(C(=O)O)c3)n2)cc1] |

TABLE X-continued
Compound
15
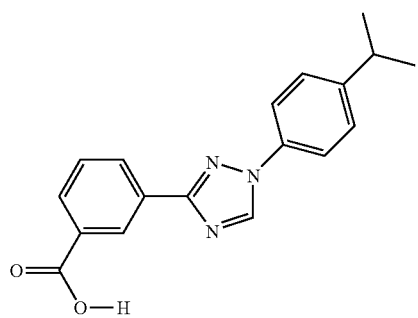 [SMILES: CC(C)c1ccc(-n2cnc(-c3cccc(C(=O)O)c3)n2)cc1]
16
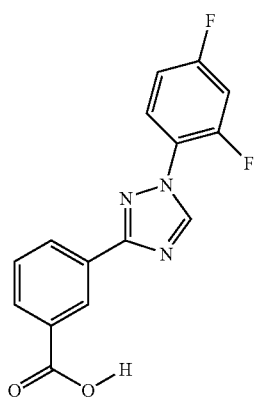 [SMILES: O=C(O)c1cccc(-c2ncn(-c3ccc(F)cc3F)n2)c1]
17
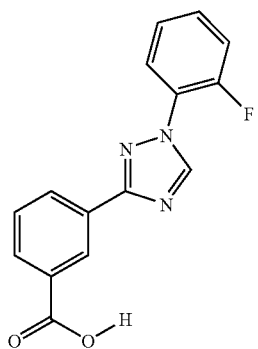 [SMILES: O=C(O)c1cccc(-c2ncn(-c3ccccc3F)n2)c1]
18
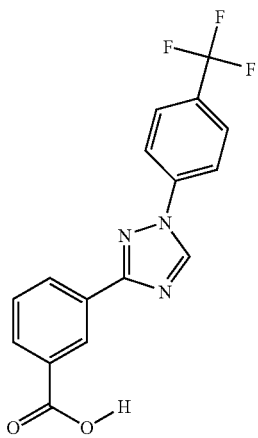 [SMILES: O=C(O)c1cccc(-c2ncn(-c3ccc(C(F)(F)F)cc3)n2)c1]
TABLE X-continued
Compound
19
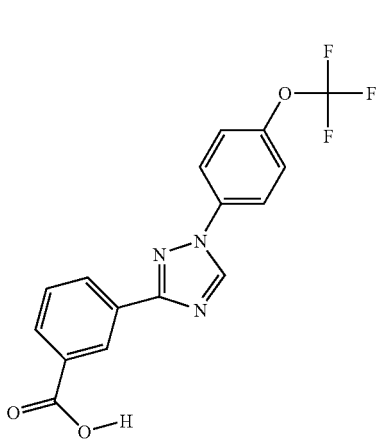 [SMILES: O=C(O)c1cccc(-c2ncn(-c3ccc(OC(F)(F)F)cc3)n2)c1]
20
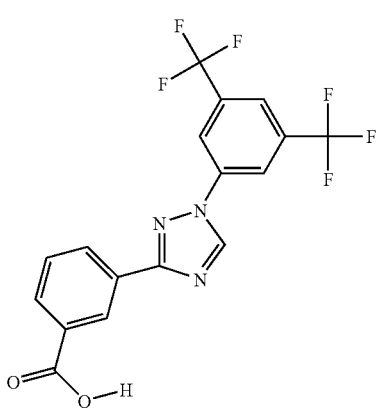 [SMILES: O=C(O)c1cccc(-c2ncn(-c3cc(C(F)(F)F)cc(C(F)(F)F)c3)n2)c1]
21
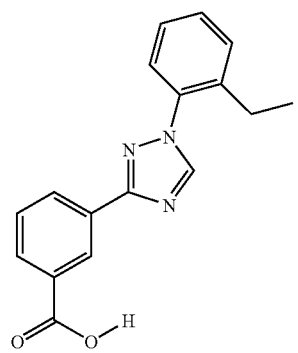 [SMILES: CCc1ccccc1-n1cnc(-c2cccc(C(=O)O)c2)n1]

TABLE X-continued
Compound
22
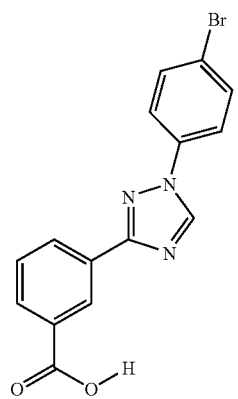 [SMILES: O=C(O)c1cccc(-c2ncn(-c3ccc(Br)cc3)n2)c1]
23
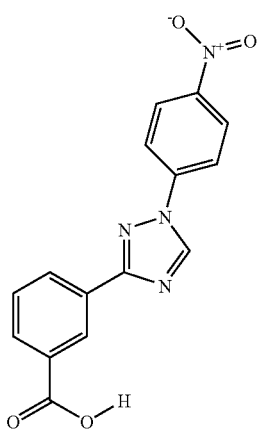
24
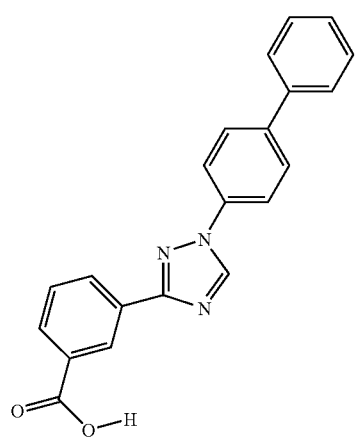 [SMILES: O=C(O)c1cccc(-c2ncn(-c3ccc(-c4ccccc4)cc3)n2)c1]
TABLE X-continued
Compound
25
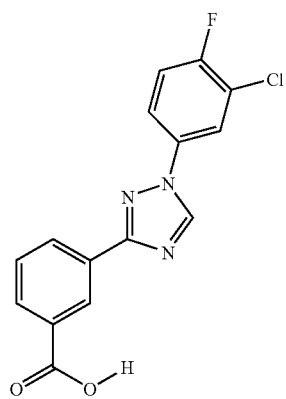 [SMILES: O=C(O)c1cccc(-c2ncn(-c3ccc(F)c(Cl)c3)n2)c1]
26
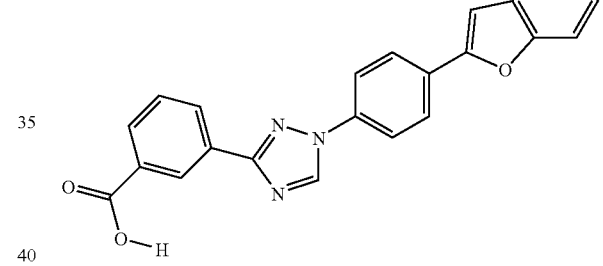
27
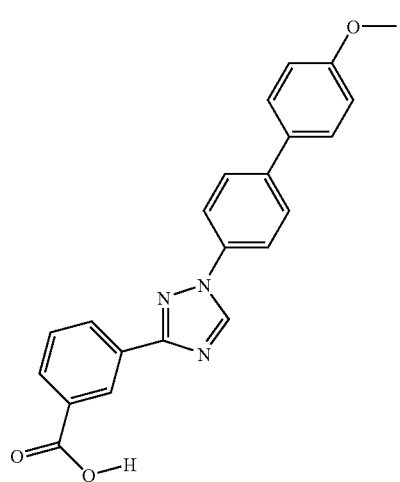 [SMILES: COc1ccc(-c2ccc(-n3cnc(-c4cccc(C(=O)O)c4)n3)cc2)cc1]

TABLE X-continued
Compound
28
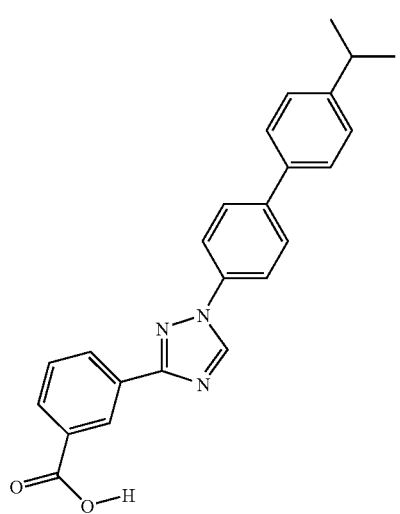 [SMILES: CC(C)c1ccc(-c2ccc(-n3cnc(-c4cccc(C(=O)O)c4)n3)cc2)cc1]
29
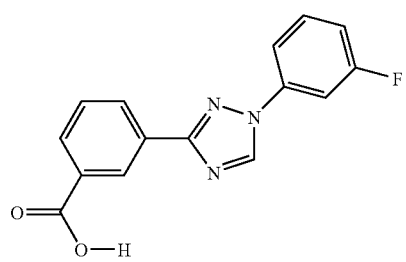 [SMILES: O=C(O)c1cccc(-c2ncn(-c3cccc(F)c3)n2)c1]
30
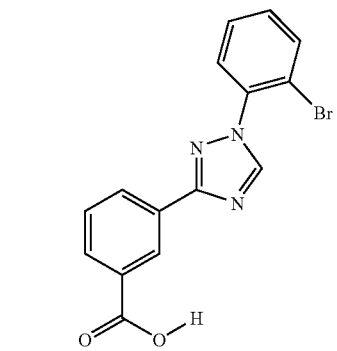 [SMILES: O=C(O)c1cccc(-c2ncn(-c3ccccc3Br)n2)c1]
31
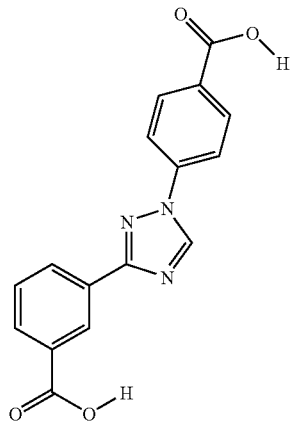 [SMILES: O=C(O)c1ccc(-n2cnc(-c3cccc(C(=O)O)c3)n2)cc1]
32
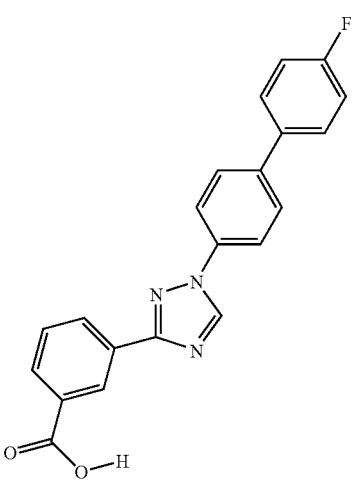 [SMILES: O=C(O)c1cccc(-c2ncn(-c3ccc(-c4ccc(F)cc4)cc3)n2)c1]
33
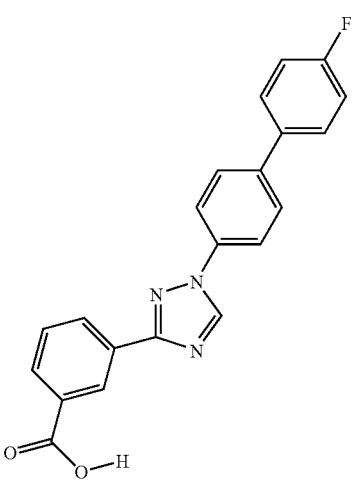 [SMILES: O=C(O)c1cccc(-c2ncn(-c3ccc(-c4ccc(F)cc4)cc3)n2)c1]

TABLE X-continued

Compound

34: 3-[1-(3-fluorophenyl)-5-methyl-1H-1,2,4-triazol-3-yl]benzoic acid

35: 3-[1-(3-bromophenyl)-1H-1,2,4-triazol-3-yl]benzoic acid

36: 3-[1-(pyridin-2-yl)-1H-1,2,4-triazol-3-yl]benzoic acid

37: 3-(1-phenyl-1H-1,2,4-triazol-3-yl)benzoic acid

38: 3-[1-(3-chloro-4-methylphenyl)-1H-1,2,4-triazol-3-yl]benzoic acid

39: 3-[1-(3-methylphenyl)-1H-1,2,4-triazol-3-yl]benzoic acid

40: 3-[1-(2-methylphenyl)-1H-1,2,4-triazol-3-yl]benzoic acid

41: 3-[1-(2-methylphenyl)-5-oxo-4,5-dihydro-1H-1,2,4-triazol-3-yl]benzoic acid

TABLE X-continued
Compound
42
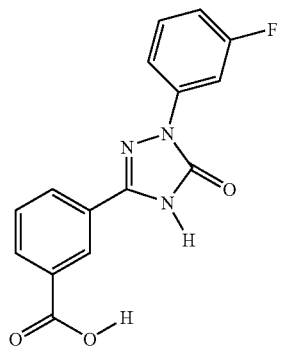 [SMILES: O=C(O)c1cccc(-c2nn(-c3cccc(F)c3)c(=O)[nH]2)c1]
43
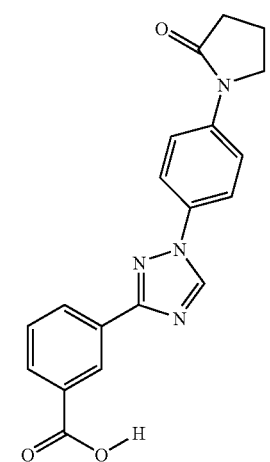 [SMILES: O=C(O)c1cccc(-c2ncn(-c3ccc(N4CCCC4=O)cc3)n2)c1]
44
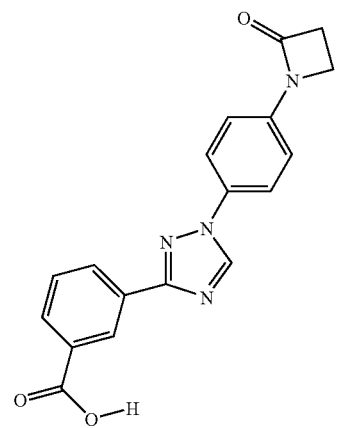 [SMILES: O=C(O)c1cccc(-c2ncn(-c3ccc(N4CCC4=O)cc3)n2)c1]
TABLE X-continued
Compound
45
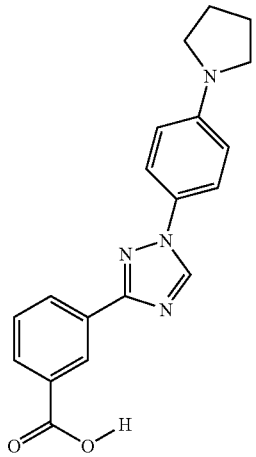 [SMILES: O=C(O)c1cccc(-c2ncn(-c3ccc(N4CCCC4)cc3)n2)c1]
46
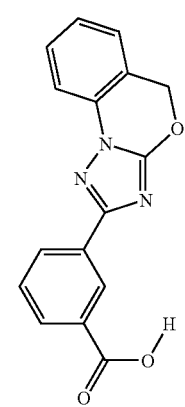 [SMILES: O=C(O)c1cccc(-c2nc3n(n2)-c2ccccc2CO3)c1]
47
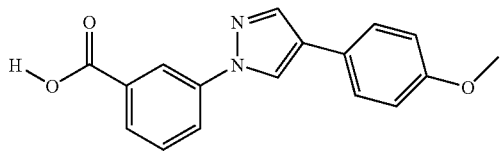 [SMILES: COc1ccc(-c2cnn(-c3cccc(C(=O)O)c3)c2)cc1]
48
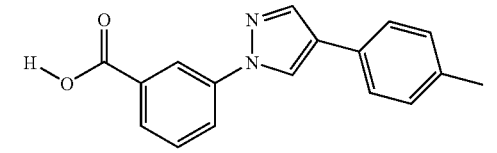 [SMILES: Cc1ccc(-c2cnn(-c3cccc(C(=O)O)c3)c2)cc1]
49
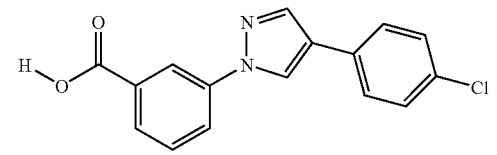 [SMILES: O=C(O)c1cccc(-n2cc(-c3ccc(Cl)cc3)cn2)c1]

TABLE X-continued

| Compound | |
|---|---|
| 50 | (structure) |
| 51 | (structure) |
| 52 | (structure) |
| 53 | (structure) |
| 54 | (structure) |
| 55 | (structure) |
| 56 | (structure) |
| 57 | (structure) |
| 58 | (structure) |
| 59 | (structure) |
| 60 | (structure) |
| 61 | (structure) |
| 62 | (structure) |
| 63 | (structure) |

TABLE X-continued
Compound
64
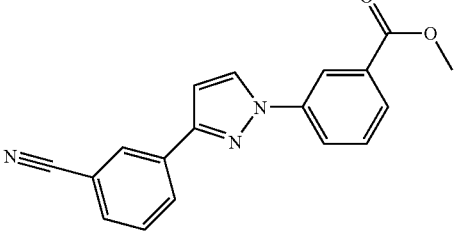
65
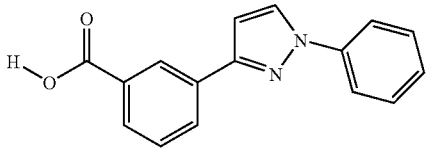 [SMILES: O=C(O)c1cccc(-c2ccn(-c3ccccc3)n2)c1]
66
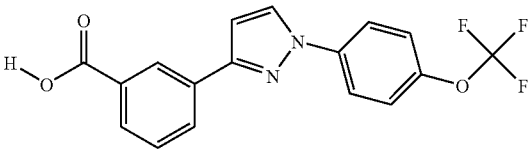 [SMILES: O=C(O)c1cccc(-c2ccn(-c3ccc(OC(F)(F)F)cc3)n2)c1]
67
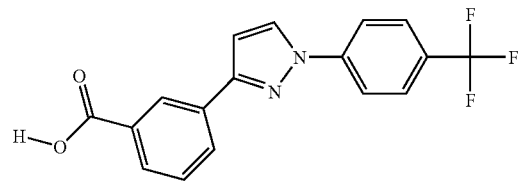 [SMILES: O=C(O)c1cccc(-c2ccn(-c3ccc(C(F)(F)F)cc3)n2)c1]
68
69
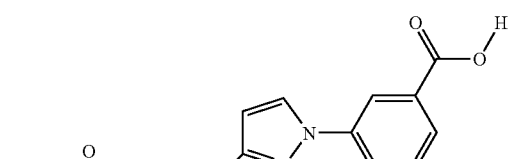
70
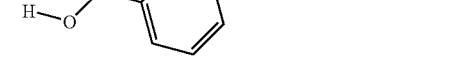
71
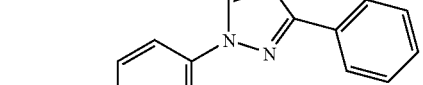
72
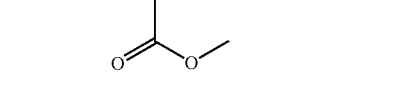
73
74
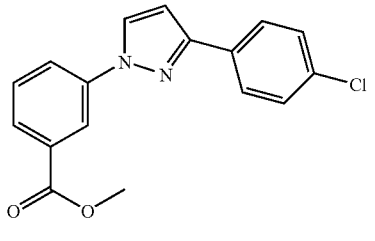 [SMILES: COC(=O)c1cccc(-n2ccc(-c3ccc(Cl)cc3)n2)c1]
75
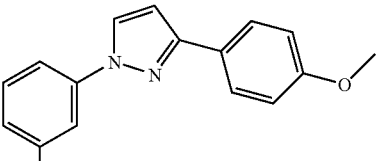
76
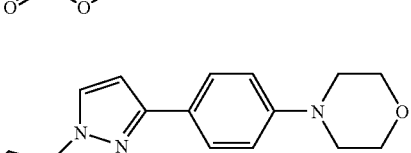

TABLE X-continued

| Compound | # |
|---|---|
| (structure) | 77 |
| (structure) | 78 |
| (structure) | 79 |
| (structure) | 80 |
| (structure) | 81 |
| (structure) | 82 |
| (structure) | 83 |
| (structure) | 84 |
| (structure) | 85 |
| (structure) | 86 |
| (structure) | 87 |
| (structure) | 88 |
| (structure) | 89 |

TABLE X-continued
Compound
90
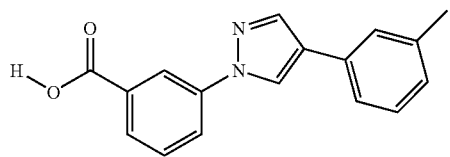 [SMILES: Cc1cccc(-c2cnn(-c3cccc(C(=O)O)c3)c2)c1]
91
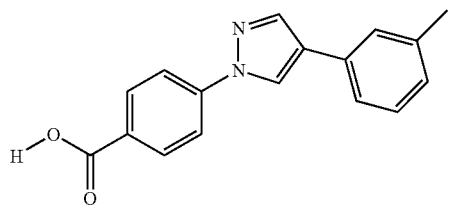 [SMILES: Cc1cccc(-c2cnn(-c3ccc(C(=O)O)cc3)c2)c1]
92
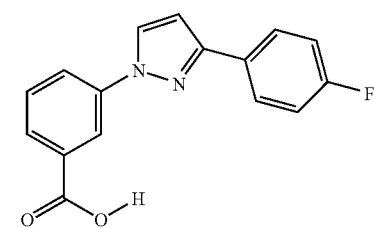 [SMILES: O=C(O)c1cccc(-n2ccc(-c3ccc(F)cc3)n2)c1]
93
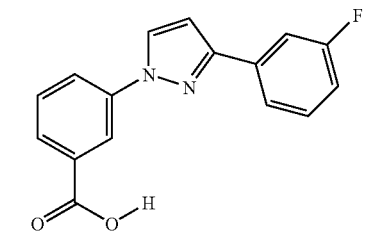 [SMILES: O=C(O)c1cccc(-n2ccc(-c3cccc(F)c3)n2)c1]
94
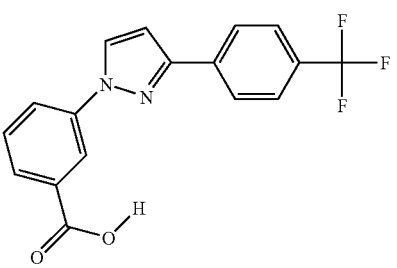 [SMILES: O=C(O)c1cccc(-n2ccc(-c3ccc(C(F)(F)F)cc3)n2)c1]
95
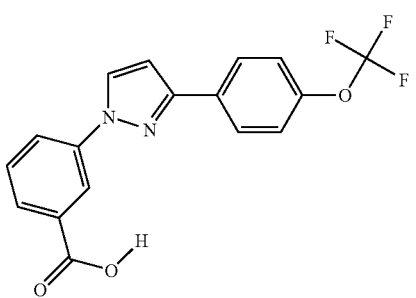 [SMILES: O=C(O)c1cccc(-n2ccc(-c3ccc(OC(F)(F)F)cc3)n2)c1]
TABLE X-continued
Compound
96
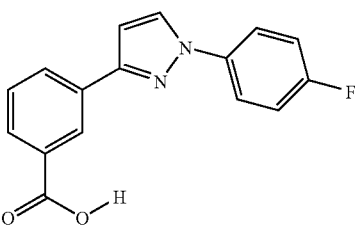 [SMILES: O=C(O)c1cccc(-c2ccn(-c3ccc(F)cc3)n2)c1]
97
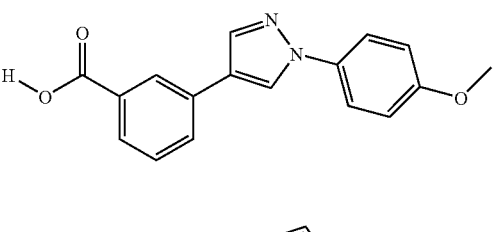
98
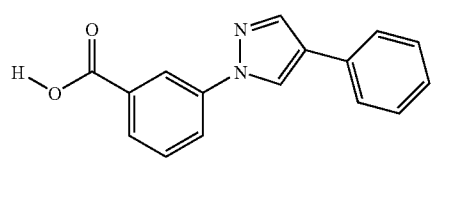 [SMILES: O=C(O)c1cccc(-n2cc(-c3ccccc3)cn2)c1]
99
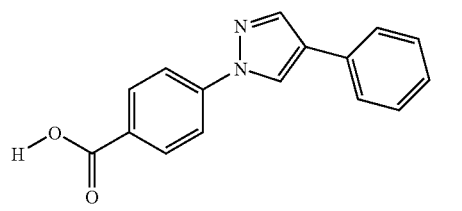 [SMILES: O=C(O)c1ccc(-n2cc(-c3ccccc3)cn2)cc1]
100
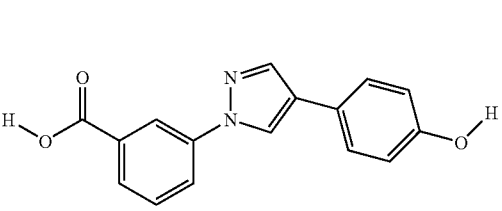 [SMILES: O=C(O)c1cccc(-n2cc(-c3ccc(O)cc3)cn2)c1]
101
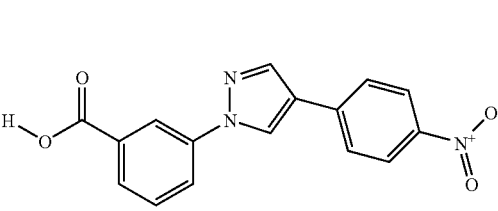
102
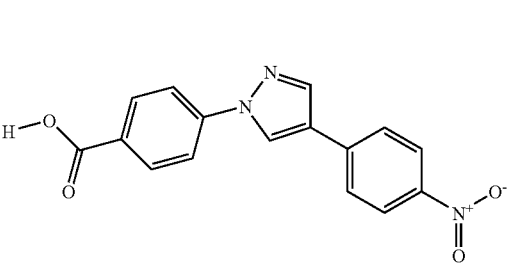 [SMILES: O=C(O)c1ccc(-n2cc(-c3ccc([N+](=O)[O-])cc3)cn2)cc1]

TABLE X-continued
Compound
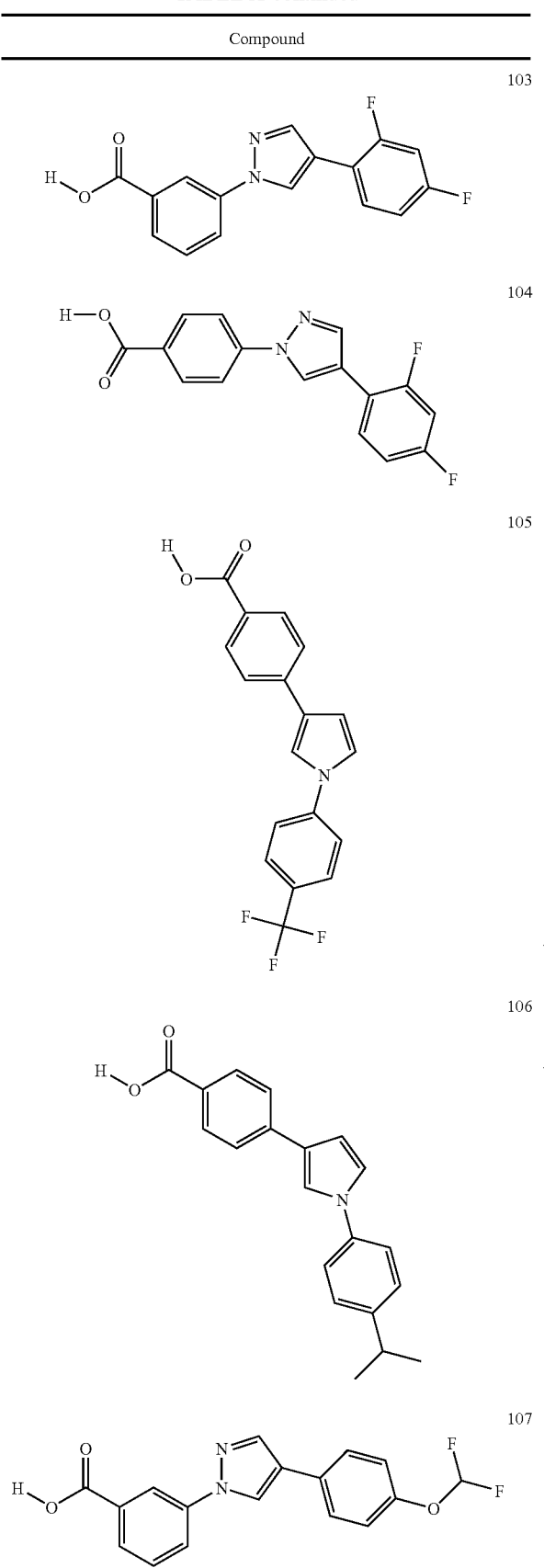
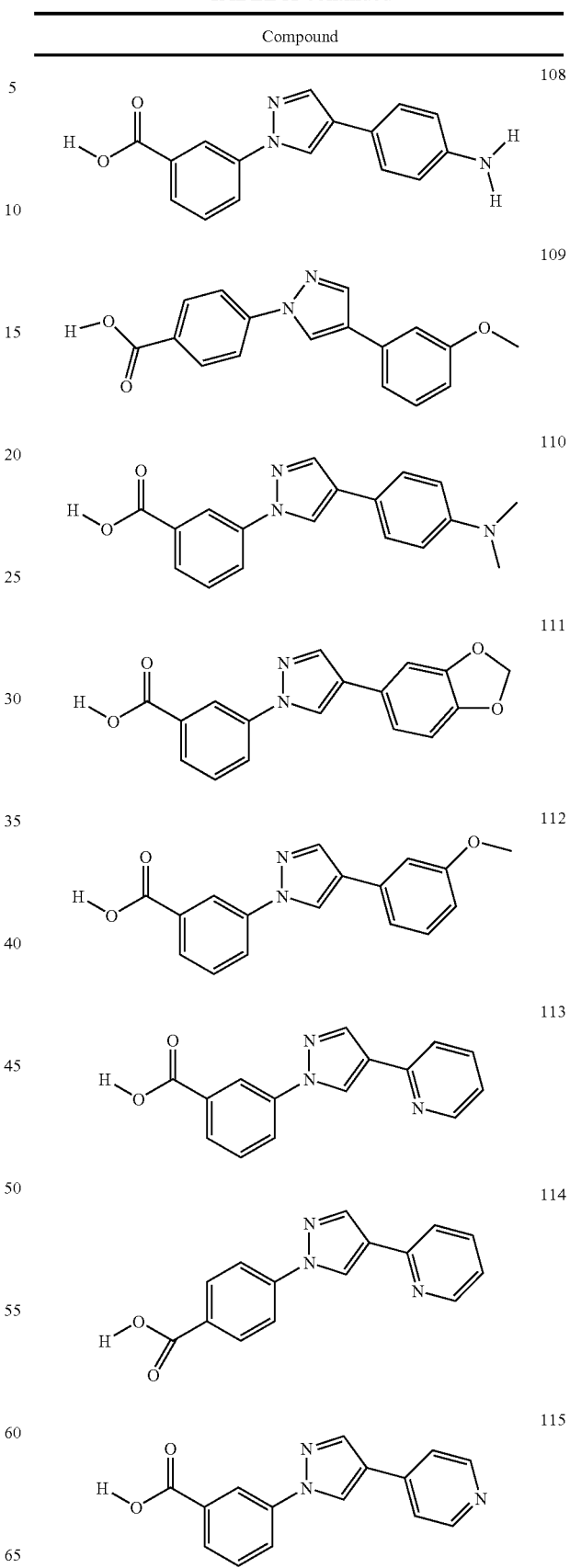

TABLE X-continued
| Compound | |
|---|---|
| 116 | 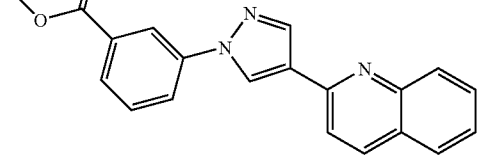 |
| 117 | |
| 118 | |
| 119 | |
| 120 | |
| 121 | |
| 122 | |
| 123 | 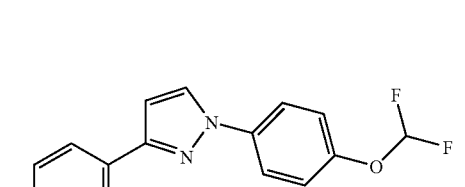 |
| 124 | |
| 125 | |
| 126 | |

TABLE X-continued
| Compound | |
|---|---|
| 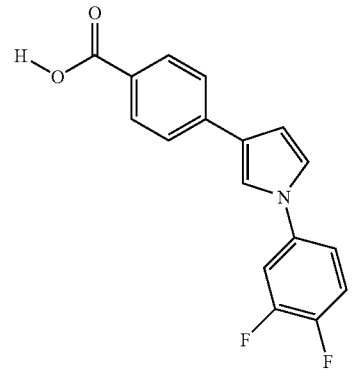 [SMILES: O=C(O)c1ccc(-c2ccn(-c3ccc(F)c(F)c3)c2)cc1] | 127 |
| 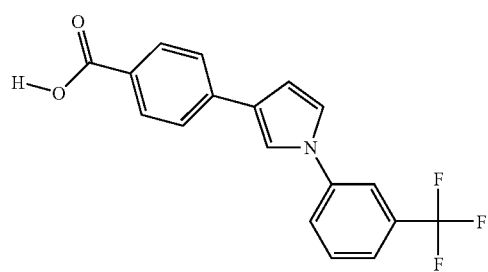 [SMILES: O=C(O)c1ccc(-c2ccn(-c3cccc(C(F)(F)F)c3)c2)cc1] | 128 |
| 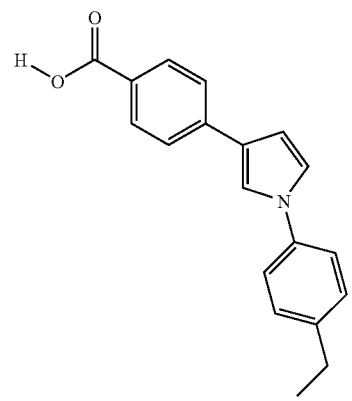 [SMILES: CCc1ccc(-n2ccc(-c3ccc(C(=O)O)cc3)c2)cc1] | 129 |
| 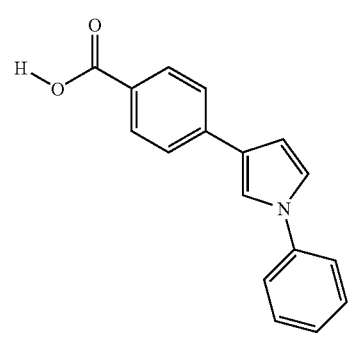 [SMILES: O=C(O)c1ccc(-c2ccn(-c3ccccc3)c2)cc1] | 130 |
| 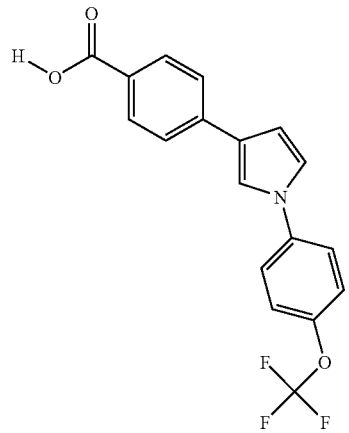 [SMILES: O=C(O)c1ccc(-c2ccn(-c3ccc(OC(F)(F)F)cc3)c2)cc1] | 131 |
| 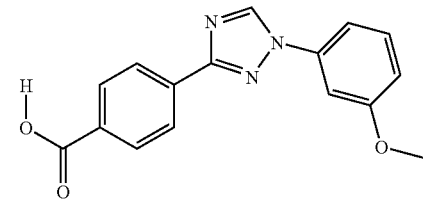 [SMILES: COc1cccc(-n2cnc(-c3ccc(C(=O)O)cc3)n2)c1] | 132 |
| 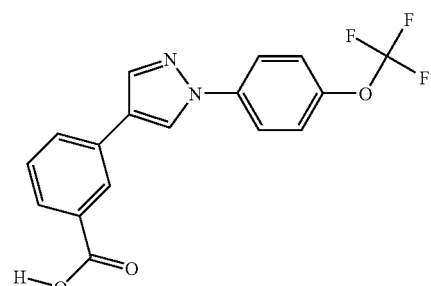 | 133 |
| 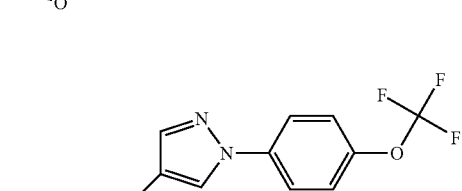 | 134 |
| 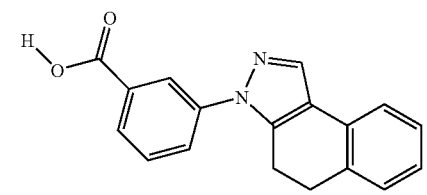 [SMILES: O=C(O)c1cccc(-n2ncc3c2CCc2ccccc2-3)c1] | 135 |

TABLE X-continued
Compound
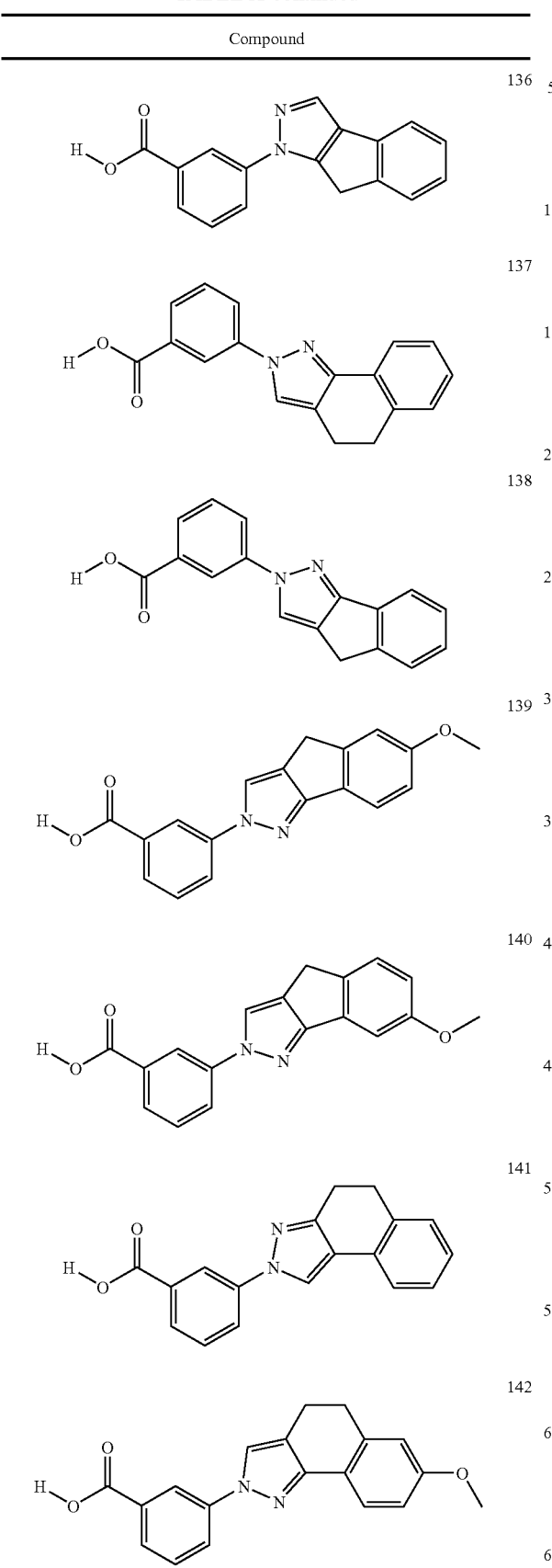
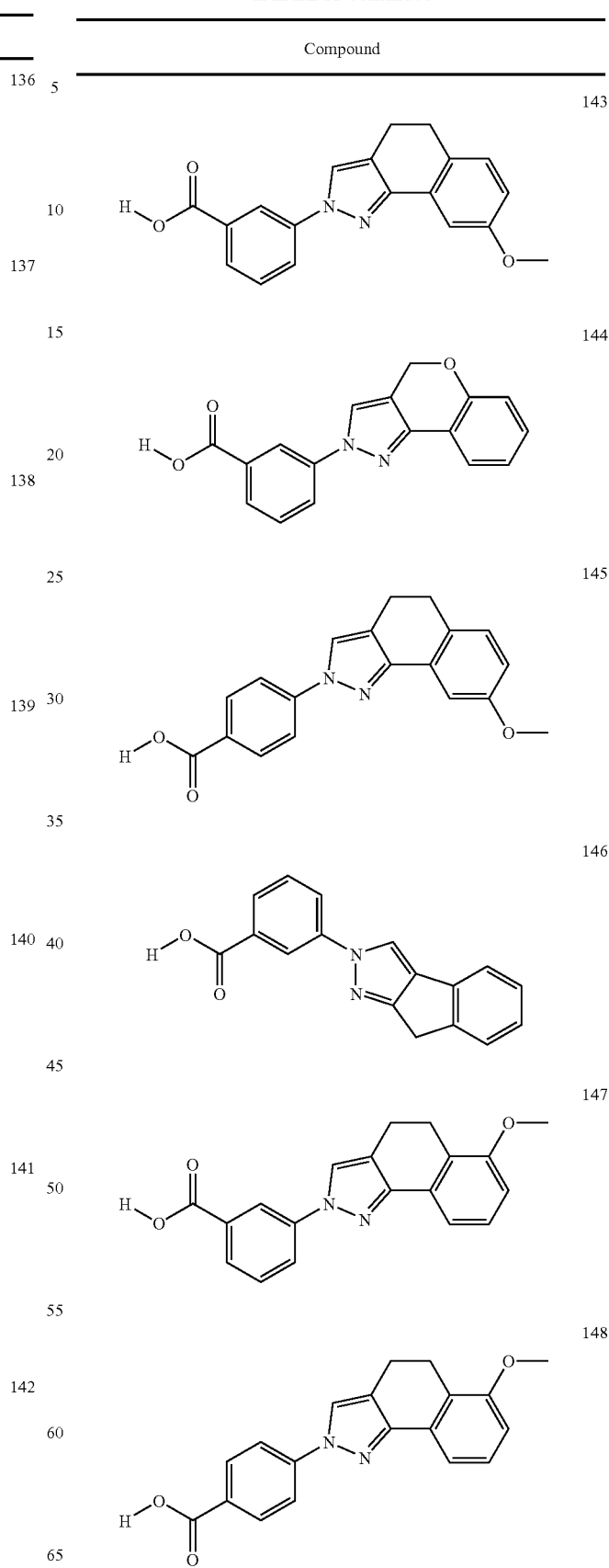

TABLE X-continued

Compound

149: 4-(7-methoxy-4H-indeno[1,2-c]pyrazol-2-yl)benzoic acid

150: 4-(1-(2,3-dihydrobenzo[b][1,4]dioxin-6-yl)-1H-pyrrol-3-yl)benzoic acid

151: 4-(1-(2-fluorophenyl)-1H-pyrrol-3-yl)benzoic acid

152: 4-(1-(3-fluorophenyl)-1H-pyrrol-3-yl)benzoic acid

153: 4-(1-(3,5-difluorophenyl)-1H-pyrrol-3-yl)benzoic acid

154: 3-(1-(4-(trifluoromethyl)phenyl)-1H-pyrrol-3-yl)benzoic acid

155: 3-(1-(4-chlorophenyl)-1H-pyrrol-3-yl)benzoic acid

TABLE X-continued
Compound
156
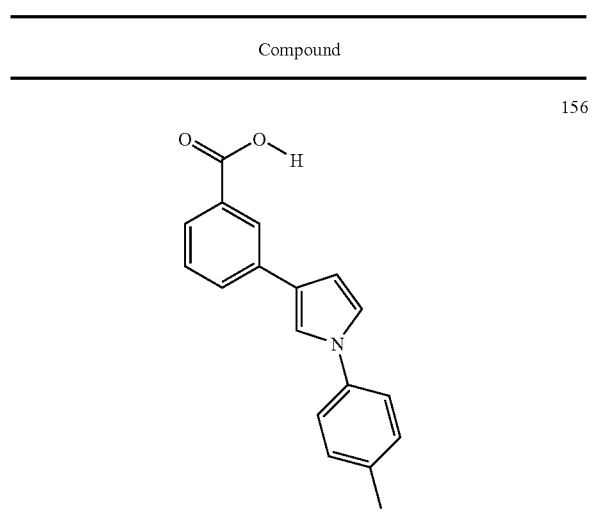
157
158
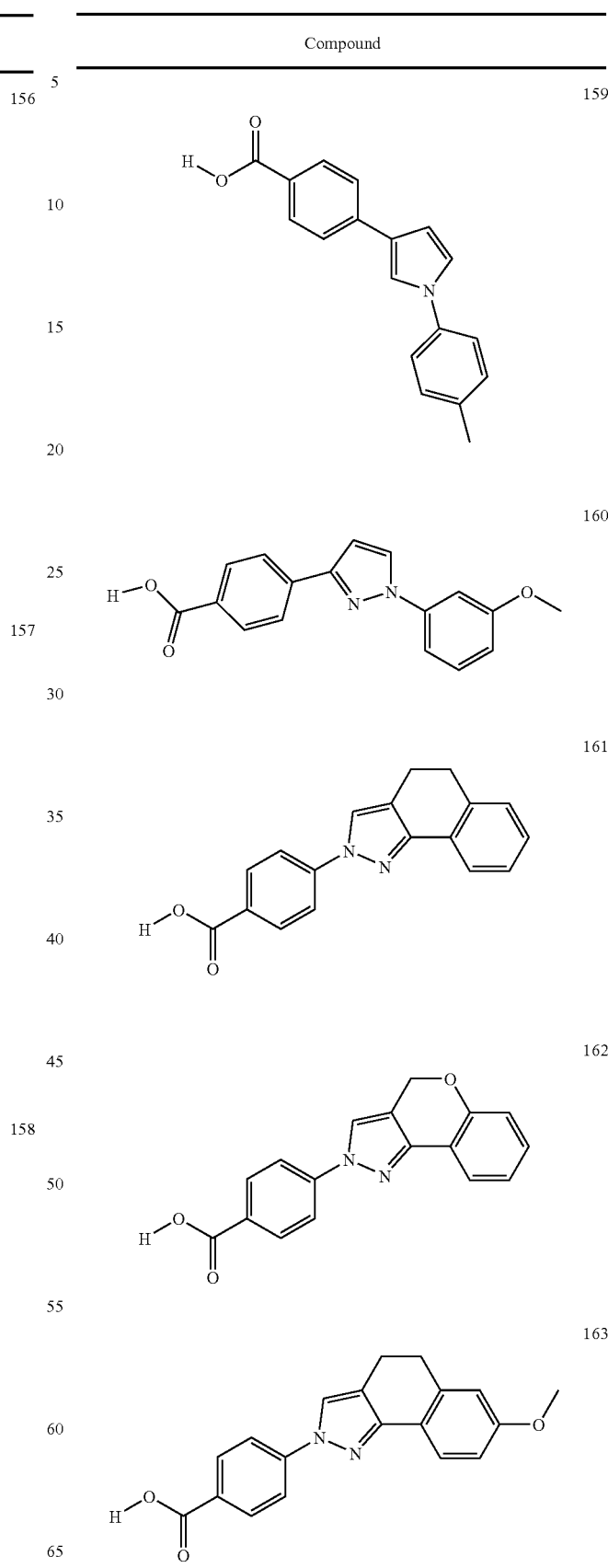
159
160
161
162
163

TABLE X-continued
Compound
164
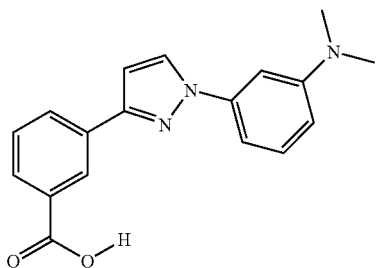 [SMILES: CN(C)c1cccc(-n2ccc(-c3cccc(C(=O)O)c3)n2)c1]
165
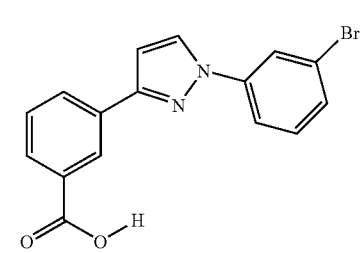 [SMILES: O=C(O)c1cccc(-c2ccn(-c3cccc(Br)c3)n2)c1]
166
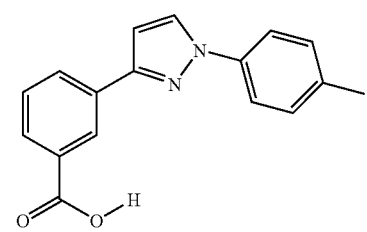 [SMILES: Cc1ccc(-n2ccc(-c3cccc(C(=O)O)c3)n2)cc1]
167
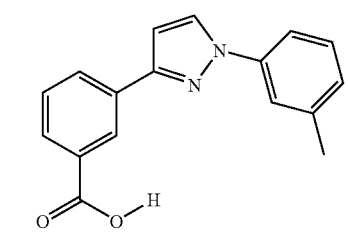 [SMILES: Cc1cccc(-n2ccc(-c3cccc(C(=O)O)c3)n2)c1]
168
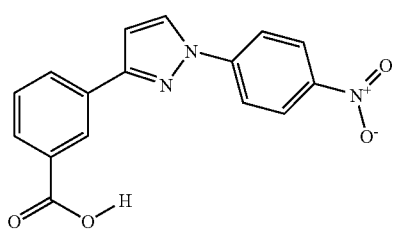 [SMILES: O=C(O)c1cccc(-c2ccn(-c3ccc([N+](=O)[O-])cc3)n2)c1]
169
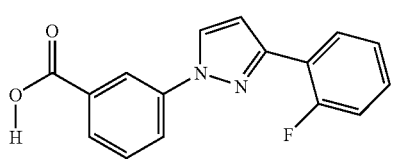 [SMILES: O=C(O)c1cccc(-n2ccc(-c3ccccc3F)n2)c1]
TABLE X-continued
Compound
170
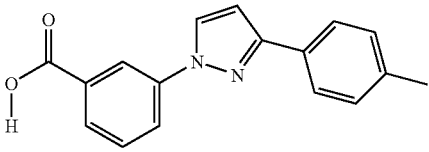 [SMILES: Cc1ccc(-c2ccn(-c3cccc(C(=O)O)c3)n2)cc1]
171
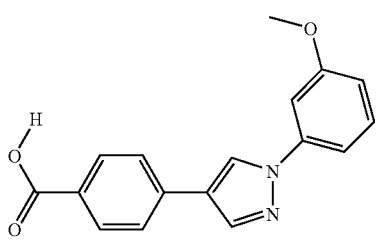 [SMILES: COc1cccc(-n2cc(-c3ccc(C(=O)O)cc3)cn2)c1]
172
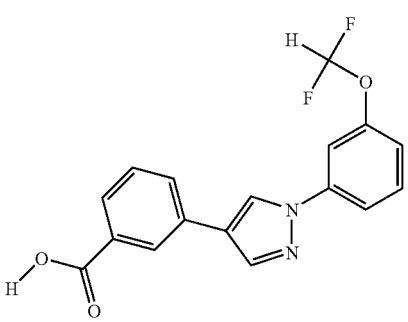 [SMILES: O=C(O)c1cccc(-c2cnn(-c3cccc(OC(F)F)c3)c2)c1]
173
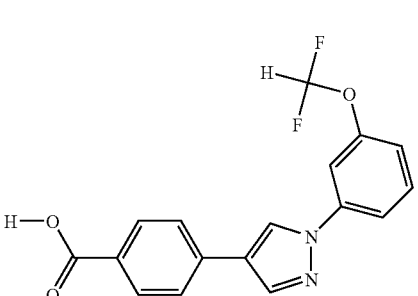
174
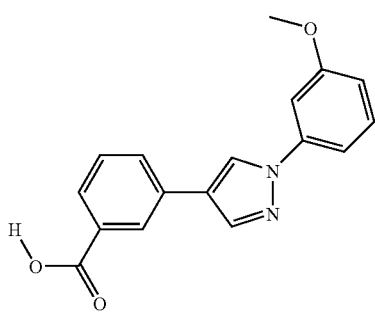 [SMILES: COc1cccc(-n2cc(-c3cccc(C(=O)O)c3)cn2)c1]

TABLE X-continued
Compound
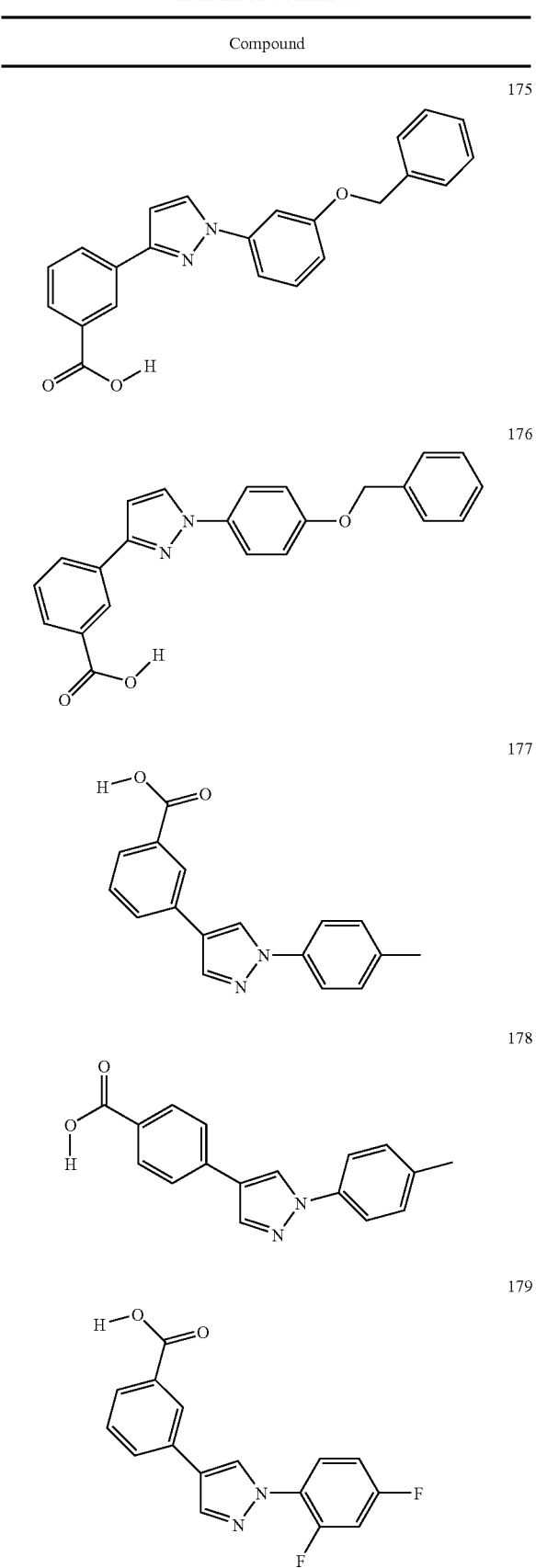
175
176
177
178
179
TABLE X-continued
Compound
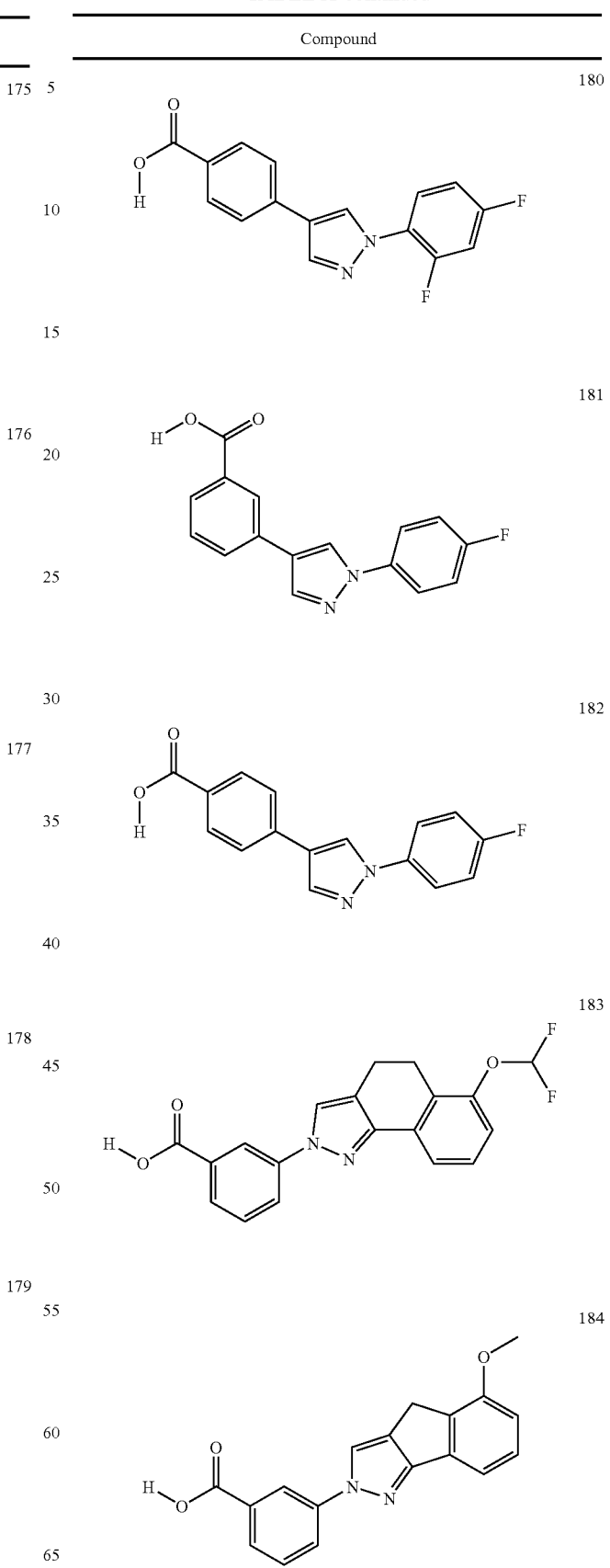
180
181
182
183
184

TABLE X-continued
Compound
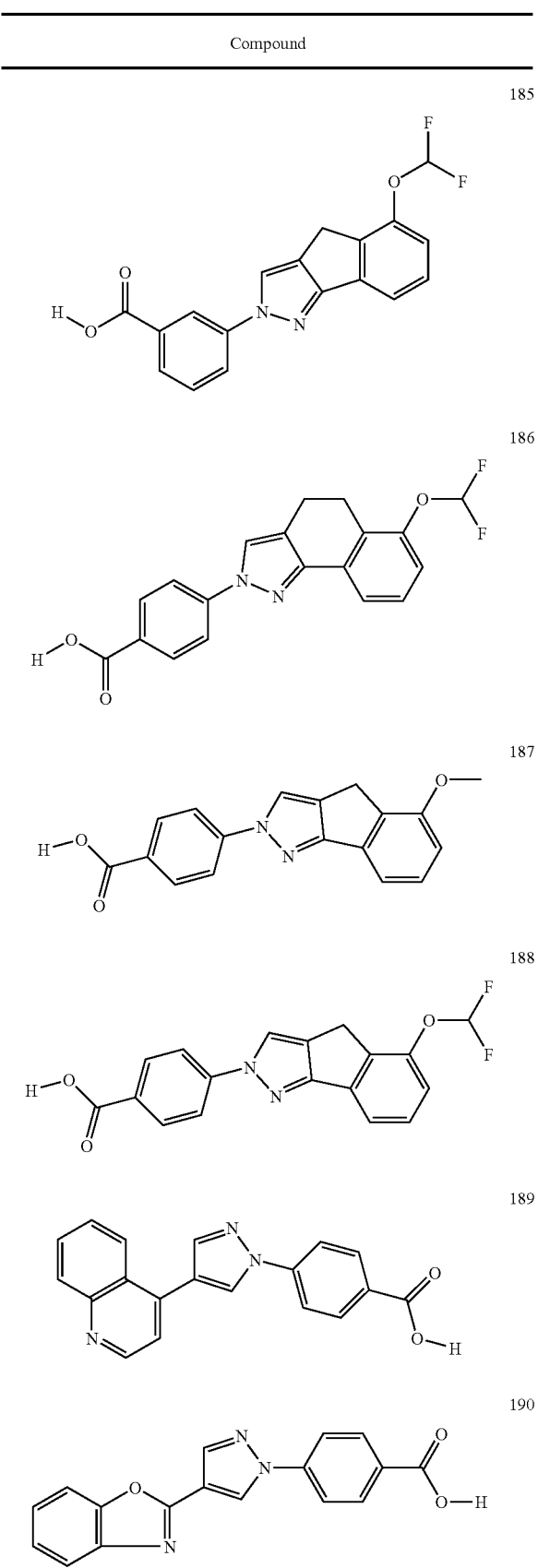
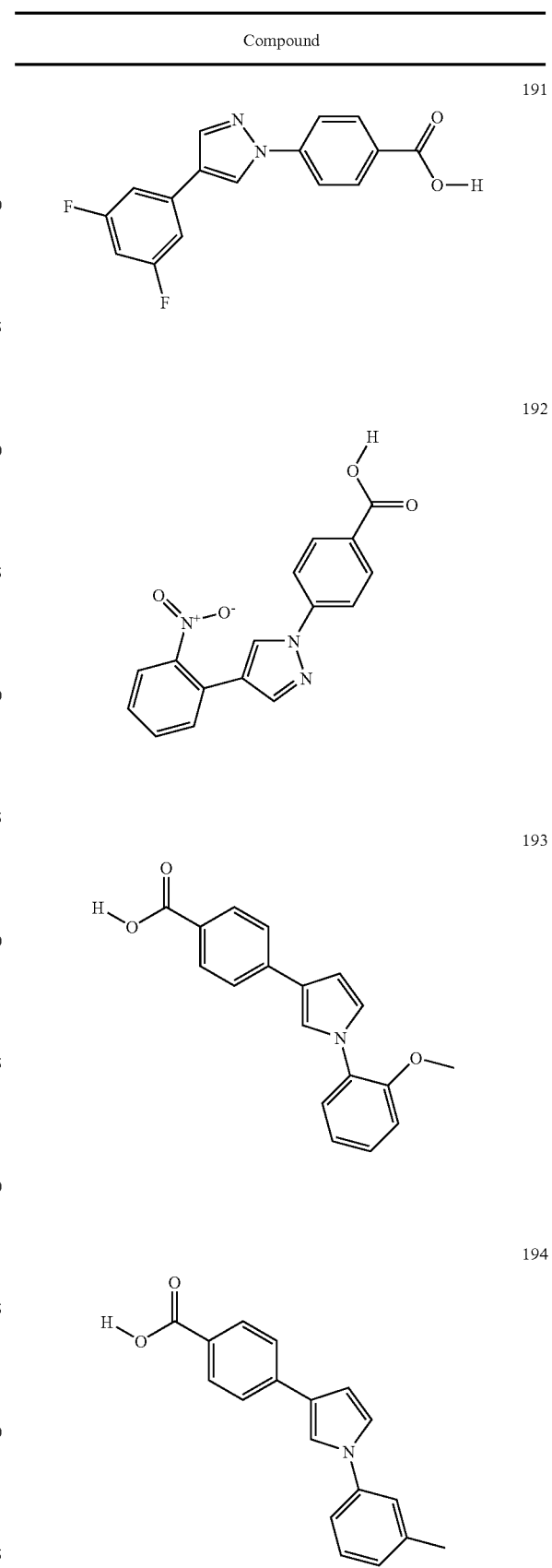

TABLE X-continued
| Compound | |
|---|---|
| 195 | 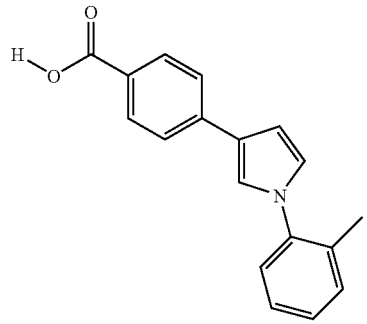 [SMILES: Cc1ccccc1-n1ccc(-c2ccc(C(=O)O)cc2)c1] |
| 196 | 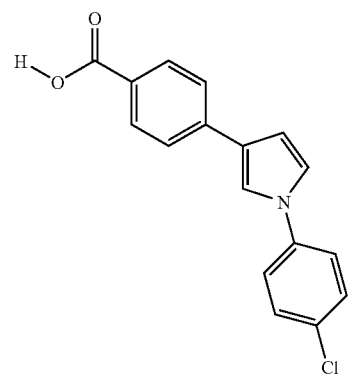 [SMILES: O=C(O)c1ccc(-c2ccn(-c3ccc(Cl)cc3)c2)cc1] |
| 197 | 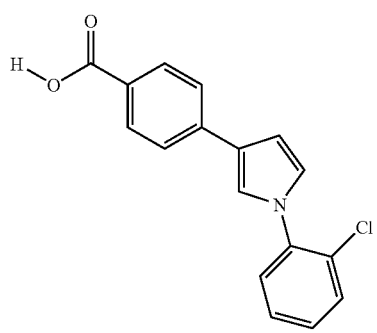 [SMILES: O=C(O)c1ccc(-c2ccn(-c3ccccc3Cl)c2)cc1] |
| 198 | 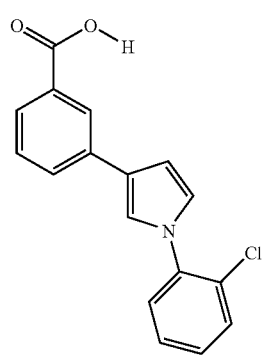 [SMILES: O=C(O)c1cccc(-c2ccn(-c3ccccc3Cl)c2)c1] |
| 199 | 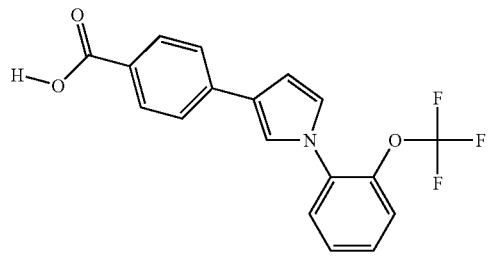 [SMILES: O=C(O)c1ccc(-c2ccn(-c3ccccc3OC(F)(F)F)c2)cc1] |
| 200 | 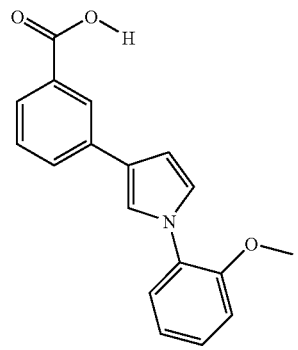 [SMILES: COc1ccccc1-n1ccc(-c2cccc(C(=O)O)c2)c1] |
| 201 | 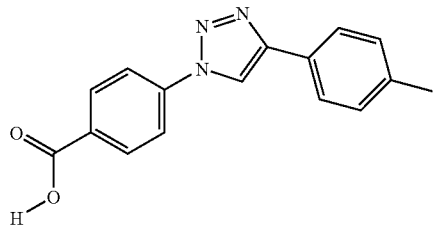 [SMILES: Cc1ccc(-c2cn(-c3ccc(C(=O)O)cc3)nn2)cc1] |
| 202 | 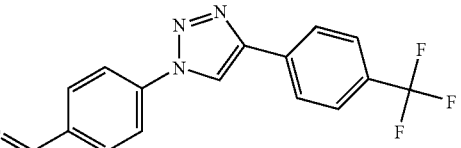 |
| 203 | 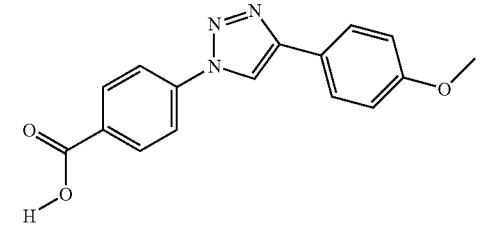 [SMILES: COc1ccc(-c2cn(-c3ccc(C(=O)O)cc3)nn2)cc1] |

TABLE X-continued

| Compound | |
|---|---|
| 204 | (structure) |
| 205 | (structure) |
| 206 | (structure) |
| 207 | (structure) |
| 208 | (structure) |
| 209 | (structure) |
| 210 | (structure) |
| 211 | (structure) |
| 212 | (structure) |
| 213 | (structure) |

TABLE X-continued
Compound
214
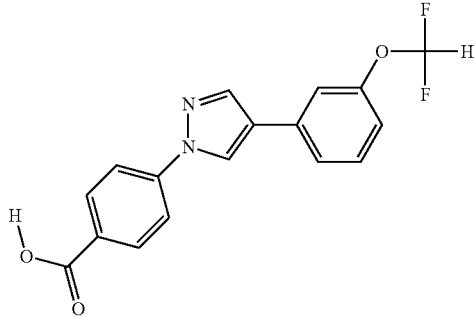 [SMILES: O=C(O)c1ccc(-n2cc(-c3cccc(OC(F)F)c3)cn2)cc1]
215
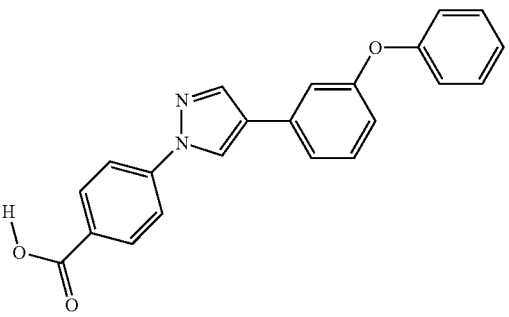 [SMILES: O=C(O)c1ccc(-n2cc(-c3cccc(Oc4ccccc4)c3)cn2)cc1]
216
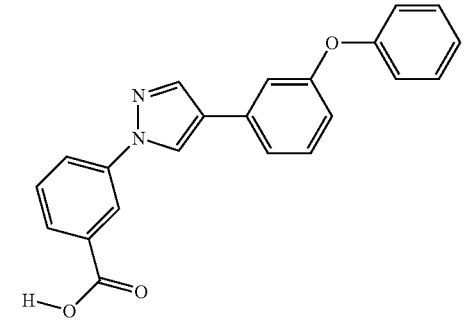 [SMILES: O=C(O)c1cccc(-n2cc(-c3cccc(Oc4ccccc4)c3)cn2)c1]
217
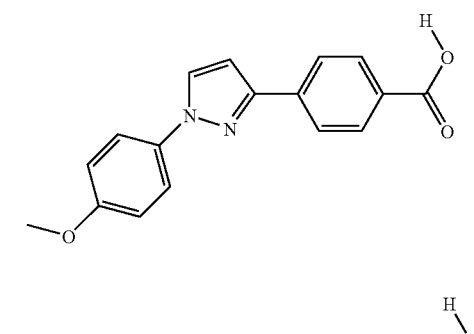
218
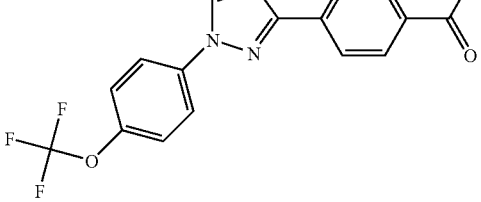
TABLE X-continued
Compound
219
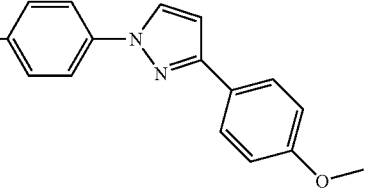
220
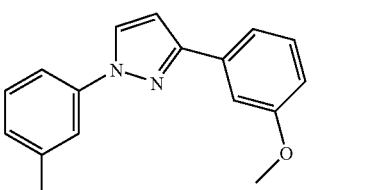
221
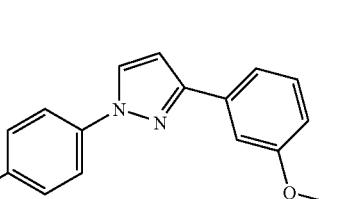
222
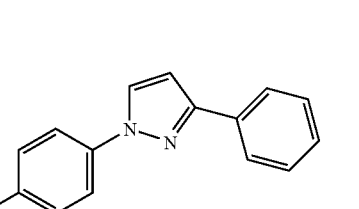
223
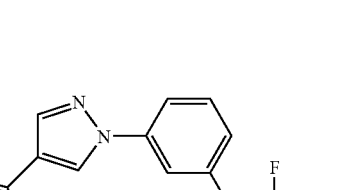
224
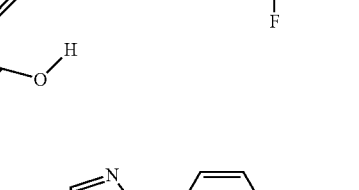

TABLE X-continued

| Compound | |
|---|---|
| (structure) | 225 |
| (structure) | 226 |
| (structure) | 227 |
| (structure) | 228 |
| (structure) | 229 |
| (structure) | 230 |
| (structure) | 231 |
| (structure) | 232 |
| (structure) | 233 |
| (structure) | 234 |
| (structure) | 235 |

TABLE X-continued
| Compound | |
|---|---|
| 236 | 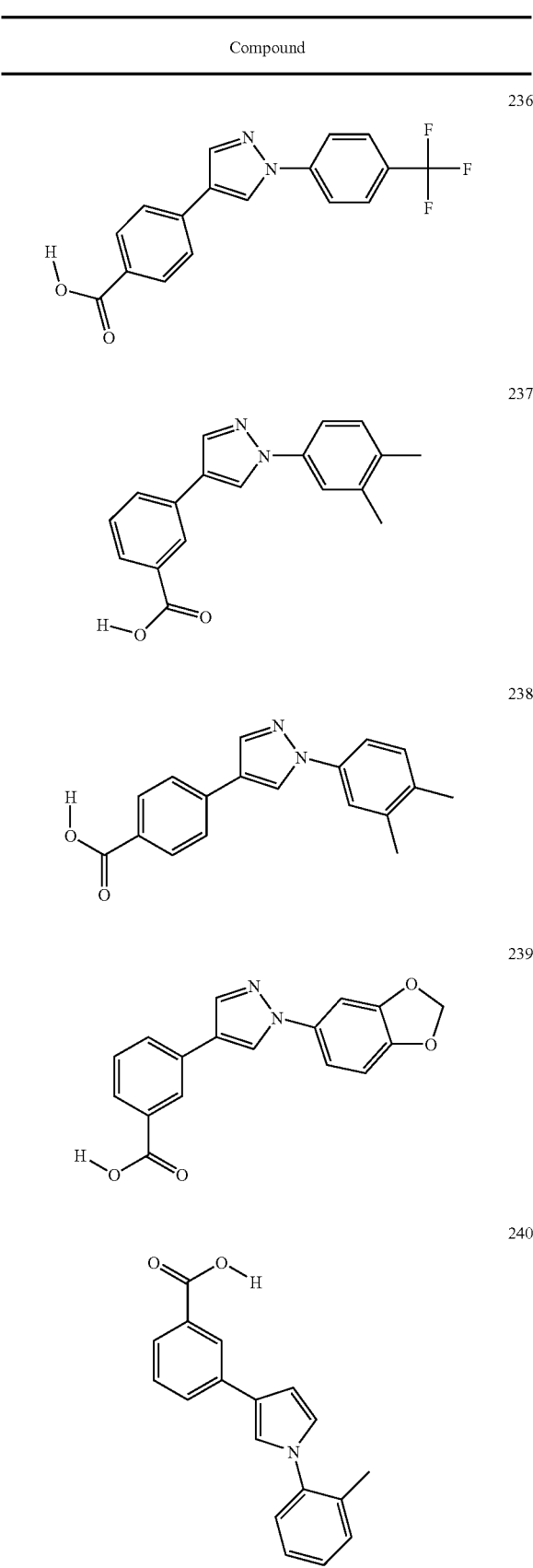 |
| 237 | |
| 238 | |
| 239 | |
| 240 | |
TABLE X-continued
| Compound | |
|---|---|
| 241 | 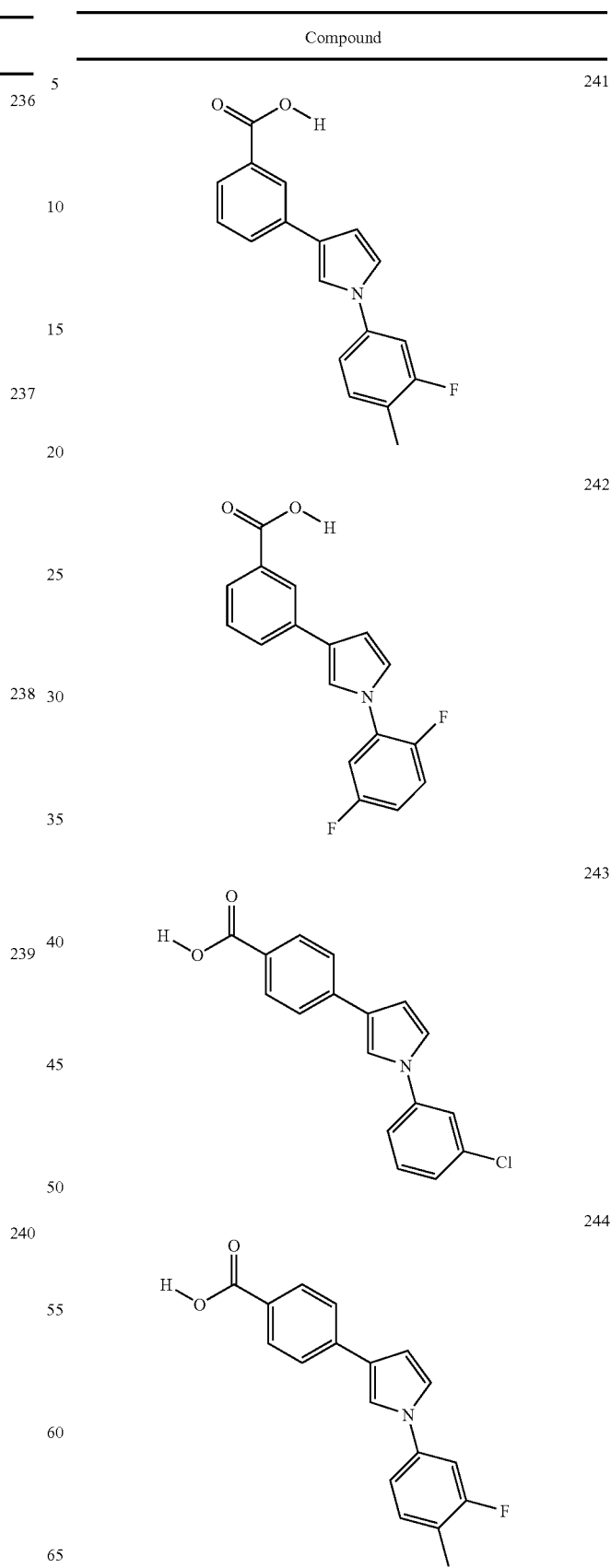 |
| 242 | |
| 243 | |
| 244 | |

TABLE X-continued

| Compound |
|---|
| 245 |
| 246 |
| 247 |
| 248 |
| 249 |
| 250 |
| 251 |
| 252 |
| 253 |
| 254 |
| 255 |
| 256 |

TABLE X-continued
Compound
257
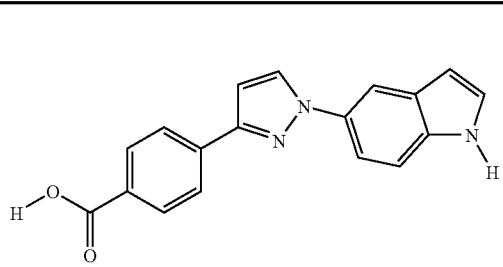
258
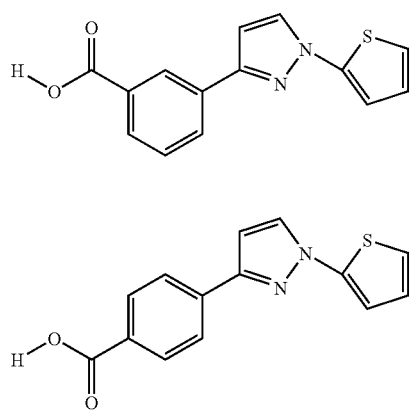
259
260
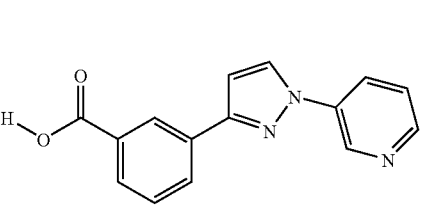
261
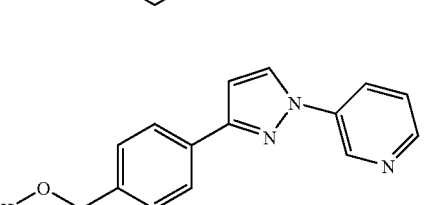
262
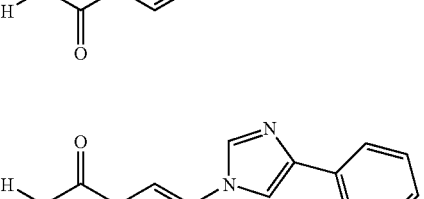
263
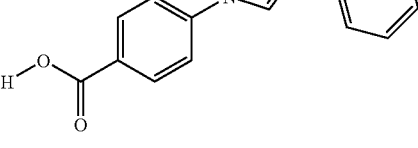
264
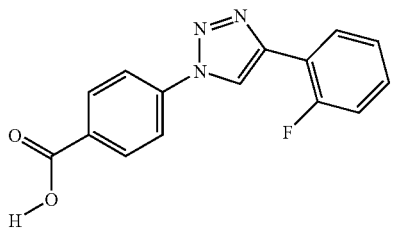 [SMILES: O=C(O)c1ccc(-n2cc(-c3ccccc3F)nn2)cc1]
265
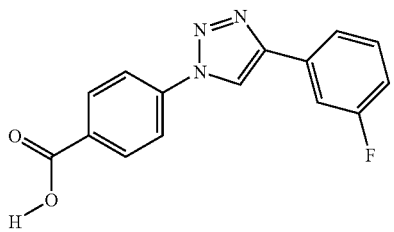 [SMILES: O=C(O)c1ccc(-n2cc(-c3cccc(F)c3)nn2)cc1]
266
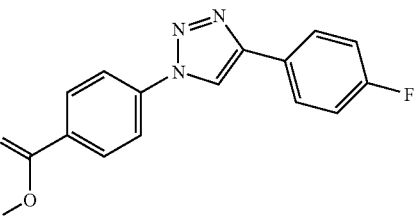
267
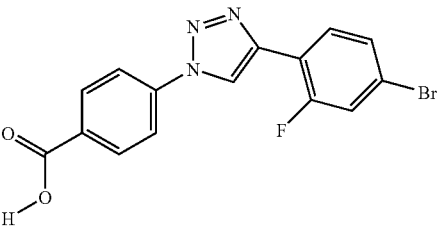 [SMILES: O=C(O)c1ccc(-n2cc(-c3ccc(Br)cc3F)nn2)cc1]
268
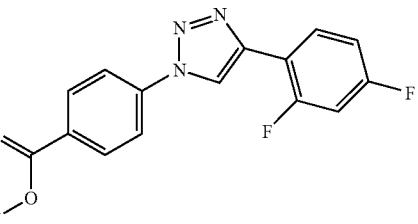
269
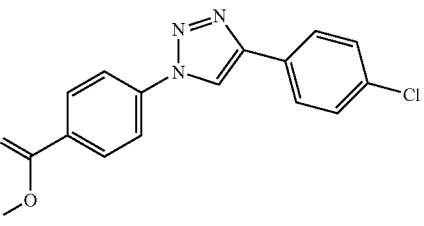

TABLE X-continued
Compound
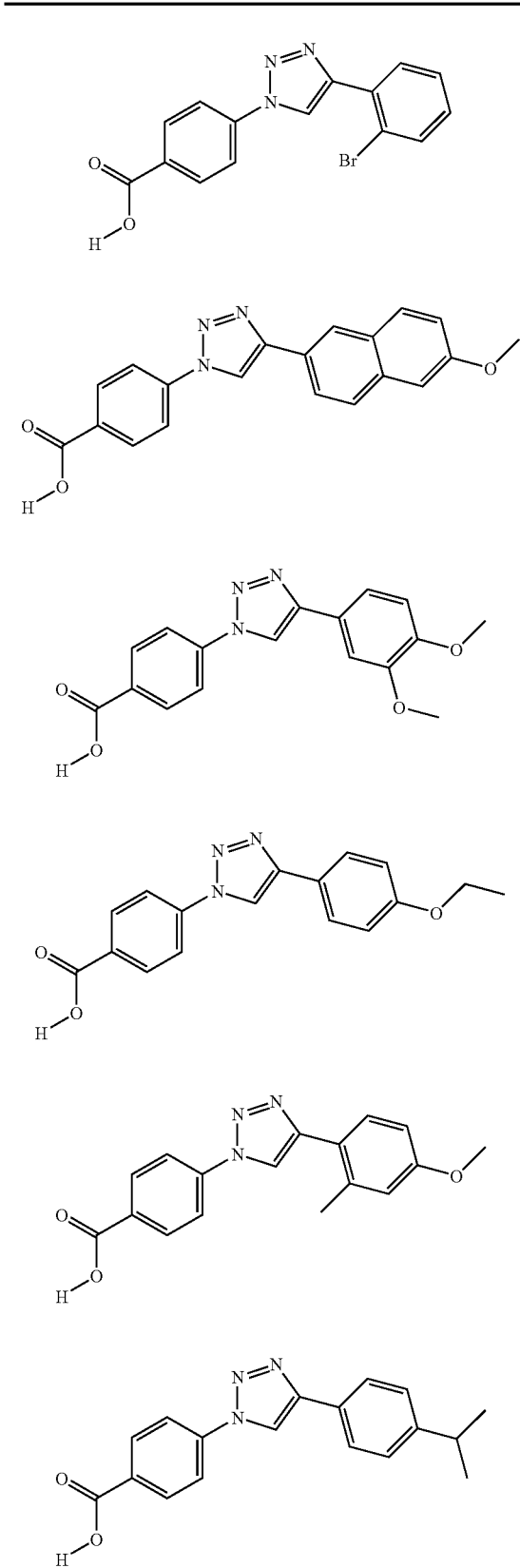
270
271
272
273
274
275
TABLE X-continued
Compound
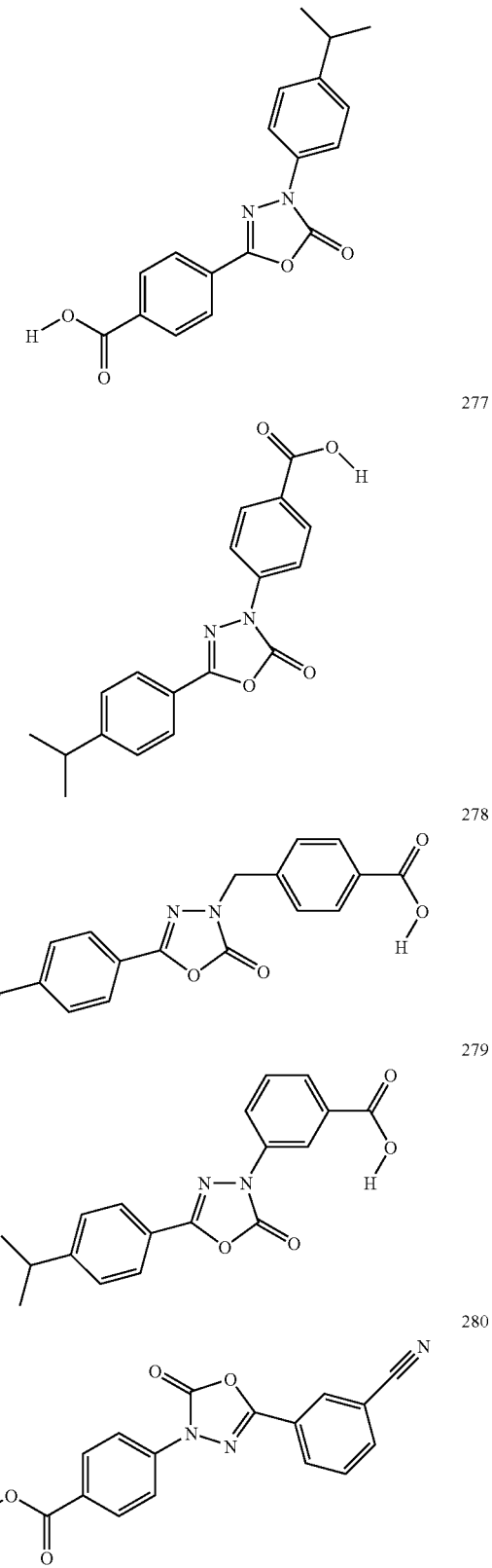
276
277
278
279
280

TABLE X-continued
Compound
281
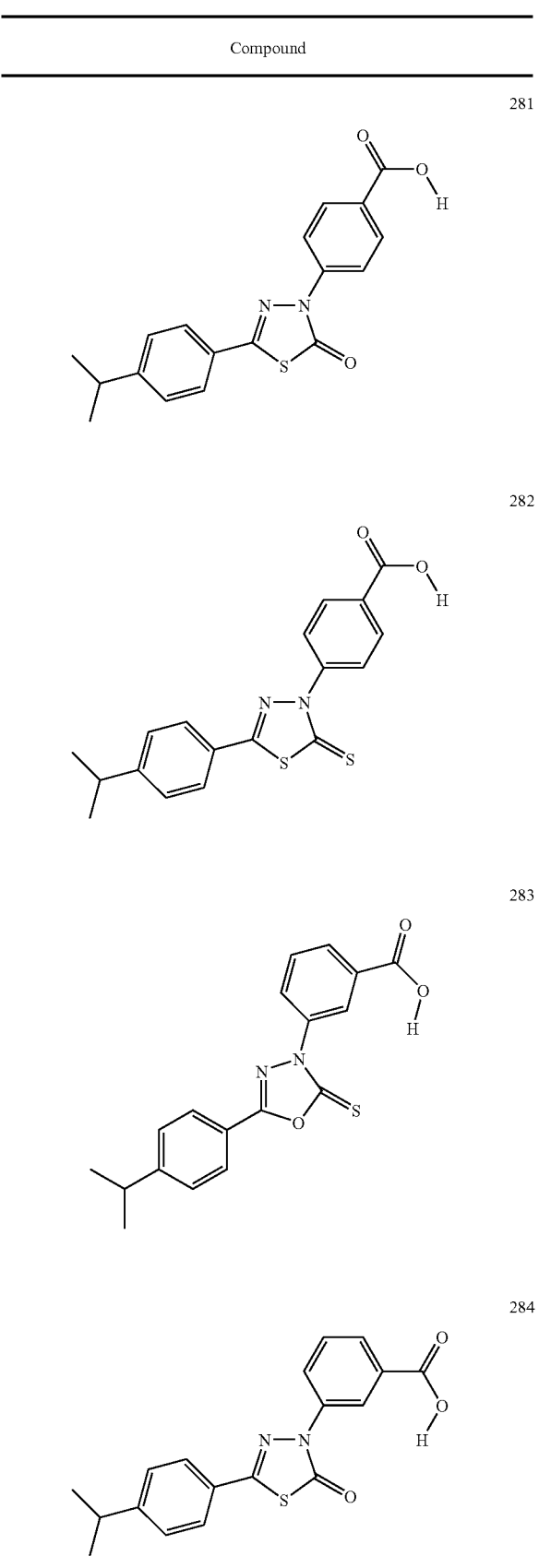
282
283
284
285
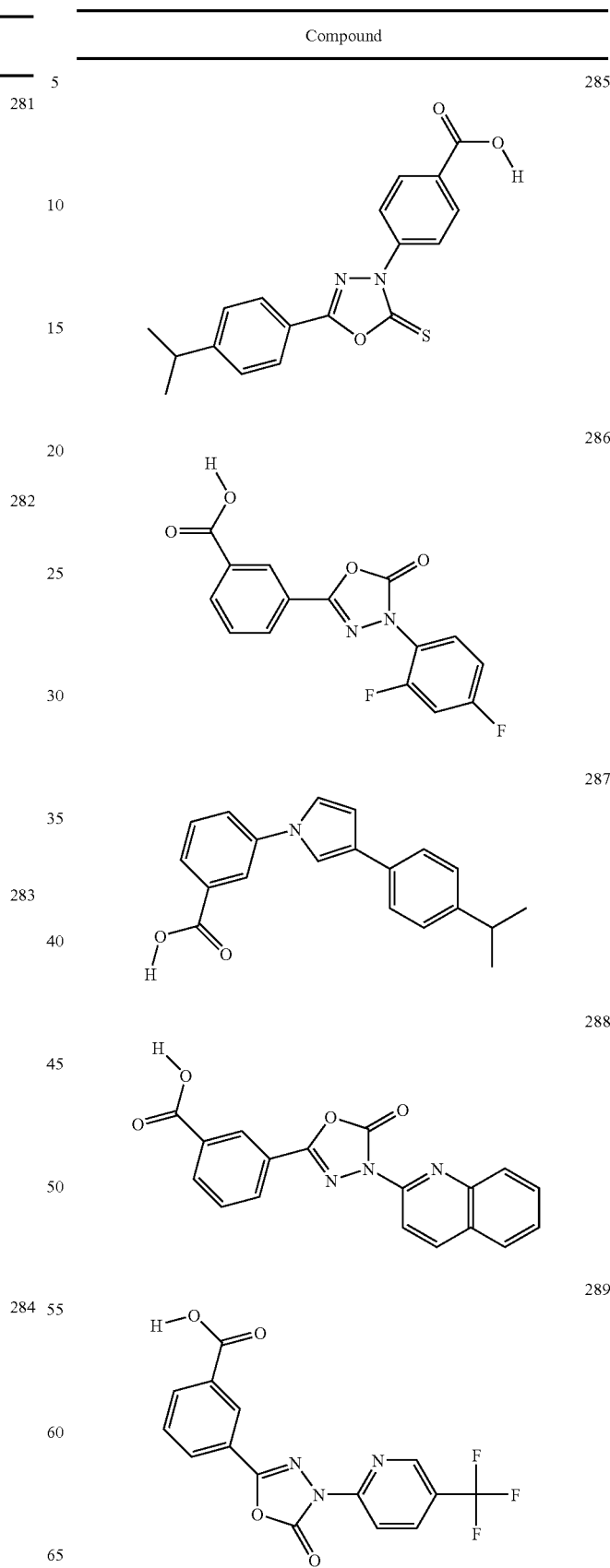
286
287
288
289

TABLE X-continued
Compound
290 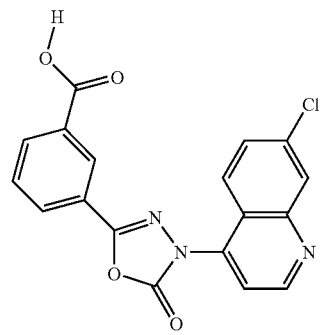 [SMILES: O=C(O)c1cccc(-c2nn(-c3ccnc4cc(Cl)ccc34)c(=O)o2)c1]
291 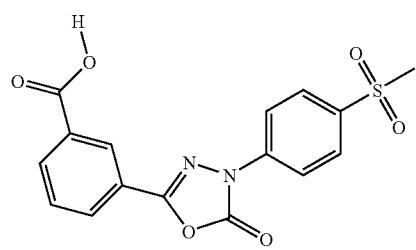 [SMILES: CS(=O)(=O)c1ccc(-n2nc(-c3cccc(C(=O)O)c3)oc2=O)cc1]
292 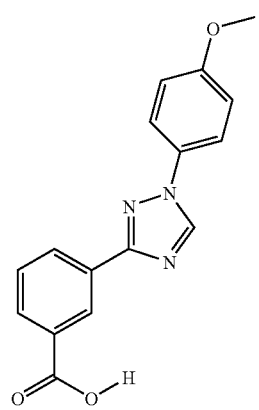 [SMILES: COc1ccc(-n2cnc(-c3cccc(C(=O)O)c3)n2)cc1]
293 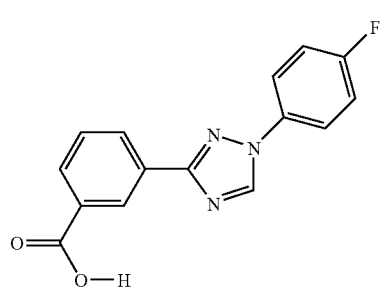 [SMILES: O=C(O)c1cccc(-c2ncn(-c3ccc(F)cc3)n2)c1]
TABLE X-continued
Compound
294 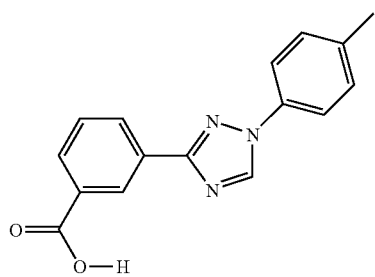 [SMILES: Cc1ccc(-n2cnc(-c3cccc(C(=O)O)c3)n2)cc1]
295 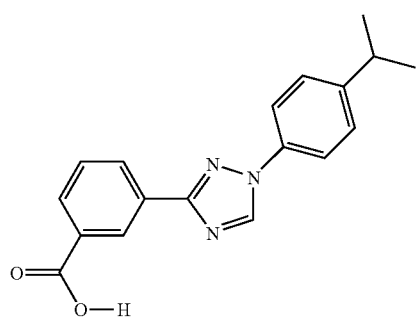 [SMILES: CC(C)c1ccc(-n2cnc(-c3cccc(C(=O)O)c3)n2)cc1]
296 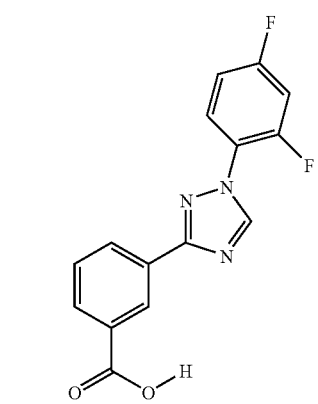 [SMILES: O=C(O)c1cccc(-c2ncn(-c3ccc(F)cc3F)n2)c1]
297 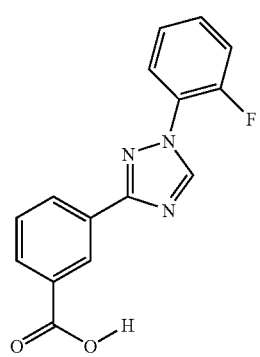 [SMILES: O=C(O)c1cccc(-c2ncn(-c3ccccc3F)n2)c1]

| Compound | Compound |
|---|---|
| 298 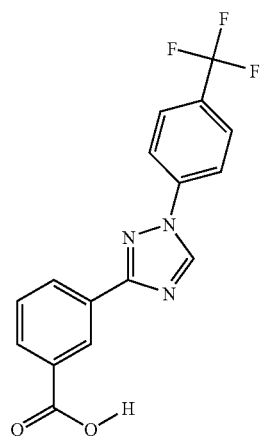 [SMILES: O=C(O)c1cccc(-c2ncn(-c3ccc(C(F)(F)F)cc3)n2)c1] | 301 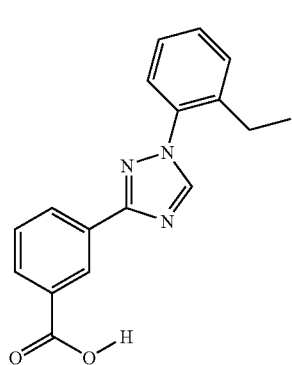 |
| 299 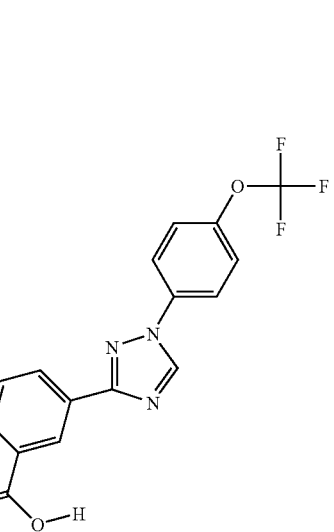 | 302 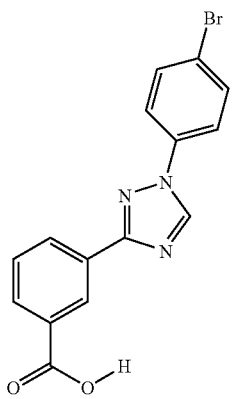 |
| 300 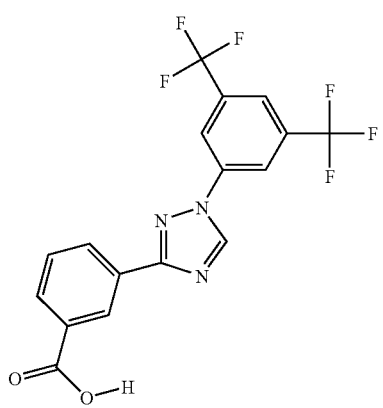 [SMILES: O=C(O)c1cccc(-c2ncn(-c3cc(C(F)(F)F)cc(C(F)(F)F)c3)n2)c1] | 303 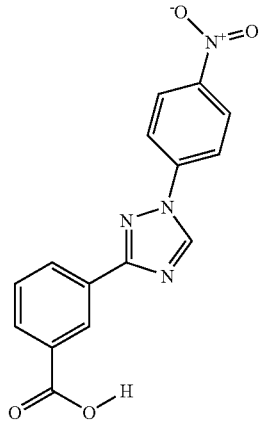 |

TABLE X-continued
Compound
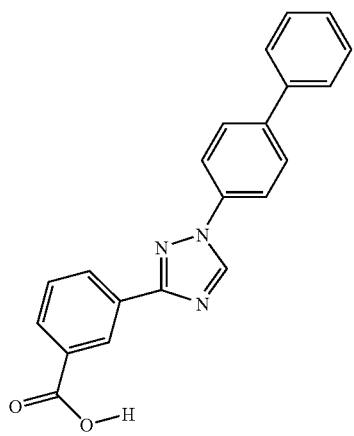 [SMILES: O=C(O)c1cccc(-c2ncn(-c3ccc(-c4ccccc4)cc3)n2)c1]
304
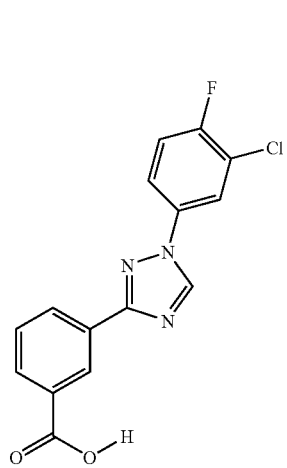 [SMILES: O=C(O)c1cccc(-c2ncn(-c3ccc(F)c(Cl)c3)n2)c1]
305
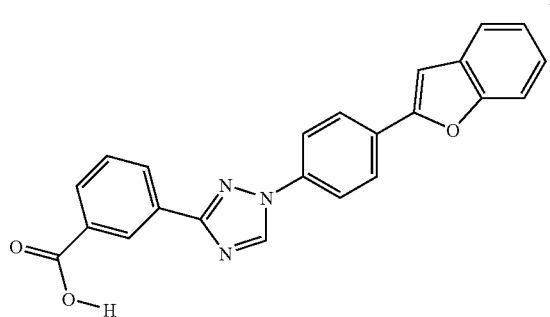 [SMILES: O=C(O)c1cccc(-c2ncn(-c3ccc(-c4cc5ccccc5o4)cc3)n2)c1]
306
TABLE X-continued
Compound
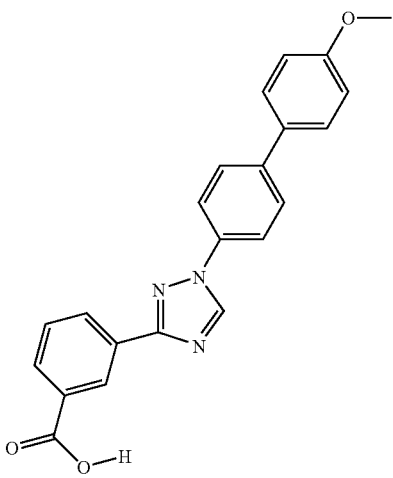 [SMILES: COc1ccc(-c2ccc(-n3cnc(-c4cccc(C(=O)O)c4)n3)cc2)cc1]
307
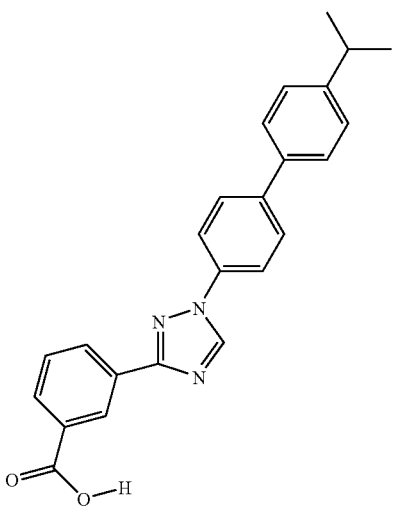 [SMILES: CC(C)c1ccc(-c2ccc(-n3cnc(-c4cccc(C(=O)O)c4)n3)cc2)cc1]
308
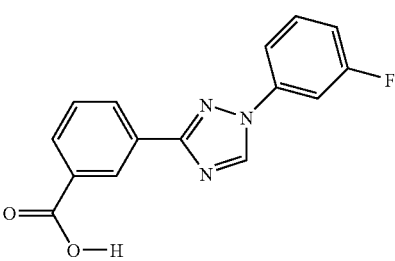 [SMILES: O=C(O)c1cccc(-c2ncn(-c3cccc(F)c3)n2)c1]
309

TABLE X-continued
Compound
310
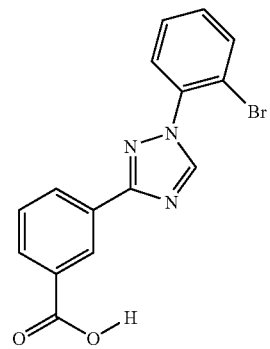 [SMILES: O=C(O)c1cccc(-c2ncn(-c3ccccc3Br)n2)c1]
311
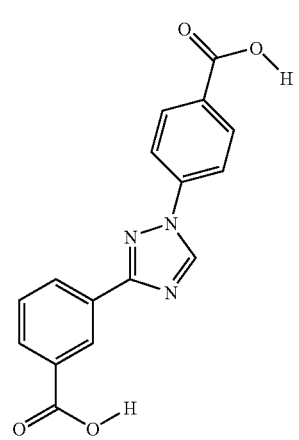 [SMILES: O=C(O)c1ccc(-n2cnc(-c3cccc(C(=O)O)c3)n2)cc1]
312
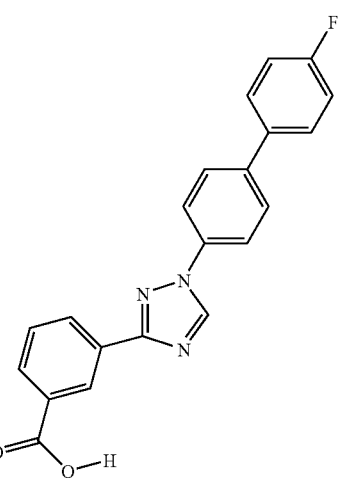
TABLE X-continued
Compound
313
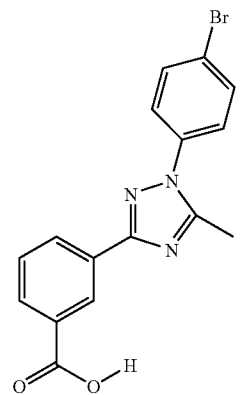 [SMILES: Cc1nc(-c2cccc(C(=O)O)c2)nn1-c1ccc(Br)cc1]
314
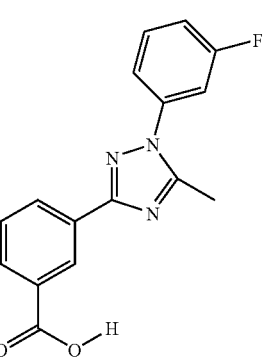
315
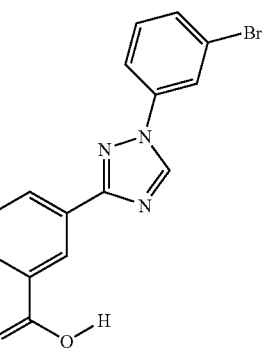
316
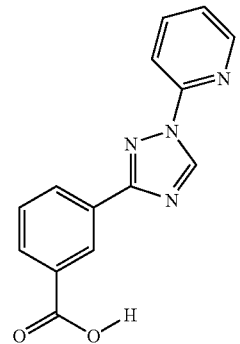 [SMILES: O=C(O)c1cccc(-c2ncn(-c3ccccn3)n2)c1]

TABLE X-continued
Compound
317
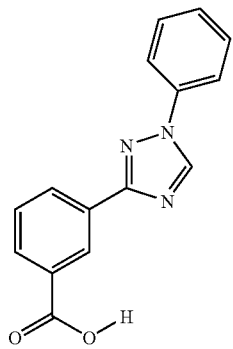 [SMILES: O=C(O)c1cccc(-c2ncn(-c3ccccc3)n2)c1]
318
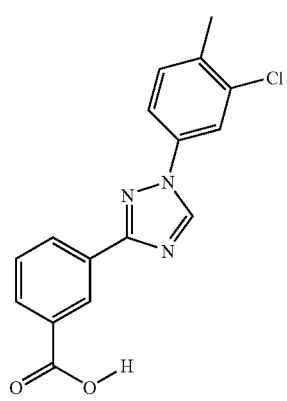 [SMILES: Cc1ccc(-n2cnc(-c3cccc(C(=O)O)c3)n2)cc1Cl]
319
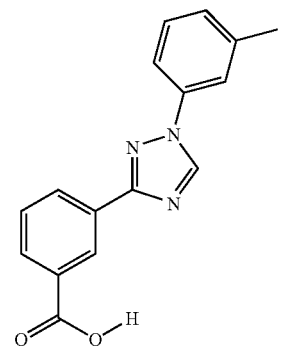 [SMILES: Cc1cccc(-n2cnc(-c3cccc(C(=O)O)c3)n2)c1]
320
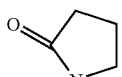
TABLE X-continued
Compound
321
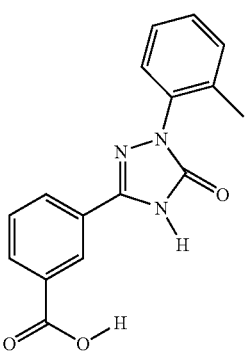 [SMILES: Cc1ccccc1-n1nc(-c2cccc(C(=O)O)c2)[nH]c1=O]
322
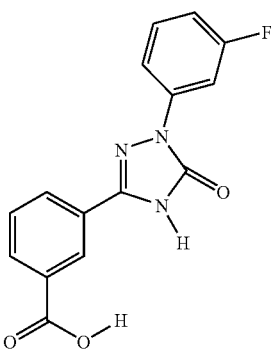 [SMILES: O=C(O)c1cccc(-c2nn(-c3cccc(F)c3)c(=O)[nH]2)c1]
323

TABLE X-continued
Compound
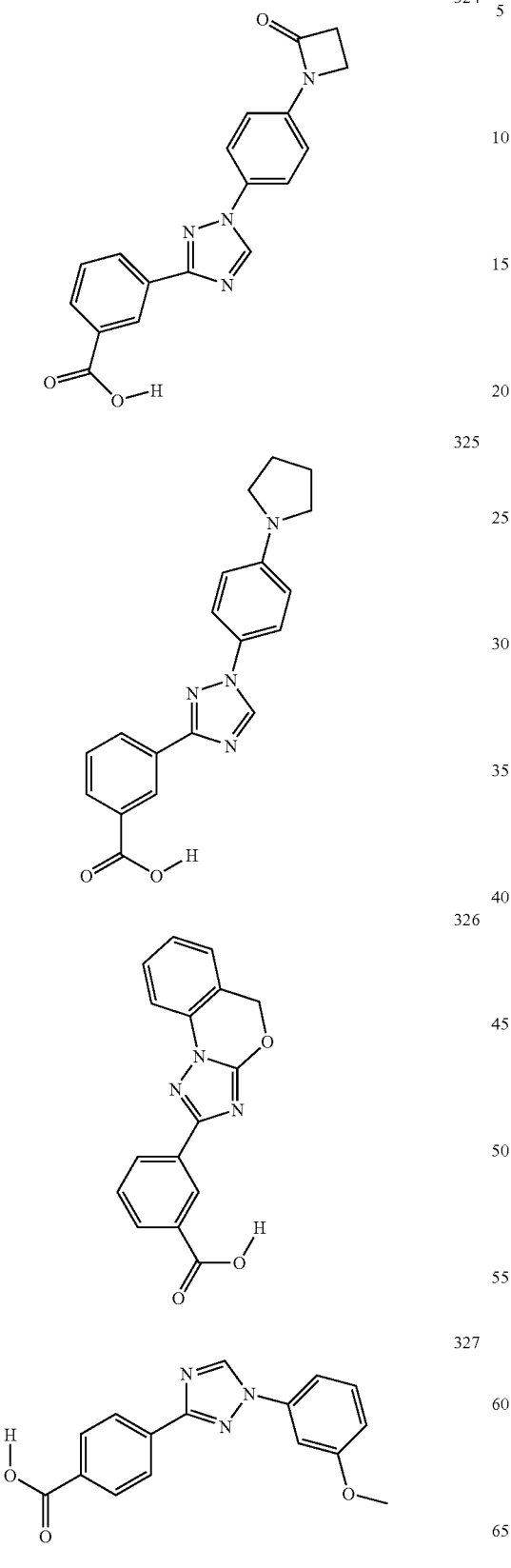
324
325
326
327
TABLE X-continued
Compound
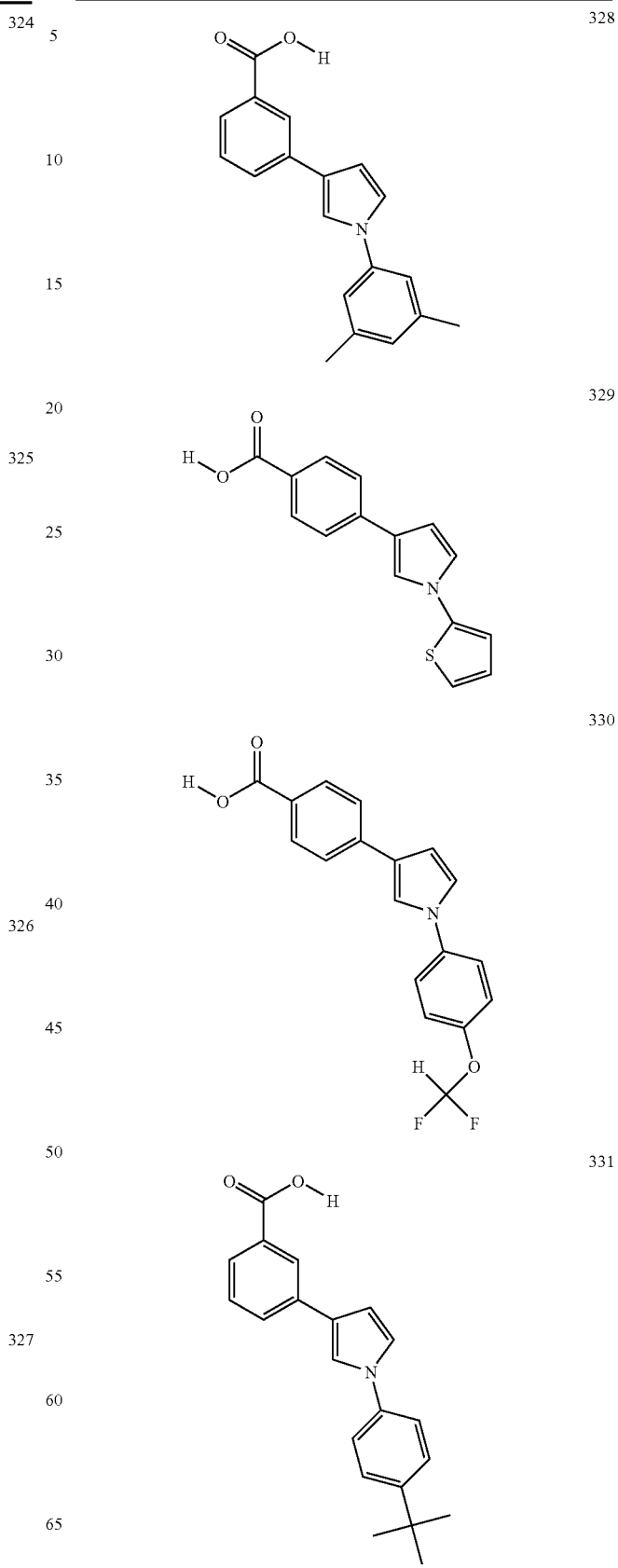
328
329
330
331

TABLE X-continued

Compound 332, 333, 334, 335, 336, 337, 338, 339, 340, 341, 342

TABLE X-continued
Compound
343
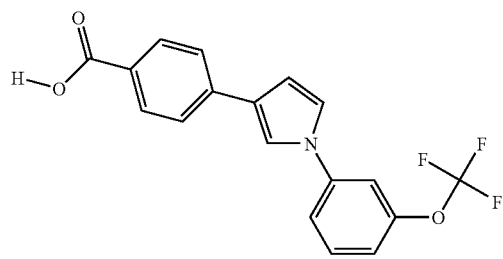 [SMILES: O=C(O)c1ccc(-c2ccn(-c3cccc(OC(F)(F)F)c3)c2)cc1]
344
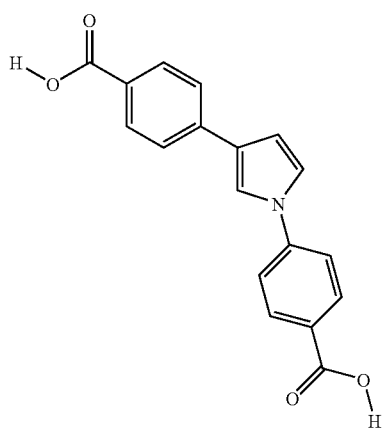 [SMILES: O=C(O)c1ccc(-c2ccn(-c3ccc(C(=O)O)cc3)c2)cc1]
345
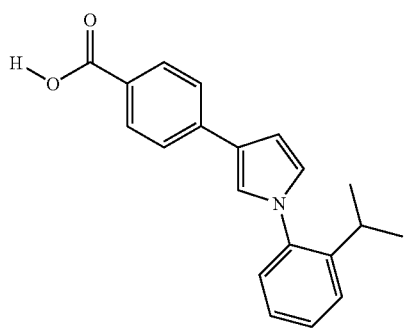 [SMILES: CC(C)c1ccccc1-n1ccc(-c2ccc(C(=O)O)cc2)c1]
346
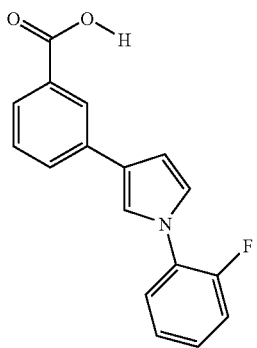 [SMILES: O=C(O)c1cccc(-c2ccn(-c3ccccc3F)c2)c1]
TABLE X-continued
Compound
347
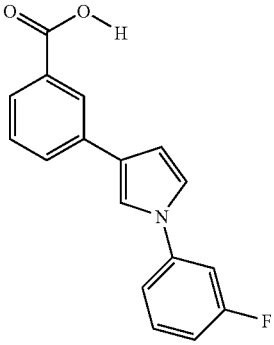 [SMILES: O=C(O)c1cccc(-c2ccn(-c3cccc(F)c3)c2)c1]
348
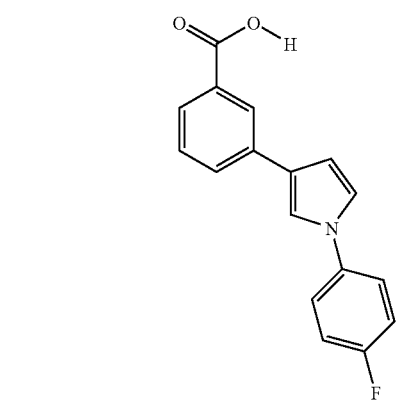 [SMILES: O=C(O)c1cccc(-c2ccn(-c3ccc(F)cc3)c2)c1]
349
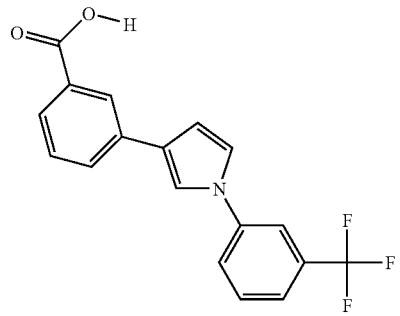 [SMILES: O=C(O)c1cccc(-c2ccn(-c3cccc(C(F)(F)F)c3)c2)c1]
350
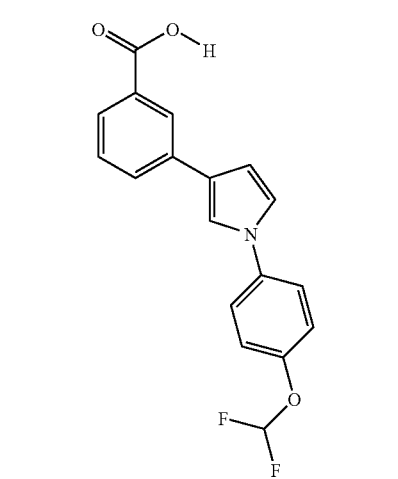 [SMILES: O=C(O)c1cccc(-c2ccn(-c3ccc(OC(F)F)cc3)c2)c1]

TABLE X-continued
Compound
351
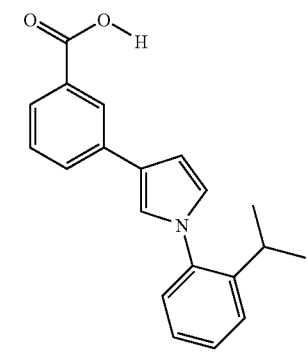 [SMILES: CC(C)c1ccccc1-n1ccc(-c2cccc(C(=O)O)c2)c1]
352
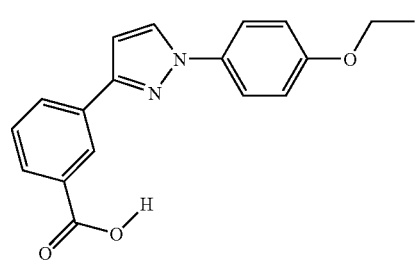 [SMILES: CCOc1ccc(-n2ccc(-c3cccc(C(=O)O)c3)n2)cc1]
353
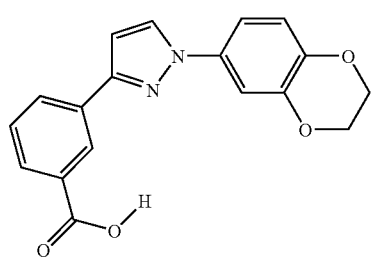 [SMILES: O=C(O)c1cccc(-c2ccn(-c3ccc4c(c3)OCCO4)n2)c1]
354
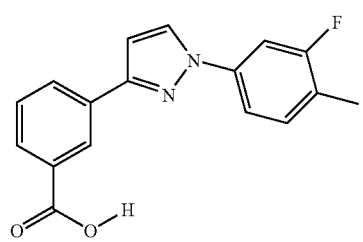 [SMILES: Cc1ccc(-n2ccc(-c3cccc(C(=O)O)c3)n2)cc1F]
355
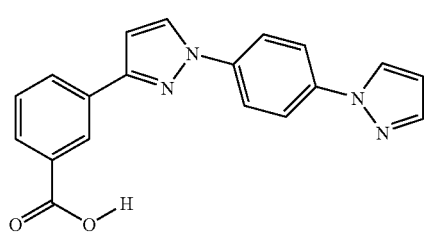 [SMILES: O=C(O)c1cccc(-c2ccn(-c3ccc(-n4cccn4)cc3)n2)c1]
TABLE X-continued
Compound
356
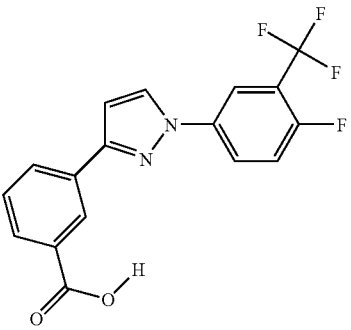 [SMILES: O=C(O)c1cccc(-c2ccn(-c3ccc(F)c(C(F)(F)F)c3)n2)c1]
357
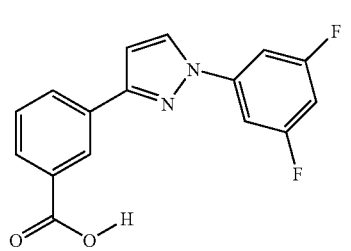 [SMILES: O=C(O)c1cccc(-c2ccn(-c3cc(F)cc(F)c3)n2)c1]
358
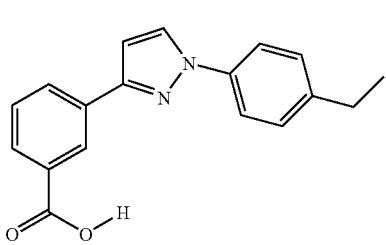
359
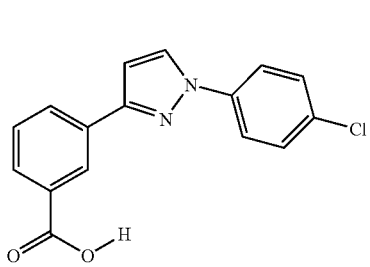 [SMILES: O=C(O)c1cccc(-c2ccn(-c3ccc(Cl)cc3)n2)c1]
360
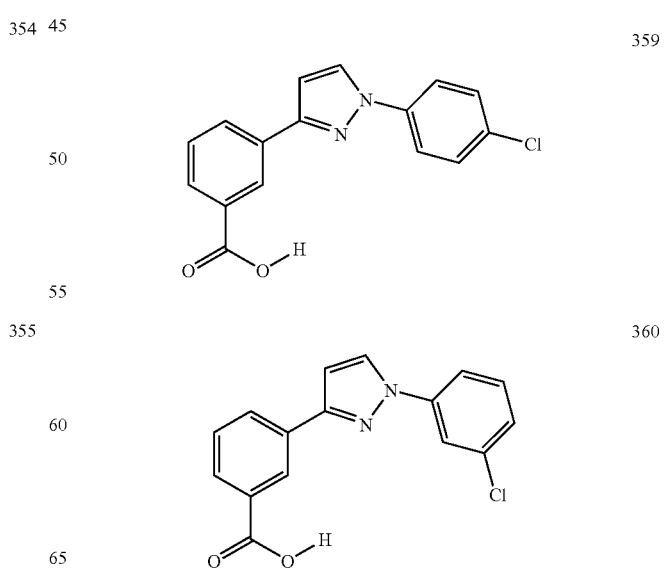

TABLE X-continued
Compound
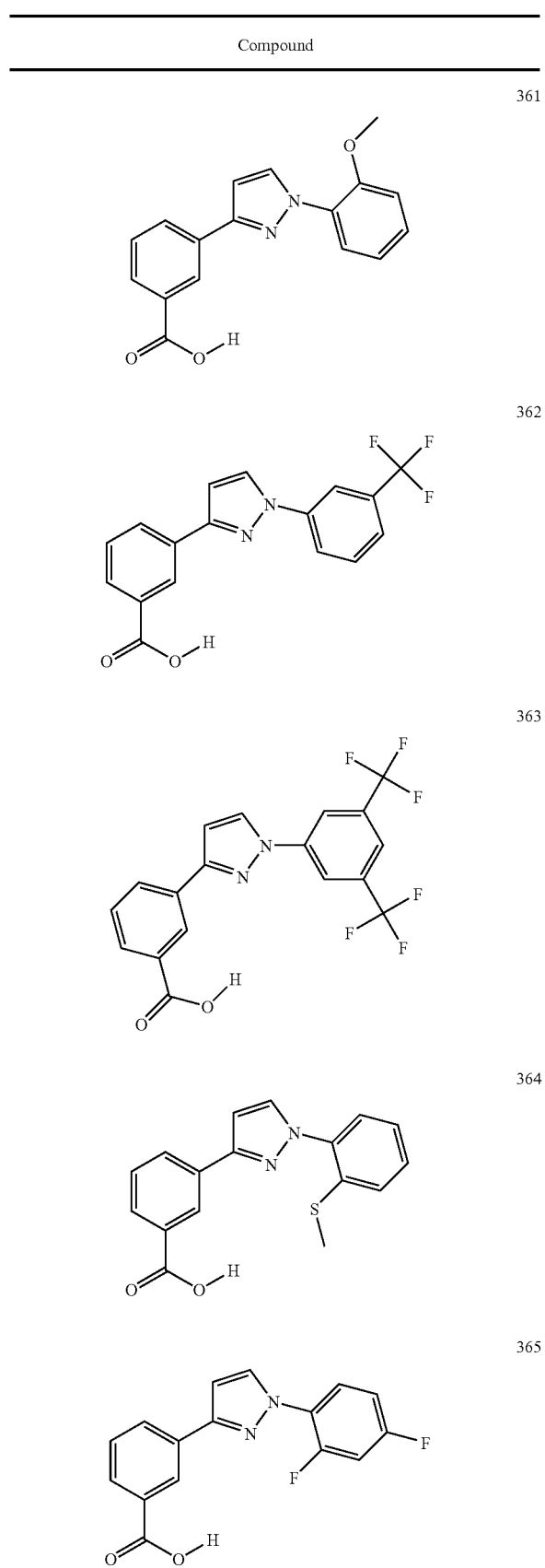
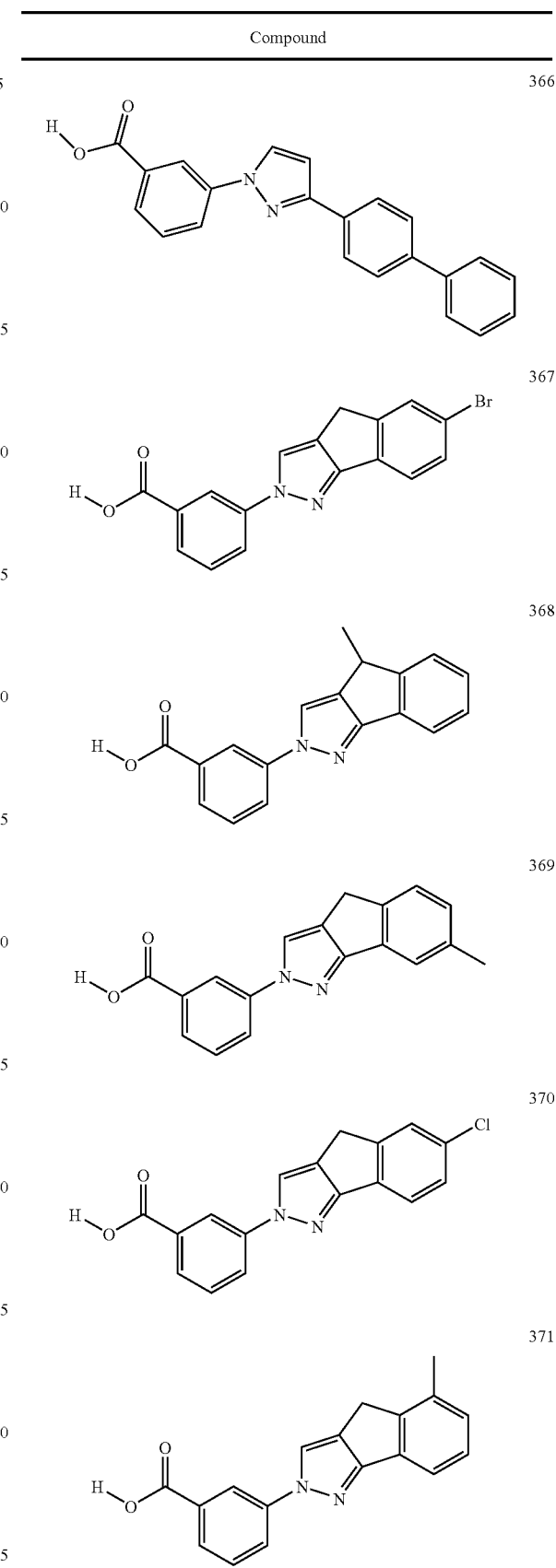

TABLE X-continued

Compound

372–384 (chemical structures)

TABLE X-continued
| Compound | |
|---|---|
| 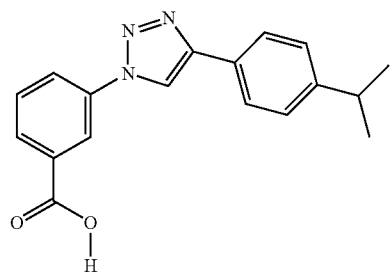 [SMILES: CC(C)c1ccc(-c2cn(-c3cccc(C(=O)O)c3)nn2)cc1] | 385 |
| 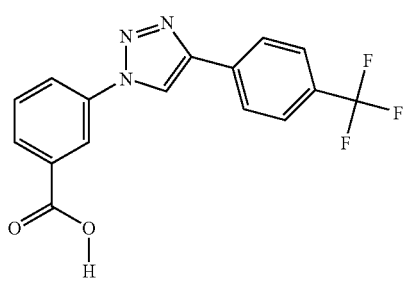 [SMILES: O=C(O)c1cccc(-n2cc(-c3ccc(C(F)(F)F)cc3)nn2)c1] | 386 |
| 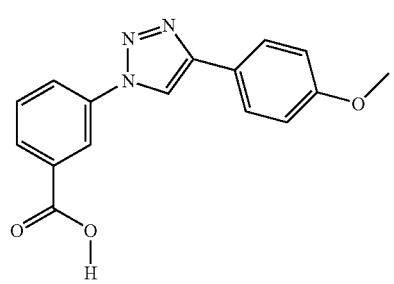 [SMILES: COc1ccc(-c2cn(-c3cccc(C(=O)O)c3)nn2)cc1] | 387 |
| 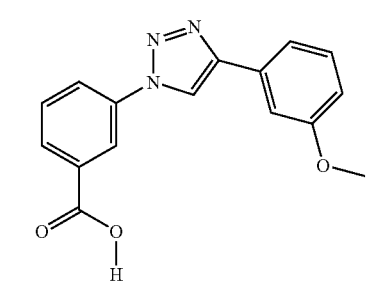 [SMILES: COc1cccc(-c2cn(-c3cccc(C(=O)O)c3)nn2)c1] | 388 |
| 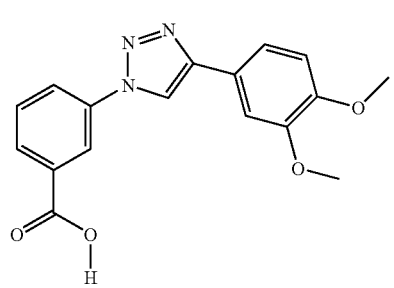 [SMILES: COc1ccc(-c2cn(-c3cccc(C(=O)O)c3)nn2)cc1OC] | 389 |
| 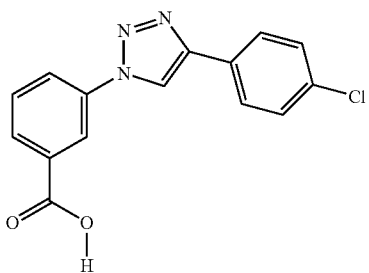 [SMILES: O=C(O)c1cccc(-n2cc(-c3ccc(Cl)cc3)nn2)c1] | 390 |
| 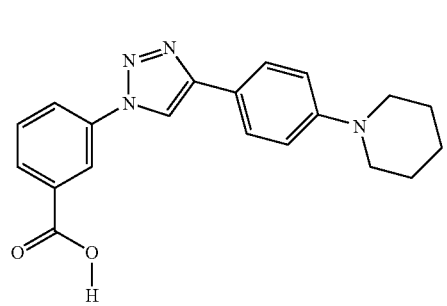 [SMILES: O=C(O)c1cccc(-n2cc(-c3ccc(N4CCCCC4)cc3)nn2)c1] | 391 |
| 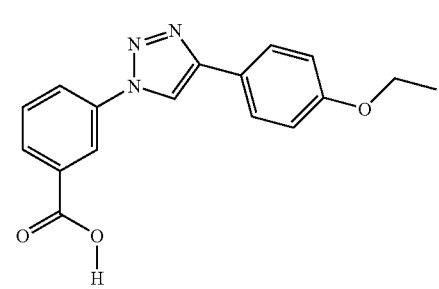 [SMILES: CCOc1ccc(-c2cn(-c3cccc(C(=O)O)c3)nn2)cc1] | 392 |
| 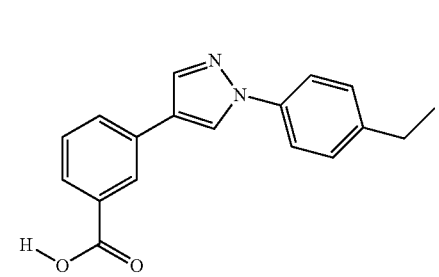 [SMILES: CCc1ccc(-n2cc(-c3cccc(C(=O)O)c3)cn2)cc1] | 393 |
| 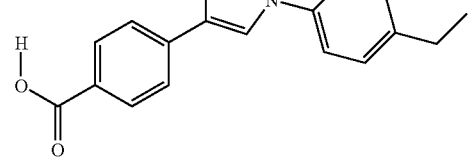 | 394 |

TABLE X-continued
| Compound | |
|---|---|
| 395 | 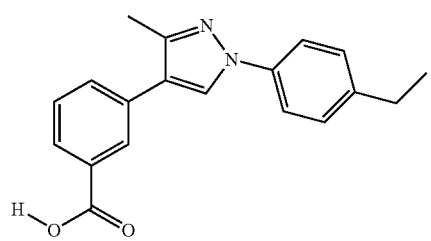 [SMILES: CCc1ccc(-n2cc(-c3cccc(C(=O)O)c3)c(C)n2)cc1] |
| 396 | 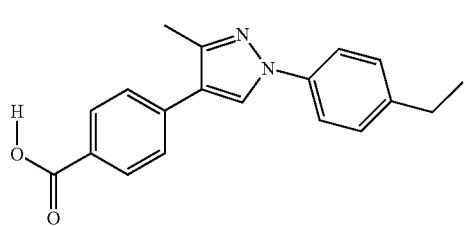 [SMILES: CCc1ccc(-n2cc(-c3ccc(C(=O)O)cc3)c(C)n2)cc1] |
| 397 | 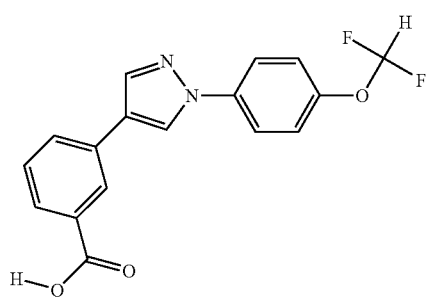 [SMILES: O=C(O)c1cccc(-c2cnn(-c3ccc(OC(F)F)cc3)c2)c1] |
| 398 | 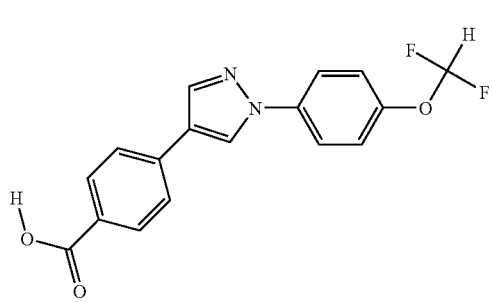 [SMILES: O=C(O)c1ccc(-c2cnn(-c3ccc(OC(F)F)cc3)c2)cc1] |
| 399 | 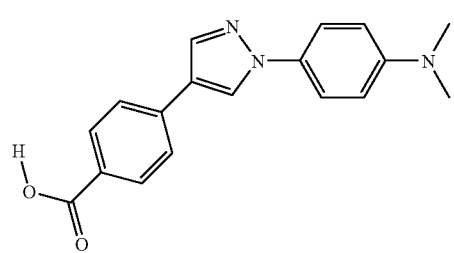 [SMILES: CN(C)c1ccc(-n2cc(-c3ccc(C(=O)O)cc3)cn2)cc1] |
| 400 | 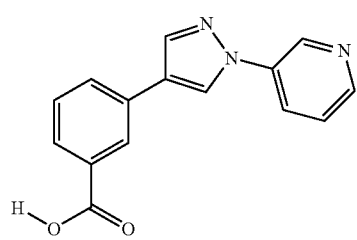 [SMILES: O=C(O)c1cccc(-c2cnn(-c3cccnc3)c2)c1] |
| 401 | 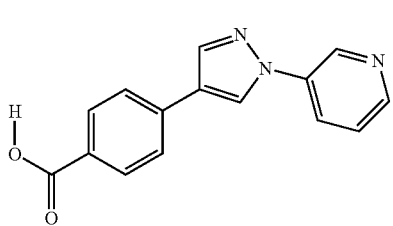 [SMILES: O=C(O)c1ccc(-c2cnn(-c3cccnc3)c2)cc1] |
| 402 | 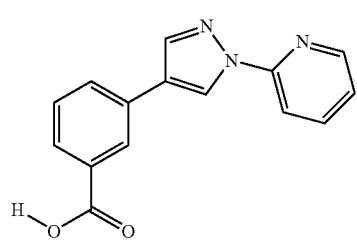 [SMILES: O=C(O)c1cccc(-c2cnn(-c3ccccn3)c2)c1] |
| 403 | 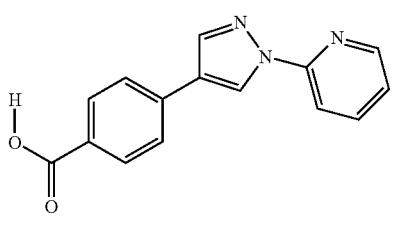 [SMILES: O=C(O)c1ccc(-c2cnn(-c3ccccn3)c2)cc1] |
| 404 | 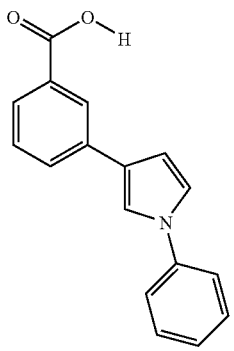 [SMILES: O=C(O)c1cccc(-c2ccn(-c3ccccc3)c2)c1] |

TABLE X-continued
Compound
405
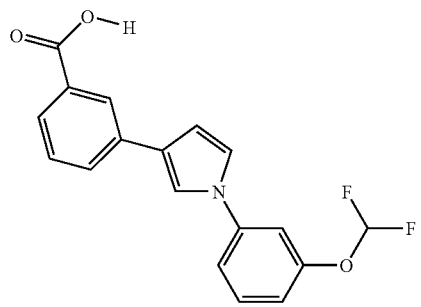 [SMILES: O=C(O)c1cccc(-c2ccn(-c3cccc(OC(F)F)c3)c2)c1]
406
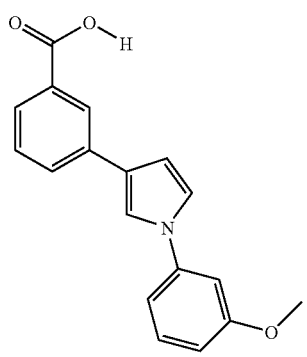 [SMILES: COc1cccc(-n2ccc(-c3cccc(C(=O)O)c3)c2)c1]
407
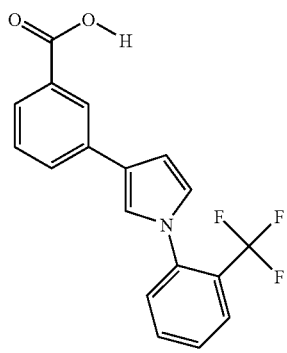 [SMILES: O=C(O)c1cccc(-c2ccn(-c3ccccc3C(F)(F)F)c2)c1]
408
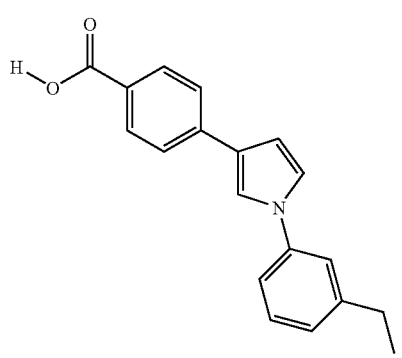 [SMILES: CCc1cccc(-n2ccc(-c3ccc(C(=O)O)cc3)c2)c1]
TABLE X-continued
Compound
409
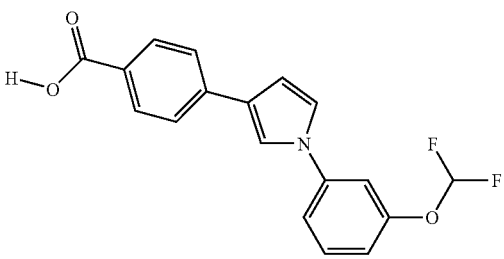 [SMILES: O=C(O)c1ccc(-c2ccn(-c3cccc(OC(F)F)c3)c2)cc1]
410
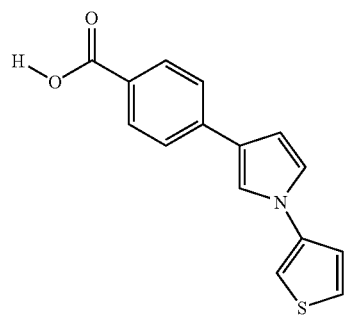 [SMILES: O=C(O)c1ccc(-c2ccn(-c3ccsc3)c2)cc1]
411
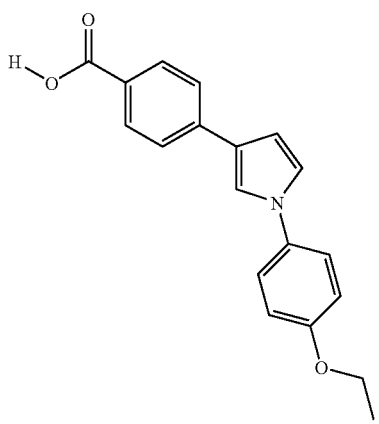 [SMILES: CCOc1ccc(-n2ccc(-c3ccc(C(=O)O)cc3)c2)cc1]
412
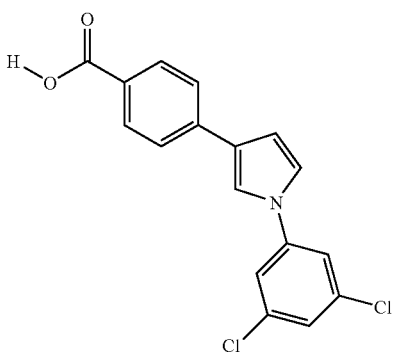 [SMILES: O=C(O)c1ccc(-c2ccn(-c3cc(Cl)cc(Cl)c3)c2)cc1]

TABLE X-continued
| Compound | |
|---|---|
| 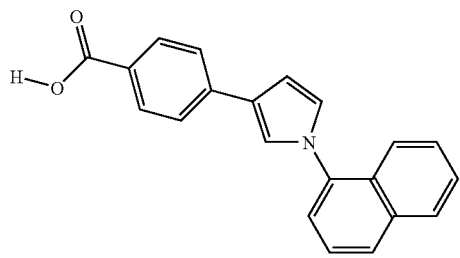 [SMILES: O=C(O)c1ccc(-c2ccn(-c3cccc4ccccc34)c2)cc1] | 413 |
| 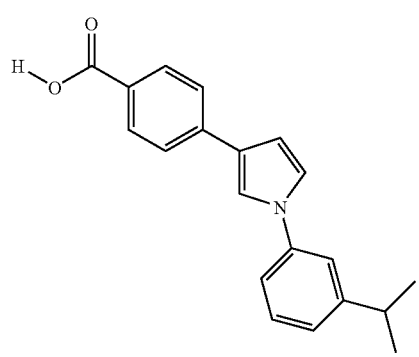 [SMILES: CC(C)c1cccc(-n2ccc(-c3ccc(C(=O)O)cc3)c2)c1] | 414 |
| 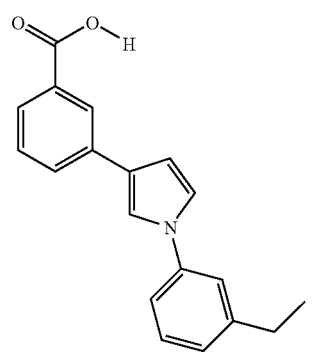 [SMILES: CCc1cccc(-n2ccc(-c3cccc(C(=O)O)c3)c2)c1] | 415 |
| 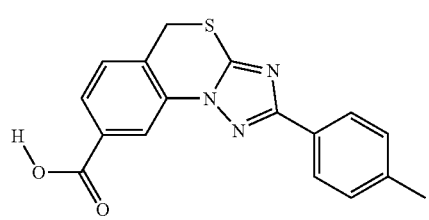 [SMILES: Cc1ccc(-c2nc3n(n2)-c2cc(C(=O)O)ccc2CS3)cc1] | 416 |
| 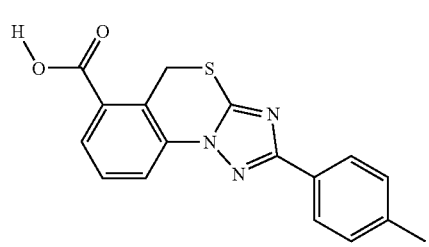 [SMILES: Cc1ccc(-c2nc3n(n2)-c2cccc(C(=O)O)c2CS3)cc1] | 417 |
TABLE X-continued
| Compound | |
|---|---|
| 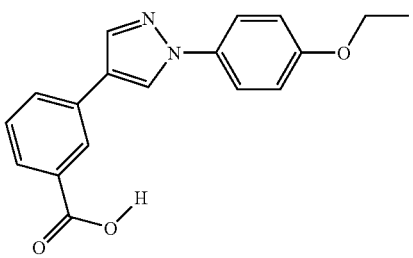 [SMILES: CCOc1ccc(-n2cc(-c3cccc(C(=O)O)c3)cn2)cc1] | 418 |
| 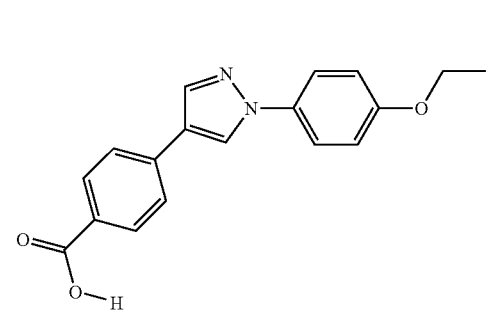 [SMILES: CCOc1ccc(-n2cc(-c3ccc(C(=O)O)cc3)cn2)cc1] | 419 |
| 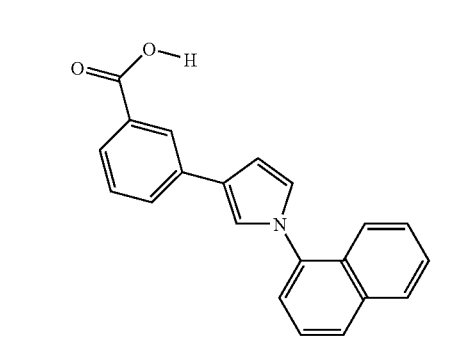 [SMILES: O=C(O)c1cccc(-c2ccn(-c3cccc4ccccc34)c2)c1] | 420 |
|  | 421 |

TABLE X-continued
Compound
422
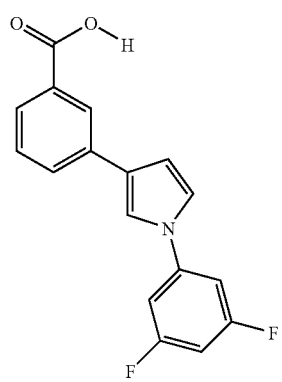 [SMILES: O=C(O)c1cccc(-c2ccn(-c3cc(F)cc(F)c3)c2)c1]
423
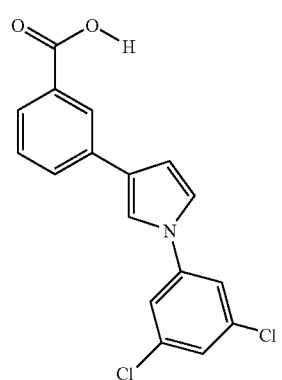 [SMILES: O=C(O)c1cccc(-c2ccn(-c3cc(Cl)cc(Cl)c3)c2)c1]
424
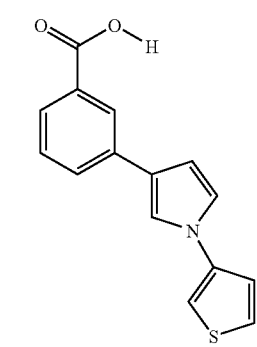 [SMILES: O=C(O)c1cccc(-c2ccn(-c3ccsc3)c2)c1]
425
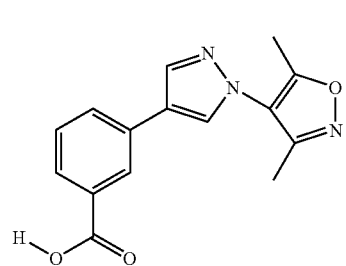 [SMILES: Cc1noc(C)c1-n1cc(-c2cccc(C(=O)O)c2)cn1]
426
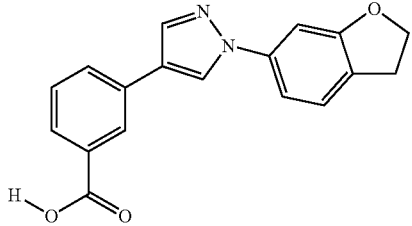 [SMILES: O=C(O)c1cccc(-c2cnn(-c3ccc4c(c3)OCC4)c2)c1]
427
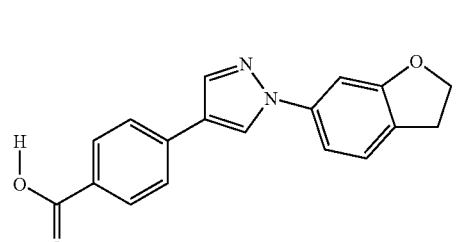
428
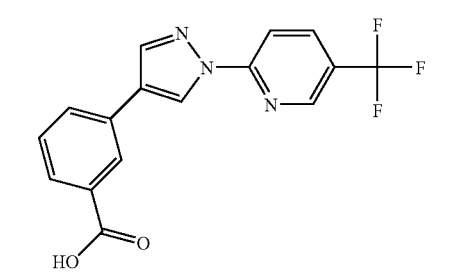 [SMILES: O=C(O)c1cccc(-c2cnn(-c3ccc(C(F)(F)F)cn3)c2)c1]
429
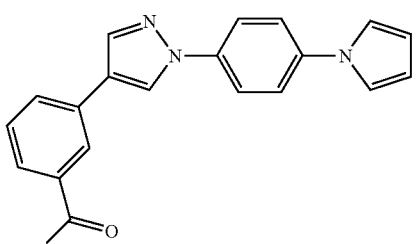
430
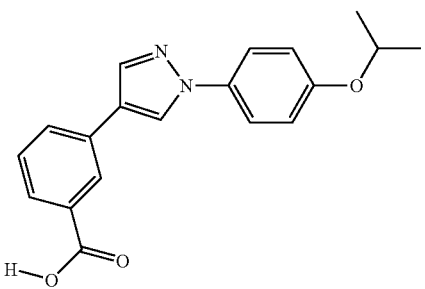 [SMILES: CC(C)Oc1ccc(-n2cc(-c3cccc(C(=O)O)c3)cn2)cc1]

TABLE X-continued
Compound
431 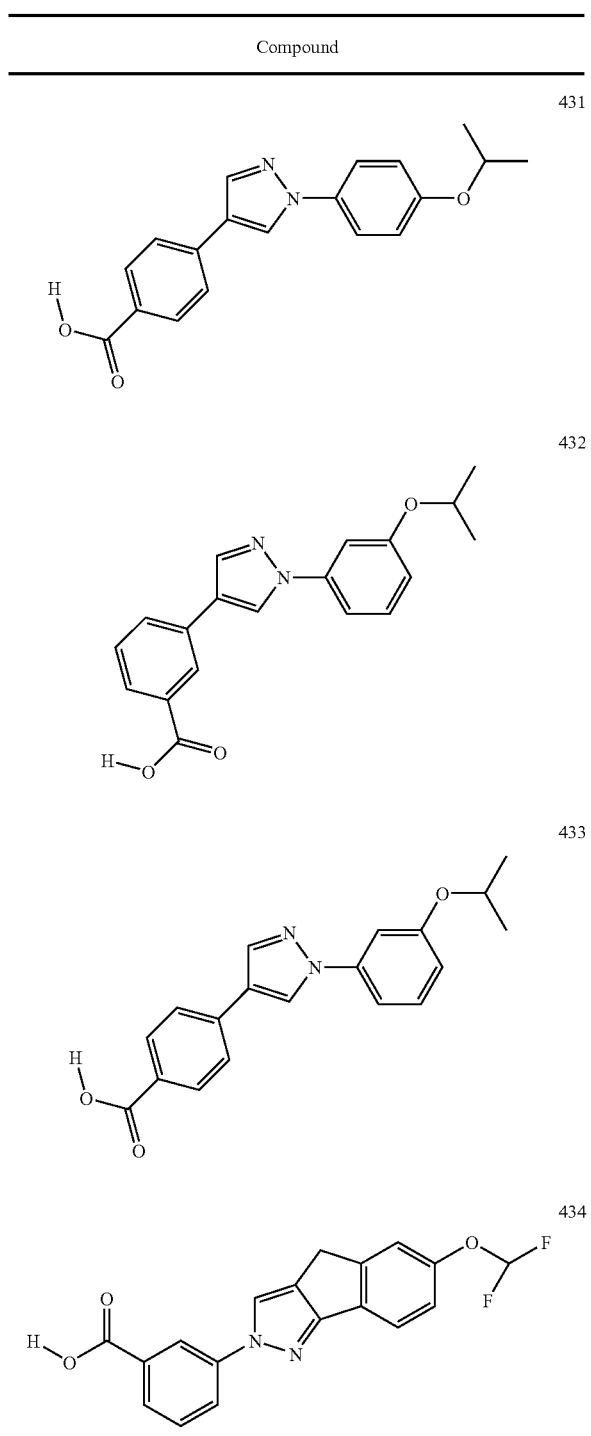
432
433
434
435
436 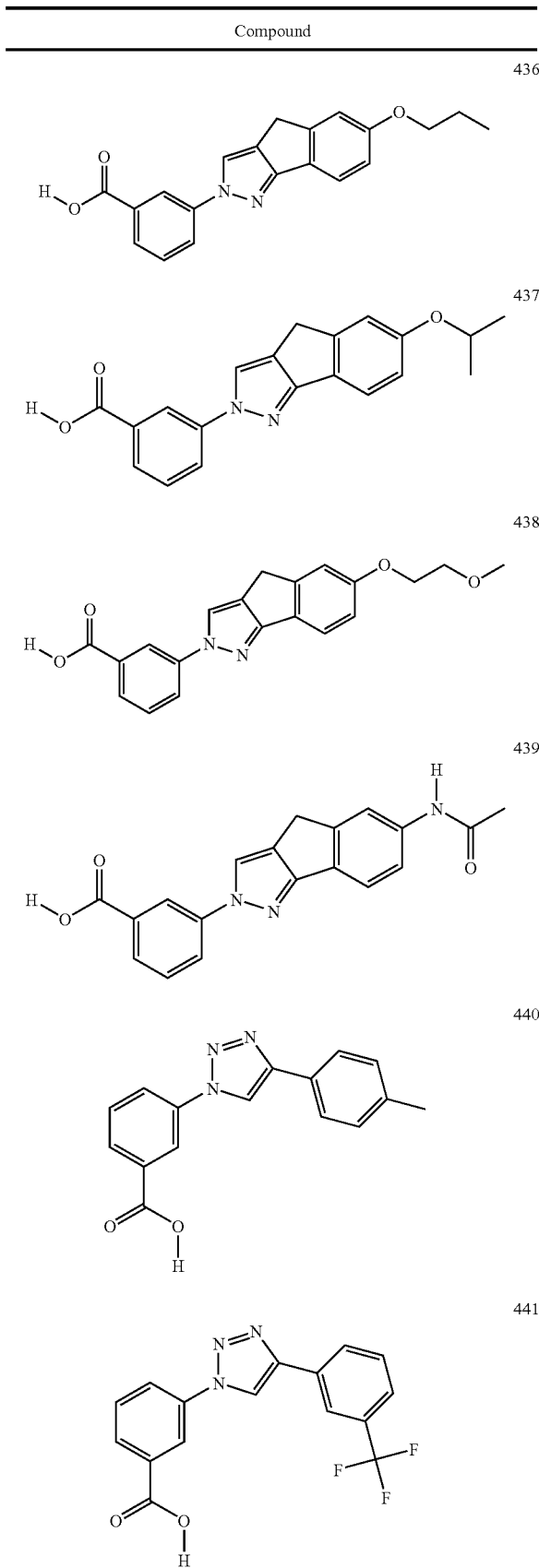
437
438
439
440
441

TABLE X-continued
Compound
442
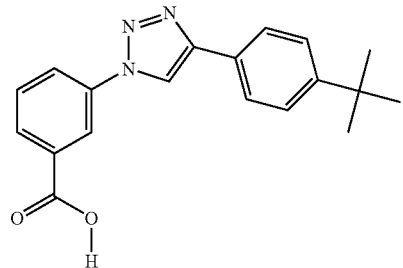 [SMILES: CC(C)(C)c1ccc(-c2cn(-c3cccc(C(=O)O)c3)nn2)cc1]
443
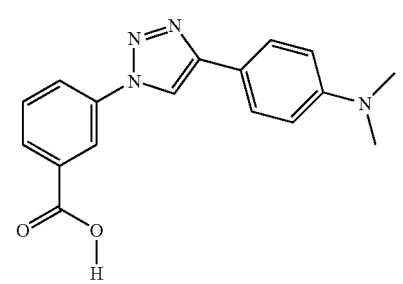 [SMILES: CN(C)c1ccc(-c2cn(-c3cccc(C(=O)O)c3)nn2)cc1]
444
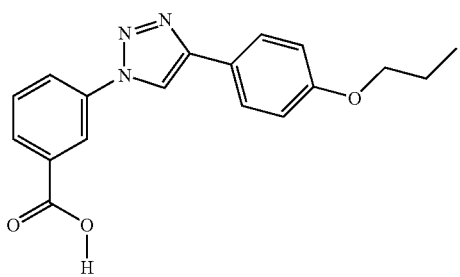 [SMILES: CCCOc1ccc(-c2cn(-c3cccc(C(=O)O)c3)nn2)cc1]
445
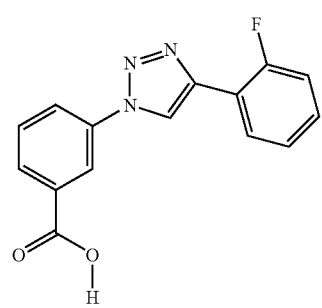 [SMILES: O=C(O)c1cccc(-n2cc(-c3ccccc3F)nn2)c1]
446
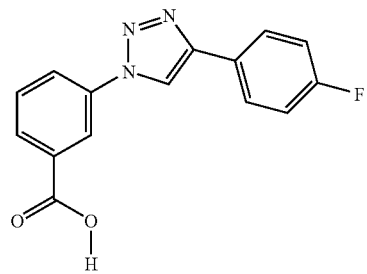 [SMILES: O=C(O)c1cccc(-n2cc(-c3ccc(F)cc3)nn2)c1]
TABLE X-continued
Compound
447
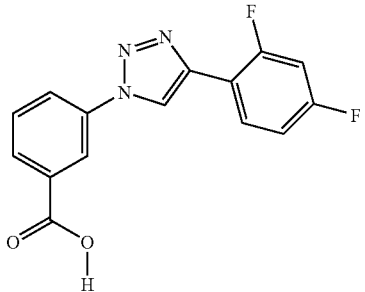 [SMILES: O=C(O)c1cccc(-n2cc(-c3ccc(F)cc3F)nn2)c1]
448
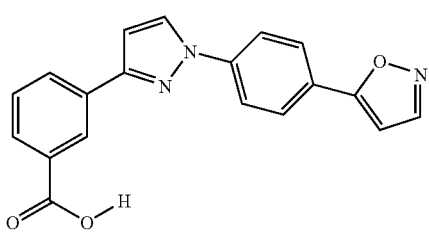 [SMILES: O=C(O)c1cccc(-c2ccn(-c3ccc(-c4ccno4)cc3)n2)c1]
449
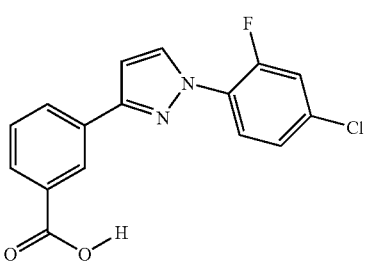 [SMILES: O=C(O)c1cccc(-c2ccn(-c3ccc(Cl)cc3F)n2)c1]
450
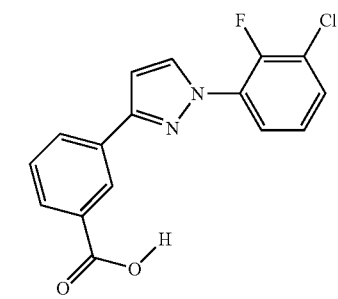 [SMILES: O=C(O)c1cccc(-c2ccn(-c3cccc(Cl)c3F)n2)c1]
451
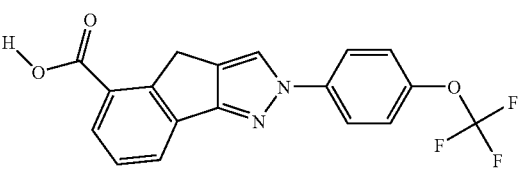 [SMILES: O=C(O)c1cccc2c1Cc1cn(-c3ccc(OC(F)(F)F)cc3)nc1-2]
452
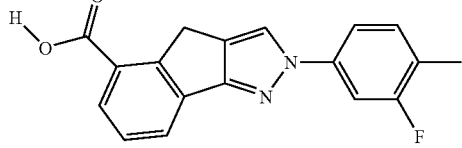

US 9,051,342 B2
TABLE X-continued
Compound
453
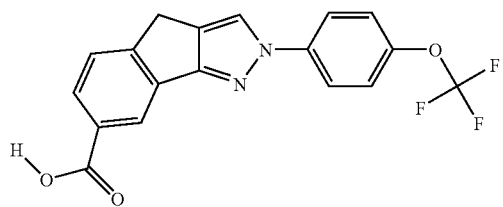 [SMILES: O=C(O)c1ccc2c(c1)-c1nn(-c3ccc(OC(F)(F)F)cc3)cc1C2]
454
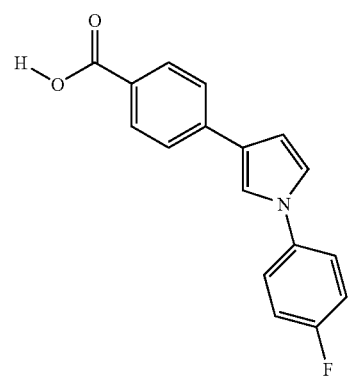 [SMILES: O=C(O)c1ccc(-c2ccn(-c3ccc(F)cc3)c2)cc1]
455
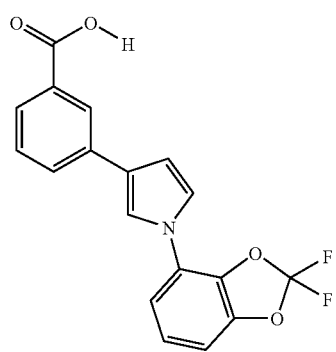 [SMILES: O=C(O)c1cccc(-c2ccn(-c3cccc4c3OC(F)(F)O4)c2)c1]
456
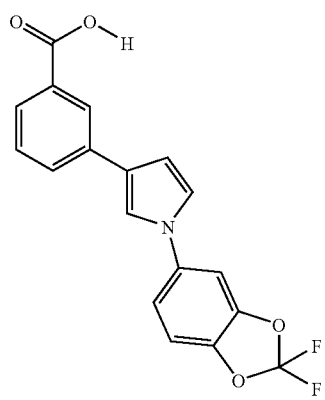 [SMILES: O=C(O)c1cccc(-c2ccn(-c3ccc4c(c3)OC(F)(F)O4)c2)c1]
457
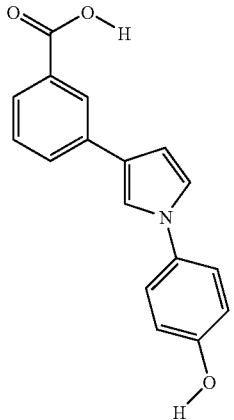 [SMILES: O=C(O)c1cccc(-c2ccn(-c3ccc(O)cc3)c2)c1]
458
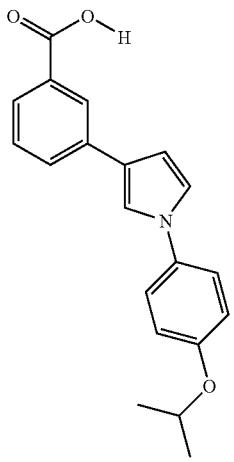 [SMILES: CC(C)Oc1ccc(-n2ccc(-c3cccc(C(=O)O)c3)c2)cc1]
459
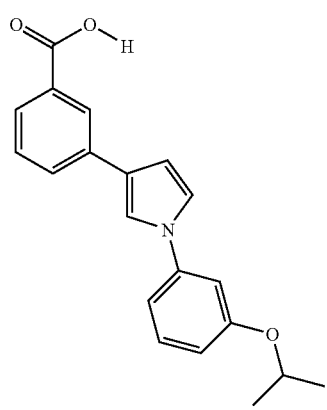 [SMILES: CC(C)Oc1cccc(-n2ccc(-c3cccc(C(=O)O)c3)c2)c1]
460
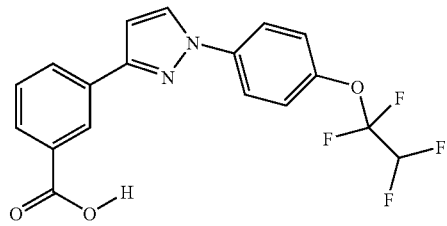 [SMILES: O=C(O)c1cccc(-c2ccn(-c3ccc(OC(F)(F)C(F)F)cc3)n2)c1]

TABLE X-continued

| Compound | |
|---|---|
| 461 | (structure) |
| 462 | (structure) |
| 463 | (structure) |
| 464 | (structure) |
| 465 | (structure) |
| 466 | (structure) |
| 467 | (structure) |
| 468 | (structure) |

TABLE X-continued

Compound

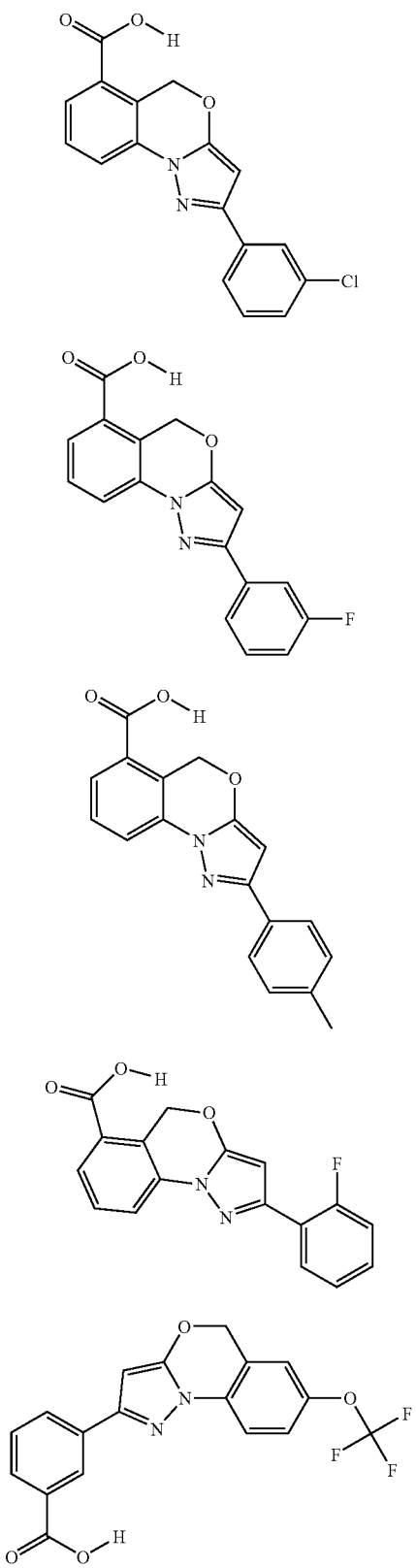

As illustrated in Table X: As used herein, Compound 12 is the same structure as Compound 292. As used herein, Compound 13 is the same structure as Compound 293. As used herein, Compound 14 is the same structure as Compound 294. As used herein, Compound 15 is the same structure as Compound 295. As used herein, Compound 16 is the same structure as Compound 296. As used herein, Compound 17 is the same structure as Compound 297. As used herein, Compound 18 is the same structure as Compound 298. As used herein, Compound 19 is the same structure as Compound 299. As used herein, Compound 20 is the same structure as Compound 300. As used herein, Compound 21 is the same structure as Compound 301. As used herein, Compound 22 is the same structure as Compound 302. As used herein, Compound 23 is the same structure as Compound 303, As used herein, Compound 24 is the same structure as Compound 304. As used herein, Compound 25 is the same structure as Compound 305. As used herein, Compound 26 is the same structure as Compound 306. As used herein, Compound 27 is the same structure as Compound 307. As used herein, Compound 28 is the same structure as Compound 308. As used herein, Compound 29 is the same structure as Compound 309. As used herein, Compound 30 is the same structure as Compound 310. As used herein, Compound 31 is the same structure as Compound 311. As used herein, Compound 32 is the same structure as Compound 312. As used herein, Compound 33 is the same structure as Compound 313. As used herein, Compound 34 is the same structure as Compound 314. As used herein, Compound 35 is the same structure as Compound 315. As used herein, Compound 36 is the same structure as Compound 316. As used herein, Compound 37 is the same structure as Compound 317. As used herein, Compound 38 is the same structure as Compound 318. As used herein, Compound 39 is the same structure as Compound 319. As used herein, Compound 40 is the same structure as Compound 320. As used herein, Compound 41 is the same structure as Compound 321. As used herein, Compound 42 is the same structure as Compound 322. As used herein, Compound 43 is the same structure as Compound 323. As used herein, Compound 44 is the same structure as Compound 324. As used herein, Compound 45 is the same structure as Compound 325. As used herein, Compound 46 is the same structure as Compound 326.

Particularly preferred compounds are Compound NOs: 47, 48, 66, 76, 81, 87, 105, 106, 109, 110, 133, 138, 139, 140, 146, 148, 154, 157, 167, 174, 177, 186, 196, 204. The above compounds are listed only to provide examples that may be used in the methods of the invention. Based upon the instant disclosure, the skilled artisan would recognize other compounds intended to be included within the scope of the presently claimed invention that would be useful in the methods recited herein.

B. Preparation of Compounds of the Invention

Compounds of the invention may be produced in any manner known in the art. By way of example, compounds of the invention may be prepared according to the following general schemes with reference to the individual azine ring core structures. For example, compounds of Formula 1 wherein V is N can be prepared by the method shown in Scheme A.

Scheme A

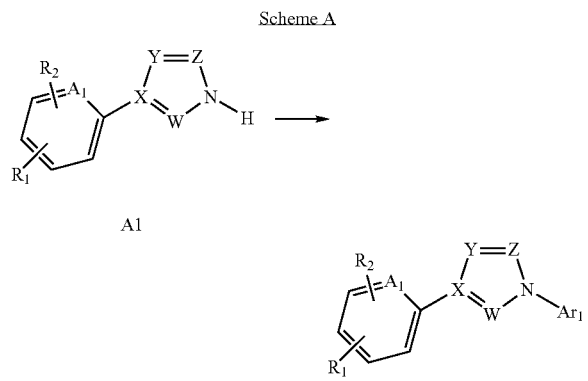

In accordance with Scheme A, an unsubstituted nitrogen atom on the azole ring of compound A1 can be substituted in a cross-coupling reaction. This type of reaction may be accomplished with the use of substrates such as $Ar_1$—X (where X is a halogen like bromide or iodide, or a pseudohalide such as methanesulfonate) or $Ar_1$-M (where M is a group such as a boronic acid or trialkoxysilane). Catalysts for the reaction may include copper salts (such as copper (II) oxide, copper (II) acetate, etc.), palladium salts (such as palladium (II) acetate, tetrakistriphenylphosphine palladium, etc.), and other catalytic transition metal salts with catalytic properties. One specific example of such a cross-coupling reaction comes from the reports of Buchwald, et al., *J. Am. Chem. Soc.* 2001, 123, 7727, which involves the reaction of aryl bromides or iodides with azoles catalyzed by the presence of copper iodide with a diamine ligand, also in the presence of an appropriate base such as potassium phosphate or potassium carbonate, usually in a higher-boiling solvent such as 1,4-dioxane, dimethoxyethane, toluene, etc. Another specific example of an azole cross-coupling reaction is the method of Lam, et al., *Tetrahedron Lett.* 2001, 42, 3415. This method involves the reaction of an azole compound such as A1 with an arylboronic acid reagent in the presence of copper (II) acetate, an amine reagent (such as pyridine, triethylamine, etc.) and molecular sieves. Such cross-coupling reactions useful for the synthesis of the compounds in this invention are not limited to these two specific examples.

Certain functional groups may be carried through the syntheses described in this invention in protected form, then liberated in a later step. Protecting group strategy is well-known to those skilled in the art of organic synthesis, and is reviewed in such texts as Greene, *Protective Groups in Organic Synthesis*, John Wiley and Sons, New York. For example, carboxylic acids may be carried through various organic syntheses as a carboxylic ester compound, then cleaved at an appropriate point to the carboxylic acid. The cleavage reaction may involve the reaction with hydroxide (sodium hydroxide, lithium hydroxide, etc.) in appropriate solvents (water, ethanol, tetrahydrofuran or mixtures thereof) at temperatures ranging from ambient to the reflux point of the solvent. Alternatively, some ester groups may be cleaved by nucleophilic reagents (lithium iodide, lithium thiophenylate, etc.) in solvents such as pyridine, dimethylsulfoxide or dimethylformamide. Another group which is a convenient masked form of a carboxylate group is cyano. An aryl nitrile compound may be hydrolyzed under acidic (e.g., concentrated hydrochloric acid or dry hydrogen chloride gas, followed by alcoholysis/hydrolysis) or basic (e.g., sodium hydroxide) conditions.

Traditional heterocyclic syntheses may be employed for the various embodiments of Formula 1. For example, with reference to compounds comprising a central pyrrole ring, the acylation methodology discussed above can be employed for a pyrrole compound of formula B1 (Scheme B).

Scheme B

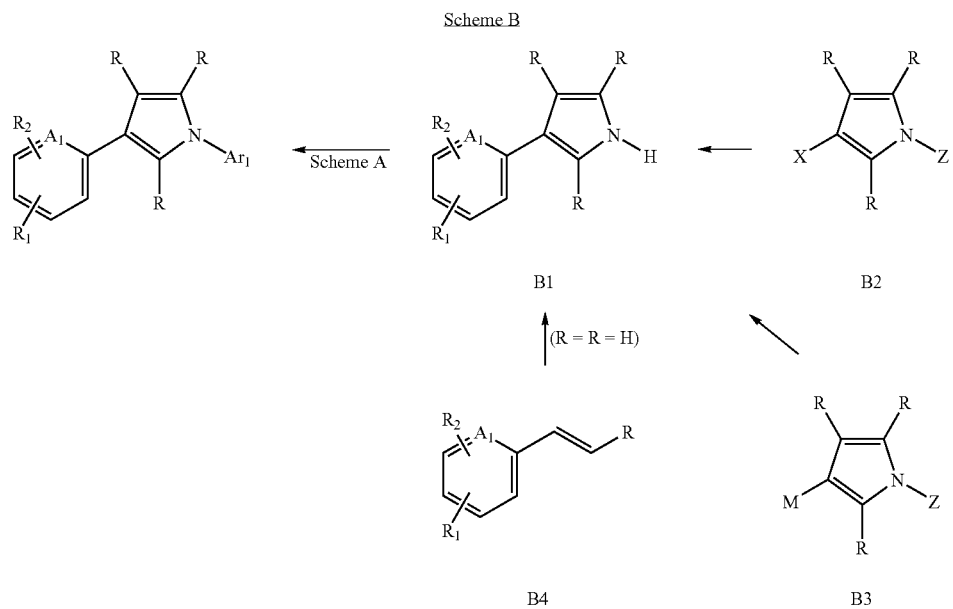

In accordance with Scheme B, compound B1 may be prepared by one of two routes. The first involves the cross-coupling of a compound of formula B2, where X represents a halogen or pseudohalogen group and Z represents either a hydrogen atom or a protecting group. Suitable protecting groups include but are not limited to tert-butoxycarbonyl, trityl, triisopropylsilyl, etc. The other cross-coupling component consists of a reagent Ar-M, where M represents a metal or other atom which will undergo the cross-coupling reaction, and may be chosen from the list consisting of Mg, Zn, B or Si, the atoms listed here also bonded to various other groups as fitting the valence of the selected M atom. The cross-coupling reaction may be performed in the presence of a catalyst. Suitable catalysts include various compounds containing Pd, Cu, or Ni. After the coupling reaction, the arylated product may be deprotected by removing the Z group to form B1. Deprotection conditions will depend on the chosen Z group and are familiar to those skilled in the art of organic synthesis. A variation of this first approach begins with a pyrrole reagent bearing the M group (B3), and the cross-coupling is performed as described above with a reagent of the formula Ar—X. One method which uses this route has the M group as $B(OH)_2$ and X as Br or I; the catalyst of choice for this reaction is a Pd(0) compound (such as $Pd(PPh_3)_4$) or a Pd(II) compound (such as $Pd(PPh_3)_2Cl_2$ or $Pd(OAc)_2$), and a base such as $Na_2CO_3$ or CsF is present. A third synthesis of the compound of formula B1 begins with an olefinic compound of formula B4. This is treated with the reagent toluenesulfonylmethyl isocyanide (TosMIC) under basic conditions. The resulting product is the version of compound B1 where R and R are both hydrogen atoms. Compound B1 is then subjected to the arylation methodology discussed above for Scheme A.

For compounds of Formula 1 comprised of a central pyrazole ring, the arylation methodology discussed above can be employed for a pyrazole compound of formula C1 (Scheme C).

In accordance with Scheme C, compound C1 can be derived from either a vinylogous amide compound of formula C2 or a dicarbonyl compound of formula C4. Either substrate can be treated with hydrazine hydrate in a protic solvent such as ethanol or acetic acid, optionally in the presence of an acid catalyst such as hydrochloric acid. The reactions are typically performed at elevated temperatures. The vinylogous amide compound of formula C2 may be prepared by the condensation of a ketone compound of formula C3 with an acetal of an amide. This reaction is typically performed with one or greater equivalents of the acetal reagent neat or in an appropriate solvent at the reflux temperature of the solvent. Diketone reagents of the formula C4 may be prepared by the condensation of an aroyl ester of formula C5 with a ketone of formula C6. This condensation reaction is usually performed under basic conditions (for example, sodium hydride) in various solvents, or the enolate anion of C6 can first be generated under strong base conditions (e.g., lithium diisopropylamide, low temperatures, aprotic solvents) and the ester C5 is subsequently added.

For the variation of the pyrazole class of compounds where there is one of the aryl groups attached at the 4-position of the pyrazole ring, the arylation methodology discussed above can be employed for a compound for a formula D1 (Scheme D).

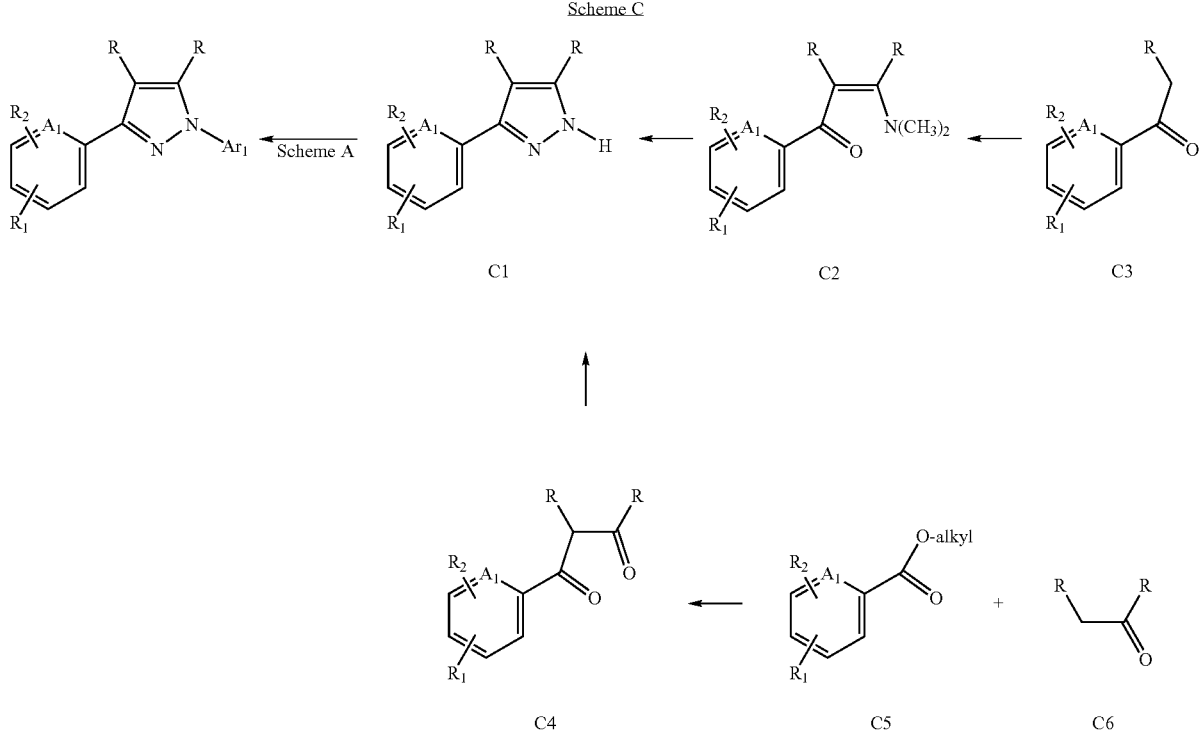

Scheme C

Scheme D

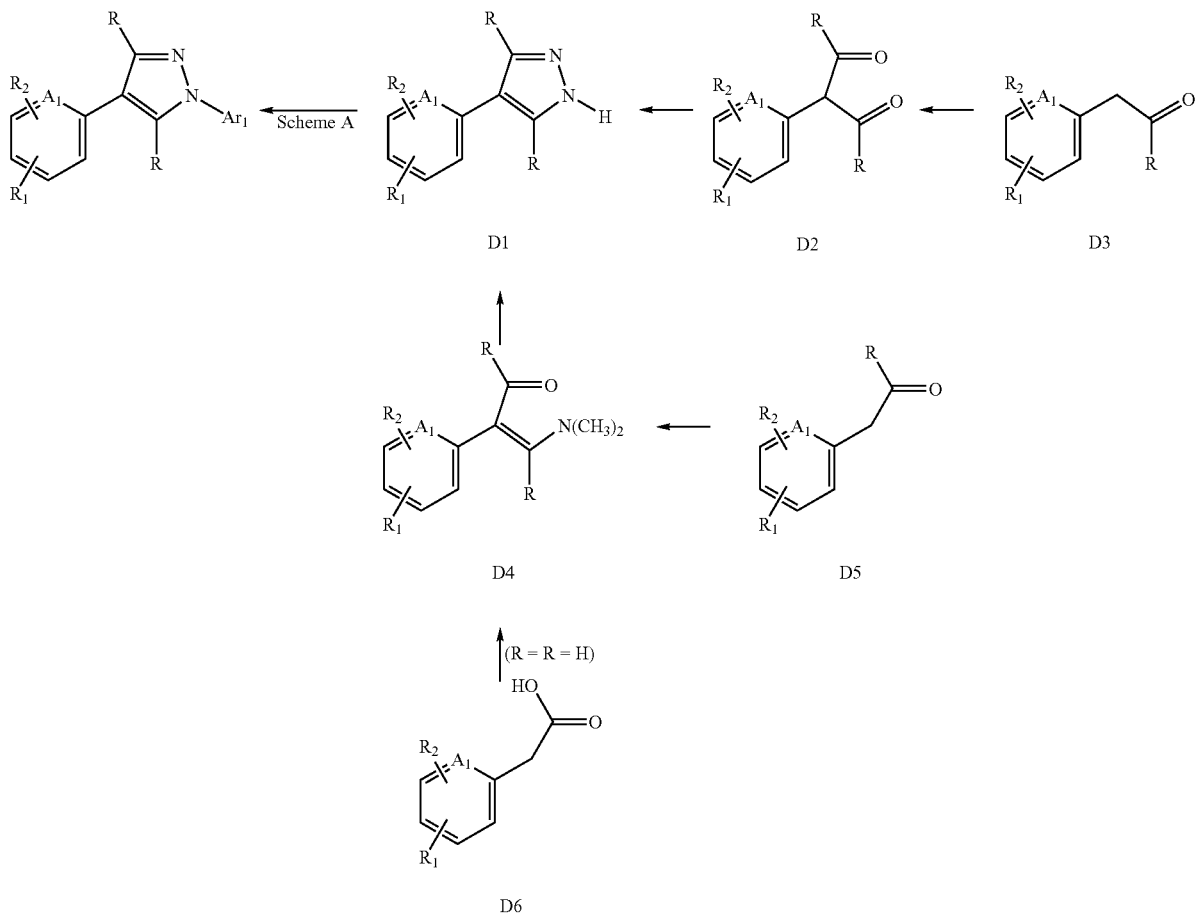

In accordance with Scheme D, as above, the N-unsubstituted pyrazole can be formed by the cyclocondensation reaction of hydrazine with either a dicarbonyl compound of formula D2 or a vinylogous amide compound of formula D4. These reagents are in turn derived from ketones D3 and D5, respectively, analogously to the method described above. For the case when R=R=H, the methodology of Coppola et al., J. Het. Chem. 1974, 11, 51-56 may be employed. This involves the treatment of an arylacetic acid reagent of formula D6 with a preformed mixture of phosphorus oxychloride and dimethylformamide. Basic workup then affords the formyl enamine product D4.

An alternative synthesis of the reagent of Formula 1 where one of the aryl groups is attached at the 4-position of the pyrazole ring is shown in Scheme E.

Scheme E

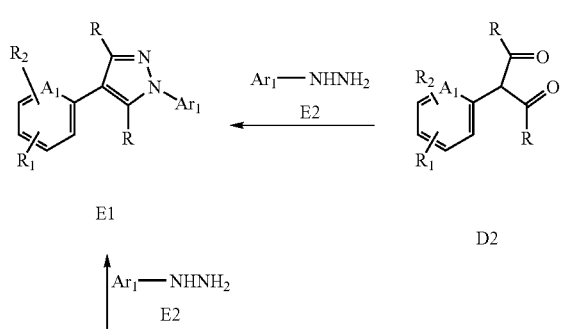

-continued

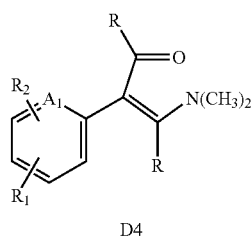

D4

In accordance with Scheme E, the previously-described compounds D2 and D4 may be condensed directly with an arylhydrazine compound of formula E2, under similar conditions as employed for the reaction of unsubstituted hydrazine itself. In the case of R≠R, the regioselectivity may be controlled by the size of the R groups, and chromatographic methods familiar to those skilled in the art may be necessary to separate the products.

For compounds of Formula 1 comprised of a central imidazole ring, the arylation methodology discussed above can be employed for an imidazole compound of formula F1 (Scheme F).

Scheme F

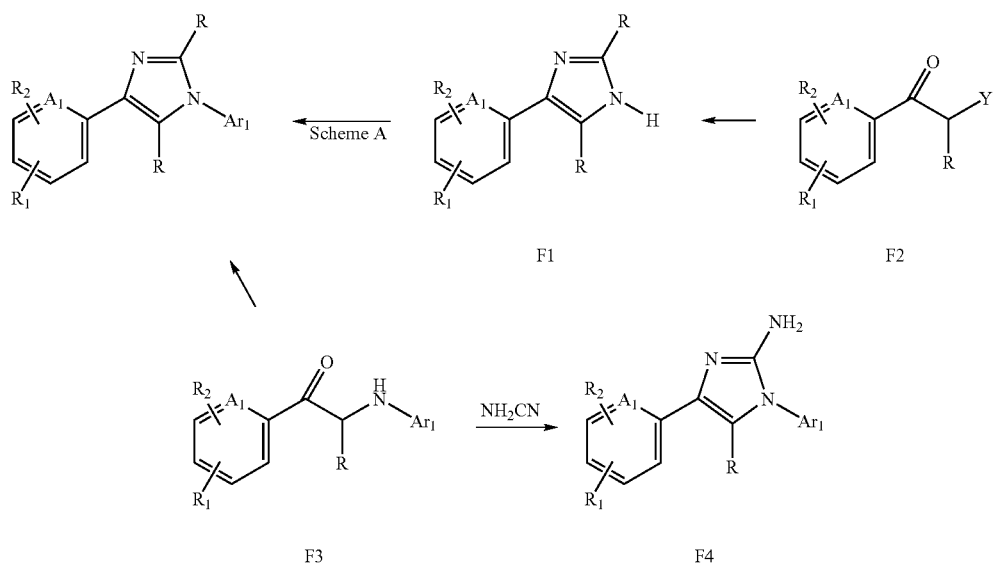

In accordance with Scheme F, a reagent of formula F2, where Y represents a halogen, amine or hydroxyl group, may be converted to compound F1 through a cyclocondensation reaction. In the case where R=H, α-bromoketones (F2, Y=Br) may be treated with formamide at high temperatures (>150° C.) to afford the imidazole product. The cross-coupling reaction of imidazole F1 may proceed with good to excellent regioselectivity if aryl and R are different in size; otherwise two regioisomers may result, which may be separable by chromatography. Imidazoles of this invention may also be prepared by cyclocondensation reaction of an arylamino ketone substrate (F3) with a reagent such as a nitrile or an imidate. For compounds with 2-amino substitution, compound F3 may also be treated with cyanamide to afford a 2-aminoimidazole. The primary amino group may then be functionalized as one chooses.

For compounds of Formula 1 comprised of a central 1,2,4-triazole ring, the arylation methodology discussed above can be employed for a compound of formula G1 (Scheme G).

Scheme G

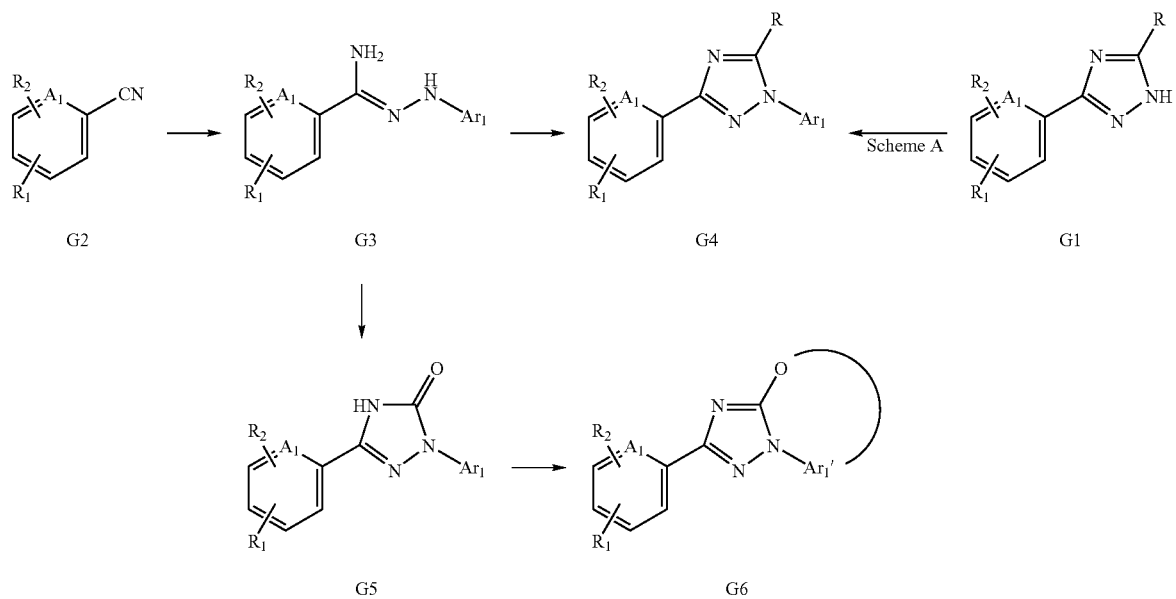

In accordance with Scheme G, another route starts with nitrile reagent G2, which is first treated in alcohol solvent with dry acid (gaseous HCl or in situ-genreated HCl from an acid chloride). The intermediate imidate salt is then treated with an arylhydrazine reagent to afford compound G3. This compound is then allowed to undergo a cyclocondensation reaction with an orthoester reagent of formula R—C(OR')$_3$ to afford the product G4, or with a reagent such as carbonyldiimidazole to give G5. In the case where compound G5 bears an $Ar_1$ group with functionality that can react with the 1,2,4-triazolone oxygen atom (e.g. a $CH_2$—Br group at the ortho position of the $Ar_1$ ring), then another ring may be formed by such an alkylation reaction. Basic reagents and/or conditions such as sodium hydride or potassium carbonate in dimethylformamide solvent at temperatures from ambient to 100° C. may be used to perform this internal alkylation to provide the compound of formula G6. An ortho-$CH_2Br$ group may be prepared on the $Ar_1$ ring by the conversion of a $CH_3$ group to $CH_2Br$ by free radical bromination. This reaction may be performed with reagents such as N-bromosuccinimide in a refluxing solution with a solvent such as carbon tetrachloride or chloroform. The presence of a catalytic amount of a free-radical initiator, such as 2,2'azobis(2-methylpropionitrile), may prove beneficial in this reaction.

For compounds of Formula 1 comprised of a central 1,2,3-triazole ring, the following methodology can be employed for a compound H1 (Scheme H).

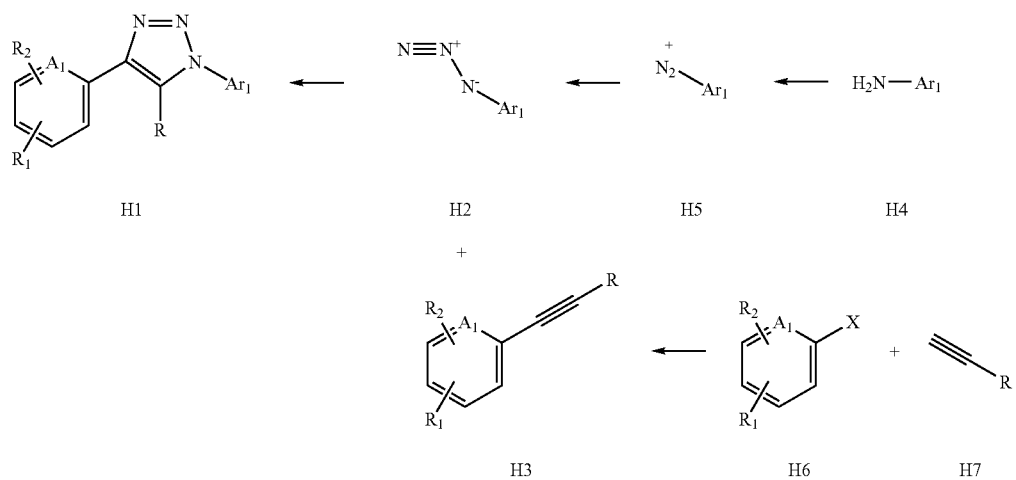

In accordance with Scheme H, the triazole can be prepared by the cycloaddition reaction of an azido reagent of formula H2 and an alkynyl reagent of formula H3. This cycloaddition reaction may be performed thermally, in appropriate aprotic solvents at elevated temperatures (in sealed vessels if necessary). Alternatively, the reaction may be performed in the presence of a catalyst, such as copper sulfate pentahydrate-ascorbic acid, according to the method of Sharpless et al., Angew. Chem., Int. Ed. Engl. 2002, 41 2596-2599. These conditions allow for higher product yields and better regioselectivity. Azide compounds may be prepared by first converting an aniline compound of formula H4 to a diazonium salt (H5), with the use of such reagents as sodium nitrite/acid or an alkyl nitrite reagent. The diazonium salt is then treated with an azide salt, such as sodium azide, to afford the azido compound H2. An example of just such a tranformation may be found in the work of Carnazzi et al., *J. Med. Chem.* 1994, 37, 1841. The alkyne compound H3 can be prepared by the palladium-catalyzed cross-coupling reaction of an aryl halide reagent of formula H6 and a terminal acetylene reagent of formula H7. Catalysts containing either Pd(0) or Pd(II), such as bis(triphenylphosphine)palladium dichloride, are useful for this reaction. This coupling reaction is usually also mediated by the presence of a copper (I) catalyst, and a mono-, di- or trialkylamine as a copper ligand, usually as a cosolvent along with a polar solvent such as dimethylformamide. The reactions may be performed at elevated temperatures as appropriate.

Compounds of Formula 1 that contain a central oxadiazolone ring may be prepared according to the strategy shown in Schemes J and K (below).

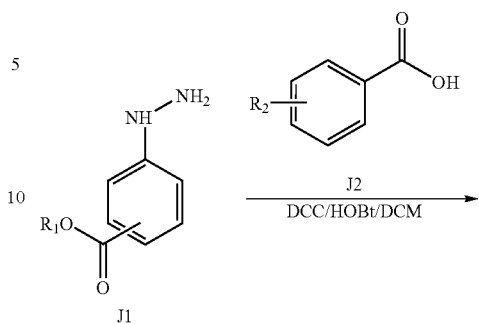

-continued

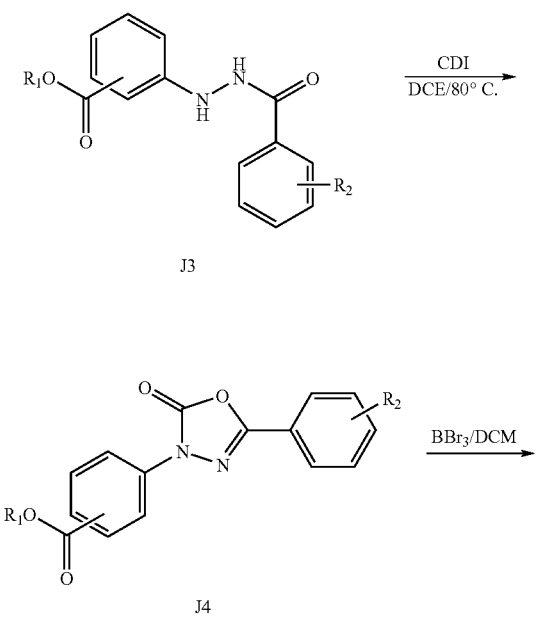

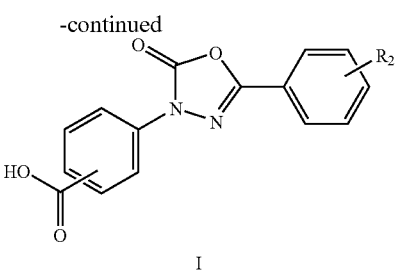

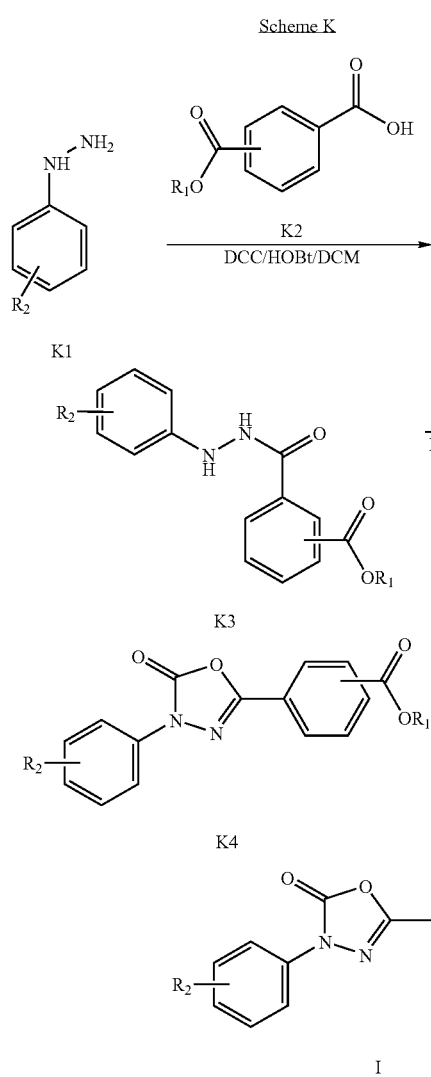

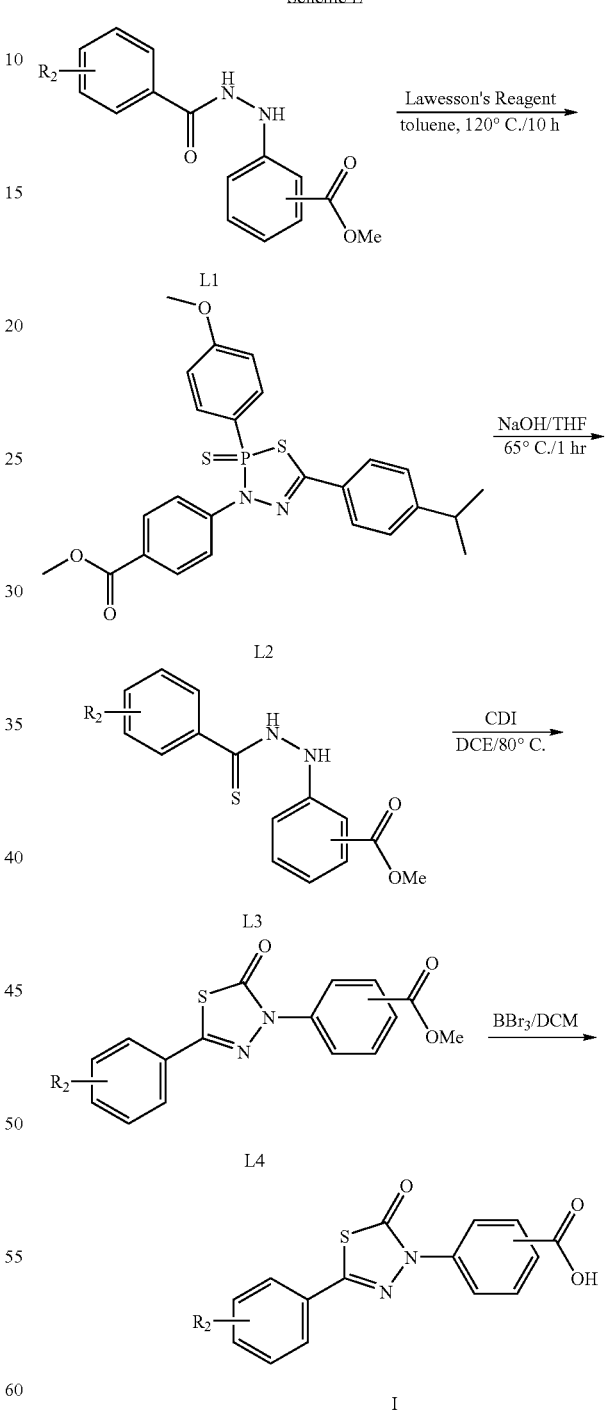

In accordance with Schemes J and K, similar conditions are used for both variations, beginning with starting materials that give final products with carboxyl substitution on one side or the other. An arylhydrazine reagent (J1 or K1) is acylated with a carboxylic acid reagent (J2 or K2) to give hydrazides J3 or K3. This condensation may also be performed using the appropriately substituted aroyl chloride reagent and an organic or inorganic base. The ring is formed in a cyclocondensation reaction using a reagent like carbonyldiimidazole, and the resulting ester compound (J4 or K4) is hydrolyzed to afford the carboxylic acid. Other non-nucleophilic ester-cleaving conditions may be employed for this transformation. This methodology may also be performed by attaching intermediates to a solid support, thus allowing rapid intermediate isolation and the liberation of pure final product.

Compounds of Formula 1 with a thiadiazolone core ring are prepared using the methodology shown in Scheme L.

In accordance with Scheme L, the hydrazide intermediates discussed above in Schemes J and K are treated with Lawesson's reagent to give an intermediate phosphorus-containing heterocyclic product (L2). The phosphorus group is removed by treatment with hydroxide, and the resulting thiohydrazide L3 is cyclocondensed in a manner analogous to the oxadiazolones to afford the thiadiazolone L4. The free carboxyl group is then liberated by the method discussed above.

In certain preferred embodiments, compounds of the invention may be resolved to enantiomerically pure compositions or synthesized as enantiomerically pure compositions using any method known in art. By way of example, compounds of the invention may be resolved by direct crystallization of enantiomer mixtures, by diastereomer salt formation of enantiomers, by the formation and separation of diasteriomers or by enzymatic resolution of a racemic mixture.

These and other reaction methodologies may be useful in preparing the compounds of the invention, as recognized by one of skill in the art. Various modifications to the above schemes and procedures will be apparent to one of skill in the art, and the invention is not limited specifically by the method of preparing the compounds of the invention.

C. Methods of the Invention

In another aspect of the invention, methods are provided for the suppression of premature translation termination, which may be associated with a nonsense mutation, and for the prevention or treatment of diseases. In a preferred embodiment, such diseases are associated with mutations of mRNA, especially nonsense mutations. Exemplary diseases include, but are not limited to, cancer, lysosomal storage disorders, the muscular dystrophies, cystic fibrosis, hemophilia, epidermolysis bullosa and classical late infantile neuronal ceroid lipofuscinosis. In this embodiment, methods for treating cancer, lysosomal storage disorders, a muscular dystrophy, cystic fibrosis, hemophilia, or classical late infantile neuronal ceroid lipofuscinosis are provided comprising administering a therapeutically effective amount of at least one compound of the invention to a subject in need thereof.

In one embodiment, the present invention is directed to methods for increasing the expression of one or more specific, functional proteins. Any compound of the invention can be used to specifically increase expression of functional protein. In another embodiment, a specific increase in expression of functional protein occurs when premature translation termination is suppressed by administering a therapeutically effective amount of at least one compound of the invention to a subject in need thereof. In a preferred embodiment premature translation termination is associated with a nonsense mutation in mRNA. In another embodiment, a specific increase in expression of functional protein occurs when mRNA decay is reduced in a patient. In a preferred embodiment, the abnormality in a patient is caused by mutation-mediated mRNA decay. In a particularly preferred embodiment, mutation-mediated mRNA decay is the result of a nonsense mutation. The methods of the present invention are not limited by any particular theory.

The invention encompasses methods of treating and preventing diseases or disorders ameliorated by the suppression of premature translation termination, nonsense-mediated mRNA decay, or premature translation termination and non-sense-mediated mRNA decay in a patient which comprise administering to a patient in need of such treatment or prevention a therapeutically effective amount of a compound of the invention.

In one embodiment, the present invention encompasses the treatment or prevention of any disease that is associated with a gene exhibiting premature translation termination, non-sense-mediated mRNA decay, or premature translation termination and nonsense-mediated mRNA decay. In one embodiment, the disease is due, in part, to the lack of or reduced expression of the gene resulting from a premature stop codon. Specific examples of genes which may exhibit premature translation termination and/or nonsense-mediated mRNA decay and diseases associated with premature translation termination and/or nonsense-mediated mRNA decay are found in U.S. Provisional Patent Application No. 60/390,747, titled: Methods For Identifying Small Molecules That Modulate Premature Translation Termination And Nonsense Mediated mRNA Decay, filed Jun. 21, 2002, and International Application PCT/US03/19760, filed Jun. 23, 2003, both of which are incorporated herein by reference in their entirety.

Diseases ameliorated by the suppression of premature translation termination, nonsense-mediated mRNA decay, or premature translation termination and nonsense-mediated mRNA decay include, but are not limited to: genetic diseases, somatic diseases, cancers, autoimmune diseases, blood diseases, collagen diseases, diabetes, neurodegenerative diseases, proliferative diseases, cardiovascular diseases, pulmonary diseases, inflammatory diseases or central nervous system diseases.

In one embodiment, diseases to be treated or prevented by administering to a patient in need thereof an effective amount of a compound of the invention include, but are not limited to, amyloidosis, hemophilia, Alzheimer's disease, Tay Sachs disease, Niemann Pick disease, atherosclerosis, giantism, dwarfism, hypothyroidism, hyperthyroidism, aging, obesity, Parkinson's disease, cystic fibrosis, muscular dystrophy, heart disease, kidney stones, ataxia-telangiectasia, familial hypercholesterolemia, retinitis pigmentosa, Duchenne muscular dystrophy, epidermolysis bullosa and Marfan syndrome. In one embodiment, the diseases are associated with a nonsense mutation.

In one embodiment, the compounds of the invention are useful for treating or preventing an autoimmune disease. In one embodiment, the autoimmune disease is associated with a nonsense mutation. In a preferred embodiment, the autoimmune disease is rheumatoid arthritis or graft versus host disease.

In another embodiment, the compounds of the invention are useful for treating or preventing a blood disease. In one embodiment, the blood disease is associated with a nonsense mutation. In a preferred embodiment, the blood disease is hemophilia, Von Willebrand disease, β-thalassemia In another embodiment, the compounds of the invention are useful for treating or preventing a collagen disease. In one embodiment, the collagen disease is associated with a nonsense mutation. In a preferred embodiment, the collagen disease is osteogenesis imperfecta or cirrhosis.

In another embodiment, the compounds of the invention are useful for treating or preventing diabetes. In one embodiment, the diabetes is associated with a nonsense mutation.

In another embodiment, the compounds of the invention are useful for treating or preventing an inflammatory disease. In one embodiment, the inflammatory disease is associated with a nonsense mutation. In a preferred embodiment, the inflammatory disease is arthritis, rheumatoid arthritis or osteoarthritis.

In another embodiment, the compounds of the invention are useful for treating or preventing a central nervous system disease. In one embodiment, the central nervous system disease is associated with a nonsense mutation. In one embodiment, the central nervous system disease is a neurodegenerative disease. In a preferred embodiment, the central nervous system disease is multiple sclerosis, muscular dystrophy, Duchenne muscular dystrophy, Alzheimer's disease, Tay Sachs disease, Niemann Pick disease, late infantile neuronal ceroid lipofuscinosis (LINCL) or Parkinson's disease.

In another preferred embodiment, the compounds of the invention are useful for treating or preventing cancer, particularly in humans. In a preferred embodiment, the cancer is of the head and neck, eye, skin, mouth, throat, esophagus, chest, bone, blood, lung, colon, sigmoid, rectum, stomach, prostate, breast, ovaries, kidney, liver, pancreas, brain, intestine, heart or adrenals. In one embodiment, the cancer is a solid tumor. In one embodiment, the cancer is associated with a nonsense mutation. In another embodiment, the cancer is associated with a genetic nonsense mutation. In another embodiment, the cancer is associated with a somatic mutation. Without being limited by any theory, the use of the compounds of the invention against cancer may relate to its action against mutations of the p53 gene.

In one embodiment, the cancer is not a blood cancer. In another embodiment, the cancer is not leukemia. In another embodiment, the cancer is not multiple myeloma. In another embodiment, the cancer is not prostate cancer.

In another preferred embodiment, the compounds of the invention are useful for treating or preventing cancer associated with a mutation of tumor suppressor gene. Such genes include, but are not limited to PTEN, BRCA1, BRCA2, Rb, and the p53 gene. In one embodiment, the mutation is a genetic mutation. In another embodiment, the mutation is a somatic mutation. The methods of the invention are particularly useful for treating or preventing a cancer associated with a nonsense mutation in the in a tumor suppressor gene. In a preferred embodiment, the methods of the invention are particularly useful for treating or preventing a cancer associated with a p53 gene due to the role of p53 in apoptosis. Without being limited by theory, it is thought that apoptosis can be induced by contacting a cell with an effective amount of a compound of the invention resulting in suppression of the nonsense mutation, which, in turn, allows the production of full-length p53 to occur. Nonsense mutations have been identified in the p53 gene and have been implicated in cancer. Several nonsense mutations in the p53 gene have been identified (see, e.g., Masuda et al., 2000, Tokai J Exp Clin Med. 25(2):69-77; Oh et al., 2000, Mol Cells 10(3):275-80; Li et al., 2000, Lab Invest. 80(4):493-9; Yang et al., 1999, Zhonghua Zhong Liu Za Zhi 21(2):114-8; Finkelstein et al., 1998, Mol Diagn. 3(1):37-41; Kajiyaina et al., 1998, Dis Esophagus. 11(4):279-83; Kawamura et al., 1999, Leuk Res. 23(2): 115-26; Radig et al., 1998, Hum Pathol. 29(11):1310-6; Schuyer et al., 1998. Int J Cancer 76(3):299-303; Wang-Gohrke et al., 1998, Oncol Rep. 5(1):65-8; Fulop et al., 1998, J Reprod Med. 43(2):119-27; Ninomiya et al., 1997, J Dermatol Sci. 14(3):173-8; Hsieh et al., 1996, Cancer Lett. 100 (1-2):107-13; Rall et al., 1996, Pancreas. 12(1):10-7; Fukutomi et al., 1995, Nippon Rinsho. 53(11):2764-8; Frebourg et al., 1995, Am J Hum Genet. 56(3):608-15; Dove et al., 1995, Cancer Surv. 25:335-55; Adamson et al., 1995, Br J Haematol. 89(1):61-6; Grayson et al., 1994, Am J Pediatr Hematol Oncol. 16(4):341-7; Lepelley et al., 1994, Leukemia. 8(8): 1342-9; McIntyre et al., 1994, J Clin Oncol. 12(5):925-30; Horio et al., 1994, Oncogene. 9(4):1231-5; Nakamura et al., 1992, Jpn J Cancer Res. 83(12):1293-8; Davidoff et al., 1992, Oncogene. 7(1):127-33; and Ishioka et al., 1991, Biochem Biophys Res Commun. 177(3):901-6; the disclosures of which are hereby incorporated by reference herein in their entireties). Any disease associated with a p53 gene encoding a premature translation codon including, but not limited to, the nonsense mutations described in the references cited above, can be treated or prevented by compounds of the invention.

In other embodiments, diseases to be treated or prevented by administering to a patient in need thereof an effective amount of a compound of the invention include, but are not limited to, solid tumors such as sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor or multiple myeloma.

In another embodiment, diseases to be treated or prevented by administering to a patient in need thereof an effective amount of a compound of the invention include, but are not limited to, a blood-born tumor such as acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, chronic lymphocytic leukemia, hairy cell leukemia, or multiple myeloma. See e.g., Harrison's Principles of Internal Medicine, Eugene Braunwald et al., eds., pp. 491-762 (15th ed. 2001).

In yet another embodiment, the invention encompasses the treatment of a human afflicted with a solid tumor or a blood tumor.

In a preferred embodiment, the invention encompasses a method of treating or preventing a disease ameliorated by modulation of premature translation termination, nonsense-mediated mRNA decay, or premature translation termination and nonsense-mediated mRNA decay, or ameliorating one or more symptoms associated therewith comprising contacting a cell with a therapeutically effective amount of a compound of the invention. Cells encompassed by the present methods include animal cells, mammalian cells, bacterial cells, and virally infected cells. In one embodiment, the nonsense mutation is a genetic mutation (i.e., the nonsense codon was present in the progenitor DNA). In another embodiment, the nonsense mutation is a somatic mutation (i.e., the nonsense codon arose spontaneously or from mutagenesis).

In certain embodiments, a compound of the invention is administered to a subject, including but not limited to a plant, reptile, avian, amphibian or preferably a mammal, more preferably a human, as a preventative measure against a disease associated with premature translation termination, nonsense-mediated mRNA decay, or premature translation termination and nonsense-mediated mRNA decay.

In a preferred embodiment, it is first determined that the patient is suffering from a disease associated with premature translation termination and/or nonsense-mediated mRNA decay. In another embodiment, the patient has undergone a screening process to determine the presence of a nonsense mutation comprising the steps of screening a subject, or cells extracted therefrom, by an acceptable nonsense mutation screening assay. In a preferred embodiment, the DNA of the patient can be sequenced or subjected to rem Blot, polymerase chain reaction (PCR), use of the Short Tandem Repeat (STR), or polymorphic length restriction fragments (RFLP) analysis to determine if a nonsense mutation is present in the DNA of the patient. In one embodiment, it is determined whether the nonsense mutation is a genetic mutation or a somatic mutation by comparison of progenitor DNA. Alternatively, it can be determined if altered levels of the protein with the nonsense mutation are expressed in the patient by western blot or other immunoassays. In another embodiment, the patient is an unborn child who has undergone screening in utero for the presence of a nonsense mutation. Administration of a compound of the invention can occur either before or after birth. In a related embodiment, the therapy is personalized in that the patient is screened for a nonsense mutation screening assay and treated by the administration of one or more compounds of the invention; particularly, the patient may be treated with a compound particularly suited for the mutations in question; e.g., depending upon the disease type, cell type, and the gene in question. Such methods are well known to one of skill in the art.

In another embodiment, the cells (e.g., animal cells, mammalian cells, bacterial cells, plant cells and virally infected cells) are screened for premature translation termination and/or nonsense-mediated mRNA decay with a method such as that described above (i.e., the DNA of the cell can be sequenced or subjected to Southern Blot, polymerase chain reaction (PCR), use of the Short Tandem Repeat (STR), or polymorphic length restriction fragments (RFLP) analysis to determine if a nonsense mutation is present in the DNA of the cell; the RNA of the cell can be subjected to quantitative real time PCR to determine transcript abundance).

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to non-opioid analgesics; non-steroid anti-inflammatory agents; steroids, antiemetics; β-adrenergic blockers; anticonvulsants; antidepressants; $Ca^{2+}$-channel blockers; anticancer agent(s) and antibiotics and mixtures thereof.

In certain embodiments, the compounds of the invention can be administered or formulated in combination with anticancer agents. Suitable anticancer agents include, but are not limited to: alkylating agents; nitrogen mustards; folate antagonists; purine antagonists; pyrimidine antagoinists; spindle poisons; topoisomerase inhibitors; apoptosis inducing agents; angiogenesis inhibitors; podophyllotoxins; nitrosoureas; cisplatin; carboplatin; interferon; asparginase; tamoxifen; leuprolide; flutamide; megestrol; mitomycin; bleomycin; doxorubicin; irinotecan and taxol.

In certain embodiments, the compounds of the invention can be administered or formulated in combination with antibiotics. In certain embodiments, the antibiotic is an aminoglycoside (e.g., tobramycin), a cephalosporin (e.g., cephalexin, cephradine, cefuroxime, cefprozil, cefaclor, cefixime or cefadroxil), a clarithromycin (e.g., clarithromycin), a macrolide (e.g., erythromycin), a penicillin (e.g., penicillin V) or a quinolone (e.g., ofloxacin, ciprofloxacin or norfloxacin). In a preferred embodiment, the antibiotic is active against *Pseudomonas aeruginosa*.

Without intending to be limited by theory, it is believed that the methods of the present invention act through a combination of mechanisms that suppress nonsense mutations. In preferred embodiments, the methods of the invention comprise administering a therapeutically effective amount of at least one compound of the invention, e.g., a compound of Formula 1. Relative activity of the compounds of the invention may be determined by any method known in the art, including the assay described in Example 2 herein.

Compounds of the invention can be characterized with an in vitro luciferase nonsense suppression assay. Luciferase assays are included in the methods of the present invention. Luciferase can be used as a functional reporter gene assay (light is only produced if the protein is functional), and luciferase is extremely sensitive (Light intensity is proportional to luciferase concentration in the nM range). In one embodiment, an assay of the present invention is a cell-based luciferase reporter assay. In a preferred cell-based luciferase reporter assay, a luciferase reporter construct containing a premature termination codon (UGA, UAA, or UAG) is stably transfected in 293 Human Embryonic Kidney cells.

In another assay of the present invention, a preferred assay is a biochemical assay consisting of rabbit reticulocyte lysate and a nonsense-containing luciferase reporter mRNA. In another assay of the present invention, the assay is a biochemical assay consisting of prepared and optimized cell extract (Lie & Macdonald, 1999, Development 126(22): 4989-4996 and Lie & Macdonald, 2000, Biochem. Biophys. Res. Commun. 270(2):473-481. In the biochemical assay, mRNA containing a premature termination codon (UGA, UAA, or UAG) is used as a reporter in an in vitro translation reaction using rabbit reticulocyte lysate supplemented with tRNA, hemin, creatine kinase, amino acids, KOAc, Mg(OAc)2, and creatine phosphate. Translation of the mRNA is initiated within a virus derived leader sequence, which significantly reduces the cost of the assay because capped RNA is not required. Synthetic mRNA is prepared in vitro using the T7 promoter and the MegaScript in vitro transcription kit (Ambion, Inc.; Austin, Tex.). In assays of the present invention, addition of gentamicin, an aminoglycoside known to allow readthrough of premature termination codons, results in increased luciferase activity and can be used as an internal standard. Assays of the present invention can be used in high-throughput screens. Hundreds of thousands of compounds can be screened in cell-based and biochemical assays of the present invention. In a preferred aspect, a functional cell-based assay similar to the one described.

Compounds of the present invention include compounds capable of increasing specific, functional protein expression from mRNA molecules comprising premature termination codons. In one embodiment, compounds of the present invention can preferentially suppress premature translation termination. For example, a compound of the present invention can be capable of suppressing a nonsense mutation if the mutation results in UAA, but not capable of suppressing a nonsense mutation if the mutation results in UAG. Another non-limiting example can occur when a compound of the present invention can be capable of suppressing a nonsense mutation if the mutation results in UAA and is followed, in-frame by a cytosine at the +1 position, but not capable of suppressing a nonsense mutation if the mutation results in UAA and is followed, in-frame by an adenine at the +1 position.

A stable cell line harboring the UGA nonsense-containing luciferase gene can be treated with a test compound. In this aspect, cells can be grown in standard medium supplemented with 1% penicillin-streptomycin (P/S) and 10% fetal bovine serum (FBS) to 70% confluency and split 1:1 the day before treatment. The next day, cells are trypsinized and 40,000 cells are added to each well of a 96-well tissue culture dish. Serial dilutions of each compound are prepared to generate a six-point dose response curve spanning 2 logs (30 μM to 0.3 μM). The final concentration of the DMSO solvent remains constant at 1% in each well. Cells treated with 1% DMSO serve as the background standard, and cells treated with gentamicin serve as a positive control.

To address the effects of the nonsense-suppressing compounds on mRNAs altered in specific inherited diseases, a bronchial epithelial cell line harboring a nonsense codon at amino acid 1282 (W1282X) can be treated with a compound of the invention and CFTR function is monitored as a cAMP-activated chloride channel using the SPQ assay (Yang et al., Hum. Mol. Genet. 2(8):1253-1261 (1993) and Howard et al., Nat. Med. 2(4):467-469(1996)). The increase in SPQ fluorescence in cells treated with a compound of the invention is compared to those treated with cAMP and untreated cells. An increase in SPQ fluorescence in cells is consistent with stimulation of CFTR-mediated halide efflux and an increase in readthrough of the nonsense codon. Full-length CFTR expression from this nonsense-containing allele following treatment with a compound of the invention demonstrates that cystic fibrosis cell lines increase chloride channel activity when treated with a compound of the invention.

D. Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

E. Pharmaceutical Compositions of the Invention

While it is possible for the compounds of the present invention to be administered neat, it may be preferable to formulate the compounds as pharmaceutical compositions. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In another embodiment, the pharmaceutical compositions of the invention may be formulated in a pH range from about pH 4 to about pH 7. In alternative embodiments, it may be preferred that the pH is adjusted to a range from about pH 5 to about pH 8.

More particularly, the pharmaceutical compositions of the invention comprise a therapeutically or prophylactically effective amount of at least one compound of the present invention, together with one or more pharmaceutically acceptable excipients. Optionally, the pharmaceutical compositions of the invention may comprise a combination of compounds of the present invention, or may include a second active ingredient useful in the treatment of cancer, diabetic retinopathy, or exudative macular degeneration.

Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The pharmaceutical compositions of the invention can be administered to the subject via any drug delivery route known in the art. Specific exemplary administration routes include oral, ocular, rectal, buccal, topical, nasal, ophthalmic, subcutaneous, intramuscular, intravenous (bolus and infusion), intracerebral, transdermal, and pulmonary.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences, $18^{th}$ Ed., Mack Publishing Co., 1990).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol heptadecacthyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

Generally, the compounds of the present invention useful in the methods of the present invention are substantially insoluble in water and are sparingly soluble in most pharmaceutically acceptable protic solvents and in vegetable oils. However, the compounds are generally soluble in medium chain fatty acids (e.g., caprylic and capric acids) or triglycerides and have high solubility in propylene glycol esters of medium chain fatty acids. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of $\alpha$-, $\beta$-, and $\gamma$-cyclodextrin. A particularly preferred cyclodextrin solubility enhancer is hydroxypropyl-$\beta$-cyclodextrin (HPBC), which may be added to any of the above-described compositions to further improve the aqueous solubility characteristics of the compounds of the present invention. In one embodiment, the composition comprises 0.1% to 20% hydroxypropyl-$\beta$-cyclodextrin, more preferably 1% to 15% hydroxypropyl-$\beta$-cyclodextrin, and even more preferably from 2.5% to 10% hydroxypropyl-$\beta$-cyclodextrin. The amount of solubility enhancer employed will depend on the amount of the compound of the present invention in the composition.

The therapeutically effective amount, as used herein, refers to an amount of a pharmaceutical composition of the invention to treat, ameliorate, or modulate an identified disease or condition, or to exhibit a detectable therapeutic or inhibitory effect. The effect can be detected by, for example, assays of the present invention. The effect can also be the prevention of a disease or condition where the disease or condition is predicted for an individual or a high percentage of a population.

The precise effective amount for a subject will depend upon the subject's body weight, size, and health; the nature and extent of the condition; the therapeutic or combination of therapeutics selected for administration, the protein half-life, the mRNA half-life and the protein localization. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 5 μg/mL to approximately 100 μg/mL, preferably from approximately 10 μg/mL to approximately 50 μg/mL, more preferably from approximately 10 μg/mL to approximately 25 μg/mL. To achieve such plasma concentrations, the compounds of the invention may be administered at doses that vary from 1 mg/kg to 150 mg/kg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 1 mg/kg to about 150 mg/kg per day. In one embodiment, the compound of the invention is given as a single once-a-day dose. In another embodiment, the compound of the invention is given as divided doses throughout a day. More specifically, the daily dose is administered in a single dose or in equally divided doses. Preferably, a daily dose range should be from about 5 mg/kg to about 100 mg/kg per day, more preferably, between about 10 mg/kg and about 90 mg/kg per day, even more preferably 20 mg/kg to 60 mg/kg per day. In managing the patient, the therapy should be initiated at a lower dose, perhaps about 200 mg to about 300 mg, and increased if necessary up to about 600 mg to about 4000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different diseases and conditions, as will be readily known by those of ordinary skill in the art. Similarly, amounts sufficient to treat or prevent such diseases, but insufficient to cause, or sufficient to reduce, adverse effects associated with conventional therapies are also encompassed by the above described dosage amounts and dose frequency schedules.

As stated before, the exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time, protein of interest half-life, RNA of interest half-life, frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

F. Combination Therapy

It is also possible to combine any compound of the present invention with one or more other active ingredients useful in the treatment of diseases associated with nonsense mutations of mRNA as described herein, including compounds in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the nonsense mutation-suppressing activity of the compounds of the invention.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

G. Gene Therapy

The compounds of the present invention or other nonsense compounds can be utilized in combination with gene therapy. In this embodiment, a gene can be introduced or provided to a mammal, preferably a human that contains a specified nonsense mutation in the desired gene. In a preferred aspect, the desired gene is selected from the group consisting of IGF1, EPO, p53, p19ARF, p21, PTEN, EI 24 and ApoAI. In order to obtain expression of the full-length polypeptide in a patient or mammal, the patient or mammal would be provided with an effective amount of a compound of the present invention or other nonsense suppression compound when such polypeptide is desired.

There are two major approaches to getting nucleic acids that contain a nonsense mutation (optionally contained in a vector) into the patient's cells: in vivo and ex vivo. For in vivo delivery the nucleic acid is injected directly into the patient, usually at the sites where the polypeptide is required, i.e., the site of synthesis of the polypeptide, if known, and the site (e.g. solid tumor) where biological activity of the polypeptide is needed. For ex vivo treatment, the patient's cells are removed, the nucleic acid is introduced into these isolated cells, and the modified cells are administered to the patient either directly or, for example, encapsulated within porous membranes that are implanted into the patient (see e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (preferably retroviral) particle with a cellular receptor, followed by introduction of the nucleic acids contained by the particle into the cell. A commonly used vector for ex vivo delivery of the gene is a retrovirus.

The currently preferred in vivo nucleic and transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinson et al., *Cancer Investigation*, 14 (1): 54-65 (1996)). The most preferred vectors for use in gene therapy are viruses, most preferably adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid sequence that, when transcribed with a gene encoding a polypeptide, is operably linked to the coding sequence and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the polypeptide from a host cell in which it is placed. Preferably the signal sequence for this purpose is a mammalian signal sequence, most preferably the native signal sequence for the polypeptide. Optionally, the vector construct may also include a signal that directs polyadenylation, as well as one or more restriction sites and a translation termination sequences. By way of example, such vectors will typically include a 5' LTR, a tRNA binding site, a packaging signal, a origin of second-strand DNA synthesis, and a 3' LTR or a portion thereof. Other vectors can be used that are non-viral, such as cationic lipids, polylysine, and dendrimers.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enchance intracellular half-life. The technique of recpto-mediated endocytosis is described, for example, by Wu et al., *J. Biol. Chem.* 262: 4429-4432 (1987); and Wagner et al., *Proc. Natl. Acad. Sci. USA,* 87: 3410-3414 (1990). For a review of the currently known gene marking and gene therapy protocols, see, Anderson et al., *Science* 256: 808-813 (1992). See also WO 93/25673 and the references cited therein.

Suitable gene therapy and methods for making retroviral particles and structural proteins can be found in, e.g. U.S. Pat. Nos. 5,681,746; 6,800,604 and 6,800,731.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of Compounds of the Invention

A. Preparation of Pyrroles
Pyrroles of the invention may be generally prepared as follows.

Preparation of 3-[1-(4-Trifluoromethyl-phenyl)-]-1H-pyrrol-3-yl]-benzoic acid sodium salt (Compound 154)

Part A.
To a solution of 1-(triisopropylsilyl)pyrrole-3-boronic acid (prepared according to the method of Alvarez, A.; Guzman, A.; Ruiz, A.; Velarde, E., *J. Org. Chem.* 1992, 57, 1653-1656) (6.12 g, 22.9 mmol) in anhydrous dimethoxyethane (76 mL) is added methyl 4-iodobenzoate (96.61 g, 25.2 mmol), dichlorobis(triphenylphosphine)palladium(II) (0.484 g, 0.69 mmol) and cesium fluoride (6.96 g, 45.8 mmol). The mixture is heated at reflux under a nitrogen atmosphere for 17 h. The reaction mixture is cooled to room temperature, diluted with water (100 mL) and extracted with ethyl acetate (4×25 mL).

The extract is washed with water, dried over MgSO$_4$ and concentrated to give the crude product. The product is purified by silica gel chromatography (5-15% ethyl acetate/hexane) to give 2.69 g of methyl 4-(1H-pyrrol-3-yl)-benzoate as a white solid (58% yield). $^1$H NMR (300 MHz, DMSO-d$_6$): δ 3.83 (s, 3H), 6.53 (m, 1H), 6.83 (m, 1H), 7.35 (m, 1H), 7.66 (d, 2H, J=8.4 Hz), 7.86 (d, 2H, J=8.4 Hz), 11.11 (br s, 1H).

Part B.

To a solution of methyl 4-(1H-pyrrol-3-yl)-benzoate in anhydrous dioxane (67 mL) is added 4-iodobenzotrifluoride (4.39 g, 16.1 mmol), cuprous iodide (0.255 g, 1.34 mmol), ethylenediamine (81 mg, 1.35 mmol) and potassium phosphate (10.16 g, 44.1 mmol). The reaction mixture is heated at reflux for 20 h. under a nitrogen atmosphere, then cooled to room temperature. The solid is filtered, washed with ethyl acetate and discarded. The filtrate is concentrated to give a dark solid which is diluted with water (50 mL) and extracted with ethyl acetate (3×20 mL). The extracts are washed with water (2×20 mL), combined, dried over MgSO$_4$ and concentrated to give the crude product. The crude product is purified by silica gel chromatography (5-20% ethyl acetate) to give 2.00 g of methyl 3-[1-(4-trifluoromethyl-phenyl)-1H-pyrrol-3-yl]-benzoate as a white solid (73% yield). $^1$H NMR (300 MHz, DMSO-d$_6$): δ 3.93 (s, 3H), 6.75 (m, 1H), 7.19 (in, 1H), 7.50 (m, 1H), 7.55 (d, 2H, J=8.7 Hz), 7.63 (d, 2H, J=6.6 Hz), 7.73 (d, 2H, J=8.4 Hz), 8.04 (d, 2H, J=6.6 Hz).

Part C.

To a suspension of methyl 3-[1-(4-trifluoromethyl-phenyl)-1H-pyrrol-3-yl]-benzoate (1.24 g, 3.59 mmol) in tert-butanol (4 mL) and water (16 mL) is added sodium hydroxide (0.215 g, 5.38 mmol). The reaction mixture is heated at reflux for 4 h, then cooled to room temperature. The solid is filtered, washed with water (3×4 mL) and dried to give 0.90 g of the title product as a gray solid (71% yield). MS (ES+): m/z 332.61.

Part D.

A portion of the sodium salt of 3-[1-(4-trifluoromethyl-phenyl)-1H-pyrrol-3-yl]-benzoic acid is neutralized with 1N aq. HCl to afford, after filtration, water washing and drying under vacuum, the free acid: m.p. 224-226° C. MS (ES+): m/e 332.28 (100). MS (ES−): m/e 330.31 (100).

Preparation of 4-[1-(4-Trifluoromethyl-phenyl)-1H-pyrrol-3-yl]-benzoic acid (Compound 105)

Part A.

To a slurry of methyltriphenylphosphonium bromide (10.88 g, 30.46 mmol, 1 eq.) and potassium tert-butoxide (31 mL, 1 M solution in THF, 30.46 mmol, 1 eq.) in THF is added methyl-4-formylbenzoate (5.0 g, 30.46 mmol, 1 eq.). The bright yellow reaction mixture is stirred at room temperature for 5 hrs. Hexane is added and after stirring for 10 minutes, the mixture is filtered and washed twice with hexanes. Solvent is removed in vacuum and the crude oily residue is purified by silica gel chromatography (0-14% ethyl acetate/hexanes) to give 3.76 g of a white oily solid, methyl 4-vinylbenzoate (23.21 mmol, 76.2% yield). $^1$H NMR (300 MHz, CDCl$_3$): δ 7.99 (2H, d, J=9 Hz), 7.45 (2H, d, J=9 Hz), 6.76 (1H, dd, J=17, 11 Hz), 5.86 (1H, d, J=17 Hz), 5.37 (1H, d, J=11 Hz), 3.91 (3H, s).

Part B.

Sodium tert-butoxide (3.681 g, 38.3 mmol, 2.0 eq.) is suspended in anhydrous DMSO under nitrogen. To this a solution of methyl 4-vinylbenzoate (3.11 g 19.15 mmol, 1.0 eq.) and tosylmethyl isocyanide (4.86 g, 24.89 mmol, 1.3 eq.) in anhydrous DMSO is transferred via cannula. The dark brown mixture is stirred at room temperature for 16 hrs. The mixture is adjusted to pH 6 by addition of 10% HCl solution, diluted with water and extracted with ethyl acetate (3×50 mL). The combined organic extract is washed with water (2×50 mL) and brine, dried over sodium sulfate and concentrated. The crude residue is purified by silica gel chromatography (20-40% ethyl acetate/hexanes) to give 990 mg (4.92 mmol, 25.7%) of methyl 4-(1H-pyrrol-3-yl)-benzoate as a cream colored solid. MS (ES+): m/e 201.08. $^1$H NMR (300 MHz, CDCl$_3$): δ 8.39 (1H, br s), 8.00 (2H, d, J=9 Hz), 7.58 (2H, d, J=9 Hz), 7.20 (1H, m), 6.85 (1H, m), 6.60 (1H, m), 3.91 (3H, s).

Part C.

To a stirred solution of methyl 4-(1H-pyrrol-3-yl)-benzoate (402 mg, 1.997 mmol, 1.0 eq.) and 4-trifluoromethyl-1-iodobenzene (652 mg, 2.39 mmol, 1.2 eq.) in anhydrous 1,4-dioxane (15 mL) is added copper(I) iodide (38 mg, 0.199 mmol, 0.1 eq.), ethylenediamine (13 μL, 0.199 mmol, 0.1 eq.) and potassium triphosphate (762 mg, 1.66 mmol, 3.31 eq.). The reaction mixture is degassed, flushed with nitrogen and heated to reflux for 18 hr. The reaction mixture is cooled, filtered and washed with ethyl acetate. The filtrate is concentrated and purified by silica gel chromatography (10% ethyl acetate/hexane) to get a white powder, methyl 4-[1-(4-trifluoromethyl-phenyl)-1H-pyrrol-3-yl]-benzoate (363.2 mg, 1.05 mmol, 52.7%). MS (ES+): m/e 345.11. $^1$H NMR (300 MHz, CDC$_3$): δ 8.04 (2H, d, J=8 Hz), 7.72 (2H, d, J=8 Hz), 7.63 (2H, d, J=8 Hz), 7.54 (2H, d, J=8 Hz), 7.50 (1H, m), 7.18 (1H, m), 6.75 (1H, m), 3.93 (3H, s).

Part D.

Methyl 4-[1-(4-trifluoromethylphenyl)-1H-pyrrol-3-yl) benzoate (150 mg, 0.434 mmol, 1 eq.) is suspended in 10 mL of 75% EtOH/water. Potassium hydroxide (73 μL of 1 M solution, 3.0 eq.) is added and the mixture heated to 60° C. for 16 hrs. The mixture is diluted with water and washed with chloroform (2×3 mL). The aqueous layer is acidified to pH 3 and the resulting precipitate is filtered and washed with water. The white solid is dried under high vacuum to give 121 mg (0.365 mmol, 84.15%) of the title product, m.p. 315-317° C. $^1$H NMR (300 MHz, DMSO-d$_6$): δ 8.03 (1H, m), 7.90 (2H, d, J=8 Hz), 7.83-7.76 (4H, m), 7.58 (1H, m), 7.52 (2H, d, J=8 Hz), 6.76 (1H, m). MS (ES+): m/e 332.24 (100). MS (ES−): m/e 330.25 (100).

Using modifications of the procedures detailed above, the following compounds may be prepared.

Compound 6

3-[1-(4-Isopropyl-phenyl)-1H-pyrrol-3-yl]-benzoic acid: m.p. 210-215° C. $^1$H NMR (400 MHz, CDCl$_3$): δ 8.30 (1H, s), 7.92 (1H, d, J=8 Hz), 7.80 (1H, d, J=8 Hz), 7.46 (1H, t, j=8 Hz), 7.44 (1H, s), 7.37 (2H, d, J=8 Hz), 7.31 (2H, d, J=8 Hz), 7.11 (1H, d, J=2 Hz), 6.69 (1H, d, J=2 Hz), 2.96 (1H, heptet, J=7 Hz), 1.29 (6H, d, J=7 Hz). MS (ES+): m/e 306 (100).

Compound 106

4-[1-(4-Isopropyl-phenyl)-1H-pyrrol-3-yl]-benzoic acid: m.p. 240-243° C. MS (ES+): m/e 306.35 (100). MS (ES−): m/e 304.26 (100).

Compound 125

3-[1-(4-Ethyl-phenyl)-1H-pyrrol-3-yl]-benzoic acid: m.p. 190-192° C. MS (ES+): m/e 292.36 (100). MS (ES−): m/e 290.37 (100).

Compound 126

4-[1-(4-Methoxy-phenyl)-1H-pyrrol-3-yl]-benzoic acid: m.p. 178-180° C. MS (ES+): m/e 294.26 (100). MS (ES−): m/e 292.26 (100).

Compound 127

4-[1-(3,4-Difluoro-phenyl)-1H-pyrrol-3-yl]-benzoic acid: m.p. 231-233° C. MS (ES+): m/e 300.27 (100). MS (ES−): m/e 298.27 (100).

Compound 128
4-[1-(3-Trifluoromethyl-phenyl)-1H-pyrrol-3-yl]-benzoic acid: m.p. 209-211° C. MS (ES+): m/e 332.34 (100). MS (ES−): m/e 330.35 (100).

Compound 129
4-[1-(4-Ethyl-phenyl)-1H-pyrrol-3-yl]-benzoic acid: m.p. 278-280° C. MS (ES+): m/e 292.34 (100). MS (ES−): m/e 290.31 (100).

Compound 130
4-(1-Phenyl-1H-pyrrol-3-yl)-benzoic acid: m.p. 239-241° C. MS (ES+): m/e 264.27 (100). MS (ES−): m/e 262.32 (100).

Compound 131
4-[1-(4-Trifluoromethoxy-phenyl)-1H-pyrrol-3-yl]-benzoic acid: m.p. 318-320° C. MS (ES+): m/e 348.30 (100). MS (ES−): m/e 346.33 (100).

Compound 150
4-[1-(2,3-Dihydro-benzo[1,4]dioxin-6-yl)-1H-pyrrol-3-yl]-benzoic acid: m.p. 273-276° C. MS (ES+): m/e 321.34 (100). MS (ES−): m/e 320.33 (100).

Compound 151
4-[1-(2-Fluoro-phenyl)-1H-pyrrol-3-yl]-benzoic acid: m.p. 202-204° C. MS (ES+): m/e 282.3 (100). MS (ES−): m/e 280.3 (100).

Compound 152
4-[1-(3-Fluoro-phenyl)-1H-pyrrol-3-yl]-benzoic acid: m.p. 211-213° C. MS (ES+): m/e 282.28 (100). MS (ES−): m/e 280.24 (100).

Compound 153
4-[1-(3,5-Difluoro-phenyl)-1H-pyrrol-3-yl]-benzoic acid: m.p. 243-245° C. MS (ES+): m/e 300.35 (100). MS (ES−): m/e 298.38 (100).

Compound 155
3-[1-(4-Chloro-phenyl)-1H-pyrrol-3-yl]-benzoic acid: m.p. 211-213° C. MS (ES+): m/e 282.28 (100). MS (ES−): m/e 280.24 (100).

Compound 156
3-(1-p-Tolyl-1H-pyrrol-3-yl)-benzoic acid: m.p. 178-181° C. MS (ES+): m/e 278.29 (100). MS (ES−): m/e 276.34 (100).

Compound 157
3-(1-m-Tolyl-1H-pyrrol-3-yl)-benzoic acid: m.p. 201-202° C. MS (ES+): m/e 348.32 (100). MS (ES−): m/e 346.32 (100).

Compound 158
3-[1-(4-Trifluoromethoxy-phenyl)-1H-pyrrol-3-yl]-benzoic acid: MS (ES+): m/e 348.32 (100). MS (ES−): m/e 346.32 (100).

Compound 159
4-(1-p-Tolyl-1H-pyrrol-3-yl)-benzoic acid: MS (ES+): m/e 278.35 (100). MS (ES−): m/e 276.37 (100).

Compound 160
4-[1-(2-Methoxy-phenyl)-1H-pyrrol-3-yl]-benzoic acid: m.p. 200-202° C. MS (ES+): m/e 294.32 (100). MS (ES−): m/e 292.36 (100).

Compound 194
4-(1-m-Tolyl-1H-pyrrol-3-yl)-benzoic acid: m.p. 212-213° C. MS (ES+): m/e 278.29 (100). MS (ES−): m/e 276.33 (100).

Compound 195
4-(1-o-Tolyl-1H-pyrrol-3-yl)-benzoic acid: m.p. 208-209° C. MS (ES+): m/e 278.30 (100). MS (ES−): m/e 276.33 (100).

Compound 196
4-[1-(4-Chloro-phenyl)-1H-pyrrol-3-yl]-benzoic acid: m.p. >350° C. MS (ES+): m/e 298.25 (100). MS (ES−): m/e 296.29 (100).

Compound 197
4-[1-(2-Chloro-phenyl)-1H-pyrrol-3-yl]-benzoic acid: m.p. 200-202° C. MS (ES+): m/e 298.25 (100). MS (ES−): m/e 296.30 (100).

Compound 198
3-[1-(2-Chloro-phenyl)-1H-pyrrol-3-yl]-benzoic acid: m.p. 198-200° C. MS (ES+): m/e 298.25 (100). MS (ES−): m/e 296.29 (100).

Compound 199
4-[1-(2-Trifluoromethoxy-phenyl)-1H-pyrrol-3-yl]-benzoic acid: m.p. 164-165° C. MS (ES+): m/e 348.24 (100). MS (ES−): m/e 346.34 (100).

Compound 200
3-[1-(2-Methoxy-phenyl)-1H-pyrrol-3-yl]-benzoic acid: m.p. >350° C. MS (ES+): m/e 294.28 (100). MS (ES−): m/e 292.35 (100).

Compound 240
3-(1-o-Tolyl-1H-pyrrol-3-yl)-benzoic acid: m.p. 161-163° C. MS (ES+): m/e 278.27 (100). MS (ES−): m/e 276.29 (100).

Compound 241
3-[1-(3-Fluoro-4-methyl-phenyl)-1H-pyrrol-3-yl]-benzoic acid: m.p. 205-208° C. MS (ES+): m/e 296.23 (100). MS (ES−): m/e 294.27 (100).

Compound 242
3-[1-(2,5-Difluoro-phenyl)-1H-pyrrol-3-yl]-benzoic acid: m.p. 193-194° C. MS (ES+): m/e 300.21 (100). MS (ES−): m/e 298.20 (100).

Compound 243
4-[1-(3-Chloro-phenyl)-1H-pyrrol-3-yl]-benzoic acid: m.p. 199-201° C. MS (ES+): m/e 298.19 (100). MS (ES−): m/e 296.27 (100).

Compound 244
4-[1-(3-Fluoro-4-methyl-phenyl)-1H-pyrrol-3-yl]-benzoic acid: m.p. 264-268° C. MS (ES+): m/e 296.23 (100). MS (ES−): m/e 294.23 (100).

Compound 245
4-[1-(2,5-Difluoro-phenyl)-1H-pyrrol-3-yl]-benzoic acid: m.p. 215-218° C. MS (ES+): m/e 300.21 (100). MS (ES−): m/e 298.20 (100).

Compound 246
3-[1-(3-Benzyloxy-phenyl)-1H-pyrrol-3-yl]-benzoic acid: m.p. 142-144° C. MS (ES+): m/e 370.28 (100). MS (ES−): m/e 368.26 (100).

Compound 247
3-(1-Benzo[1,3]dioxol-5-yl-1H-pyrrol-3-yl)-benzoic acid: m.p. 177-180° C. MS (ES+): m/e 308.26 (100). MS (ES−): m/e 306.24 (100).

B. Preparation of Imidazoles

Imidazoles of the invention may generally be prepared as follows.

Preparation of 3-[4-(4-Isopropyl-phenyl)-imidazol-1-yl]-benzoic acid (Compound 2)

Part A.

A solution of isopropylbenzene (50 g) in carbon disulfide (250 mL) is treated with aluminum chloride (170 g), and the resulting mixture is cooled to 0° C. Acetyl chloride (33 g) is added at the rate of 1 mL/min, and the resulting mixture is stirred overnight. The mixture is poured into aq. HCl (2N, 400 mL), and the layers are separated. The aqueous phase is extracted with ethyl acetate, and the organic phases are combined, washed with brine, dried over $Na_2SO_4$, filtered and concentrated to afford the product, 4-isopropylacetophenone, as an oil (66 g).

Part B.

A solution of 4-isopropylacetophenone (65 g) in ethyl acetate (250 mL) is cooled to 0° C. and treated with bromine (65 g) dropwise. The mixture is stirred for 5 h, then quenched by the addition of water (250 mL). The phases are separated, and the aqueous layer is extracted with ethyl acetate. The organic phases are washed with satd. aq. NaHCO$_3$ and brine, combined, dried over Na$_2$SO$_4$, filtered and evaporated to afford the product, 2-bromo-4'-isopropylacetophenone (64 g, 66%).

Part C.

A mixture of 2-bromo-4'-isopropylacetophenone (2.41 g) and formamide (10 mL) is heated to 180° C. for 1 h, then cooled, poured into water and extracted with ethyl acetate. The organic layer is washed with brine, dried over Na$_2$SO$_4$, filtered and evaporated. The residue is purified by column chromatography to afford the product, 4-(4-isopropyl-phenyl)-1H-imidazole, as a yellow solid (550 mg).

Part D.

A solution of 4-(4-isopropyl-phenyl)-1H-imidazole (190 mg), 3-carbomethoxy-phenylboronic acid (360 mg) and Cu(OAc)$_2$ (300 mg) in dichloromethane (15 mL) is treated with pyridine (160 mg) and 4 Å molecular sieves (500 mg). The mixture is stirred in the presence of air for 14 h then filtered through celite, and the celite pad is washed well with ethyl acetate. The filtrate and washing are combined and evaporated, and the residual material is separated by column chromatography to afford the product, methyl 3-[4-(4-isopropyl-phenyl)-imidazol-1-yl]-benzoate, as a yellow solid (190 mg).

Part E.

A solution of methyl 3-[4-(4-isopropyl-phenyl)-imidazol-1-yl]-benzoate (190 mg) in 5 mL methanol-1 mL water is treated with lithium hydroxide hydrate (125 g), and the resulting mixture is heated to reflux for 1 h. The solution is cooled and neutralized with acetic acid. The resulting precipitate is collected by filtration, washed with water, dried under vacuum and recrystallized from acetone to afford the title product as a white solid (90 mg). m.p. 248-250° C. $^1$H NMR (400 MHz, DMSO-d$_6$): δ 8.38 (1H, s), 8.31 (1H, s), 8.18 (1H, s), 7.97 (1H, d, J=8 Hz), 7.91 (1H, d. J=8 Hz), 7.78 (2H, d, J=8 Hz), 7.66 (1H, t, J=8 Hz), 7.24 (2H, d, J=8 Hz), 2.88 (1H, heptet, J=7 Hz), 1.20 (6H, d, J=7 Hz). MS (ES+): m/e 308 (21), 307 (100).

The methods described in the above example are employed (using appropriate starting materials) in the synthesis of the following compounds:

Compound 2

3-[1-(4-isopropyl-phenyl)-1H-imidazol-4-yl]-benzoic acid: m.p. 225-226° C. $^1$H NMR (400 MHz, DMSO-d$_6$): δ 12.94 (1H, br), 8.43 (1H, s), 8.35 (1H, s), 8.30 (1H, s), 8.06 (1H, d, J=8 Hz), 7.79 (1H, d, J=8 Hz), 7.63 (2H, d, J=8 Hz), 7.51 (1H, t, J=8 Hz), 7.39 (2H, d, J=8 Hz), 2.95 (1H, heptet, J=7 Hz), 1.22 (6H, d, J=7 Hz). MS (ES+): m/e 308 (18), 307 (100).

Compound 262

3-(4-Phenyl-imidazol-1-yl)-benzoic acid: m.p. 277-279° C. $^1$H NMR (300 MHz, DMSO-d$_6$): δ 13.33 (1H, br), 8.42 (1H, d, J=1.5 Hz), 8.39 (1H, d, J=1.5 Hz), 8.19 (1H, t, J=1.8 Hz), 7.98 (1H, ddd, J=8.2 2.3, 1.2 Hz), 7.91 (1H, dt, J=7.9, 1.2 Hz), 7.89-7.85 (2H, m), 7.66 (1H, t, J=7.9 Hz), 7.42-7.35 (2H, m), 7.26-7.20 (1H, m). MS (ES+): m/e 266 (44), 265 (100). MS (ES−): m/e 264 (18), 263 (100).

Compound 263

4-(4-Phenyl-imidazol-1-yl)-benzoic acid: m.p. 263-265° C. $^1$H NMR (300 MHz, DMSO-d$_6$): δ 13.11 (1H, br), 8.47 (1H, d, J=1.2 Hz), 8.40 (1H, d, J=1.2 Hz), 8.07 (2H, d, J=8.8 Hz), 7.89-7.84 (4H, m), 7.42-7.36 (2H, m), 7.27-7.21 (1H, m). MS (ES+): m/e 266 (37), 265 (100). MS (ES−): m/e 264 (19), 263 (100).

Preparation of 3-[2-amino-4-(4-isopropylphenyl)-1H-imidazol-1-yl]benzoic acid (Compound 1)

Part A.

To a suspension of methyl 3-aminobenzoate (4.76 g, 31.5 mmol) and K$_2$CO$_3$ (6.21 g, 45.0 mmol) in DMF (150 mL), is added α-bromo-4-isopropylacetophenone (7.23 g, 30.0 mmol). The mixture is stirred at room temperature for 24 hr. DMF is removed in vacuum and the residue is chromatographed to provide the amino ketone, methyl 3-{[2-(4-isopropylphenyl)-2-oxoethyl]amino}benzoate (2.15 g, 23%). (ES+): m/e 312.

Part B.

Methyl 3-{[2-(4-isopropylphenyl)-2-oxoethyl]amino}benzoate (0.62 g, 2.0 mmol) is refluxed with cyanamide (1.68 g, 40 mmol) in EtOH (15 mL) for 48 h, and the solvent is removed in vacuum. The residue is treated with water. The precipitate is collected by filtration, dried and chromatographed (silica gel, first with 1:4 ethyl acetate-hexanes, then 50:1 dichloromethane-methanol). The last fraction (0.26 g) is then treated with NaOH (1 N, 3.0 mL, 3.0 mmol) in THF (10 mL) at 65° C. overnight. After the removal of the solvent, the residue is treated with water and acidified with HCl (1 N). The precipitate is collected by filtration and washed with ethyl acetate thoroughly, dried to furnish desired product as a single component by LC/MS, 3-[2-amino-4-(4-isopropylphenyl)-1H-imidazol-1-yl]benzoic acid (0.13 g, 20%), m.p. 279-282° C. (decomp.). $^1$H NMR (CDCl$_3$, 300 MHz) δ (ppm) 1.27 (d, 6H), 2.87-2.97 (m, 1H), 4.36 (s, br, 2H), 7.01 (s, 1H), 7.21-7.26 (m, 3H), 7.59-7.69 (m, 3H), 8.05-8.12 (m, 2H). (ES+): m/e 322.

C. Preparation of 1,3-Pyrazoles 1,3-Pyrazoels of the invention may be prepared as follows.

Preparation of 3-[3-(4-Trifluoromethoxy-phenyl)-pyrazol-1-yl]-benzoic acid (Compound 95)

Part A.

A mixture of 4'-trifluoromethoxyacetophenone (1.50 g) and dimethylformamide dimethyl acetal (8.6 mL) is heated to 115° C. for 16 h, then cooled. Volatile components are evaporated, and the resulting brown oil is used directly in the next step. A solution of this material (1.90 g) and hydrazine hydrate (1.14 mL) in acetic acid (10 mL) is heated to 109° C. for 15 h, then cooled and poured into water (100 mL). This is extracted with ethyl acetate (2×100 mL), and the extracts are washed with brine, combined, dried over MgSO$_4$, filtered and evaporated to afford pure product, 3-(4-trifluoromethoxy-phenyl)-1H-pyrazole, as a solid; purity as determined by LC/MS 100%.

Part B.

A solution of 3-(4-trifluoromethoxy-phenyl)-1H-pyrazole (250 mg), 3-methoxycarbonylphenylboronic acid (540 mg) and pyridine (0.18 mL) in dimethylformamide (5 mL) is treated with copper (II) acetate (214 mg) and powdered activated 4 Å molecular sieves (0.5 g). The resulting mixture is heated to 60° C. for 16 h and cooled. The reaction mixture is poured into 1M aq. HCl (300 mL), and the resulting mixture is filtered through a glass microfiber filter pad. The pad is washed with ethyl acetate, and the filtrate is evaporated to afford the product, methyl 3-[3-(4-trifluoromethoxy-phenyl)-pyrazol-1-yl]-benzoate, as a solid (204 mg).

Part C.

A solution of methyl 3-[3-(4-trifluoromethoxy-phenyl)-pyrazol-1-yl]-benzoate (100 mg) and sodium hydroxide (0.58 mL, 1 M aq. solution) in ethanol (5 mL) is heated to reflux for 2 d. The mixture is cooled and evaporated, and the residual material is acidified with 1 M aq. HCl and extracted with ethyl acetate. The extract is washed with brine, dried over $MgSO_4$, filtered and evaporated to afford 91% pure (by LC/MS) title product (90 mg) as a powder, m.p. 191-194° C. $^1$H NMR (300 MHz, DMSO-$d_6$): δ 8.70 (1H, d, J=2.7 Hz), 8.44 (1H, t, J=1.9 Hz), 8.15 (1H, ddd, J=8.2, 2.4, 0.9 Hz), 8.05 (2H, d, J=8.8 Hz), 7.87 (1H, dt, J=7.7, 1.1 Hz), 7.64 (1H, t, J=8.0 Hz), 7.43 (2H, dd, J=8.8, 0.8 Hz), 7.11 (1H, d, J=2.7 Hz). MS (ES+): m/e 350 (20), 349 (100). MS (ES−): m/e 348 (20), 347 (100).

Slightly modified versions of this procedure may be used to prepare the following compounds.

Compound 78

3-[3-(3-Cyano-phenyl)-pyrazol-1-yl]-benzoic acid: m.p. 164-166° C. $^1$H NMR (300 MHz, DMSO-$d_6$): δ 8.73 (1H, d, J=2.5 Hz), 8.44 (1H, s), 8.37 (1H, s), 8.28 (1H, d, J=7.9 Hz), 8.17 (1H, dd, J=8.0, 2.2 Hz), 7.88 (1H, d, J=7.7 Hz), 7.82 (1H, d, J=7.7 Hz), 7.69-7.62 (2H, m), 7.22 (1H, d, J=2.7 Hz). MS (ES+): m/e 291 (20), 290 (100). MS (ES−): m/e 289 (20), 288 (100).

Compound 79

3-(3-Phenyl-pyrazol-1-yl)-benzoic acid: m.p. 180-182° C. $^1$H NMR (300 MHz, DMSO-$d_6$): δ 8.67 (1H, dd, J=2.5, 1.4 Hz), 8.43 (1H, m), 8.15 (1H, dt, J=8.2, 1.1 Hz), 7.94-7.91 (2H, m), 7.86 (1H, dd, J=7.7, 1.1 Hz), 7.63 (1H, t, J=8.0 Hz), 7.47-7.32 (3H, m), 7.06 (1H, d, J=2.7 Hz). MS (ES+): m/e 266 (20), 265 (100). MS (ES−): m/e 264 (20), 263 (100).

Compound 80

3-[3-(4-Chloro-phenyl)-pyrazol-1-yl]-benzoic acid: m.p. 230-235° C. $^1$H NMR (300 MHz, DMSO-$d_6$): δ 8.69 (1H, d, J=2.7 Hz), 8.43 (1H, narrow m), 8.16 (1H, dm, J=8 Hz), 7.96 (2H, d, J=8.5 Hz), 7.86 (1H, d, J=7.7 Hz), 7.64 (1H, t, J=8.0 Hz), 7.50 (2H, d, J=8.5 Hz), 7.10 (1H, d, J=2.5 Hz), MS (ES+): m/e 301 (35), 299 (100). MS (ES−): m/e 299 (35), 297 (100).

Compound 81

3-[3-(4-Methoxy-phenyl)-pyrazol-1-yl]-benzoic acid: m.p. 210-211° C. $^1$H NMR (300 MHz, DMSO-$d_6$): δ 8.63 (1H, d, J=2.5 Hz), 8.41 (1H, t, J=1.7 Hz), 8.13 (1H, dm, J=8 Hz), 7.85 (2H, d, J=8.8 Hz), 7.84-7.80 (1H, m), 7.62 (1H, t, J=8.0 Hz), 7.00 (2H, d, J=8.8 Hz), 6.98 (1H, d, J=2.5 Hz), 3.78 (3H, s). MS (ES+): m/e 296 (20), 295 (100). MS (ES−): m/e 294 (20), 293 (100).

Compound 82

3-[3-(4-Morpholin-4-yl-phenyl)-pyrazol-1-yl]-benzoic acid: m.p. 230-235° C. $^1$H NMR (300 MHz, DMSO-$d_6$): δ 8.61 (1H, dd, J=2.6, 1.0 Hz), 8.41 (1H, s), 8.12 (1H, dt, J=8.2, 1.2 Hz), 7.83 (1H, d, J=8 Hz), 7.80 (2H, d, J=8.2 Hz), 7.61 (1H, t, J=8.0 Hz), 7.07 (2H, d, J=8.2 Hz), 6.96 (1H, dd, J=2.3, 1.5 Hz), 3.76 (4H, br), 3.19 (4H, br), MS (ES+): m/e 351 (20), 350 (100). MS (ES−): m/e 349 (20), 348 (100).

Compound 92

3-[3-(4-Fluoro-phenyl)-pyrazol-1-yl]-benzoic acid: m.p. 237-240° C. $^1$H NMR (300 MHz, DMSO-$d_6$): δ 8.67 (1H, d, J=2.7 Hz), 8.43 (1H, t, J=1.9 Hz), 8.14 (1H, ddd, J=7.0, 2.5, 1.4 Hz), 7.97 (2H, dd, J=8.8, 5.5 Hz), 7.85 (1H, dt, J=6.6, 1.1 Hz), 7.63 (1H, t, J=7.8 Hz), 7.28 (2H, t, J=8.8 Hz), 7.06 (1H, d, J=2.5 Hz). MS (ES+): m/e 284 (20), 283 (100). MS (ES−): m/e 282 (20), 281 (100).

Compound 93

3-[3-(3-Fluoro-phenyl)-pyrazol-1-yl]-benzoic acid: m.p. 173-174° C. $^1$H NMR (300 MHz, DMSO-$d_6$): δ 8.70 (1H, d, J=2.5 Hz), 8.42 (1H, t, J=1.8 Hz), 8.16 (1H, ddd, J=8.2, 2.4, 1.1 Hz), 7.87 (1H, dt, J=7.7, 1.2 Hz), 7.79 (1H, dt, J=7.9, 1.1 Hz), 7.73 (1H, ddd, J=10.3, 2.5, 1.4 Hz), 7.64 (1H, t, J=8.0 Hz), 7.51 (1H, dt, J=8.3, 6.1 Hz), 7.19 (1H, ddt, J=8, 2, 1 Hz), 7.14 (1H, d, J=2.6 Hz). MS (ES+): m/e 284 (20), 283 (100). MS (ES−): m/e 282 (20), 281 (100).

Compound 97

3-[3-(4-Trifluoromethyl-phenyl)-pyrazol-1-yl]-benzoic acid: m.p. 225-227° C. $^1$H NMR (300 MHz, DMSO-$d_6$): δ 8.74 (1H, d, J=2.5 Hz), 8.46 (1H, t, J=1.9 Hz), 8.20-8.1.4 (3H, m), 7.88 (1H, d, J=7.7 Hz), 7.80 (2H, d, J=8.8 Hz), 7.65 (1H, t, J=8.0 Hz), 7.21 (1H, d, J=2.5 Hz). MS (ES+): m/e 334 (20), 333 (100). MS (ES−): m/e 332 (20), 331 (100).

Compound 5

3-[3-(4-Isopropyl-phenyl)-pyrazol-1-yl]-benzoic acid: m.p. 215-216° C. $^1$H NMR (400 MHz, DMSO-$d_6$): δ 13.26 (1H, br), 8.65 (1H, d, J=2 Hz), 8.43 (1H, s), 8.13 (1H, d, J=8 Hz), 7.87-7.82 (3H, m), 7.63 (1H, t, J=8 Hz), 7.30 (2H, d, J=8 Hz), 7.01 (1H, d, J=2 Hz), 2.90 (1H, heptet, J=7 Hz), 1.20 (6H, d, J=7 Hz). MS (ES+): m/e 308 (22), 307 (100).

Compound 137

3-(4,5-Dihydro-benzo[g]indazol-2-yl)-benzoic acid: m.p. 191-192° C. $^1$H NMR (300 MHz, DMSO-$d_6$): δ 13.25 (1H, br s), 8.44-8.39 (2H, m), 8.11-8.06 (1H, m), 7.84-7.80 (2H, m), 7.61 (1H, dt, J=7.9, 4.1 Hz), 7.32-7.22 (3H, m), 2.92-2.87 (2H, m), 2.83-2.78 (2H, m). MS (ES+): m/e 292 (20), 291 (100). MS (ES−): m/e 290 (21), 289 (100).

Compound 138

3-(4H-Indeno[1,2-c]pyrazol-2-yl)-benzoic acid: m.p. 249-250° C. $^1$H NMR (300 MHz, DMSO-$d_6$): δ 13.24 (1H, br), 8.54 (1H, s), 8.44 (1H, t, J=1.8 Hz), 8.12 (1H, dd, J=8.0, 2.1 Hz), 7.82 (1H, d, J=7.6 Hz), 7.78 (1H, dd, J=7.9, 1.2 Hz), 7.61 (1H, t, J=7.9 Hz), 7.57 (1H, d, J=7.6 Hz), 7.42-7.32 (2H, m), 3.76 (2H, s). MS (ES+): m/e 278 (18), 277 (100). MS (ES−): m/e 276 (20), 275 (100).

Compound 139

3-(6-Methoxy-4H-indeno[1,2-c]pyrazol-2-yl)-benzoic acid: m.p. 272-273° C. $^1$H NMR (300 MHz, DMSO-$d_6$): δ 13.16 (1H, br), 8.47 (1H, s), 8.41 (1H, s), 8.08 (1H, dd, J=8.1, 2.0 Hz), 7.80 (1H, d, J=7.6 Hz), 7.67 (1H, d, J=8.5 Hz), 7.59 (1H, t, J=7.9 Hz), 7.17 (1H, d, J=2.0 Hz), 6.95 (1H, dd, J=8.5, 2.3 Hz), 3.80 (3H, s), 3.72 (2H, s). MS (ES+): m/e 308 (20), 307 (100). MS (ES−): m/e 306 (21), 305 (100).

Compound 140

3-(7-Methoxy-4H-indeno[1,2-c]pyrazol-2-yl)-benzoic acid: m.p. 225-227° C. $^1$H NMR (300 MHz, DMSO-$d_6$): δ 13.25 (1H, br), 8.52 (1H, s), 8.45 (1H, s), 8.11 (1H, ddd, J=8.2, 2.4, 1.2 Hz), 7.82 (1H, d, J=7.6 Hz), 7.61 (1H, t, J=7.9 Hz), 7.45 (1H, d, J=8.5 Hz), 7.34 (1H, d, J=2.3 Hz), 6.90 (1H, dd, J=8.5, 2.3 Hz), 3.82 (3H, s), 3.67 (2H, s). MS (ES+): m/e 308 (20), 307 (100). MS (ES−): m/e 306 (18), 305 (100).

Compound 142

3-(7-Methoxy-4,5-dihydro-benzo[g]indazol-2-yl)-benzoic acid: m.p. 217-218° C. $^1$H NMR (300 MHz, DMSO-$d_6$): δ 13.23 (1H, br), 8.38 (1H, s), 8.37 (1H, d, J=2 Hz), 8.06 (1H, dd, J=8.2, 2.0 Hz), 7.80 (1H, d, J=7.6 Hz), 7.74 (1H, d, J=8.5 Hz), 7.59 (1H, t, J=7.9 Hz), 6.91-6.84 (2H, m), 3.77 (3H, s), 2.92-2.86 (2H, m), 2.78-2.72 (2H, m). MS (ES+): m/e 322 (20), 321 (100). MS (ES−): m/e 320 (21), 319 (100).

Compound 143

3-(8-Methoxy-4,5-dihydro-benzo[g]indazol-2-yl)-benzoic acid: m.p. 192-193° C. $^1$H NMR (300 MHz, DMSO-$d_6$): δ 13.25 (1H, br), 8.43 (1H, br), 8.38 (1H, t, J=1.8 Hz), 8.09 (1H, dd, J=8.2, 2.3 Hz), 7.83 (1H, d, J=7.6 Hz), 7.61 (1H, t, J=7.9 Hz), 7.33 (1H, d, J=3.0 Hz), 7.22 (1H, d, J=8.5 Hz), 6.83 (1H, dd, J=8.5, 3.0 Hz), 3.80 (3H, s), 2.87-2.82 (2H, m), 2.77-2.72 (2H, m). MS (ES+): m/e 322 (18), 321 (100). MS (ES−): m/e 320 (24), 319 (100).

Compound 144

3-(4H-Chromeno[4,3-c]pyrazol-2-yl)-benzoic acid: m.p. 227-228° C. $^1$H NMR (300 MHz, DMSO-d$_6$): δ 13.29 (1H, br), 8.49 (1H, s), 8.39 (1H, t, J=1.9 Hz), 8.09 (1H, dd, J=8.2, 2.3 Hz), 7.86 (1H, d, J=7.6 Hz), 7.76 (1H, dd, J=7.4, 1.6 Hz), 7.63 (1H, t, J=7.9 Hz), 7.26 (1H, dt, J=8.0, 1.8 Hz), 7.07-6.96 (2H, m), 5.33 (2H, s). MS (ES+): m/e 294 (17), 293 (100). MS (ES−): m/e 292 (18), 291 (100).

Compound 145

4-(8-Methoxy-4,5-dihydro-benzo[g]indazol-2-yl)-benzoic acid: m.p. 290-292° C. $^1$H NMR (300 MHz, DMSO-d$_6$): δ 12.98 (1H, br), 8.45 (1H, s), 8.04 (2H, d, J=8.8 Hz), 7.98 (2H, d, J=8.8 Hz), 7.34 (1H, d, J=2.9 Hz), 7.23 (1H, d, J=8.5 Hz), 6.84 (1H, dd, J=8.5, 2.9 Hz), 3.79 (3H, s), 2.86-2.81 (2H, m), 2.78-2.73 (2H, m) MS (ES+): m/e 323 (4), 322 (22), 321 (100). MS (ES−): m/e 319 (100).

Compound 147

3-(6-Methoxy-4,5-dihydro-benzo[g]indazol-2-yl)-benzoic acid: m.p. 232-233° C. $^1$H NMR (300 MHz, DMSO-d$_6$): δ 13.25 (1H, br), 8.42 (1H, s), 8.39 (1H, t, J=1.9 Hz), 8.08 (1H, dd, J=8.0, 2.2 Hz), 7.82 (1H, d, J=7.6 Hz), 7.61 (1H, t, J=7.9 Hz), 7.46 (1H, d, J=7.6 Hz), 7.27 (1H, t, J=8.0 Hz), 6.96 (1H, d, J=8.2 Hz), 3.81 (3H, s), 2.90-2.85 (2H, m), 2.77-2.72 (2H, m). MS (ES+): m/e 322 (19), 321 (100). MS (ES−): m/e 320 (18), 319 (100).

Compound 148

4-(6-Methoxy-4,5-dihydro-benzo[g]indazol-2-yl)-benzoic acid: m.p. 288-290° C. $^1$H NMR (300 MHz, DMSO-d$_6$): δ 12.97 (1H, br), 8.44 (1H, s), 8.03 (2H, d, J=8.8 Hz), 7.97 (2H, d, J=8.8 Hz), 7.46 (1H, d, J=7.3 Hz), 7.28 (1H, t, J=7.9 Hz), 6.97 (1H, d, J=8.2 Hz), 3.81 (3H, s), 2.90-2.85 (2H, m), 2.78-2.73 (2H, m). MS (ES+): m/e 323 (3), 322 (20), 321 (100).

Compound 149

4-(7-Methoxy-4H-indeno[1,2-c]pyrazol-2-yl)-benzoic acid: m.p. 304-306° C. $^1$H NMR (300 MHz, DMSO-d$_6$): δ 12.95 (1H, br), 8.55 (1H, s), 8.04 (2H, d, J=9.0 Hz), 8.00 (2H, d, J=9.0 Hz), 7.46 (1H, d, J=8.4 Hz), 7.30 (1H, d, J=2.4 Hz), 6.92 (1H, dd, J=8.4, 2.4 Hz), 3.82 (3H, s), 3.67 (2H, s). MS (ES+): m/e 308 (20), 307 (100).

Compound 161

4-(4,5-Dihydro-benzo[g]indazol-2-yl)-benzoic acid: m.p. 288-290° C. $^1$H NMR (300 MHz, DMSO-d$_6$): δ 12.98 (1H, br), 8.45 (1H, s), 8.04 (2H, d, J=8.8 Hz), 7.98 (2H, d, J=8.8 Hz), 7.82 (1H, dd, J=7.6, 2.0 Hz), 7.34-7.26 (3H, m), 2.95-2.90 (2H, m), 2.81-276 (2H, m). MS (ES+): m/e 292 (15), 291 (100). MS (ES−): m/e 290 (20), 289 (100).

Compound 162

4-(4H-Chromeno[4,3-c]pyrazol-2-yl)-benzoic acid: m.p. 308-310° C. $^1$H NMR (300 MHz, DMSO-d$_6$): δ 13.03 (1H, br), 8.50 (1H, s), 8.05 (2H, d, J=8.8 Hz), 7.98 (2H, d, J=8.8 Hz), 7.74 (1H, dd, J=7.5, 1.6 Hz), 7.27 (1H, dt, J=7.8, 1.8 Hz), 7.05 (1H, dt, J=7.3, 1.2 Hz), 6.99 (1H, d, J=8.2 Hz), 5.34 (2H, s). MS (ES+): m/e 294 (16), 293 (100). MS (ES−): m/e 292 (22), 291 (100).

Compound 163

4-(7-Methoxy-4,5-dihydro-benzo[g]indazol-2-yl)-benzoic acid: m.p. 279-280° C. $^1$H NMR (300 MHz, DMSO-d$_6$): δ 12.94 (1H, br), 8.41 (1H, s), 8.02 (2H, d, J=8.8 Hz), 7.95 (2H, d, J=8.8 Hz), 7.74 (1H, d, J=8.2 Hz), 6.91 (1H, d, J=2.6 Hz), 6.87 (1H, dd, J=8.2, 2.6 Hz), 3.77 (3H, s), 2.92-2.87 (2H, m), 2.79-2.74 (2H, m). MS (ES+): m/e 322 (20), 321 (100). MS (ES−): m/e 320 (20), 319 (100).

Compound 169

3-[3-(2-Fluoro-phenyl)-pyrazol-1-yl]-benzoic acid: m.p. 166-167° C. $^1$H NMR (300 MHz, DMSO-d$_6$): δ 8.73 (1H, d, J=2.5 Hz), 8.44 (1H, t, J=1.9 Hz), 8.17 (1H, ddd, J=8.2, 2.3, 1.1 Hz), 8.06 (1H, dt, J=7.7, 1.9 Hz), 7.88 (1H, dt, J=7.7, 1 Hz), 7.65 (1H, t, J=7.8 Hz), 7.44-7.27 (3H, m), 6.93 (1H, dd, J=3.9, 2.8 Hz). MS (ES+): m/e 284 (20), 283 (100). MS (ES−): m/e 282 (20), 281 (100).

Compound 170

3-(3-p-Tolyl-pyrazol-1-yl)-benzoic acid: m.p. 180-182° C. $^1$H NMR (300 MHz, DMSO-d$_6$): δ 13.12 (1H, br), 8.54 (1H, d, J=2.5 Hz), 8.47 (1H, t, J=1.8 Hz), 8.13 (1H, dt, J=7.9, 1.8 Hz), 7.90 (1H, dt, J=7.9, 1.3 Hz), 7.80 (2H, d, J=8.5 Hz), 7.57 (1H, t, J=7.8 Hz), 7.31 (2H, d, J=8.5 Hz), 7.09 (1H, d, J=2.5 Hz), 2.34 (3H, s). MS (ES+): m/e 280 (14), 279 (100). MS (ES−): m/e 278 (19), 277 (100).

Compound 219

4-[3-(4-Methoxy-phenyl)-pyrazol-1-yl]-benzoic acid: m.p. 268-270° C. $^1$H NMR (300 MHz, DMSO-d$_6$): δ 8.65 (1H, d, J=2.5 Hz), 8.05 (2H, d, J=9.1 Hz), 8.01 (2H, d, J=9.1 Hz), 7.87 (2H, d, J=8.5 Hz), 7.02 (1H, d, J=2.5 Hz), 7.01 (2H, d, J=8.5 Hz), 3.79 (3H, s). MS (ES+): m/e 296 (20), 295 (100). MS (ES−): m/e 294 (23), 293 (100).

Compound 220

3-[3-(3-Methoxy-phenyl)-pyrazol-1-yl]-benzoic acid: m.p. 179-180° C. $^1$H NMR (300 MHz, DMSO-d$_6$): δ 8.67 (1H, d, J=2.5 Hz), 8.42 (1H, s), 8.15 (1H, dm, J=8.0 Hz), 7.86 (1H, d, J=7.7 Hz), 7.64 (1H, t, J=7.8 Hz), 7.51 (1H, d, J=7.7 Hz), 7.46 (1H, s), 7.36 (1H, t, J=7.9 Hz), 7.08 (1H, d, J=2.5 Hz), 6.93 (1H, dd, J=8.2, 2.5 Hz), 3.82 (3H, s). MS (ES+): m/e 296 (20), 295 (100). MS (ES−): m/e 294 (20), 293 (100).

Compound 221

4-[3-(3-Methoxy-phenyl)-pyrazol-1-yl]-benzoic acid: m.p. 200-202° C. $^1$H NMR (300 MHz, DMSO-d$_6$): δ 8.69 (1H, d, J=2.5 Hz), 8.05 (4H, s), 7.52 (1H, dd, J=7.7, 1 Hz), 7.48 (1H, dd, J=2.6, 1 Hz), 7.37 (1H, t, J=7.9 Hz), 7.12 (1H, d, J=2.5 Hz), 6.94 (1H, dd, J=7.5, 2.6 Hz), 3.82 (3H, s). MS (ES+): m/e 296 (20), 295 (100). MS (ES−): m/e 294 (20), 293 (100).

Compound 222

4-(3-Phenyl-pyrazol-1-yl)-benzoic acid: m.p. 244-245° C. $^1$H NMR (300 MHz, DMSO-d$_6$): δ 8.69 (1H, d, J=2.5 Hz), 8.05 (4H, s), 7.96-7.92 (2H, m), 7.48-7.36 (3H, m), 7.11 (1H, d, J=2.5 Hz). MS (ES+): m/e 266 (20), 265 (100). MS (ES−): m/e 264 (20), 263 (100).

D. Preparation of 1,4-Pyrazoles 1,4 Pyrazoles of the invention may be prepared as follows.

Preparation of 3-[4-(4-Methoxy-phenyl)-pyrazol-1-yl]-benzoic acid (Compound 47)

A solution of 3-hydrazinobenzoic acid (300 mg, 1.97 mmol) and 4-methoxyphenylmalondialdehyde (351 mg, 1.97 mmol) in 4 mL acetic acid is heated for 20 h at 110° C. After being allowed to cool, the solution developed a tan precipitate, which is collected by filtration and washed with ethyl acetate and diethyl ether. The powder is dried under vacuum to afford the title compound (429 mg, 1.46 mmol, 74%). m.p. 238-239° C. $^1$H NMR (300 MHz, DMSO-d$_6$): δ 13.26 (1H, s), 9.02 (1H, s), 8.41 (1H, s), 8.17 (1H, s), 8.12 (1H, d, J=7.9 Hz), 7.85 (1H, d, J=7.9 Hz), 7.65 (2H, d, J=8.5 Hz), 7.64 (1H, t, J=7.9 Hz), 6.96 (2H, d, J=8.5 Hz), 3.76 (3H, s). MS (ES+): m/e 296 (18), 295 (100). MS (ES−): m/e 294 (17), 293 (100).

The following compounds may be prepared following a similar procedure as just described.

Compound 48

3-(4-p-Tolyl-pyrazol-1-yl)-benzoic acid: m.p. 208-209° C. $^1$H NMR (300 MHz, DMSO-d$_6$): δ 13.26 (1H, s), 9.08 (1H, s), 8.42 (1H, s), 8.21 (1H, s), 8.12 (1H, d, J=8.2 Hz), 7.85 (1H, d, J=7.7 Hz), 7.63 (1H, t, J=8 Hz), 7.62 (2H, d, J=8.2 Hz), 7.20 (2H, d, J=8.2 Hz), 2.30 (3H, s). MS (ES+): m/e 280 (18), 279 (100). MS (ES−): m/e 278 (17), 277 (100).

Compound 49

3-[4-(4-Chloro-phenyl)-pyrazol-1-yl]-benzoic acid: m.p. 253-254° C. $^1$H NMR (300 MHz, DMSO-d$_6$): δ 13.28 (1H, s), 9.17 (1H, s), 8.42 (1H, s), 8.27 (1H, s), 8.11 (1H, dd, J=8.0, 1.3 Hz), 7.86 (1H, d, J=7.7 Hz), 7.76 (2H, d, J=8.2 Hz), 7.63 (1H, t, J=8.0 Hz), 7.44 (2H, d, J=8.2 Hz). MS (ES+): m/e 301 (35), 300 (19), 299 (100). MS (ES−): m/e 299 (40), 298 (17), 297 (100).

Compound 50

4-[4-(4-Methoxy-phenyl)-pyrazol-1-yl]-benzoic acid: m.p. 289-290° C. $^1$H NMR (300 MHz, DMSO-d$_6$): δ 13.02 (1H, s), 9.00 (1H, s), 8.20 (1H, s), 8.06 (2H, d, J=8.4 Hz), 7.99 (2H, d, J=8.4 Hz), 7.64 (2H, d, J=8.5 Hz), 6.96 (2H, d, J=8.5 Hz), 3.76 (3H, s). MS (ES+): m/e 296 (16), 295 (100). MS (ES−): m/e 294 (19), 293 (100).

Compound 51

4-(4-p-Tolyl-pyrazol-1-yl)-benzoic acid: m.p. 298-299° C. $^1$H NMR (300 MHz, DMSO-d$_6$): δ 13.02 (1H, s), 9.07 (1H, s), 8.25 (1H, s), 8.06 (2H, d, J=8.8 Hz), 8.00 (2H, d, J=8.8 Hz), 7.61 (2H, d, J=8.2 Hz), 7.20 (2H, d, J=8.2 Hz), 2.30 (3H, s). MS (ES+): m/e 280 (20), 279 (100). MS (ES−): m/e 278 (14), 277 (100).

Compound 52

4-[4-(4-Chloro-phenyl)-pyrazol-1-yl]-benzoic acid: m.p. 300-302° C. $^1$H NMR (300 MHz, DMSO-d$_6$): δ 13.03 (1H, s), 9.14 (1H, s), 8.29 (1H, s), 8.06 (2H, d, J=8.8 Hz), 7.98 (2H, d, J=8.8 Hz), 7.73 (2H, d, J=8.5 Hz), 7.44 (2H, d, J=8.5 Hz). MS (ES+): m/e 301 (35), 300 (16), 299 (100). MS (ES−): m/e 299 (39), 298 (18), 297 (100).

Compound 113

3-(4-Pyridin-2-yl-pyrazol-1-yl)-benzoic acid: m.p. 243-245° C. $^1$H NMR (300 MHz, DMSO-d$_6$): δ 9.29 (1H, s), 8.58 (1H, d, J=5.0 Hz), 8.44 (1H, t, J=1.8 Hz), 8.38 (1H, s), 8.17 (1H, dd, J=8.0, 1.3 Hz), 7.90-7.87 (3H, m), 7.65 (1H, t, J=7.9 Hz), 7.30 (1H, q, J=4.4 Hz). MS (ES+): m/e 267 (24), 266 (100). MS (ES−): m/e 265 (19), 264 (100).

Compound 114

4-(4-Pyridin-2-yl-pyrazol-1-yl)-benzoic acid: m.p. 260-262° C. $^1$H NMR (300 MHz, DMSO-d$_6$): δ 9.39 (1H, s), 8.61 (1H, dd, J=5.0, 0.6 Hz), 8.50 (1H, s), 8.10-7.95 (6H, m), 7.40 (1H, dt, J=6.0, 1.5 Hz). MS (ES+): m/e 267 (29), 266 (100). MS (ES−): m/e 265 (18), 264 (100).

Compound 115

3-(4-Pyridin-4-yl-pyrazol-1-yl)-benzoic acid: m.p. 300-302° C. $^1$H NMR (300 MHz, DMSO-d$_6$): δ 9.37 (1H, s), 8.55 (2H, d, J=5.0 Hz), 8.43 (2H, s), 8.14 (1H, dd, J=8.2, 1.5 Hz), 7.89 (1H, d, J=7.6 Hz), 7.73 (2H, d, J=6.1 Hz), 7.66 (1H, t, J=7.9 Hz). MS (ES+): m/e 267 (21), 266 (100). MS (ES−): m/e 265 (18), 264 (100).

Compound 116

4-(4-Pyridin-4-yl-pyrazol-1-yl)-benzoic acid: m.p. >350° C. $^1$H NMR (300 MHz, DMSO-d$_6$): δ 9.36 (1H, s), 8.56 (2H, d, J=6.2 Hz), 8.46 (1H, s), 8.09 (2H, d, J=8.8 Hz), 8.02 (2H, d, J=8.8 Hz), 7.71 (2H, d, J=6.2 Hz). MS (ES+): m/e 267 (30), 266 (100). MS (ES−): m/e 265 (17), 264 (100).

Compound 117

3-(4-Pyrimidin-4-yl-pyrazol-1-yl)-benzoic acid: m.p. 297-299° C. $^1$H NMR (300 MHz, DMSO-d$_6$): δ 12.95 (1H, br), 9.45 (1H, s), 9.12 (1H, d, J=1.2 Hz), 8.77 (1H, d, J=5.2 Hz), 8.47 (1H, s), 8.45 (1H, t, J=1.8 Hz), 8.18 (1H, ddd, J=8.2, 2.3, 0.9 Hz), 7.94-7.89 (2H, m), 7.66 (1H, t, J=7.9 Hz). MS (ES+): m/e 268 (15), 267 (100). MS (ES−): m/e 266 (18), 265 (100).

Compound 118

4-(4-Pyrimidin-4-yl-pyrazol-1-yl)-benzoic acid: m.p. >350° C. $^1$H NMR (300 MHz, DMSO-d$_6$): δ 9.44 (1H, s), 9.13 (1H, dd, J=4, 1.4 Hz), 8.79 (1H, t, J=4.5 Hz), 8.51 (1H, s), 8.07 (4H, s), 7.90 (1H, m). MS (ES+): m/e 268 (17), 267 (100). MS (ES−): m/e 266 (15), 265 (100).

Compound 119

3-(4-Pyrazin-2-yl-pyrazol-1-yl)-benzoic acid: m.p. 310-311° C. $^1$H NMR (300 MHz, DMSO-d$_6$): δ 13.31 (1H, br), 9.38 (1H, s), 9.13 (1H, d, J=1.4 Hz), 8.60 (1H, dd, J=2.5, 1.6 Hz), 8.48-8.42 (3H, m), 8.17 (1H, dt, J=7.9, 1.1 Hz), 7.90 (1H, dd, J=6.4, 1.2 Hz), 7.66 (1H, t, J=7.9 Hz). MS (ES+): m/e 268 (13), 267 (100). MS (ES−): m/e 266 (15), 265 (100).

Compound 120

4-(4-Pyrazin-2-yl-pyrazol-1-yl)-benzoic acid: m.p. 319-321° C. $^1$H NMR (300 MHz, DMSO-d$_6$): δ 13.08 (1H, br), 9.37 (1H, s), 9.12 (1H, d, J=1.6 Hz), 8.62 (1H, dd, J=2.5, 1.6 Hz), 8.49 (1H, d, J=2.5 Hz), 8.47 (1H, s), 8.08 (2H, d, J=9.0 Hz), 8.05 (2H, d, J=9.0 Hz). MS (ES−): m/e 268 (11), 267 (100). MS (ES−): m/e 266 (13), 265 (100).

Compound 121

3-(4-Benzooxazol-2-yl-pyrazol-1-yl)-benzoic acid: m.p. 331-333° C. $^1$H NMR (300 MHz, DMSO-d$_6$): δ 13.31 (1H, br), 9.48 (1H, s), 8.49 (1H, t, J=1.9 Hz), 8.46 (1H, s), 8.23 (1H, dd, J=8.1, 2.3 Hz), 7.93 (1H, d, J=7.9 Hz), 7.77-7.71 (2H, m), 7.67 (1H, t, J=7.9 Hz), 7.42-7.34 (2H, m). MS (ES+): m/e 307 (19), 306 (100). MS (ES−): m/e 305 (22), 304 (100).

Compound 122

3-(4-Quinoxalin-2-yl-pyrazol-1-yl)-benzoic acid: m.p. 325-326° C. $^1$H NMR (300 MHz, DMSO-d$_6$): δ 13.32 (1H, br), 9.60 (1H, s), 9.46 (1H, s), 8.59 (1H, s), 8.49 (1H, t, J=1.8 Hz), 8.22 (1H, dt, J=7.9, 1.2 Hz), 8.08-8.03 (2H, m), 7.92 (1H, dt, J=7.7, 1.6 Hz), 7.87-7.75 (2H, m), 7.69 (1H, t, J=7.9 Hz). MS (ES+): m/e 318 (20), 317 (100). MS (ES−): m/e 316 (22), 315 (100).

Compound 123

3-(4-Quinolin-2-yl-pyrazol-1-yl)-benzoic add: m.p. 250-252° C. $^1$H NMR (300 MHz, DMSO-d$_6$): δ 9.44 (1H, s), 8.51 (1H, s), 8.49 (1H, t, J=1.8 Hz), 8.41 (1H, d, J=8.8 Hz), 8.22 (1H, dt, J=6.7, 1.0 Hz), 8.04 (1H, d, J=8.5 Hz), 8.00 (1H, d, J=8.4 Hz), 7.92 (1H, dt, J=8.2, 1.0 Hz), 7.74 (1H, dt, J=7.8, 1.5 Hz), 7.67 (1H, t, J=7.9 Hz), 7.54 (1H, di, J=7.9, 1.1 Hz). MS (ES+): m/e 317 (37), 316 (100). MS (ES−): m/e 315 (18), 314 (100).

Preparation of 3-[4-(2-Fluoro-phenyl)-pyrazol-1-yl]-benzoic acid (Compound 84)

Part A.

A flask containing phosphorus oxychloride (3.25 mL, 34.9 mmol) is cooled to ca. 10° C., and dimethylformamide (3.25 mL) is added dropwise. After stirring for 30 min, the resulting mixture is treated dropwise with a solution of 2-fluorophenylacetic acid (1.79 g, 11.6 mmol) in dimethylformamide (6 mL). This solution is heated to 70° C. for 18 h, then cooled and poured into ice. After being allowed to melt, the mixture is neutralized with solid NaHCO$_3$, and then made basic with 50% aq. NaOH solution. After stirring for 1 h, the mixture is extracted twice with diethyl ether (100 mL), and the ether extracts are washed with brine, combined, dried over anhydrous magnesium sulfate, filtered and evaporated to afford 3-dimethylamino-2-(2-fluorophenyl)-acrolein (1.72 g, 8.92 mmol, 77%) as a yellow-brown oil. TLC R$_F$ 0.30 (ethyl acetate). $^1$H NMR (300 MHz, CDCl$_3$): δ 9.08 (1H, s), 7.29-

7.19 (2H, m), 7.14-7.01 (2H, m), 6.91 (1H, s), 2.88 (6H, br). MS (ES+): m/e 216 (18), 195 (23), 194 (100).

Part B.

A solution of 3-dimethylamino-2-(2-fluorophenyl)-acrolein (812 mg, 4.20 mmol) and 3-hydrazinobenzoic acid (639 mg, 4.20 mmol) in acetic acid (8 mL) is heated to 110° C. for 18 h and cooled. The resulting tan-colored precipitate is collected by filtration, washed with ethyl acetate and diethyl ether, and dried under vacuum to afford the title product as a powder (833 mg, 2.95 mmol, 70%). m.p. 225-226° C. $^1$H NMR (300 MHz, acetone-$d_6$): δ 8.90 (1H, dd, J=1.5, 0.6 Hz), 8.55 (1H, t, J=1.8 Hz), 8.21 (1H, dd, J=2.0, 0.6 Hz), 8.18 (1H, ddd, J=8.1 2.4, 1.1 Hz), 7.98 (1H, ddd, J=7.9 1.6, 1.0 Hz), 7.90-7.83 (1H, m), 7.65 (1H, t, j=7.7 Hz), 7.35-7.20 (3H, m), 1H missing. MS (ES+): m/e 285 (2), 284 (18), 283 (100).

This procedure may be adapted to prepare the following compounds.

Compound 85

4-[4-(2-Fluoro-phenyl)-pyrazol-1-yl]-benzoic acid: m.p. 260-261° C. $^1$H NMR (300 MHz, acetone-$d_6$): δ 8.97 (1H, dd, J=1.5, 0.6 Hz), 8.25 (1H, dd, J=2.0, 0.6 Hz), 8.15 (2H, d, J=9.4 Hz), 8.09 (2H, d, J=9.4 Hz), 7.91-7.85 (1H, m), 7.38-7.23 (3H, m), 1H missing. MS (ES−): m/e 282 (20), 281 (100).

Compound 88

3-[4-(3-Bromo-phenyl)-pyrazol-1-yl]-benzoic acid: m.p. 177-178° C. $^1$H NMR (300 MHz, DMSO-$d_6$): δ 9.24 (1H, s), 8.43 (1H, s), 832 (1H, s), 8.13 (1H, dd, J=8.5, 0.5 Hz), 8.00 (1H, s), 7.87 (1H, d, =7.6 Hz), 7.75 (1H, d, J=7.6 Hz), 7.64 (1H, t, J=7.9 Hz), 7.42 (1H, d, J=8.2 Hz), 7.34 (1H, t, J=7.7 Hz), 1H missing. MS (ES+): m/e 346 (16), 345 (100), 344 (18), 343 (99). MS (ES−): m/e 344 (16), 343 (92), 342 (18), 341 (100).

Compound 89

4-[4-(3-Bromo-phenyl)-pyrazol-1-yl]-benzoic acid: m.p. 247-248° C. $^1$H NMR (300 MHz, DMSO-$d_6$): δ 13.06 (1H, br), 9.23 (1H, s), 8.36 (1H, s), 8.09-7.98 (5H, m), 7.74 (1H, d, J=7.6 Hz), 7.42 (1H, d, J=7.9 Hz), 7.35 (1H, t, J=7.8 Hz). MS (ES+): m/e 346 (14), 345 (100), 344 (15), 343 (90). MS (ES−): m/e 344 (14), 343 (100), 342 (13), 341 (91).

Compound 90

3-(4-m-Tolyl-pyrazol-1-yl)-benzoic acid: m.p. 181-182° C. $^1$H NMR (300 MHz, DMSO-$d_6$): δ 13.28 (1H, br), 9.12 (1H, s), 8.44 (1H, t, J=1.9 Hz), 8.24 (1H, s), 8.14 (1H, dt, J=8.2, 1.3 Hz), 7.86 (1H, dd, J=7.9, 1.0 Hz), 7.67-7.51 (3H, m), 7.27 (1H, t, J=7.6 Hz), 7.05 (1H, d, J=7.6 Hz), 2.33 (3H, s). MS (ES+): m/e 280 (19), 279 (100). MS (ES−): m/e 278 (20), 277 (100).

Compound 91

4-(4-m-Tolyl-pyrazol-1-yl)-benzoic acid: m.p. 251-252° C. $^1$H NMR (300 MHz, DMSO-$d_6$): δ 13.02 (1H, br), 9.10 (1H, s), 8.27 (1H, s), 8.09-7.99 (4H, m), 7.57-7.50 (2H, m), 7.28 (1H, t, J=7.8 Hz), 7.06 (1H, d, J=7.3 Hz), 2.33 (3H, s). MS (ES+): m/e 280 (19), 279 (100). MS (ES−): m/e 278 (21), 277 (100).

Compound 98

3-(4-Phenyl-pyrazol-1-yl)-benzoic acid: m.p. 225-226° C. $^1$H NMR (300 MHz, DMSO-$d_6$): δ 13.19 (1H, br s), 9.14 (1H, s), 8.43 (1H, d, J=1.7 Hz), 8.26 (1H, s), 8.14 (1H, dd, J=7.3, 1.4 Hz), 7.87 (1H, d, J=7.6 Hz), 7.74 (2H, d, J=7.3 Hz), 7.64 (1H, t, J=8.0 Hz), 7.42-7.36 (2H, m), 7.24 (1H, t, J=7.5 Hz). MS (ES+): m/e 266 (16), 265 (100). MS (ES−): m/e 264 (13), 263 (100).

Compound 99

4-(4-Phenyl-pyrazol-1-yl)-benzoic acid: m.p. 267-269° C. $^1$H NMR (300 MHz, DMSO-$d_6$): δ 13.04 (1H, br s), 9.13 (1H, s), 8.30 (1H, s), 8.07 (2H, d, J=8.8 Hz), 8.01 (2H, d, J=8.8 Hz), 7.73 (2H, d, J=7.3 Hz), 7.40 (2H, t, J=7.6 Hz), 7.25 (1H, t, J=7.5 Hz). MS (ES+): m/e 266 (19), 265 (100). MS (ES−): m/e 264 (13), 263 (100).

Compound 100

3-[4-(4-Hydroxy-phenyl)-pyrazol-1-yl]-benzoic acid: m.p. 282-284° C. $^1$H NMR (300 MHz, DMSO-$d_6$): δ 8.95 (1H, s), 8.40 (1H, s), 8.12 (1H, s), 8.12-8.09 (1H, m), 7.84 (1H, d, J=7.6 Hz), 7.62 (1H, t, J=7.9 Hz), 7.53 (2H, d, J=8.5 Hz), 6.78 (2H, d, J=8.5 Hz). MS (ES+): m/e 282 (18), 281 (100). MS (ES−): m/e 280 (17), 279 (100).

Compound 101

3-[4-(4-Nitro-phenyl)-pyrazol-1-yl]-benzoic acid: m.p. 274-276° C. $^1$H NMR (300 MHz, DMSO-$d_6$): δ 13.01 (1H, br s), 9.39 (1H, s), 8.44 (2H, s), 8.25 (2H, d, J=8.8 Hz), 8.14 (1H, dd, J=8.0, 1.7 Hz), 8.01 (2H, d, J=8.8 Hz), 7.89 (1H, d, J=7.6 Hz), 7.66 (1H, t, J=8.0 Hz). MS (ES−): m/e 309 (17), 308 (100).

Compound 102

4-[4-(4-Nitro-phenyl)-pyrazol-1-yl]-benzoic acid: m.p. 276-277° C. $^1$H NMR (300 MHz, DMSO-$d_6$): δ 12.72 (1H, br s), 9.37 (1H, s), 8.47 (1H, s), 8.26 (2H, d, J=8.8 Hz), 8.09-7.97 (6H, m). MS (ES−): m/e 309 (24), 308 (100).

Compound 103

3-[4-(2,4-Difluoro-phenyl)-pyrazol-1-yl]-benzoic acid: m.p. 283-285° C. $^1$H NMR (300 MHz, DMSO-$d_6$): δ 13.31 (1H, br s), 9.02 (1H, s), 8.42 (1H, s), 8.19 (1H, d, J=1.5 Hz), 8.14 (1H, dt, J=8.0, 1.0 Hz), 7.94-7.86 (2H, m), 7.64 (1H, t, J=7.9 Hz), 7.35 (1H, dt, J=10.1, 2.6 Hz), 7.17 (1H, dt, J=8.5, 2.6 Hz). MS (ES+): m/e 302 (17), 301 (100). MS (ES−): m/e 300 (19), 299 (100).

Compound 104

4-[4-(2,4-Difluoro-phenyl)-pyrazol-1-yl]-benzoic acid: m.p. 291-293° C. $^1$H NMR (300 MHz, DMSO-$d_6$): δ 13.04 (1H, br s), 9.01 (1H, s), 8.23 (1H, d, J=1.7 Hz), 8.06 (2H, d, J=6.7 Hz), 8.02 (2H, d, J=6.7 Hz), 7.92-7.84 (1H, m), 7.40-7.32 (1H, m), 7.22-7.15 (1H, m). MS (ES+): m/e 302 (21), 301 (100). MS (ES−): m/e 300 (21), 299 (100).

Compound 107

3-[4-(4-Difluoromethoxy-phenyl)-pyrazol-1-yl]-benzoic acid: m.p. 118-120° C. $^1$H NMR (300 MHz, DMSO-$d_6$): δ 13.18 (1H, br s), 9.15 (1H, s), 8.42 (1H, t, J=1.9 Hz), 8.26 (1H, s), 8.13 (1H, dt, J=8.2, 2.3 Hz), 7.86 (1H, dd, J=8.8, 1.2 Hz), 7.80 (2H, d, J=8.8 Hz), 7.65 (1H, t, J=7.9 Hz), 7.25 (1H, t, J=74.2 Hz), 7.22 (2H, d, J=8.8 Hz). MS (ES+): m/e 332 (20), 331 (100). MS (ES−): m/e 330 (20), 329 (100).

Compound 108

3-[4-(4-Amino-phenyl)-pyrazol-1-yl]-benzoic acid: m.p. 209-210° C. $^1$H NMR (300 MHz, DMSO-$d_6$): δ 8.85 (1H, s), 8.39 (1H, q, J=2.0 Hz), 8.11-8.06 (1H, m), 8.05 (1H, s), 7.82 (1H, dt, J=8.2, 1.3 Hz), 7.61 (1H, t, J=8.0 Hz), 7.38 (2H, d, J=8.4 Hz), 6.58 (2H, d, J=8.4 Hz). MS (ES+): m/e 281 (32), 280 (100). MS (ES−): m/e 279 (18), 278 (100).

Compound 109

4-[4-(3-Methoxy-phenyl)-pyrazol-1-yl]-benzoic acid: m.p. 222-223° C. $^1$H NMR (300 MHz, DMSO-$d_6$): δ 13.03 (1H, br s), 9.14 (1H, s), 8.31 (1H, s), 8.07 (2H, d, J=9.0 Hz), 8.01 (2H, d, J=9.0 Hz), 7.34-7.29 (3H, m), 6.85-6.80 (1H, m), 3.80 (3H, s). MS (ES+): m/e 296 (18), 295 (100). MS (ES−): m/e 294 (19), 293 (100).

Compound 110

3-[4-(4-Dimethylamino-phenyl)-pyrazol-1-yl]-benzoic acid: m.p. 224-225° C. TLC $R_F$ 0.41 (ethyl acetate). $^1$H NMR (300 MHz, DMSO-$d_6$): δ 13.27 (1H, br s), 8.93 (1H, s), 8.40 (1H, t, J=1.8 Hz), 8.12 (1H, s), 8.11 (1H, ddd, J=8.2, 2.3, 1.1 Hz), 7.83 (1H, dd, J=8.0, 1.2 Hz), 7.62 (1H, t, J=7.9 Hz), 7.55

(2H, d, J=8.8 Hz), 6.75 (2H, d, J=8.8 Hz), 2.90 (6H, s). MS (ES+): m/e 309 (48), 308 (100). MS (ES−): m/e 307 (23), 306 (100).

Compound 111

3-(4-Benzo[1,3]dioxol-5-yl-pyrazol-1-yl)-benzoic acid: m.p. 264-265° C. $^1$H NMR (300 MHz, DMSO-d$_6$): δ 13.12 (1H, br s), 9.04 (1H, s), 8.40 (1H, t, J=1.9 Hz), 8.19 (1H, s), 8.10 (1H, ddd, J=8.2, 2.3, 0.9 Hz), 7.85 (1H, dt, J=7.6, 1.2 Hz), 7.63 (1H, t, J=7.9 Hz), 7.36 (1H, d, J=1.8 Hz), 7.23 (1H, dd, J=7.9, 1.8 Hz), 6.94 (1H, d, J=7.9 Hz), 6.02 (2H, s). MS (ES+): m/e 310 (18), 309 (100). MS (ES−): m/e 308 (22), 307 (100).

Compound 112

3-[4-(3-Methoxy-phenyl)-pyrazol-1-yl]-benzoic acid: m.p. 157-158° C. TLC R$_F$ 0.20 (50:50 ethyl acetate-hexane). $^1$H NMR (300 MHz, DMSO-d$_6$): δ 13.27 (1H, br s), 9.15 (1H, s), 8.43 (1H, t, J=1.9 Hz), 8.27 (1H, s), 8.13 (1H, ddd, J=8.2, 2.4, 1.2 Hz), 7.86 (1H, dt, J=7.6, 1.2 Hz), 7.64 (1H, t, J=7.9 Hz), 7.33-7.27 (3H, m), 6.80 (1H, dt, J=6.4, 2.8 Hz), 3.80 (3H, s). MS (ES+): m/e 296 (18), 295 (100). MS (ES−): m/e 294 (20), 293 (100).

Compound 205

4-(4-Benzo[1,3]dioxol-5-yl-pyrazol-1-yl)-benzoic acid: m.p. 286-288° C. $^1$H NMR (300 MHz, DMSO-d$_6$): δ 9.03 (1H, s), 8.22 (1H, s), 8.05 (2H, d, J=8.5 Hz), 7.96 (2H, d, J=8.5 Hz), 7.33 (1H, s), 7.22 (1H, d, j=8.3 Hz), 6.95 (1H, d, J=8.3 Hz), 6.02 (2H, s). MS (ES+): m/e 310 (30), 309 (100). MS (ES−): m/e 308 (20), 307 (100).

Compound 206

4-[4-(3-Hydroxy-phenyl)-pyrazol-1-yl]-benzoic acid: m.p. 273-275° C. $^1$H NMR (300 MHz, DMSO-d$_6$): δ 9.47 (1H, s), 9.05 (1H, s), 8.20 (1H, s), 8.06 (2H, d, J=8.8 Hz), 8.00 (2H, d, J=8.8 Hz), 7.17 (2H, m), 7.09 (1H, s), 6.66 (1H, dd, J=8.6, 1.2 Hz). MS (ES+): m/e 282 (10), 281 (100). MS (ES−): m/e 280 (20), 279 (100).

Compound 207

3-[4-(3-Hydroxy-phenyl)-pyrazol-1-yl]-benzoic acid: m.p. 272-274° C. $^1$H NMR (300 MHz, DMSO-d$_6$): δ 9.45 (1H, s), 9.06 (1H, s), 8.43 (1H, s), 8.15 (2H, m), 7.86 (1H, dd, J=7.7, 1.0 Hz), 7.63 (1H, t, J=7.7 Hz), 7.20 (2H, m), 7.11 (1H, s), 6.66 (1H, m). MS (ES+): m/e 282 (20), 281 (100). MS (ES−): m/e 280 (20), 279 (100).

Compound 208

4-[4-(3-Trifluoromethoxy-phenyl)-pyrazol-1-yl]-benzoic acid: m.p. 225-227° C. $^1$H NMR (300 MHz, DMSO-d$_6$): δ 926 (1H, s), 8.39 (1H, s), 8.08 (2H, d, J=8.8 Hz), 8.00 (2H, d, J=8.8 Hz), 7.78 (2H, m), 7.53 (1H, t, J=8.0 Hz), 7.22 (1H, m). MS (ES+): m/e 350 (20), 349 (100). MS (ES−): m/e 348 (20), 347 (100).

Compound 209

3-[4-(3-Trifluoromethoxy-phenyl)-pyrazol-1-yl]-benzoic acid: m.p. 166-168° C. $^1$H NMR (300 MHz, DMSO-d$_6$): δ 9.28 (1H, s), 8.43 (1H, s), 8.36 (1H, s), 8.14 (1H, dd, J=8.0, 1.1 Hz), 7.88 (1H, dd, J=7.7, 0.8 Hz), 7.80 (2H, m), 7.66 (1H, t, J=7.7 Hz), 7.53 (1H, t, J=7.8 Hz), 7.21 (1H, m). MS (ES+): m/e 350 (30), 349 (100). MS (ES−): m/e 348 (20), 347 (100).

Compound 210

3-[4-(3-Chloro-phenyl)-pyrazol-1-yl]-benzoic acid: m.p. 178-180° C. $^1$H NMR (300 MHz, DMSO-d$_6$): δ 9.25 (1H, s), 8.43 (1H, s), 8.33 (1H, s), 8.13 (1H, dd, J=7.4, 1.0 Hz), 7.87 (2H, m), 7.72 (1H, dd, J=7.7, 1.0 Hz), 7.67 (1H, t, J=8.0 Hz), 7.43 (1H, t, J=8.0 Hz), 7.26 (1H, dd, J=8.0, 0.9 Hz). MS (ES+): m/e 301 (60), 299 (100). MS (ES−): m/e 299 (30), 297 (100).

Compound 211

4-[4-(3-Chloro-phenyl)-pyrazol-1-yl]-benzoic acid: m.p. 252-255° C. $^1$H NMR (300 MHz, DMSO-d$_6$): δ 9.23 (1H, s), 8.36 (1H, s), 8.07 (2H, d, J=8.8 Hz), 7.99 (2H, d, J=8.8 Hz), 7.84 (1H, s), 7.70 (1H, dd, J=7.7, 1.0 Hz), 7.43 (1H, t, J=8.0 Hz), 7.29 (1H, dd, J=8.0 Hz). MS (ES+): m/e 301 (30), 299 (100). MS (ES−): m/e 299 (30), 297 (100).

Compound 212

4-[4-(3-Fluoro-phenyl)-pyrazol-1-yl]-benzoic acid: m.p. 261-265° C. $^1$H NMR (300 MHz, DMSO-d$_6$): δ 9.21 (1H, s), 8.36 (1H, s), 8.08 (2H, d, J=8.8 Hz), 8.00 (2H, d, J=8.8 Hz), 7.59 (2H, m), 7.46 (1H, m), 7.05 (1H, m). MS (ES+): m/e 284 (20), 283 (100). MS (ES−): m/e 282 (20), 281 (100).

Compound 213

3-[4-(3-Fluoro-phenyl)-pyrazol-1-yl]-benzoic acid: m.p. 228-230° C. $^1$H NMR (300 MHz, DMSO-d$_6$): δ 9.22 (1H, s), 8.43 (1H, s), 8.32 (1H, s), 8.12 (1H, dd, J=9.1, 2.2 Hz), 7.87 (1H, dd, J=7.7, 0.9 Hz), 7.62 (3H, m), 7.41 (1H, m), 7.05 (1H, m). MS (ES+): m/e 284 (30), 283 (100). MS (ES−): m/e 282 (20), 281 (100).

Compound 214

4-[4-(3-Trifluoromethoxy-phenyl)-pyrazol-1-yl]-benzoic acid: m.p. 220-222° C. $^1$H NMR (300 MHz, DMSO-d$_6$): δ 9.21 (1H, s), 8.35 (1H, s), 8.07 (2H, d, J=8.8 Hz), 7.99 (2H, d, J=8.8 Hz), 7.59 (2H, m), 7.45 (1H, t, J=8.0 Hz), 7.28 (1H, s), 7.05 (1H, m). MS (ES+): m/e 332 (20), 331 (100). MS (ES−): m/e 330 (20), 329 (100).

Compound 215

4-[4-(3-Phenoxy-phenyl)-pyrazol-1-yl]-benzoic acid: m.p. 211-213° C. $^1$H NMR (300 MHz, DMSO-d$_6$): δ 9.16 (1H, s), 8.31 (1H, s), 8.05 (2H, d, J=9.1 Hz), 7.99 (2H, d, J=9.1 Hz), 7.51 (2H, m), 7.39 (3H, m), 7.12 (1H, m), 7.05 (2H, m), 6.85 (1H, m). MS (ES+): m/e 358 (25), 357 (100). MS (ES−): m/e 356 (25), 355 (100).

Compound 216

3-[4-(3-Phenoxy-phenyl)-pyrazol-1-yl]-benzoic acid: m.p. 164-165° C. $^1$H NMR (300 MHz, DMSO-d$_6$): δ 9.18 (1H, s), 8.43 (1H, t, J=1.2 Hz), 8.27 (1H, s), 8.13 (1H, dd, J=8.0, 1.3 Hz), 7.86 (1H, dd, 7.7, 0.9 Hz), 7.63 (1H, t, J=8.0 Hz), 7.56 (2H, m), 7.12 (1H, m), 7.02 (2H, m), 6.84 (1H, dd, J=8.0, 2.5 Hz). MS (ES+): m/e 359 (10), 358 (60), 357 (100). MS (ES−): m/e 356 (25), 355 (100).

Preparation of
3-(4,5-Dihydro-benzo[e]indazol-3-yl)-benzoic acid
(Compound 135)

A mixture of 2-tetralone (2.00 mL, 14.7 mmol) and dimethylformamide dimethyl acetal (2.10 mL, 15.0 mmol) is heated to reflux for 14 h. The mixture is cooled and evaporated, and approximately half of the residue is dissolved in acetic acid (10 mL) and treated with 3-hydrazinobenzoic acid (750 mL, 4.93 mmol). The solution is heated to reflux for 12 h, then cooled and poured into water (100 mL). The resulting precipitate is collected by filtration, washed with water, and evaporated under high vacuum to afford the title compound (900 mg, 3.10 mmol, 63%) as a tan solid, m.p. 273-275° C. $^1$H NMR (300 MHz, DMSO-d$_6$): δ 13.30 (1H, br), 8.15 (1H, s), 8.10 (1H, t, J=1.9 Hz), 7.95 (1H, dt, J=7.6, 1.3 Hz), 7.82 (1H, ddd, J=8.0, 2.2, 1.0 Hz), 7.66 (1H, t, J=7.9 Hz), 7.53 (1H, dd, J=7.6, 1.2 Hz), 7.26-7.22 (2H, m), 7.10 (1H, dt, J=7.3, 1.2 Hz), 3.05-3.02 (2H, m), 3.00-2.87 (2H, m). MS (ES+): m/e 292 (21), 291 (100). MS (ES−): m/e 290 (20), 289 (100).

Using these procedures, the following compounds may be prepared.

Compound 136

3-(8H-Indeno[2,1-c]pyrazol-1-yl)-benzoic acid: m.p. 241-243° C. $^1$H NMR (300 MHz, DMSO-d$_6$): δ 8.40 (1H, t, J=1.7 Hz), 8.08 (1H, dd, J=8.2, 1.4 Hz), 8.01 (1H, s), 7.88 (1H, dt, J=7.9, 1.2 Hz), 7.67 (1H, t, J=7.9 Hz), 7.57 (1H, d, J=7.3 Hz), 7.52 (1H, d, J=8.4 Hz), 7.31 (1H, dt, J=7.9, 0.9 Hz), 7.18 (1H, dt, J=7.6, 1.1 Hz), 4.21 (2H, s). MS (ES+): m/e 278 (19), 277 (100). MS (ES−): m/e 276 (19), 275 (100).

Compound 141

3-(4,5-Dihydro-benzo[e]indazol-2-yl)-benzoic acid: m.p. 233-234° C. $^1$H NMR (300 MHz, DMSO-d$_6$): δ 13.22 (1H, br), 8.99 (1H, s), 8.38 (1H, t, J=1.8 Hz), 8.07 (1H, dd, J=7.9, 2.0 Hz), 7.82 (1H, d, J=7.6 Hz), 7.61 (1H, t, J=7.9 Hz), 7.58 (1H, d, J=7.6 Hz), 7.26 (1H, d, J=7.6 Hz), 7.23 (1H, d, J=7.9 Hz), 7.13 (1H, dt, J=7.9, 1.0 Hz), 3.00-2.95 (2H, m), 2.89-2.84 (2H, m). MS (ES+): m/e 292 (18), 291 (100). MS (ES−): m/e 290 (19), 289 (100).

Compound 146

3-(8H-Indeno[2,1-c]pyrazol-2-yl)-benzoic acid: m.p. 246-248° C. $^1$H NMR (300 MHz, DMSO-d$_6$): δ 13.24 (1H, br), 8.75 (1H, s), 8.39 (1H, t, J=1.8 Hz), 8.10 (1H, dd, J=8.0, 2.2 Hz), 7.82 (1H, d, J=7.6 Hz), 7.62 (1H, t, J=7.9 Hz), 7.56 (1H, d, J=7.3 Hz), 7.51 (1H, d, J=7.6 Hz), 7.33 (1H, t, J=7.8 Hz), 7.22 (1H, t, J=7.2 Hz), 3.85 (2H, s). MS (ES+): m/e 278 (18), 277 (100). MS (ES−): m/e 276 (21), 275 (100).

Compound 183

3-(6-Difluoromethoxy-4,5-dihydro-benzo[g]indazol-2-yl)-benzoic acid: m.p. 235-237° C. $^1$H NMR (300 MHz, DMSO-d$_6$): δ 13.27 (1H, br), 8.47 (1H, s), 8.40 (1H, t, J=1.8 Hz), 8.09 (1H, ddd, J=8.2, 2.3, 1.2 Hz), 7.84 (1H, dt, J=8.2, 1.3 Hz), 7.75 (1H, dd, J=7.6, 1.1 Hz), 7.62 (1H, t, J=7.9 Hz), 7.36 (1H, t, J=7.9 Hz), 7.22 (1H, t, J=74.1 Hz), 7.15 (1H, dd, J=8.2, 0.9 Hz), 2.96-2.90 (2H, m), 2.82-2.77 (2H, m). $^{19}$F NMR (300 MHz, DMSO-d$_6$): δ −81.44 (2F, d, J=74.1 Hz). MS (ES+): m/e 358 (18), 357 (100). MS (ES−): m/e 356 (23), 355 (100).

Compound 184

3-(5-Methoxy-4H-indeno[1,2-c]pyrazol-2-yl)-benzoic acid: m.p. 277-278° C. $^1$H NMR (300 MHz, DMSO-d$_6$): δ 13.24 (1H, br), 8.53 (1H, s), 8.42 (1H, t, J=1.9 Hz), 8.10 (1H, dd, J=8.0, 2.0 Hz), 7.82 (1H, d, J=7.6 Hz), 7.61 (1H, t, J=7.9 Hz), 7.41 (1H, d, J=8 Hz), 7.37 (1H, d, J=8 Hz), 7.03-6.97 (1H, m), 3.87 (3H, s), 3.62 (2H, s). MS (ES+): m/e 308 (24), 307 (100). MS (ES−): m/e 306 (19), 305 (100).

Compound 185

3-(5-Difluoromethoxy-4H-indeno[1,2-c]pyrazol-2-yl)-benzoic acid: m.p. 240-241° C. $^1$H NMR (300 MHz, DMSO-d$_6$): δ 13.27 (1H, br), 8.60 (1H, s), 8.44 (1H, t, J=1.9 Hz), 8.13 (1H, ddd, J=8.2, 2.3, 0.9 Hz), 7.84 (1H, dt, J=7.9, 1.3 Hz), 7.69 (1H, d, J=7.4 Hz), 7.62 (1H, t, J=7.9 Hz), 7.48 (1H, t, J=7.9 Hz), 7.34 (1H, t, J=74.1 Hz), 7.19 (1H, dd, J=7.9, 0.6 Hz), 3.77 (2H, s). $^{19}$F NMR (300 MHz, DMSO-d$_6$): δ −81.57 (2F, d, J=74.1 Hz). MS (ES+): m/e 344 (23), 343 (100). MS (ES−): m/e 342 (21), 341 (100).

Compound 186

4-(6-Difluoromethoxy-4,5-dihydro-benzo[g]indazol-2-yl)-benzoic acid: m.p. 282-283° C. $^1$H NMR (300 MHz, DMSO-d$_6$): δ 13.00 (1H, br), 8.48 (1H, s), 8.05 (2H, d, J=9.0 Hz), 7.99 (2H, d, J=9.0 Hz), 7.74 (1H, dd, J=7.6, 0.9 Hz), 7.38 (1H, t, J=7.9 Hz), 7.23 (1H, t, J=74.2 Hz), 7.16 (1H, d, J=8.2 Hz), 2.96-2.91 (2H, m), 2.83-2.77 (2H, m). $^{19}$F NMR (300 MHz, DMSO-d$_6$): δ −81.48 (2F, d, J=74.2 Hz). MS (ES+): m/e 358 (17), 357 (100). MS (ES−): m/e 356 (23), 355 (100).

Compound 187

4-(5-Methoxy-4H-indeno[1,2-c]pyrazol-2-yl)-benzoic acid: m.p. 311-313° C. $^1$H NMR (300 MHz, DMSO-d$_6$): δ 12.97 (1H, br), 8.54 (1H, s), 8.04 (2H, d, J=9.0 Hz), 7.99 (2H, d, J=9.0 Hz), 7.43-7.35 (2H, m), 7.01 (1H, dd, J=7.0, 1.8 Hz), 3.87 (3H, s), 3.63 (2H, s). MS (ES+): m/e 308 (19), 307 (100). MS (ES−): m/e 306 (22), 305 (100).

Compound 188

4-(5-Difluoromethoxy-4H-indeno[1,2-c]pyrazol-2-yl)-benzoic acid: m.p. 277-278° C. $^1$H NMR (300 MHz, DMSO-d$_6$): δ 13.00 (1H, br), 8.60 (1H, s), 8.05 (2H, d, J=9.4 Hz), 8.01 (2H, d, J=9.4 Hz), 7.66 (1H, d, J=7.4 Hz), 7.49 (1H, t, J=7.9 Hz), 7.34 (1H, t, J=74.0 Hz), 7.20 (1H, d, J=7.6 Hz), 3.77 (2H, s). $^{19}$F NMR (300 MHz, DMSO-d$_6$): δ −81.60 (2F, d, J=74.0 Hz). MS (ES+): m/e 345 (13), 344 (33), 343 (100). MS (ES−): m/e 342 (22), 341 (100).

Compound 253

3-(8-Methoxy-4,5-dihydro-benzo[e]indazol-2-yl)-benzoic acid: m.p. 239-241° C. $^1$H NMR (300 MHz, DMSO-d$_6$): δ 9.01 (1H, s), 8.35 (1H, t, J=1.8 Hz), 8.06 (1H, ddd, J=8.0, 2.3, 0.9 Hz), 7.82 (1H, dt, J=7.6, 1.3 Hz), 7.61 (1H, t, J=7.9 Hz), 7.21 (1H, d, J=2.9 Hz), 7.16 (1H, d, J=8.4 Hz), 6.70 (1H, dd, J=8.4, 2.9 Hz), 3.77 (3H, s), 2.93-2.80 (4H, m). MS (ES+): m/e 322 (21), 321 (100). MS (ES−): m/e 320 (23), 319 (100).

Compound 254

3-(8-Methoxy-4,5-dihydro-benzo[e]indazol-3-yl)-benzoic acid: m.p. 269-271° C. $^1$H NMR (300 MHz, DMSO-d$_6$): δ 8.18 (1H, s), 8.09 (1H, t, J=1.9 Hz), 7.94 (1H, dt, J=7.9, 1.3 Hz), 7.81 (1H, ddd, J=8.2, 2.3, 1.2 Hz), 7.66 (1H, t, =7.9 Hz), 7.16 (1H, d, J=8.5 Hz), 7.15 (1H, d, J=2.6 Hz), 6.67 (1H, dd, J=8.5, 2.6 Hz), 3.76 (3H, s), 3.05-2.99 (2H, m), 2.91-2.85 (2H, m). MS (ES+): m/e 322 (23), 321 (100). MS (ES−): m/e 320 (21), 319 (100).

E. Preparation of 3,1-Pyrazoles 3,1 Pyrazoles of the invention may be prepared as follows.

Preparation of 3-[1-(4-Difluoromethoxy-phenyl)-1H-pyrazol-3-yl]-benzoic acid (Compound 124)

Part A.

A mixture of 3-acetylbenzonitrile (40.0 g, 276 mmol) and dimethylformamide dimethyl acetal (321 mL) is heated with stirring to 100° C. for 72 h. The volatiles are distilled off, and the crude product (55 g) is taken up in acetic acid (250 mL). Hydrazine hydrate (42.6 mL) is added, and the mixture is heated to 100° C. for 36 h. The mixture is cooled, and poured into ethyl acetate (500 mL). This is washed with 1M aq. HCl (1 L) and said. aq. brine (250 mL). The aqueous phases are back-extracted in sequence with ethyl acetate (3×500 mL), and the extracts are combined, dried over MgSO$_4$, filtered and evaporated. The residual material is filtered to afford the product, 3-(1H-pyrazol-3-yl)-benzonitrile, as an orange solid (45.0 g), which is 88% pure by HPLC analysis.

Part B.

A solution of 4-difluoromethoxy-1-iodobenzene (1.50 g, 5.56 mmol) and triisopropylborate (2.06 mL, 8.89 mmol) in tetrahydrofuran (50 mL) is cooled to −78° C., and n-butyl-lithium (9.8 mL, 1.6 M solution in hexane, 6.11 mmol) is added dropwise with stirring. After 20 min, the cooling bath is removed, and the solution is allowed to warm to ambient temperature. The solvent is evaporated, and the residual material is taken up in 1M aq. HCl (100 mL). This is extracted with ethyl acetate (100 mL), and the extract is dried over MgSO$_4$, filtered and evaporated. Analysis by HPLC shows the product, 4-difluoromethoxybenzeneboronic acid, of sufficient purity for the next step (1.02 g).

Part C.

A solution of 3-(1H-pyrazol-3-yl)-benzonitrile (400 mg, 2.36 mmol) and 4-difluoromethoxybenzeneboronic acid (1.02 g, 5.44 mmol) in dimethylformamide (20 mL) is treated with copper (II) acetate (472 mg), pyridine (0.36 mL), and powdered, activated 4 Å molecular sieves (1 g). The resulting mixture is heated to 35° C. for 3 h, cooled and partially evaporated. The residue is partitioned between 1 M aq. HCl and ethyl acetate (200 mL each), and the extract is washed with brine (100 mL), dried over MgSO$_4$, filtered and evaporated. The residue is separated by column chromatography (silica gel, 1:1 CH$_2$Cl$_2$-hexane) to afford 3-[1-(4-difluoromethoxy-phenyl)-1H-pyrazol-3-yl]-benzonitrile (200 mg, 23%).

Part D.

A solution of 3-[1-(4-difluoromethoxy-phenyl)-1H-pyrazol-3-yl]-benzonitrile (100 mg) and conc. aq. HCl (5 mL) in acetic acid (5 mL) is heated to reflux for 16 h. The mixture is cooled and poured into water (100 mL). This is extracted with ethyl acetate, and the extract ias washed with brine, dried over MgSO$_4$, filtered and evaporated. The residue is separated by column chromatography (silica gel, 1:25:74 acetic acid-CH$_2$Cl$_2$-hexane) to afford the title product (12 mg, 11%) as a powder (m.p. 182-183° C.), after evaporation. $^1$H NMR (300 MHz, acetone-d$_6$): δ 11.35 (1H, br s), 8.64 (1H, dt, J=1.6, 0.5 Hz), 8.44 (1H, dd, J=2.6, 1.4 Hz), 8.22 (1H, ddd, J=7.8, 1.9, 1.1 Hz), 8.06-7.99 (3H, m), 7.60 (1H, t, J=8 Hz), 7.38 (2H, d, J=9.1 Hz), 7.09 (1H, d, J=2.6 Hz), 7.07 (1H, t, J=74.0 Hz). MS (ES+): m/e 332 (20), 331 (100). MS (ES−): m/e 330 (20), 329 (100).

This procedure may be used in slightly modified forms to prepare the following compounds.

Compound 86

3-[1-(2-Fluoro-phenyl)-1H-pyrazol-3-yl]-benzoic acid: m.p. 157-158° C. $^1$H NMR (300 MHz, DMSO-d$_o$): δ 8.46 (1H, t. J=1.6 Hz), 8.28 (1H, t, J=2.6 Hz), 8.13 (1H, dt, J=8.0, 1.4 Hz), 7.93-7.86 (2H, m), 7.57 (1H, t, J=7.7 Hz), 7.53-7.34 (3H, m), 7.13 (1H, d, J=2.6 Hz). MS (ES+): m/e 284 (20), 283 (100). MS (ES−): m/e 282 (20), 281 (100).

Compound 57

3-(1-Phenyl-1H-pyrazol-3-yl)-benzonitrile: m.p. 78-80° C. MS (ES+): m/e 246 (100).

Compound 58

3-[1-(4-Methoxy-phenyl)-1H-pyrazol-3-yl]-benzonitrile: m.p. 110-112° C. MS (ES+): m/e 276 (100).

Compound 59

3-[1-(3-Methoxy-phenyl)-1H-pyrazol-3-yl]-benzonitrile: m.p. 100-101° C. MS (ES+): m/e 276 (100).

Compound 60

3-(1-Benzo[1,3]dioxol-5-yl-1H-pyrazol-3-yl)-benzonitrile: m.p. 144-147° C. MS (ES+): m/e 290 (100).

Compound 61

3-[1-(4-Trifluoromethoxy-phenyl)-1H-pyrazol-3-yl]-benzonitrile: m.p. 83-84° C. MS (ES+): m/e 330 (100).

Compound 62

3-[1-(4-Trifluoromethyl-phenyl)-1H-pyrazol-3-yl]-benzonitrile: m.p. 70-74° C. MS (ES+): m/e 314 (100).

Compound 63

3-[1-(3,4-Difluoro-phenyl)-1H-pyrazol-3-yl]-benzonitrile: m.p. 142-145° C. MS (ES+): m/e 282 (100).

Compound 64

3-[3-(3-Cyano-phenyl)-pyrazol-1-yl]-benzoic acid methyl ester: m.p. 143-145° C. MS (ES+): m/e 304 (100).

Compound 65

3-(1-Phenyl-1H-pyrazol-3-yl)-benzoic acid: m.p. 202-204° C. $^1$H NMR (300 MHz, DMSO-d$_6$): δ 8.59 (1H, d, J=2.5 Hz), 8.47 (1H, t, J=1.7 Hz), 8.14 (1H, dt, J=8.0, 1.5 Hz), 7.93 (1H, t, J=1.5 Hz), 7.91-7.88 (1H, m), 7.57 (1H, t, J=7.8 Hz), 7.54-7.48 (1H, m), 7.32 (1H, tt, J=7.4, 1.1 Hz), 7.11 (1H, d, J=2.5 Hz). MS (ES+): m/e 266 (20), 265 (100). MS (ES−): m/e 264 (20), 263 (100).

Compound 74

3-[1-(4-Hydroxy-phenyl)-1H-pyrazol-3-yl]-benzoic acid: m.p. 228-230° C. $^1$H NMR (300 MHz, DMSO-d$_6$): δ 9.63 (1H, s), 8.44 (1H, t, J=1.7 Hz), 8.38 (1H, d, J=2.5 Hz), 8.10 (1H, dt, J=8.0, 1.5 Hz), 7.88 (1H, dt, J=7.7, 1.4 Hz), 7.67 (2H, d, J=9.0 Hz), 7.55 (1H, t, J=7.7 Hz), 7.03 (1H, d, J=2.5 Hz), 6.86 (2H, d, J=9.0 Hz). MS (ES+): m/e 282 (20), 281 (100). MS (ES−): m/e 280 (20), 279 (100).

Compound 75

3-[1-(3-Hydroxy-phenyl)-1H-pyrazol-3-yl]-benzoic acid: m.p. 178-190° C. $^1$H NMR (300 MHz, DMSO-d$_6$): δ 9.80 (1H, s), 8.51 (1H, d, J=2.5 Hz), 8.48 (1H, s), 8.12 (1H, d, J=7.7 Hz), 7.90 (1H, d, J=7.7 Hz), 7.57 (1H, t, J=7.7 Hz), 7.36-7.25 (3H, m), 7.08 (1H, d, J=2.5 Hz), 6.70 (1H, dt, J=6.9, 2.2 Hz). MS (ES+): m/e 282 (20), 281 (100). MS (ES−): m/e 280 (20), 279 (100).

Compound 66

3-[1-(4-Trifluoromethoxy-phenyl)-1H-pyrazol-3-yl]-benzoic acid: m.p. 171-174° C. $^1$H NMR (300 MHz, DMSO-d$_6$): δ 8.63 (1H, t, J=2.6 Hz), 8.48 (1H, m), 8.15 (1H, d, J=8.0 Hz), 8.04 (2H, dd, J=9.0, 2.5 Hz), 7.91 (1H, d, J=7.7 Hz), 7.58 (1H, dd, J=7.7, 2.2 Hz), 7.53 (2H, d, J=9.0 Hz), 7.15 (1H, t, J=2.5 Hz). MS (ES+): m/e 350 (20), 349 (100). MS (ES−): m/e 348 (20), 347 (100).

Compound 67

3-[1-(4-Trifluoromethyl-phenyl)-1H-pyrazol-3-yl]-benzoic acid: m.p. 225-227° C. $^1$H NMR (300 MHz, DMSO-d$_6$): δ 8.75 (1H, d. J=2.5 Hz), 8.50 (1H, t, J=1.5 Hz), 8.20-8.17 (3H, m), 7.94 (1H, dt, J=8.2, 1.4 Hz), 7.88 (2H, d, J=8.5 Hz), 7.59 (1H, t, J=7.6 Hz), 7.21 (1H, d, J=2.5 Hz). MS (ES+): m/e 334 (20), 333 (100). MS (ES−): m/e 332 (20), 331 (100).

Compound 68

3-[1-(3,4-Difluoro-phenyl)-1H-pyrazol-3-yl]-benzoic acid: m.p. 240-244° C. $^1$H NMR (300 MHz, DMSO-d$_6$): δ 8.62 (1H, d, J=2.5 Hz), 8.47 (1H, t, J=1.7 Hz), 8.15 (1H, dt, J=8.2, 1.5 Hz), 8.05 (1H, ddd, J=12.1, 7.1, 2.6 Hz), 7.92 (1H, dt, J=8.0, 1.4 Hz), 7.84-7.78 (1H, m), 7.66-7.55 (2H, m), 7.15 (1H, d, J=2.5 Hz). MS (ES+): m/e 302 (20), 301 (100). MS (ES−): m/e 300 (20), 299 (100).

Compound 69**

1,3-Bis(3-carboxyphenyl)-1H-pyrazole: m.p. >300° C. $^1$H NMR (300 MHz, DMSO-d$_6$): δ 8.71 (1H, d, J=1.7 Hz), 8.48 (1H, s), 8.44 (1H, s), 8.16 (2H, d, J=7.2 Hz), 7.93-7.85 (2H, m), 7.64 (1H, t, J=8.0 Hz), 7.57 (1H, t, J=8.2 Hz), 7.14 (1H, d, J=2.7 Hz). MS (ES+): m/e 310 (20), 309 (100). MS (ES−): m/e 308 (20), 307 (100).

Compound 76

3-[1-(4-Methoxy-phenyl)-1H-pyrazol-3-yl]-benzoic acid: m.p. 160-161° C. $^1$H NMR (300 MHz, acetone-d$_6$): δ 11.40 (1H, br s), 8.63 (1H, t, J=1.5 Hz), 8.33 (1H, d, J=2.5 Hz), 8.21 (1H, d, J=7 Hz), 8.02 (1H, d, J=7 Hz), 7.86 (2H, d, J=9.1 Hz), 7.59 (1H, t, J=7.7 Hz), 7.09 (2H, d, J=9.1 Hz), 7.03 (1H, d, J=2.5 Hz), 3.87 (3H, s). MS (ES+): m/e 296 (20), 295 (100). MS (ES−): m/e 294 (20), 293 (100).

Compound 77

3-[1-(3-Methoxy-phenyl)-1H-pyrazol-3-yl]-benzoic acid: m.p. 153-154° C. $^1$H NMR (300 MHz, DMSO-d$_6$): δ 8.60 (1H, dd, J=2.5, 1.5 Hz), 8.45 (1H, d, J=1.1 Hz), 8.14 (1H, dd, J=7.9, 1.3 Hz), 7.90 (1H, dd, J=7.7, 1.1 Hz), 7.60-7.38 (4H, m), 7.11 (1H, dd, J=2.5, 1.4 Hz), 6.89 (1H, d, J=8.0 Hz), 3.83 (3H, s). MS (ES+): m/e 296 (20), 295 (100). MS (ES−): m/e 294 (20), 293 (100).

Compound 87

3-(1-Benzo[1,3]dioxol-5-yl-1H-pyrazol-3-yl)-benzoic acid: m.p. 210-215° C. $^1$H NMR (300 MHz, acetone-d$_6$): δ 8.61 (1H, dt, J=1.7, 0.5 Hz), 8.32 (1H, d, J=2.5 Hz), 8.21 (1H, ddd, J=7.7, 1.7, 1.1 Hz), 8.02 (1H, dt, J=8.3, 1.5 Hz), 7.59 (1H, dt, J=7.7, 0.6 Hz), 7.49 (1H, dd, J=2.2 Hz), 7.41 (1H, dd, J=8.5, 2.2 Hz), 7.03 (1H, d, J=2.7 Hz), 6.98 (1H, d, J=8.3 Hz), 6.11 (2H, s) MS (ES+): m/e 310 (20), 309 (100). MS (ES−): m/e 308 (10), 307 (100).

Compound 96

3-[1-(4-Fluoro-phenyl)-1H-pyrazol-3-yl]-benzoic acid: m.p. 245-246° C. $^1$H NMR (300 MHz, DMSO-d$_6$): δ 8.57 (1H, d, J=2.5 Hz), 8.47 (1H, t, J=1.8 Hz), 8.14 (1H, dt, J=7.7, 1.5 Hz), 7.98-7.88 (3H, m), 7.57 (1H, t, J=7.7 Hz), 7.36 (2H, t, J=8.8 Hz), 7.11 (1H, d, J=2.5 Hz). MS (ES+): m/e 284 (20), 283 (100). MS (ES−): m/e 282 (20), 281 (100).

Compound 4

3-[1-(4-Isopropyl-phenyl)-1H-pyrazol-3-yl]-benzoic acid: $^1$H NMR (400 MHz, CDCl$_3$): δ 8.62 (1H, s), 8.21 (1H, d, J=8 Hz), 8.08 (1H, d, J=8 Hz), 7.95 (1H, d, J=2 Hz), 7.69 (2H, d, J=8 Hz), 7.55 (1H, t, J=8 Hz), 7.33 (2H, d, J=8 Hz), 6.84 (1H, d, J=2 Hz), 2.97 (1H, heptet, J=7 Hz), 1.27 (6H, d, J=7 Hz). MS (ES+): m/e 308 (22), 307 (100).

The following compounds may be prepared by copper iodide-catalyzed cross-coupling of a 3-(carbomethoxyphenyl)-1H-pyrazole with an aryl iodide reagent, followed by hydrolysis of the methyl ester, as described elsewhere in this invention:

Compound 160

4-[1-(3-Methoxy-phenyl)-1H-pyrazol-3-yl]-benzoic acid: m.p. 190-191° C. $^1$H NMR (300 MHz, DMSO-d$_6$): δ 12.99 (1H, br), 8.63 (1H, d, J=2.6 Hz), 8.05 (2H, d, J=8.5 Hz), 7.99 (2H, d, J=8.5 Hz), 7.53-7.48 (2H, m), 7.42 (1H, t, J=7.9 Hz), 7.14 (1H, d, J=2.6 Hz), 6.90 (1H, ddd, J=8, 2.2, 1.2 Hz), 3.84 (3H, s). MS (ES+): m/e 296 (21), 295 (100).

Compound 164

3-[1-(3-Dimethylamino-phenyl)-1H-pyrazol-3-yl]-benzoic acid: m.p. 180-183° C. $^1$H NMR (300 MHz, DMSO-d$_6$): δ 8.56 (1H, d, J=2.7 Hz), 8.44 (1H, t, J=1.7 Hz), 8.13 (1H, dt, J=7.9, 1.5 Hz), 7.90 (1H, dt, J=7.7, 1.5 Hz), 7.56 (1H, t, J=7.8 Hz), 7.28 (1H, t, J=8.5 Hz), 7.16 (1H, s), 7.16-7.13 (1H, m), 7.07 (1H, d, J=2.5 Hz), 6.68-6.64 (1H, m), 2.97 (6H, s). MS (ES+): m/e 309 (20), 308 (100). MS (ES−): m/e 307 (15), 306 (100).

Compound 165

3-[1-(3-Bromo-phenyl)-1H-pyrazol-3-yl]-benzoic acid: m.p. 180-183° C. $^1$H NMR (300 MHz, DMSO-d$_6$): δ 8.68 (1H, d, J=2.5 Hz), 8.47 (1H, s), 8.18-8.15 (2H, m), 7.98-7.90 (2H, m), 7.58 (1H, t, J=7.7 Hz), 7.54-7.44 (2H, m), 7.16 (1H, d, J=2.5 Hz). MS (ES+): m/e 345 (100), 343 (95). MS (ES−): r/e 343 (98), 341 (100).

Compound 166

3-(1-p-Tolyl-1H-pyrazol-3-yl)-benzoic acid: m.p. 192-193° C. $^1$H NMR (300 MHz, DMSO-d$_6$): δ 8.54 (1H, d, J=2.5 Hz), 8.47 (1H, t, J=2 Hz), 8.13 (1H, dm, J=7.7 Hz), 7.90 (1H, dm, J=8.0 Hz), 7.80 (2H, d, J=8.3 Hz), 7.57 (1H, t, J=7.7 Hz), 7.32 (2H, d, J=8.5 Hz), 7.09 (1H, d, J=2.5 Hz), 2.34 (3H, s). MS (ES+): m/e 280 (20), 279 (100). MS (ES−): m/e 278 (20), 277 (100).

Compound 167

3-(1-m-Tolyl-1H-pyrazol-3-yl)-benzoic acid: m.p. 162-164° C. $^1$H NMR (300 MHz, DMSO-d$_6$): δ 8.56 d, J=2.5 Hz), 8.47 (1H, t, J=2 Hz), 8.14 (1H, d, J=7.7 Hz), 7.91 (1H, d, J=8.0 Hz), 7.76 (1H, s), 7.70 (1H, d, J=8.0 Hz), 7.57 (1H, t, J=7.7 Hz), 7.39 (1H, t, J=7.8 Hz), 7.13 (1H, d, J=7.2 Hz), 7.10 (1H, d, J=2.5 Hz), 2.40 (3H, s). MS (ES+): m/e 280 (23), 279 (100). MS (ES−): m/e 278 (20), 277 (100).

Compound 168

3-[1-(4-Nitro-phenyl)-1H-pyrazol-3-yl]-benzoic acid: m.p. 280-281° C. $^1$H NMR (300 MHz, DMSO-d$_6$): δ 8.83 (1H, d, J=2.7 Hz), 8.52 (1H, s), 8.39 (2H, d, J=9.3 Hz), 8.22 (2H, d, J=9.3 Hz), 8.18 (1H, d, J=8 Hz), 7.95 (1H, d, J=8.0 Hz), 7.60 (1H, t, J=8 Hz), 7.27 (1H, d, J=2.5 Hz). MS (ES+): m/e 311 (30), 310 (100). MS (ES−): m/e 309 (20), 308 (100).

Compound 175

3-[1-(3-Benzyloxy-phenyl)-1H-pyrazol-3-yl]-benzoic acid: m.p. 152-153° C. $^1$H NMR (300 MHz, DMSO-d$_6$): δ 8.61 (1H, d, J=2.7 Hz), 8.47 (1H, t, J=1.6 Hz), 8.15 dt, J=7.7, 1.2 Hz), 7.91 (1H, dt, J=7.7, 1.2 Hz), 7.60-7.30 (9H, m), 7.12 (1H, d, J=2.7 Hz), 6.97 (1H, dd, J=7.7, 2.2 Hz), 5.20 (2H, s). MS (ES+): m/e 372 (25), 371 (100). MS (ES−): m/e 370 (20), 369 (100).

Compound 176

3-[1-(4-Benzyloxy-phenyl)-1H-pyrazol-3-yl]-benzoic acid: m.p. 210-212° C. $^1$H NMR (300 MHz, DMSO-d$_6$): δ 8.47 (1H, d, J=2.5 Hz), 8.45 (1H, t, J=1.8 Hz), 8.12 (1H, dt, J=7.9, 1.3 Hz), 7.89 (1H, dt, J=7.7, 1.3 Hz), 7.82 (2H, d, J=9.1 Hz), 7.56 (1H, t, J=7.8 Hz), 7.49-7.30 (5H, m), 7.15 (2H, d, J=9.1 Hz), 7.07 (1H, d, J=2.5 Hz), 5.15 (2H, s). MS (ES+): m/e 372 (20), 371 (100). MS (ES−): m/e 370 (25), 369 (100).

Compound 217

4-[1-(4-Methoxy-phenyl)-1H-pyrazol-3-yl]-benzoic acid: m.p. 252-253° C. $^1$H NMR (300 MHz, DMSO-d$_6$): δ 8.49 (1H, d, J=2.5 Hz), 8.03 (2H, d, J=8.7 Hz), 7.99 (2H, d, J=8.7 Hz), 7.82 (2H, d, J=9.0 Hz), 7.09 (1H, d, J=2.5 Hz), 7.07 (2H, d, J=9.0 Hz), 3.79 (3H, s). MS (ES+): m/e 296 (20), 295 (100). MS (ES−): m/e 294 (20), 293 (100).

Compound 218

4-[1-(4-Trifluoromethoxy-phenyl)-1H-pyrazol-3-yl]-benzoic acid: m.p. 214-215° C. $^1$H NMR (300 MHz, DMSO-d$_6$): δ 8.66 (1H, d, J=2.5 Hz), 8.06-8.01 (6H, m), 7.54 (2H, d, J=8.5 Hz), 7.18 (1H, d, J=2.5 Hz). MS (ES+): m/e 350 (20), 349 (100). MS (ES−): m/e 348 (20), 347 (100).

Compound 255

3-[1-(4-Acetyl-phenyl)-1H-pyrazol-3-yl]-benzoic acid: m.p. 215-216° C. $^1$H NMR (300 MHz, DMSO-d$_6$): δ 12.99 (1H, br), 8.75 (1H, d, J=2.6 Hz), 8.50 (1H, t, J=1.6 Hz), 8.17 (1H, dt, J=8.2, 1.5 Hz), 8.10 (2H, d, J=9.3 Hz), 8.07 (2H, d, J=9.3 Hz), 7.93 (1H, dt, J=7.9, 1.5 Hz), 7.59 (1H, t, J=7.9 Hz), 7.20 (1H, d, J=2.6 Hz), 2.60 (3H, s). MS (ES+): m/e 308 (19), 307 (100). MS (ES−): m/e 306 (20), 305 (100).

Compound 256

4-[1-(4-Acetyl-phenyl)-1H-pyrazol-3-yl]-benzoic acid: m.p. 278-279° C. $^1$H NMR (300 MHz, DMSO-d$_6$): δ 13.00 (1H, br), 8.76 (1H, d, J=2.6 Hz), 8.10 (2H, d, J=9.3 Hz), 8.08 (2H, d, J=9.3 Hz), 8.07 (2H, d, J=8.8 Hz), 8.01 (2H, d, J=8.8 Hz), 7.22 (1H, d, J=2.6 Hz), 2.60 (3H, s). MS (ES+): m/e 308 (23), 307 (100). MS (ES−): m/e 306 (20), 305 (100).

Compound 257

4-[1-(1H-Indol-5-yl)-1H-pyrazol-3-yl]-benzoic acid: m.p. 281-282° C. $^1$H NMR (300 MHz, DMSO-d$_6$): δ 12.90 (1H, br), 11.27 (1H, br), 8.49 (1H, d, J=2.6 Hz), 8.04 (2H, d, J=8.8 Hz), 8.03-8.00 (1H, m), 7.99 (2H, d, J=8.8 Hz), 7.64 (1H, dd, J=8.8, 2.3 Hz), 7.50 (1H, d, J=8.8 Hz), 7.44 (1H, t, J=2.8 Hz), 7.08 (1H, d, J=2.6 Hz), 6.52-6.49 (1H, m). MS (ES+): m/e 305 (19), 304 (100). MS (ES−): m/e 303 (22), 302 (100).

Compound 258

3-(1-Thiophen-2-yl-1H-pyrazol-3-yl)-benzoic acid: m.p. 198-199° C. $^1$H NMR (300 MHz, DMSO-d$_6$): δ 13.12 (1H, br), 8.48 (1H, d, J=2.4 Hz), 8.42 (1H, s), 8.09 (1H, d, J=7.6 Hz), 7.91 (1H, d, J=7.9 Hz), 7.57 (1H, t, J=7.9 Hz), 7.36 (1H, dd, J=3.8, 1.1 Hz), 7.31 (1H, d, J=5.2 Hz), 7.11 (1H, d, J=2.4 Hz), 7.03 (1H, dd, J=5.2, 3.8 Hz). MS (ES+): m/e 273 (8), 272 (21), 271 (100). MS (ES−): m/e 271 (6), 270 (16), 269 (100).

Compound 259

4-(1-Thiophen-2-yl-1H-pyrazol-3-yl)-benzoic acid: m.p. 200-202° C. $^1$H NMR (300 MHz, DMSO-d$_6$): δ 12.97 (1H, br), 8.50 (1H, d, J=2.6 Hz), 8.00 (2H, d, J=9.3 Hz), 7.97 (2H, d, J=9.3 Hz), 7.38 (1H, dd, J=3.8, 1.4 Hz), 7.32 (1H, dd, J=5.6, 1.5 Hz), 7.13 (1H, d, J=2.6 Hz), 7.03 (1H, dd, J=5.6, 3.8 Hz). MS (ES+): m/e 273 (5), 272 (15), 271 (100). MS (ES−): m/e 271 (5), 270 (16), 269 (100).

Compound 260

3-(1-Pyridin-3-yl-1H-pyrazol-3-yl)-benzoic acid: m.p. 235-236° C. $^1$H NMR (300 MHz, DMSO-d$_6$): δ 13.12 (1H, br), 9.18 (1H, d, J=2.6 Hz), 8.69 (1H, d, J=2.6 Hz), 8.53 (1H, dd, J=4.7, 1.2 Hz), 8.49 (1H, t, J=1.6 Hz), 8.31 (1H, ddd, J=8.5, 2.6, 1.5 Hz), 8.17 (1H, dt, J=8.2, 1.6 Hz), 7.93 (1H, dt, J=7.9, 1.6 Hz), 7.59 (1H, t, J=7.9 Hz), 7.56 (1H, ddd, J=8.2, 4.7, 0.6 Hz), 7.19 (1H, d, J=2.6 Hz). MS (ES+): m/e 267 (34), 266 (100). MS (ES−): m/e 265 (17), 264 (100).

Compound 261

4-(1-Pyridin-3-yl-1H-pyrazol-3-yl)-benzoic acid: m.p. 280-282° C. $^1$H NMR (300 MHz, DMSO-d$_6$): δ 12.99 (1H, br), 9.21 (1H, br), 8.71 (1H, d, J=2.6 Hz), 8.56 (1H, br), 8.32 (1H, br d, J=9.0 Hz), 8.07 (2H, d, J=8.8 Hz), 8.01 (2H, d, J=8.8 Hz), 7.60-7.55 (1H, br m), 7.21 (2H, d, J=2.6 Hz). MS (ES+): m/e 267 (30), 266 (100). MS (ES−): m/e 265 (20), 264 (100).

F. Preparation of 4,1-Pyrazoles 4,1-pyrazoles of the invention may be prepared as follows.

Preparation of 6-[1-(4-Methoxy-phenyl)-1H-pyrazol-4-yl]-pyridine-2-carboxylic acid (Compound 53)

A solution of 6-(diformylmethyl)-pyridin-2-carboxylic acid (315 mg, 1.63 mmol), 4-methoxyphenylhydrazine hydrochloride (285 mg, 1.63 mmol) and sodium acetate (134 mg, 1.63 mmol) in acetic acid (5 mL) is heated to 110° C. for 18 h. After being allowed to cool, the solution is filtered. The solid product is washed with ethyl acetate and diethyl ether, and dried under vacuum to afford the title product (294 mg, 0.99 mmol, 61%) as a beige powder. m.p. 122-123° C. $^1$H NMR (300 MHz, DMSO-d$_6$): δ 9.11 (1H, s), 8.38 (1H, s), 7.99 (2H, d, J=4.7 Hz), 7.86 (1H, t, J=4.4 Hz), 7.80 (2H, d, J=9.1 Hz), 7.08 (2H, d, J=9.1 Hz), 3.80 (3H, s), 1H missing. MS (ES+): m/e 297 (18), 296 (100). MS (ES−): m/e 295 (14), 294 (100).

The procedure above may be slightly modified to prepare the following compounds.

Compound 54

6-[1-(4-Chloro-phenyl)-1H-pyrazol-4-yl]-pyridine-2-carboxylic acid: m.p. 194-196° C. $^1$H NMR (300 MHz, DMSO-d$_6$): δ 9.25 (1H, s), 8.45 (1H, s), 8.01-7.86 (5H, m), 7.59 (2H, d, J=8.5 Hz), 1H missing. MS (ES+): m/e 302 (36), 301 (16), 300 (100). MS (ES−): m/e 300 (36), 299 (16), 298 (100).

Compound 55

3-[1-(4-Methoxy-phenyl)-1H-pyrazol-4-yl]-4-nitro-benzoic acid: m.p. 249-250° C. $^1$H NMR (300 MHz, DMSO-d$_6$): δ 13.68 (1H, br s), 8.81 (1H, s), 8.20 (1H, s), 8.02 (2H, s), 7.79 (2H, d, J=9.1 Hz), 7.79 (1H, s), 7.06 (2H, d, J=9.1 Hz), 3.79 (3H, s). MS (ES+): m/e 341 (20), 340 (100). MS (ES−): m/e 339 (21), 338 (100).

Compound 56

3-[1-(4-Chloro-phenyl)-1H-pyrazol-4-yl]-4-nitro-benzoic acid: m.p. 270-271° C. $^1$H NMR (300 MHz, DMSO-d$_6$): δ 13.70 (1H, br s), 8.96 (1H, s), 8.20 (1H, s), 8.03 (2H, s), 7.92 (2H, d, J=8.8 Hz), 7.86 (1H, s), 7.57 (2H, d, J=8.8 Hz). MS (ES+): m/e 346 (37), 345 (14), 344 (100). MS (ES−): m/e 344 (42), 343 (15), 342 (100).

Preparation of 3-[1-(4-Chloro-phenyl)-1H-pyrazol-4-yl]-benzoic acid (Compound 83)

Part A.

A solution of 4-chlorophenylhydrazine hydrochloride (2.02 g, 11.3 mmol), 1,1,3,3-tetramethoxypropane (2.00 mL, 12.1 mmol) and sodium acetate (1.00 g, 12.2 mmol) in acetic acid (25 mL) is heated to gentle reflux overnight. The solution is cooled and poured into water (125 mL). Solid sodium bicarbonate is added in portions until the pH of the mixture is slightly basic. This is then extracted twice with ethyl acetate (125 mL), and the extracts are washed with brine, combined, dried over anhydrous magnesium sulfate, filtered and evaporated to afford 1-(4-chlorophenyl)pyrazole in two crops (1.13 g+0.24 g, 7.65 mmol, 68%). m.p. 50-53° C. TLC R$_F$ 0.19 (10:90 ethyl acetate-hexane), $^1$H NMR (300 MHz, CDCl$_3$): δ 7.89 (1H, dd, J=2.4, 0.6 Hz), 7.72 (1H, d, J=1.5 Hz), 7.64 (2H, d, J=8.7 Hz), 7.42 (2H, d, J=8.7 Hz), 6.47 (1H, dd, J=2.4, 1.8 Hz). MS (ES+): m/e 182 (3), 181 (34), 180 (6), 179 (100).

Part B.

A solution of 1-(4-chlorophenyl)pyrazole (834 mg, 4.67 mmol) in acetic acid (10 mL) is treated with bromine (0.26 mL, 5.08 mmol). After stirring for 18 h, the solution is diluted with 40 mL water, and satd. aq. NaHSO$_3$ solution is added until the bromine color had dissipated. Then, solid sodium bicarbonate is added until a neutral pH is obtained. This mixture is extracted with ethyl acetate (2×50 mL), and the extracts are washed with brine, combined, dried over MgSO$_4$, filtered and evaporated. The solid residue is recrystallized from cyclohexane to afford pure product, 4-bromo-1-(4-chlorophenyl)-pyrazole (797 mg, 3.10 mmol, 66%). m.p. 75-76° C. (cyclohexane), $^1$H NMR (300 MHz, CDCl$_3$): δ 7.89 (1H, s), 7.66 (1H, s), 7.57 (2H, d, J=9.0 Hz), 7.41 (2H, d, J=9.0 Hz). MS (ES+): m/e 261 (26), 259 (100), 257 (77).

Part C.

A solution of 4-bromo-1-(4-chlorophenyl)-pyrazole (422 mg, 1.64 mmol), 3-carboxybenzeneboronic acid (326 mg, 1.96 mmol), palladium acetate (20 mg, 0.089 mmol), triphenylphosphine (93 mg, 0.355 mmol) and aq. Na$_2$CO$_3$ solution (2.50 mL, 2.0 M, 5.00 mmol) in dimethoxyethane (25 mL) is degassed by three cycles of vacuum pumping/nitrogen purging. The solution is then heated to reflux for 18 h. The resulting black mixture is allowed to cool, filtered through celite and poured into 120 mL HCl (0.5 N). This is extracted with ethyl acetate (2×120 mL), and the extracts are washed with brine, combined, dried over MgSO$_4$, filtered and partially evaporated. A small amount (50 mg) of a solid product is collected by filtration, which is pure title product by spectroscopic analysis. m.p. 205-206° C. $^1$H NMR (300 MHz, acetone-d$_6$): δ 9.03 (1H, s), 8.32 (1H, t, J=1.6 Hz), 8.26 (1H, s), 8.01 (2H, d, J=9.0 Hz), 7.97-7.87 (2H, m), 7.56 (2H, d, J=9.0 Hz), 7.53 (1H, t, J=8.2 Hz), 1H missing. MS (ES+): m/e 302 (4), 301 (31), 300 (19), 299 (100). MS (ES−): m/e 300 (2), 299 (31), 298 (23), 297 (100).

The procedure above may be slightly modified to prepare the following compounds.

Compound 97

3-[1-(4-Methoxy-phenyl)-1H-pyrazol-4-yl]-benzoic acid: m.p. 223-225° C. $^1$H NMR (300 MHz, DMSO-d$_6$): δ 13.07 (1H, s), 9.01 (1H, s), 8.24 (1H, s), 8.22 (1H, s), 7.94 (1H, d, J=7.6 Hz), 7.82 (2H, d, J=9.9 Hz), 7.81 (1H, d, J=7.8 Hz), 7.52 (1H, t, J=7.7 Hz), 7.06 (2H, d, J=9.9 Hz), 3.79 (3H, s). MS (ES+): m/e 296 (19), 295 (100). MS (ES−): m/e 294 (17), 293 (100).

Compound 133

3-[1-(4-Trifluoromethoxy-phenyl)-1H-pyrazol-4-yl]-benzoic acid: m.p. 213-215° C. $^1$H NMR (300 MHz, DMSO-d$_6$): δ 9.18 (1H, s), 8.32 (1H, s), 8.26 (1H, s), 7.99 (3H, m), 7.81 (1H, d, J=6.3 Hz), 7.53 (3H, m). MS (ES+): m/e 350 (20), 349 (100). MS (ES−): m/e 348 (20), 347 (100).

Compound 134

4-[1-(4-Trifluoromethoxy-phenyl)-1H-pyrazol-4-yl]-benzoic acid: m.p. 246-248° C. $^1$H NMR (300 MHz, DMSO-d$_6$):

δ 9.18 (1H, s), 8.35 (1H, s), 8.01 (2H, d, J=8.9 Hz), 7.96 (2H, d, J=8.2 Hz), 7.83 (2H, d, J=8.2 Hz), 7.55 (2H, d, J=8.9 Hz). MS (ES+): m/e 350 (20), 349 (100). MS (ES−): m/e 348 (20), 347 (100).

Compound 171

4-[1-(3-Methoxy-phenyl)-1H-pyrazol-4-yl]-benzoic acid: m.p. 211-212° C. $^1$H NMR (300 MHz, DMSO-d$_6$): δ 9.16 (1H, s), 8.31 (1H, s), 7.95 (2H, d, J=8.5 Hz), 7.83 (2H, d, J=8.5 Hz), 7.44 (3H, m), 6.90 (1H, m), 3.84 (3H, s). MS (ES+): m/e 297 (5), 296 (45), 295 (100). MS (ES−): m/e 294 (20), 293 (100).

Compound 172

3-[1-(3-Trifluoromethoxy-phenyl)-1H-pyrazol-4-yl]-benzoic acid: m.p. 179-181° C. $^1$H NMR (300 MHz, DMSO-d$_6$): δ 9.21 (1H, s), 8.33 (1H, s), 8.27 (1H, s), 7.95 (1H, dd, J=8.0, 1.2 Hz), 7.80 (3H, m), 7.55 (2H, m), 7.35 (1H, s), 7.12 (1H, m). MS (ES+): m/e 332 (60), 331 (100). MS (ES−): m/e 330 (20), 329 (100).

Compound 173

4-[1-(3-Trifluoromethoxy-phenyl)-1H-pyrazol-4-yl]-benzoic acid: m.p. 255-257° C. $^1$H NMR (300 MHz, DMSO-d$_6$): δ 9.20 (1H, s), 8.34 (1H, s), 7.96 (2H, d, J=8.5 Hz), 7.82 (2H, d, J=8.5 Hz), 7.77 (1H, m), 7.73 (1H, m), 7.57 (1H, m), 7.36 (1H, s), 7.14 (1H, m). MS (ES+): m/e 333 (10), 332 (60), 331 (100). MS (ES−): m/e 330 (20), 329 (100).

Compound 174

3-[1-(3-Methoxy-phenyl)-1H-pyrazol-4-yl]-benzoic acid: m.p. 156-157° C. $^1$H NMR (300 MHz, DMSO-d$_6$): δ 9.15 (1H, s), 8.27 (2H, s, overlapping), 7.96 (1H, dd, J=7.7, 1.1 Hz), 7.81 (1H, dd, J=7.4, 1.1 Hz), 7.50 (3H, m), 7.43 (1H, m), 6.88 (1H, dd, J=8.0, 1.1 Hz), 3.83 (3H, s). MS (ES+): m/e 296 (20), 295 (100). MS (ES−): m/e 294 (20), 293 (100).

Compound 177

3-(1-p-Tolyl-1H-pyrazol-4-yl)-benzoic acid: m.p. 229-231° C. $^1$H NMR (300 MHz, DMSO-d$_6$): δ 9.07 (1H, s), 8.25 (2H, s, overlapping), 7.94 (1H, d, J=7.4 Hz), 7.78 (3H, m), 7.51 (1H, t, J=7.4 Hz), 7.30 (2H, d, J=8.0 Hz), 2.33 (3H, s). MS (ES+): m/e 280 (20), 279 (100). MS (ES−): m/e 278 (20), 277 (100).

Compound 178

4-(1-p-Tolyl-1H-pyrazol-4-yl)-benzoic acid: m.p. 280-282° C. $^1$H NMR (300 MHz, DMSO-d$_6$): δ 9.08 (1H, s), 8.28 (1H, s), 7.95 (2H, d, J=8.3 Hz), 7.83 (2H, d, J=8.3 Hz), 7.77 (2H, d, J=8.6 Hz), 7.32 (2H, d, J=8.6 Hz), 2.33 (3H, s). MS (ES+): m/e 280 (20), 279 (100). MS (ES−): m/e 278 (20), 277 (100).

Compound 179

3-[1-(2,4-Difluoro-phenyl)-1H-pyrazol-4-yl]-benzoic acid: m.p. 200-202° C. $^1$H NMR (300 MHz, DMSO-d$_6$): δ 8.74 (1H, d, J=1.9 Hz), 8.32 (1H, s), 8.21 (1H, s), 7.87 (3H, m), 7.58 (2H, m), 7.28 (1H, m). MS (ES+): m/e 302 (20), 301 (100). MS (ES−): m/e 300 (20), 299 (100).

Compound 180

4-[1-(2,4-Difluoro-phenyl)-1H-pyrazol-4-yl]-benzoic acid: m.p. 258-260° C. $^1$H NMR (300 MHz, DMSO-d$_6$): δ 8.76 (1H, d, J=2.2 Hz), 8.36 (1H, s), 7.94 (2H, d, J=8.3 Hz), 7.88 (1H, m), 7.83 (2H, d, J=8.3 Hz), 7.61 (1H, m), 7.29 (1H, m). MS (ES+): m/e 302 (20), 301 (100). MS (ES−): m/e 300 (20), 299 (100).

Compound 181

3-[1-(4-Fluoro-phenyl)-1H-pyrazol-4-yl]-benzoic acid: m.p. 235-237° C. $^1$H NMR (300 MHz, DMSO-d$_6$): δ 9.11 (1H, s), 8.26 (2H, d, J=6.3 Hz), 7.94 (3H, m), 7.81 (1H, d, J=7.7 Hz), 7.52 (1H, t, J=7.7 Hz), 7.36 (2H, m). MS (ES+): m/e 284 (40), 283 (100). MS (ES−): m/e 282 (20), 281 (100).

Compound 182

4-[1-(4-Fluoro-phenyl)-1H-pyrazol-4-yl]-benzoic acid: m.p. 266-268° C. $^1$H NMR (300 MHz, DMSO-d$_6$): δ 9.11 (1H, s), 8.31 (1H, s), 7.95 (2H, d, J=8.4 Hz), 7.92 (2H, m), 7.83 (2H, d, J=8.4 Hz), 7.38 (2H, m). MS (ES+): m/e 284 (40), 283 (100). MS (ES−): m/e 282 (20), 281 (100).

Compound 223

3-[1-(3-Trifluoromethoxy-phenyl)-1H-pyrazol-4-yl]-benzoic acid: m.p. 143-145° C. $^1$H NMR (300 MHz, DMSO-d$_6$): δ 8.30 (1H, s), 8.21 (1H, s), 8.03 (2H, m), 7.76 (1H, dd, J=6.9, 1.0 Hz), 7.65 (2H, m), 7.49 (2H, m), 7.17 (1H, dd, J=8.3, 1.3 Hz). MS (ES+): m/e 350 (30), 349 (100). MS (ES−): m/e 348 (20), 347 (100).

Compound 224

4-[1-(3-Trifluoromethoxy-phenyl)-1H-pyrazol-4-yl]-benzoic acid: m.p. 230-231° C. $^1$H NMR (300 MHz, DMSO-d$_6$): δ 8.24 (1H, s), 7.90 (1H, s), 7.86 (2H, m), 7.53 (2H, m), 7.45 (2H, m), 7.33 (1H, m), 6.98 (1H, m). MS (ES+): m/e 350 (30), 349 (100). MS (ES−): m/e 348 (20), 347 (100).

Compound 225

3-[1-(2,3-Dihydro-benzo[1,4]dioxin-6-yl)-1H-pyrazol-4-yl]-benzoic acid: m.p. 201-203° C. $^1$H NMR (300 MHz, DMSO-d$_6$): δ 9.01 (1H, s), 8.23 (1H, s), 8.20 (1H, s), 7.91 (1H, dd, J=7.7, 1.1 Hz), 7.79 (1H, dd, J=7.4, 1.0 Hz), 7.50 (1H, t, J=7.7 Hz), 7.36 (2H, m), 6.97 (1H, d, J=8.8 Hz), 4.28 (4H, t, J=1.2 Hz). MS (ES+): m/e 324 (20), 323 (100). MS (ES−): m/e 322 (20), 321 (100).

Compound 226

4-[1-(2,3-Dihydro-benzo[1,4]dioxin-6-yl)-1H-pyrazol-4-yl]-benzoic acid: m.p. 238-240° C. $^1$H NMR (300 MHz, DMSO-d$_6$): δ 9.01 (1H, s), 8.23 (1H, s), 7.93 (2H, d, J=8.3 Hz), 7.75 (2H, d, J=8.3 Hz), 7.36 (2H, m), 6.98 (1H, d, J=8.8 Hz), 4.28 (4H, t, J=1.9 Hz). MS (ES+): m/e 324 (20), 323 (100). MS (ES−): m/e 322 (20), 321 (100).

Compound 227

4-(1-Benzo[1,3]dioxol-5-yl-1H-pyrazol-4-yl)-benzoic acid: m.p. 266-268° C. $^1$H NMR (300 MHz, DMSO-d$_6$): δ 9.00 (1H, s), 8.25 (1H, s), 7.94 (2H, d, J=8.2 Hz), 7.80 (2H, d, J=8.2 Hz), 7.47 (1H, d, J=2.2 Hz), 7.35 (1H, dd, J=8.5, 2.2 Hz), 7.04 (1H, d, J=8.5 Hz), 6.09 (2H, s). MS (ES+): m/e 310 (20), 309 (100). MS (ES−): m/e 308 (15), 307 (70), 242 (100).

Compound 228

3-[1-(4-Isopropyl-phenyl)-1H-pyrazol-4-yl]-benzoic acid: m.p. 212-215° C. $^1$H NMR (300 MHz, DMSO-d$_6$): δ 9.06 (1H, s), 8.25 (1H, t, J=2.2 Hz), 8.24 (1H, s), 7.94 (1H, dd, J=7.1, 1.1 Hz), 7.81 (2H, d, J=8.6 Hz), 7.79 (1H, s), 7.51 (1H, m), 7.36 (2H, d, J=8.6 Hz), 2.91 (1H, heptet, J=6.9 Hz), 1.21 (6H, d, J=6.9 Hz). MS (ES+): m/e 308 (20), 307 (100). MS (ES−): m/e 306 (20), 305 (100).

Compound 229

4-[1-(4-Isopropyl-phenyl)-1H-pyrazol-4-yl]-benzoic acid: m.p. 215-218° C. $^1$H NMR (300 MHz, DMSO-d$_6$): δ 9.08 (1H, s), 8.28 (1H, s), 7.94 (2H, d, J=8.3 Hz), 7.83 (2H, d, J=8.3 Hz), 7.79 (2H, d, J=8.5 Hz), 7.38 (2H, d, J=8.5 Hz), 2.93 (1H, heptet, J=6.9 Hz), 1.21 (6H, d, J=6.9 Hz). MS (ES+): m/e 308 (20), 307 (100). MS (ES−): m/e 306 (20), 305 (100).

Compound 230

3-[1-(3-Chloro-4-methyl-phenyl)-1H-pyrazol-4-yl]-benzoic acid: m.p. 209-211° C. $^1$H NMR (300 MHz, DMSO-d$_6$): δ 9.16 (1H, s), 8.33 (1H, s), 7.93 (3H, m), 7.85 (2H, m), 7.58 (2H, m), 2.31 (3H, s). MS (ES+): m/e 315 (30), 313 (100). MS (ES−): m/e 313 (30), 311 (100), 277 (10).

Compound 231

4-[1-(3-Chloro-4-methyl-phenyl)-1H-pyrazol-4-yl]-benzoic acid: m.p. 285-288° C. $^1$H NMR (300 MHz, DMSO-d$_6$): δ 9.17 (1H, s), 8.31 (1H, s), 7.97 (1H, s), 7.94 (2H, d, J=8.3

Hz), 7.81 (2H, d, J=8.3 Hz), 7.77 (1H, d, J=8.5 Hz), 7.49 (1H, d, J=8.3 Hz), 2.34 (3H, s). MS (ES+): m/e 315 (30), 313 (100). MS (ES−): m/e 313 (30), 311 (100).

Compound 232

3-[1-(3,4-Dichloro-phenyl)-1H-pyrazol-4-yl]-benzoic acid: m.p. 135-138° C. $^1$H NMR (300 MHz, DMSO-d$_6$): δ 9.24 (1H, s), 8.34 (1H, s), 8.27 (1H, s), 8.23 (1H, d, J=2.5 Hz), 7.93 (2H, m), 7.80 (2H, m), 7.51 (1H, t, J=7.7 Hz). MS (ES−): m/e 337 (10), 335 (60), 333 (100). MS (ES−): m/e 335 (10), 333 (60), 331 (100).

Compound 233

4-[1-(3,4-Dichloro-phenyl)-1H-pyrazol-4-yl]-benzoic acid: m.p. 286-289° C. $^1$H NMR (300 MHz, DMSO-d$_6$): δ 9.23 (1H, s), 8.36 (1H, s), 8.19 (1H, d, J=1.1 Hz), 7.95 (2H, d, J=7.2 Hz), 7.90 (1H, m), 7.82 (2H, d, J=7.2 Hz), 7.80 (1H, s). MS (ES+): m/e 337 (10), 335 (50), 333 (100). MS (ES−): m/e 335 (10), 333 (60), 331 (100).

Compound 234

4-[1-(4-Chloro-phenyl)-1H-pyrazol-4-yl]-benzoic acid: m.p. 259-261° C. $^1$H NMR (300 MHz, DMSO-d$_6$): δ 9.16 (1H, s), 8.33 (1H, s), 7.95 (2H, d, J=7.6 Hz), 7.91 (2H, d, J=8.5 Hz), 7.82 (2H, d, J=7.6 Hz), 7.58 (2H, d, J=8.5 Hz). MS (ES+): m/e 301 (30), 299 (100). MS (ES−): m/e 299 (30), 297 (100).

Compound 235

3-[1-(4-Trifluoromethyl-phenyl)-1H-pyrazol-4-yl]-benzoic acid: m.p. 218-220° C. $^1$H NMR (300 MHz, DMSO-d$_6$): δ 9.30 (1H, s), 8.38 (1H, s), 8.30 (1H, s), 8.15 (2H, d, J=8.1 Hz), 7.96 (1H, dd, J=7.7, 1.1 Hz), 7.89 (2H, d, J=8.1 Hz), 7.83 (1H, dd, J=7.8, 1.2 Hz), 7.53 (1H, m). MS (ES+): m/e 334 (20), 333 (100). MS (ES−): m/e 332 (20), 331 (100).

Compound 236

4-[1-(4-Trifluoromethyl-phenyl)-1H-pyrazol-4-yl]-benzoic acid: m.p. 271-273° C. $^1$H NMR (300 MHz, DMSO-d$_6$): δ 9.28 (1H, s), 8.40 (1H, s), 8.10 (2H, d, J=7.7 Hz), 7.96 (2H, d, J=7.7 Hz), 7.89 (4H, m). MS (ES+): m/e 334 (20), 333 (100). MS (ES−): m/e 332 (20), 331 (100), 287 (10).

Compound 237

3-[1-(3,4-Dimethyl-phenyl)-1H-pyrazol-4-yl]-benzoic acid: m.p. 196-197° C. $^1$H NMR (300 MHz, DMSO-d$_6$): δ 9.03 (1H, s), 8.25 (1H, s), 8.22 (1H, s), 7.91 (1H, d, J=7.4 Hz), 7.80 (1H, dd, J=7.2, 1.1 Hz), 7.72 (1H, s), 7.60 (1H, dd, J=8.3, 2.2 Hz), 7.49 (1H, m), 7.23 (1H, d, J=8.0 Hz), 2.29 (3H, s), 2.23 (3H, s). MS (ES+): m/e 294 (20), 293 (100). MS (ES−): m/e 292 (20), 291 (100).

Compound 238

4-[1-(3,4-Dimethyl-phenyl)-1H-pyrazol-4-yl]-benzoic acid: m.p. 254-256° C. $^1$H NMR (300 MHz, DMSO-d$_6$): δ 9.05 (1H, s), 8.25 (1H, s), 7.93 (2H, d, J=6.9 Hz), 7.88 (2H, d, J=6.9 Hz), 7.68 (1H, s), 7.57 (1H, d, J=8.0 Hz), 7.25 (1H, d, J=8.0 Hz), 2.28 (3H, s), 2.23 (3H, s). MS (ES+): m/e 294 (20), 293 (100). MS (ES−): m/e 292 (20), 291 (100), 247 (10).

Compound 239

3-(1-Benzo[1,3]dioxol-5-yl-1H-pyrazol-4-yl)-benzoic acid: m.p. 221-223° C. $^1$H NMR (300 MHz, DMSO-d$_6$): δ 9.01 (1H, s), 8.23 (1H, t, J=1.7 Hz), 8.22 (1H, s), 7.92 (1H, d, J=7.7 Hz), 7.79 (1H, dd, J=7.7, 1.1 Hz), 7.53-7.48 (2H, m), 7.37 (1H, dd, J=8.3, 2.2 Hz), 7.03 (1H, d, J=8.3 Hz), 6.09 (2H, s). MS (ES+): m/e 310 (20), 309 (100). MS (ES−): m/e 308 (20), 307 (100).

G. Preparation of 1,2,4-Triazoles

Preparation of 3-[1-(4-Methoxy-phenyl)-1H-[1,2,4] triazol-3-yl]-benzoic acid (Compound 12)

Part A.

A solution of methyl 3-cyanobenzoate (1.06 g, 6.58 mmol) in methanol (8 mL) is cooled to 0° C., and treated dropwise with acetyl chloride (10.0 mL, 140 mmol). The resulting mixture is stirred for 6 h and allowed to warm to ambient temperature. The solution is evaporated of volatile components, and the resulting white solid is purified by washing with diethyl ether. After drying under vacuum, the solid is used immediately in the next step.

Part B.

4-Methoxyphenylhydrazine hydrochloride (1.30 g, 7.44 mmol) is treated with satd. aq. NaHCO$_3$ solution (15 mL), and stirred for 10 min. This is extracted with ethylene dichloride (2×20 mL), and the extracts are washed with brine, combined, dried over MgSO$_4$, filtered and evaporated to afford the free base as a white powder. This is suspended in 1,4-dioxane (10 mL), and the imidate salt prepared in Part A above is added. The resulting solution is heated to 110° C. for 3.5 h and allowed to cool. The mixture is diluted with diethyl ether, and the resulting white precipitate is collected by filtration and dried under vacuum to afford methyl 3-[imino(2-(4-methoxy)phenylhydrazino)methyl]benzoate (0.48 g, 21%). MS (ES+): m/e 300 (100).

Part C.

A solution of methyl 3-[imino(2-(4-methoxy)phenylhydrazino)methyl]benzoate (0.28 g, 0.94 mmol) is treated with conc. aq. formic acid (3.5 mL). The solution is heated to reflux for 12 h, cooled, poured into water, and stirred for 1 h. A white solid (methyl 3-[1-(4-methoxy-phenyl)-1H-[1,2,4] triazol-3-yl]-benzoate) forms, which is collected by filtration, washed with water and hexane, and dried under vacuum (0.22 g, 76%). MS (ES+): m/e 310.

Part D.

A mixture of methyl 3-[1-(4-methoxy-phenyl)-1H-[1,2,4] triazol-3-yl]-benzoate (0.21 g, 6.8 mmol) and aq. NaOH solution (5 mL) in THF (5 mL) is heated to reflux for 5 h. The solution is cooled and evaporated, and the residue is treated with 1 N HCl until the pH is slightly acidic. This causes the precipitation of a white solid, which is recrystallized from ethanol/water to afford the title product (0.13 g, 65%). m.p. 230-232° C. $^1$H NMR (300 MHz, DMSO-d$_6$): δ 9.26 (1H, s), 8.64 (1H, s), 8.29 (1H, d, J=8 Hz), 8.00 (1H, d, J=8 Hz), 7.84 (2H, d, J=8.8 Hz), 7.63 (1H, t, J=8 Hz), 7.12 (2H, d, J=8.8 Hz), 3.82 (3H, s). MS (ES+): m/e 297 (20), 296 (100), MS (ES−): m/e 295 (20), 294 (100).

This procedure may be used in the synthesis of the following compounds.

Compound 8

3-(3-Phenyl-[1,2,4]triazol-1-yl)-benzoic acid: m.p. 268-271° C. $^1$H NMR (300 MHz, acetone-d$_6$): δ 9.27 (1H, s), 8.57 (1H, t, J=1.9 Hz), 8.26-8.19 (3H, m), 8.09 (1H, dt, J=7.9, 1.3 Hz), 7.75 (1H, t, J=7.9 Hz), 7.54-7.43 (3H, m). MS (ES+): m/e 267 (18), 266 (100). MS (ES−): m/e 265 (17), 264 (100). Analysis calculated for C$_{15}$H$_{11}$N$_3$O$_2$.1.52H$_2$O: C, 61.57; H, 4.83; N, 14.36. found: C, 62.79; H, 4.27; N, 13.00.

Compound 9

3-[3-(4-Hydroxy-phenyl)-[1,2,4]triazol-1-yl]-benzoic acid: m.p. 307-311° C. $^1$H NMR (300 MHz, DMSO-d$_6$): δ 9.41 (1H, s), 8.41 (1H, s), 8.16 (1H, dd, J=7.9, 2.0 Hz), 7.95-7.84 (3H, m), 7.68 (1H, t, J=7.9 Hz), 6.87 (2H, d, J=8.5 Hz). MS (ES+): m/e 283 (18), 282 (100). MS (ES−): m/e 281 (18), 280 (100). Analysis calculated for C$_{15}$H$_{11}$N$_3$O$_3$.2.03H$_2$O: C, 56.69; H, 4.78; N, 13.22. found: C, 56.38; H, 3.66; N, 13.02.

Compound 10

3-[3-(4-Benzyloxy-phenyl)-[1,2,4]triazol-1-yl]-benzoic acid: m.p. 259-261° C. $^1$H NMR (300 MHz, DMSO-d$_6$): δ 13.37 (1H, br s), 9.42 (1H, s), 8.42 (1H, s), 8.16 (1H, ddd, J=8.1, 2.3, 1.2 Hz), 8.03 (2H, d, J=9.2 Hz), 7.95 (1H, dt, J=7.9, 1.0 Hz), 7.69 (1H, t, J=7.8 Hz), 7.48-7.32 (5H, m), 7.13 (2H, d, J=9.2 Hz), 5.16 (2H, s). MS (ES+): m/e 373 (21), 372 (100). MS (ES−): m/e 371 (23), 370 (100). Analysis calculated for C$_{22}$H$_{17}$N$_3$O$_3$.0.18H$_2$O: C, 70.54; H, 4.67; N, 11.22. found: C, 70.55; H, 4.46; N, 11.07.

Compound 11
3-[3-(4-Methoxy-phenyl)-[1,2,4]triazol-1-yl]-benzoic acid: m.p. 268-270° C. $^1$H NMR (300 MHz, DMSO-d$_6$): δ 13.36 (1H, br s), 9.42 (1H, s), 8.42 (1H, s), 8.17 (1H, dt, J=8.1, 1.1 Hz), 8.03 (2H, d, J=8.2 Hz), 7.94 (1H, dd, J=7.8, 1.1 Hz), 7.69 (1H, t, J=7.6 Hz), 7.05 (2H, d, J=8.2 Hz), 3.81 (3H, s). MS (ES+): m/e 297 (23), 296 (100). MS (ES−): m/e 295 (17), 294 (100). Analysis calculated for C$_{16}$H$_{13}$N$_3$O$_3$.0.17H$_2$O: C, 64.42; H, 4.51; N, 14.08. found: C, 64.69; H, 4.43; N, 13.77.

Compound 13
3-[1-(4-Fluoro-phenyl)-1H-[1,2,4]triazol-3-yl]-benzoic acid: m.p. >310° C. $^1$H NMR (300 MHz, DMSO-d$_6$): δ 9.31 (1H, s), 8.60 (1H, s), 8.25 (1H, d, J=6.6 Hz), 8.00-7.90 (3H, m), 7.59 (1H, t, J=7.5 Hz), 7.42-7.36 (2H, m). MS (ES+): m/e 285 (25), 284 (100). MS (ES−): m/e 283 (20), 282 (100).

Compound 14
3-(1-p-Tolyl-1H-[1,2,4]triazol-3-yl)-benzoic acid: m.p. 263-265° C. $^1$H NMR (300 MHz, DMSO-d$_6$): δ 9.26 (1H, d), 8.57 (1H), 8.21 (1H), 7.91 (1H), 7.73 (1H), 7.55 (1H, d), 7.29 (2H), 2.30 (3H, s). MS (ES+): m/e 281 (25), 280 (100). MS (ES−): m/e 279 (20), 278 (100).

Compound 16
3-[1-(2,4-Difluoro-phenyl)-1H-[1,2,4]triazol-3-yl]-benzoic acid: m.p. 290-292° C. $^1$H NMR (300 MHz, DMSO-d$_6$): δ 9.09 (1H, t, J=1.9 Hz), 8.63 (1H, d, J=1.4 Hz), 8.28 (1H, d, J=6.3 Hz), 8.03-7.90 (2H, m), 7.71-7.61 (2H, m), 7.34 (1H, t, J=7 Hz). MS (ES+): m/e 303 (20), 302 (100). MS (ES−): m/e 301 (20), 300 (100).

Compound 15
3-[1-(4-Isopropyl-phenyl)-1H-[1,2,4]triazol-3-yl]-benzoic acid: m.p. 173-175° C. $^1$H NMR (300 MHz, DMSO-d$_6$): δ 9.25 (1H), 8.58 (1H), 8.22 (1H), 7.92 (1H), 7.75 (2H), 7.56 (1H), 7.34 (2H), 2.89 (1H), 1.15 (6H). MS (ES+): m/e 309 (40), 308 (100). MS (ES−): m/e 307 (20), 306 (100).

Compound 17
3-[1-(2-Fluoro-phenyl)-1H-[1,2,4]triazol-3-yl]-benzoic acid: m.p. 239-241° C. $^1$H NMR (300 MHz, DMSO-d$_6$): δ 9.12 (1H, s), 8.66 (1H, s), 8.31 (1H, d, J=7.4 Hz), 8.03 (1H, d, J=7.1 Hz), 7.91 (1H, t, J=7.5 Hz), 7.64 (1H, t, J=7.7 Hz), 7.60-7.50 (2H, m), 7.43 (1H, br). MS (ES+): m/e 285 (20), 284 (100). MS (ES−): m/e 283 (20), 282 (100).

Compound 18
3-[1-(4-Trifluoromethyl-phenyl)-1H-[1,2,4]triazol-3-yl]-benzoic acid: m.p. 141-143° C. $^1$H NMR (300 MHz, DMSO-d$_6$): δ 9.55 (1H, s), 8.67 (1H, s), 8.32 (1H, d, J=7.7 Hz), 8.19 (2H, d, J=8.5 Hz), 8.02 (1H, d, J=7.7 Hz), 7.95 (2H, d, J=8.5 Hz), 7.65 (1H, t, J=7.7 Hz). MS (ES+): m/e 335 (20), 334 (100). MS (ES−): m/e 333 (20), 332 (100).

Compound 19
3-[1-(4-Trifluoromethoxy-phenyl)-1H-[1,2,4]triazol-3-yl]-benzoic acid: m.p. 219-221° C. $^1$H NMR (300 MHz, DMSO-d$_6$): δ 9.43 (1H, s), 8.66 (1H, s), 8.28 (1H, d, J=7.4 Hz), 8.13-8.00 (3H, m), 7.67-7.58 (3H, m). MS (ES+): m/e 351 (15), 350 (100). MS (ES−): m/e 349 (15), 348 (100).

Compound 20
3-[1-(3,5-Bis-trifluoromethyl-phenyl)-1H-[1,2,4]triazol-3-yl]-benzoic acid: m.p. 271-273° C. $^1$H NMR (300 MHz, DMSO-d$_6$): δ 9.68 (1H, s), 8.65 (1H, s), 8.62 (2H, s), 8.34 (1H, d, J=7.7 Hz), 8.16 (1H, s), 8.02 (1H, d, J=7.7 Hz), 7.63 (1H, t, J=7.7 Hz). MS (ES+): m/e 403 (25), 402 (100).

Compound 21
3-[1-(2-Ethyl-phenyl)-1H-[1,2,4]triazol-3-yl]-benzoic acid: m.p. 176-178° C. $^1$H NMR (300 MHz, DMSO-d$_6$): δ 8.96 (1H, s), 8.64 (1H, s), 8.28 (1H, dd, J=7.7, 1.1 Hz), 8.01 (1H, dd, J=7.7, 1.1 Hz), 7.63 (1H, t, J=7.7 Hz), 7.52-7.40 (4H, m), 2.55 (2H, q, J=7.7 Hz), 1.06 (3H, t, J=7.7 Hz). MS (ES+): m/e 295 (30), 294 (100).

Compound 22
3-[1-(4-Bromo-phenyl)-1H-[1,2,4]triazol-3-yl]-benzoic acid: m.p. >310° C. $^1$H NMR (300 MHz, DMSO-d$_6$): δ 9.39 (1H, s), 8.65 (1H, s), 8.03-7.93 (4H, m), 7.76 (2H, d, J=8.2 Hz), 7.40 (1H, t, J=7.3 Hz). MS (ES+); m/e 347 (15), 346 (100), 345 (15), 344 (100).

Compound 23
3-[1-(4-Nitro-phenyl)-1H-[1,2,4]triazol-3-yl]-benzoic acid: m.p. 284-286° C. $^1$H NMR (300 MHz, DMSO-d$_6$): δ 9.41 (1H, s), 8.65 (1H, s), 8.31 (1H, d, J=7.7 Hz), 8.30-8.25 (1H, m), 8.05-7.95 (2H, m), 7.70-7.60 (3H, m). MS (ES+): m/e 312 (20), 311 (100).

Compound 25
3-[1-(3-Chloro-4-fluoro-phenyl)-1H-[1,2,4]triazol-3-yl]-benzoic acid: m.p. 270-272° C. $^1$H NMR (300 MHz, DMSO-d$_6$): δ 9.42 (1H, s), 8.65 (1H, s), 8.31 (1H, dd, J=7.7, 1.1 Hz), 8.25-8.22 (1H, m), 8.04-7.95 (2H, m), 7.68-7.61 (2H, m). MS (ES+): m/e 320 (35), 318 (100).

Compound 29
3-[1-(3-Fluoro-phenyl)-1H-[1,2,4]triazol-3-yl]-benzoic acid: m.p. 266-268° C. $^1$H NMR (300 MHz, DMSO-d$_6$): δ 9.45 (1H, s), 8.66 (1H, s), 8.31 (1H, d, J=7.8 Hz), 8.02 (1H, d, J=7.6 Hz), 7.89-7.80 (2H, m), 7.66-7.58 (2H, m), 7.28 (1H, t, J=8.3 Hz). MS (ES+): m/e 285 (20), 284 (100).

Compound 30
3-[1-(2-Bromo-phenyl)-1H-[1,2,4]triazol-3-yl]-benzoic acid: m.p. 245-247° C. $^1$H NMR (300 MHz, DMSO-d$_6$): δ 9.04 (1H, s), 8.62 (1H, d, J=1.2 Hz), 8.27 (1H, dd, J=7.8, 1.2 Hz), 8.00 (1H, dd, J=7.8, 1.3 Hz), 7.90 (1H, dt, J=8.0, 2.2 Hz), 7.74-7.49 (4H, m). MS (ES+): m/e 347 (20), 346 (100), 345 (20), 344 (100).

Compound 31
4-[3-(3-Carboxy-phenyl)-[1,2,4]triazol-1-yl]-benzoic acid: m.p. >300° C. $^1$H NMR (300 MHz, DMSO-d$_6$): δ 9.53 (1H, s), 8.67 (1H, s), 8.32 (1H, d, J=7.6 Hz), 8.10 (4H, s), 8.02 (1H, d, J=7.6 Hz), 7.65 (1H, t, J=7.6 Hz). MS (ES+): m/e 311 (20), 310 (100).

Compound 35
3-[1-(3-Bromo-phenyl)-1H-[1,2,4]triazol-3-yl]-benzoic acid: m.p. 253-255° C. $^1$H NMR (300 MHz, DMSO-d$_6$): δ 9.48 (1H, s), 8.67 (1H, s), 8.33 (1H, d, J=7.8 Hz), 8.22 (1H, s), 8.05-7.97 (2H, m), 7.68-7.62 (2H, m), 7.54 (1H, t, J=7.8 Hz). MS (ES+): 347 (20), 346 (100), 345 (20), 344 (100). MS (ES−): m/e 345 (15), 344 (95), 343 (15), 342 (100).

Compound 36
3-(1-Pyridin-2-yl-1H-[1,2,4]triazol-3-yl)-benzoic acid: m.p. 241-244° C. $^1$H NMR (300 MHz, DMSO-d$_6$): δ 9.47 (1H, s), 8.68 (1H, s), 8.56 (1H, br), 8.34 (1H, d, J=7.3 Hz), 8.10-7.98 (3H, m), 7.66 (1H, t, J=7.3 Hz), 7.50 (1H, br). MS (ES+): m/e 268 (25), 267 (100). MS (ES−): m/e 266 (20), 265 (100).

Compound 37
3-(1-Phenyl-1H-[1,2,4]triazol-3-yl)-benzoic acid: m.p. 257-259° C. $^1$H NMR (300 MHz, DMSO-d$_6$): δ 9.41 (1H, s), 8.68 (1H, s), 8.33 (1H, d, J=7.6 Hz), 8.03 (1H, d, J=7.6 Hz), 8.01-7.93 (2H, m), 7.68-7.55 (3H, m), 7.44 (1H, t, J=7.1 Hz). MS (ES+): m/e 267 (25), 266 (100). MS (ES−): m/e 265 (20), 264 (100).

Compound 38
3-[1-(3-Chloro-4-methyl-phenyl)-1H-[1,2,4]triazol-3-yl]-benzoic acid: m.p. 269-272° C. $^1$H NMR (300 MHz, DMSO-d$_6$): δ 9.43 (1H, s), 8.66 (1H, s), 8.32 (1H, d, J=6.8 Hz), 8.06 (1H, s), 8.02 (1H, d, J=7.5 Hz), 7.85 (1H, t, J=7.6 Hz), 7.65 (1H, t, J=7.5 Hz), 7.57 (1H, d, J=8.5 Hz), 2.39 (3H, s). MS (ES+): m/e 314 (100). MS (ES−): m/e 312 (100).

Compound 39

3-(1-m-Tolyl-1H-[1,2,4]triazol-3-yl)-benzoic acid: m.p. 223-225° C. $^1$H NMR (300 MHz, DMSO-d$_6$): δ 9.37 (1H, s), 8.66 (1H, s), 8.31 (1H, d, J=7.5 Hz), 8.01 (1H, d, J=7.5 Hz), 7.78 (1H, s), 7.73 (1H, d, J=8.3 Hz), 7.64 (1H, t, J=7.5 Hz), 7.45 (1H, t, J=7.8 Hz), 7.24 (1H, d, J=7.5 Hz), 2.41 (3H, s). MS (ES+): m/e 281 (30), 280 (100). MS (ES−): m/e 279 (20), 278 (100).

Compound 40

3-(1-o-Tolyl-1H-[1,2,4]triazol-3-yl)-benzoic acid: m.p. 209-211° C. $^1$H NMR (300 MHz, DMSO-d$_6$): δ 8.98 (1H, s), 8.64 (1H, s), 8.29 (1H, d, J=7.3 Hz), 8.01 (1H, d, J=7.3 Hz), 7.63 (1H, t, J=7.3 Hz), 7.53-7.41 (4H, m), 2.27 (3H, s). MS (ES+): m/e 280 (100).

Compound 45

4-[1-(3-Methoxy-phenyl)-1H-[1,2,4]triazol-3-yl]-benzoic acid: m.p. 203-205° C. $^1$H NMR (300 MHz, DMSO-d$_6$): δ 9.43 (1H, s), 8.21 (2H, d, J=8 Hz), 8.06, 2H, d, J=8 Hz), 7.51-7.47 (3H, m), 7.02-6.99 (1H, m), 3.85 (3H, s). MS (ES+): m/e 297 (20), 296 (100). MS (ES−): m/e 295 (20), 294 (100).

Preparation of 3-(1-Biphenyl-4-yl-1H-[1,2,4]triazol-3-yl)-benzoic acid (Compound 24)

A 10 mL glass tube with a stirbar is charged with methyl 3-[1-(4-bromo-phenyl)-1H-[1,2,4]triazol-3-yl]-benzoate (265 mg, 0.74 mmol), benzeneboronic acid (90.2 mg, 0.74 mmol), sodium carbonate (235 mg), tetrabutylammonium iodide (273 mg), palladium acetate (0.8 mg) and 6 mL water. The vessel is sealed and placed into the reaction cavity of a microwave reactor. The reaction is performed with 60 W power at 150° C., with monitoring by LC/MS. After the reaction is determined to be complete, the mixture is filtered through celite and acidified using 1N HCl until the pH of the medium is less than 7. The resulting solid is collected by filtration and recrystallized to purity from THF-hexane to afford the title product (200 mg, 79%) as a white powder, m.p. 263-265° C. $^1$H NMR (300 MHz, DMSO-d$_6$): δ 9.47 (1H, s), 8.69 (1H, s), 8.34 (1H, d, J=7.5 Hz), 8.05-7.39 (1H, m). MS (ES+): m/e 343 (30), 342 (100).

The following examples may be prepared using the above procedure, slightly modified as necessary.

Compound 26

3-[1-(4-Benzofuran-2-yl-phenyl)-1H-[1,2,4]triazol-3-yl]-benzoic acid: m.p. 293-295° C. $^1$H NMR (300 MHz, DMSO-d$_6$): δ 9.50 (1H, s), 8.69 (1H, s), 8.34 (1H, d, J=7.8 Hz), 8.14-7.99 (4H, m), 7.66 (2H, t, J=7.8 Hz), 7.56 (1H, s), 7.36-7.24 (4H, m). MS (ES+): m/e 383 (25), 382 (100).

Compound 27

3-[1-(4'-Methoxy-biphenyl-4-yl)-1H-[1,2,4]triazol-3-yl]-benzoic acid: m.p. 243-246° C. $^1$H NMR (300 MHz, DMSO-d$_6$): δ 9.44 (1H, s), 8.68 (1H, s), 8.29 (1H, d, J=7.5 Hz), 8.01 (1H, d, J=7.7 Hz), 7.99 (2H, d, J=8.8 Hz), 7.82 (2H, d, J=8.8 Hz), 7.68 (2H, d, J=8.8 Hz), 7.61 (1H, t, J=7.7 Hz), 7.04 (2H, d, J=8.8 Hz), 3.80 (3H, s). MS (ES+): m/e 373 (30), 372 (100).

Compound 28

3-[1-(4'-Isopropyl-biphenyl-4-yl)-1H-[1,2,4]triazol-3-yl]-benzoic acid: m.p. 225-228° C. $^1$H NMR (300 MHz, DMSO-d$_6$): δ 9.44 (1H, s), 8.69 (1H, s), 8.26 (1H, d, J=7.3 Hz), 8.01 (2H, d, J=8.0 Hz), 8.00 (1H, obscurred), 7.84 (2H, d, J=8.5 Hz), 7.64 (2H, d, J=8.1 Hz), 7.62 (1H, t, J=7.7 Hz), 7.34 (2H, d, J=7.8 Hz), 2.95 (1H, heptet, J=6.6 Hz), 1.22 (6H, d, J=6.6 Hz). MS (ES+): m/e 385 (25), 384 (100).

Compound 32

3-[1-(4'-Fluoro-biphenyl-4-yl)-1H-[1,2,4]triazol-3-yl]-benzoic acid: m.p. 272-275° C. $^1$H NMR (300 MHz, DMSO-d$_6$): δ 9.46 (1H, s), 8.68 (1H, s), 8.33 (1H, d, J=7.8 Hz), 8.05-7.60 (9H, m), 7.31 (1H, t, J=8.7 Hz). MS (ES+): m/e 361 (25), 360 (100). MS (ES−): m/e 359 (25), 358 (100).

Preparation of 3-[1-(3-Fluoro-phenyl)-5-methyl-1H-[1,2,4]triazol-3-yl]-benzoic acid (Compound 34)

A solution of methyl 3-[imino-2-(3-fluorophenylhydrazino)methyl]benzoate (0.43 g, 1.50 mmol) and triethyl orthoacetate (6.07 g, 37.4 mmol) in ethanol (8 mL) is heated to reflux overnight. After cooling, the solution is poured into water, and the resulting solid is collected by filtration. This ester compound (230 mg, 0.73 mmol) is then subjected to hydrolysis (3 mL 1N aq. sodium hydroxide in 3 mL THF, reflux, 3 h). After evaporation and acidification of the reaction mixture, the resulting residue is collected by filtration and dried under vacuum to afford the solid product (153 mg, 70%), m.p. 236-238° C. $^1$H NMR (300 MHz, DMSO-d$_6$): δ 8.61 (1H, s), 8.24 (1H, d, J=7.6 Hz), 7.99 (1H, d, J=7.6 Hz), 7.68-7.53 (4H, m), 7.39 (1H, t, J=7.6 Hz), 2.57 (3H, s).

The following compound may be prepared by this method.

Compound 33

3-[1-(4-Bromo-phenyl)-5-methyl-1H-[1,2,4]triazol-3-yl]-benzoic acid: m.p. 295-298° C. $^1$H NMR (300 MHz, DMSO-d$_6$): δ 8.60 (1H, s), 8.24 (1H, d, J=7 Hz), 7.98 (1H, d, J=7 Hz), 7.78 (2H, d, J=8 Hz), 7.66 (2H, d, J=8 Hz), 7.64 (1H, t, J=7 Hz), 2.55 (3H, s). MS (ES+): m/e 361 (15), 360 (100), 359 (15), 358 (100). MS (ES−): m/e 359 (15), 358 (100), 357 (15), 356 (95).

Preparation of 3-(5-Oxo-1-o-tolyl-4,5-dihydro-1H-[1,2,4]triazol-3-yl)-benzoic acid (Compound 41)

Part A.

A solution of methyl 3-[imino-2-(2-methylphenylhydrazino)methyl]benzoate (1.13 g, 36.4 mmol) in toluene (8 mL) is treated with N,N'-carbonyldiimidazole (0.61 g, 37.6 mmol). The solution is heated to reflux for 14 h with stirring and monitoring by TLC. After cooling, the reaction mixture is poured into water (50 mL) and extracted with ethyl acetate (2×50 mL). The extracts are combined, dried over magnesium sulfate, filtered and evaporated. The residual solid is suspended in diethyl ether, collected by filtration and dried under vacuum to afford methyl 3-(5-oxo-1-o-tolyl-4,5-dihydro-1H-[1,2,4]triazol-3-yl)-benzoate as a white powder (92.0 mg).

Part B.

A solution of methyl 3-(5-oxo-1-o-tolyl-4,5-dihydro-1H-[1,2,4]triazol-3-yl)-benzoate (92 mg, 0.30 mmol) and lithium iodide (478 mg, 3.57 mmol) in pyridine (3 mL) is heated at reflux for 12 h. The cooled reaction mixture is poured into water and acidified by the addition of 1 N HCl. The resulting solid is collected by filtration, washed with water and ether, and dried under vacuum to afford the title product (72.8 mg, 83%) as a white powder, m.p. >310° C. $^1$H NMR (300 MHz, DMSO-d$_6$): δ 8.80 (1H, br), 8.44 (1H, s), 8.29 (1H, t, J=7.7 Hz), 8.15-8.05 (2H, m), 7.85-7.75 (1H, m), 7.64 (1H, t, J=7.8 Hz), 7.42-7.30 (3H, m), 2.25 (3H, s). MS (ES+): m/e 297 (20), 296 (100). MS (ES−): m/e 295 (29), 294 (100).

The above method may be used to produce the following compound.

Compound 42

3-[1-(3-Fluoro-phenyl)-5-oxo-4,5-dihydro-1H-[1,2,4]triazol-3-yl]-benzoic acid: m.p. >310° C. $^1$H NMR (300 MHz, DMSO-d$_6$): δ 8.68 (1H, s), 8.03 (2H, d, J=7.5 Hz), 7.86

(2H, d, J=7.3 Hz), 7.56-7.46 (2H, m), 7.04 (1H, t, J=8.0 Hz). MS (ES+): m/e 301 (15), 300 (100). MS (ES−): m/e 299 (15), 298 (100).

Preparation of 3-{1-[4-(2-Oxo-pyrrolidin-1-yl)-phenyl]-1H-[1,2,4]triazol-3-yl}-benzoic acid (Compound 43)

Part A.

A 50 mL culture tube containing methyl 3-[1-(4-bromophenyl)-1H-[1,2,4]triazol-3-yl]benzoate (407 mg, 1.14 mmol), copper (I) iodide (10.8 mg, 0.057 mmol), pyrrolidin-2-one (121 mg, 1.42 mmol) and potassium carbonate (138 mg, 2.28 mmol) is evacuated and back charged with nitrogen. N,N'-Dimethylethylenediamine (10 mg, 0.12 mmol) and toluene (5 mL) are added, the tube is sealed with a PTFE cap, and the reaction mixture is heated to 110° C. with stirring for 12 h. The cooled reaction mixture is partitioned between water and ethyl acetate, and the organic extract is washed with water, dried over $MgSO_4$, filtered and evaporated. The residual material is separated by column chromatography (silica gel, 1:20 methanol-dichloromethane) to provide methyl 3-{1-[4-(2-oxo-pyrrolidin-1-yl)-phenyl]-1H-[1,2,4]triazol-3-yl}-benzoate as a tan solid (380 mg, 92%).

Part B.

A solution of methyl 3-{1-[4-(2-oxo-pyrrolidin-1-yl)-phenyl]-1H-[1,2,4]triazol-3-yl}-benzoate (101.6 mg, 0.28 mmol) and lithium iodide (451 mg, 3.37 mmol) in pyridine (3 mL) is heated under dry $N_2$ atmosphere to reflux for 6 h, then cooled and poured into 1N aq. HCl. The resulting solid is collected by filtration, washed with water and ether, and dried under vacuum to afford the title product as a tan solid (75.3 mg, 77%), m.p. 270-273° C. $^1$H NMR (300 MHz, DMSO-$d_6$): δ 9.36 (1H, s), 8.66 (1H, s), 8.31 (1H, d, J=7.6 Hz), 8.02 (1H, d, J=7.1 Hz), 7.93 (2H, d, J=8.5 Hz), 7.86 (2H, d, J=8.5 Hz), 7.64 (1H, t, J=7.8 Hz), 3.88 (2H, m), 2.53 (2H, m), 2.08 (2H, m). MS (ES+): m/e 350 (30), 349 (100). MS (ES−): m/e 348 (25), 347 (100).

The following compound may be prepared using a minor modification of the procedure above.

Compound 44

3-{1-[4-(2-Oxo-azetidin-1-yl)-phenyl]-1H-[1,2,4]triazol-3-yl}-benzoic acid: m.p. 295-297° C. $^1$H NMR (300 MHz, DMSO-$d_6$): δ 9.33 (1H, s), 8.65 (1H, s), 8.31 (1H, d, J=7.8 Hz), 8.01 (1H, d, J=6.8 Hz), 7.93 (2H, d, J=8.0 Hz), 7.64 (1H, t, J=7.3 Hz), 7.51 (2H, d, J=8.0 Hz), 3.68 (2H, br), 3.11 (2H, br). MS (ES+): m/e 336 (30), 335 (100). MS (ES−): m/e 334 (20), 333 (100).

Preparation of 3-[1-(4-Pyrrolidin-1-yl-phenyl)-1H-[1,2,4]triazol-3-yl]-benzoic acid (Compound 45)

Part A.

A solution of methyl 3-{1-[4-(2-oxo-pyrrolidin-1-yl)-phenyl]-1H-[1,2,4]triazol-3-yl}-benzoate (278 mg, 0.77 mmol) in THF (5 mL) is treated with borane.tetrahydrofuran complex (3.85 mmol) at ambient temperature. The resulting solution is stirred for 16 h, and quenched by the addition of 6N aq. HCl. After being allowed to stir for 30 min, the mixture is made basic with the addition of 1N aq. sodium hydroxide solution. The mixture is partially evaporated until a precipitate formed, which is collected by filtration, washed with water, and dried under vacuum to afford 226 mg (84%) of methyl 3-[1-(4-pyrrolidin-1-yl-phenyl)-1H-[1,2,4]triazol-3-yl]-benzoate.

Part B.

The lithium iodide-pyridine ester cleavage method described above is employed to convert methyl 3-[1-(4-pyrrolidin-1-yl-phenyl)-1H-[1,2,4]triazol-3-yl]-benzoate to the title compound, m.p. 263-265° C. $^1$H NMR (300 MHz, DMSO-$d_6$): δ 9.14 (1H, s), 8.64 (1H, s), 8.28 (1H, d, J=7.3 Hz), 7.98 (1H, d, J=6.9 Hz), 7.68-7.59 (3H, m), 6.64 (2H, d, J=8.5 Hz), 3.26 (4H, s), 1.96 (4H, s). MS (ES+): m/e 336 (40), 335 (100). MS (ES−): m/e 334 (30), 333 (100).

Preparation of 3-(5H-4-Oxa-1,3,9b-triaza-cyclopenta[a]naphthalen-2-yl)-benzoic acid (Compound 46)

Part A.

A suspension of methyl 3-(5-oxo-1-o-tolyl-4,5-dihydro-1H-[1,2,4]triazol-3-yl)-benzoate (0.58 g, 1.88 mmol), N-bromosuccinimide (368 mg, 2.07 mmol) and azoisobutyronitrile (5 g) in 2:1 $CCl_4/CHCl_3$ (23 mL) is heated to reflux for 3 d. After cooling, the solution is partitioned between water and ethyl acetate, and the organic extract is dried over magnesium sulfate, filtered and evaporated. The residual material (0.62 g) is taken up in tetrahydrofuran (6 mL), and treated with sodium hydride (7 mg of 60% w/w suspension in mineral oil, 0.29 mmol). The resulting mixture is heated to reflux for 6 h, cooled and evaporated. The residue is separated by column chromatography (5:95 ethyl acetate-hexane) to afford the cyclized compound (66 mg).

Part B.

A solution of the ester compound of Part A above (66 mg) in 1:1 aq. tetrahydrofuran (6 mL) is treated with lithium hydroxide (7.7 mg), and the resulting mixture is heated to reflux for 1 h. The solution is cooled and poured into 1 N HCl. The resulting solid is collected by filtration and separated by column chromatography to afford the title product (2.2 mg). $^1$H NMR (300 MHz, $CDCl_3$): δ 8.50 (1H, s), 8.00 (1H, d, J=7.8 Hz), 7.80 (1H, d, J=7.5 Hz), 7.43 (1H, d, J=7.8 Hz), 7.28-7.21 (2H, m), 7.03-6.99 (2H, m), 5.31 (2H, s). MS (ES+): m/e 295 (30), 294 (100). MS (ES−): m/e 293 (20), 292 (100).

H. 1,2,3-Triazoles 1,2,3-triazoles of the invention may be prepared as follows.

Preparation of 4-[4-(3-Methoxyphenyl)-[1,2,3]triazol-1-yl]benzoic acid (Compound 204)

To a solution of 1-ethynyl-3-methoxybenzene (396 mg, 3.00 mmol, Aldrich) in 50% tert-butanol/water (4.0 mL) is added 300 μL (0.30 mmol) of an aqueous solution of sodium ascorbate (594 mg in 3 mL $H_2O$), 100 μL (0.030 mmol) of an aqueous $CuSO_4.5H_2O$ solution (75 mg in 1 mL $H_2O$), followed by 4-azidobenzoic acid (489 mg, 3 mmol). The resulting mixture is stirred for 7 days, the resulting suspension filtered and washed with $H_2O$ (3×30 mL), $Et_2O$ (2×15 mL), and hexanes (3×30 mL). The solid is dried overnite in vacuo (70° C., 10 torr) to afford 880 mg (99%) of 4-[4-(3-methoxyphenyl)-[1,2,3]triazol-1-yl]benzoic acid as a pale yellow powder: m.p. 276-277° C. $^1$H NMR (300 MHz, DMSO-$d_6$) δ 9.44 (s, 1H), 8.16 (d, J=8.5 Hz, 2H), 8.08 (d, J=8.3 Hz, 2H), 7.52 (m, 2H), 7.40 (t, J=7.8 Hz, 1H), 6.95 (ddd, J=8.3, 2.5, 0.8 Hz, 1H), 3.82 (s, 3H). MS m/z 296.29, calcd for $C_{16}H_{13}N_3O_3$ (M+H$^+$) 296.

This method may be used in the synthesis of the following compounds.

Compound 201

4-(4-p-Tolyl-[1,2,3]triazol-1-yl)-benzoic acid: m.p. 302-303° C. $^1$H NMR (300 MHz, DMSO-$d_6$) δ 9.40 (s, 1H), 8.15 (d, J=8.5 Hz, 2H), 8.08 (d, J=8.5 Hz, 2H), 7.82 (d, J=8.0 Hz, 2H), 7.30 (d, J=8.0 Hz, 2H), 2.33 (s, 3H). MS (ES+): m/e 280.36 (100).

Compound 202

4-[4-(4-Trifluoromethyl-phenyl)-[1,2,3]triazol-1-yl]-benzoic acid: m.p. 305-306° C. $^1$H NMR (300 MHz, DMSO-$d_6$) δ 9.60 (s, 1H), 8.14 (m, 6H), 7.87 (m, 2H). MS (ES+): m/e 334.30 (100).

Compound 203

4-[4-(4-Methoxy-phenyl)-[1,2,3]triazol-1-yl]-benzoic acid: m.p. 294-295° C. $^1$H NMR (300 MHz, DMSO-$d_6$) δ 9.30 (s, 1H), 8.11 (m, 4H), 7.86 (d, J=8.5 Hz, 2H), 7.05 (d, J=8.3 Hz, 2H), 3.79 (s, 3H). MS (ES+): m/e 296.35 (100).

Compound 264

4-[4-(2-Fluoro-phenyl)-[1,2,3]triazol-1-yl]-benzoic acid: m.p. 292-294° C. $^1$H NMR (DMSO-$d_6$): δ 9.17 (1H, s), 8.15 (5H, m), 7.90 (3H, m). MS (ES+) m/e 284.20 (100).

Compound 265

4-[4-(3-Fluoro-phenyl)-[1,2,3]triazol-1-yl]-benzoic acid: m.p. 327-328° C. $^1$H NMR (DMSO-$d_6$): δ 9.49 (1H, s), 8.16 (2H, d, J=8.5 Hz), 8.07 (2H, d, J=8.5 Hz), 7.76 (2H, m), 7.54 (1H, m), 7.22 (1H, tm, J=7.6 Hz). MS (ES+) m/e 284.22 (100).

Compound 266

4-[4-(4-Fluoro-phenyl)-[1,2,3]triazol-1-yl]-benzoic acid: m.p. 321-323° C. $^1$H NMR (DMSO-$d_6$): δ 9.41 (1H, s), 8.16 (2H, d, J=8.5 Hz), 8.07 (2H, d, J=8.5 Hz), 7.97 (2H, m), 7.34 (2H, t, J=8.8 Hz). MS (ES+) m/e 284.26 (100).

Compound 267

4-[4-(4-Bromo-2-fluoro-phenyl)-[1,2,3]triazol-1-yl]-benzoic acid: m.p. 327-328° C. $^1$H NMR (DMSO-$d_6$): δ 9.21 (1H, s), 8.14 (5H, m), 7.76 (1H, dm, J=9.9 Hz), 7.57 (1H, dm, J=7.4 Hz). MS (ES+) m/e 366 (100), 364.15 (100).

Compound 268

4-[4-(2,4-Difluoro-phenyl)-[1,2,3]triazol-1-yl]-benzoic acid: m.p. 312-313° C. $^1$H NMR (DMSO-$d_6$): δ 9.17 (1H, s), 8.14 (5H, m) 7.97 (2H, tm, J=9.5 Hz), 7.25 (1H, m). MS (ES+) m/e 302.19 (100).

Compound 269

4-[4-(4-Chloro-phenyl)-[1,2,3]triazol-1-yl]-benzoic acid: m.p. 313-314° C. $^1$H NMR (DMSO-$d_6$): δ 9.46 (1H, s), 8.16 (2H, d, J=8.4 Hz), 8.07 (2H, d, J=8.4 Hz), 7.95 (2H, d, J=8.4 Hz), 7.56 (2H, d, J=8.4 Hz). MS (ES+) m/e 300.29 (100).

Compound 270

4-[4-(2-Bromo-phenyl)-[1,2,3]triazol-1-yl]-benzoic acid: m.p. 261-262° C. $^1$H NMR (DMSO-$d_6$): δ 9.32 (1H, s), 8.14 (4H, m), 7.90 (1H, d, J=6.6 Hz), 7.78 (1H, d, J=7.7 Hz), 7.52 (1H, t, J=7.5 Hz), 7.37 (1H, t, J=7.7 Hz). MS (ES+) m/e 346.11 (100), 348 (100).

Compound 271

4-(4-Naphthalen-1-yl-[1,2,3]triazol-1-yl)-benzoic acid: m.p. 265-266° C. $^1$H NMR (DMSO-$d_6$): δ 9.38 (1H, s), 8.53 (1H, m), 8.18 (4H, m), 8.00 (2H, m), 7.86 (1H, m) 7.59 (3H, m). MS (ES+) m/e 316.23 (100).

Compound 272

4-[4-(3,4-Dimethoxy-phenyl)-[1,2,3]triazol-1-yl]-benzoic acid: m.p. 253-254° C. $^1$H NMR (DMSO-$d_6$): δ 9.33 (1H, s), 8.15 (1H, d, J=8.0 Hz), 8.07 (1H, d, J=8.0 Hz), 7.48 (2H, m), 7.06 (1H, d, J=8.3 Hz), 3.83 (3H, s), 3.78 (3H, s). MS (ES+) m/e 326.23 (100).

Compound 273

4-[4-(4-Ethoxy-phenyl)-[1,2,3]triazol-1-yl]-benzoic acid: m.p. 310-311° C. MS (ES+) m/e 310 (100).

Compound 274

4-[4-(4-Methoxy-2-methyl-phenyl)-[1,2,3]triazol-1-yl]-benzoic acid: m.p. 244-245° C. $^1$H NMR (DMSO-$d_6$): δ 9.04 (1H, s), 8.16 (4H, m), 7.71 (2H, d, J=8.0 Hz), 6.89 (2H, m), 3.77 (3H, s), 2.48 (3H, s). MS (ES+) m/e 310.26 (100).

Compound 275

4-[4-(4-Isopropyl-phenyl)-[1,2,3]triazol-1-yl]-benzoic acid: m.p. 311-312° C. $^1$H NMR (DMSO-$d_6$): δ 9.36 (1H, s), 8.15 (2H, d, J=8.5 Hz), 8.09 (2H, d, J=8.5 Hz), 7.85 (2H, d, J=8.0 Hz), 7.36 (2H, d, J=8.2 Hz), 2.91 (1H, heptet, J=6.9 Hz), 1.21 (6H, d, J=6.9 Hz). MS (ES+) m/e 308.26 (100).

I. Preparation of Oxadiazolones

Oxadiazolones of the invention may be prepared as follows.

Preparation of 4-[5-(3-cyanophenyl)-2-oxo-1,3,4-oxadiazol-3(2H)-yl]benzoic acid (Compound 280)

Part A.

At 0° C., to a suspension of 3-cyanobenzoic acid (0.62 g, 4.2 mmol) in dichloromethane (15 mL) is added THF dropwise until the system became homogenous, which is followed by the addition of 1-hydroxybenzotriazole (0.57 g, 4.2 mmol) and dicyclohexylcarbodiimide (0.87 g, 4.2 mmol). The mixture is brought to room temperature slowly and stirred for 0.5 h. To the mixture, methyl 4-hydrazinobenzoate (0.63 g, 3.8 mmol) is added and the mixture is stirred for 2 hr. The precipitate is then removed by filtration and washed with dichloromethane. The filtrate is washed with water and brine, dried over anhydrous $Na_2SO_4$, which is discarded later. The crude product obtained after the removal of the solvent is separated by column chromatography (silica gel, 1:19 ethyl acetate-dichloromethane) to provide the intermediate, methyl 4-[2-(3-cyanobenzoyl)hydrazino]benzoate (0.68 g, 61%). MS (ES+) m/z: 296.

Part B.

Methyl 4-[2-(3-cyanobenzoyl)hydrazino]benzoate (0.59 g, 2.0 mmol) and carbonyldiimidazole (0.49 g, 3.0 mmol) are stirred at 80° C. in dichloroethane (20 mL) overnight, and the mixture is then subjected to chromatography directly (silica gel, 1:9 ethyl acetate-dichloromethane) to provide methyl 4-[5-(3-cyanophenyl)-2-oxo-1,3,4-oxadiazol-3(2H)-yl]benzoate (0.63 g, 98%). MS (ES+) m/z: 322.

Part C.

Methyl 4-[5-(3-cyanophenyl)-2-oxo-1,3,4-oxadiazol-3(2H)-yl]benzoate (0.60 g, 1.87 mmol) is then treated with boron tribromide (1M in dichloromethane, 5.6 mL, 5.6 mmol) in dichloromethane (20 mL) at room temperature overnight. The volatiles are removed in vacuum and the residue is treated with water. The crude product is separated by column chromatography (silica gel, 1:9 methanol-dichloromethane) to furnish the desired product, 4-[5-(3-cyanophenyl)-2-oxo-1,3,4-oxadiazol-3(2H)-yl]benzoic acid (0.46 g, 81%). m.p. 294-295° C. (decomp.). $^1$H NMR (CDCl$_3$, 300 MHz) δ (ppm) 7.47 (t, 1H), 7.77 (d, 2H), 7.88-8.00 (m, 4H). (ES+) m/z: 307.

The following compounds may be prepared in the same fashion as described above. For thio-1,3,4-oxadizolone analogues, thiocarbonyldiimidazole may be used instead of carbonyldiimidazole. Compound 276 is also prepared similarly by using 4-methoxycarbonylbenzoic acid and 4-isopropylphenylhydrazine as the starting materials.

Compound 276

4-[4-(4-Isopropyl-phenyl)-5-oxo-4,5-dihydro-[1,3,4]oxadiazol-2-yl]-benzoic acid: m.p. 263-267° C. $^1$H NMR (300

MHz, CDCl$_3$): δ 1.15 (d, 2H), 2.80-2.88 (m, 1H), 7.20 (d, 2H), 7.69 (d, 2H), 7.87 (d, 2H), 8.05 (d, 2H). MS (ES−): m/e 323.

Compound 277

4-[5-(4-Isopropyl-phenyl)-2-oxo-[1,3,4]oxadiazol-3-yl]-benzoic acid: m.p. 252-254° C. $^1$H NMR (300 MHz, CDCl$_3$): δ 1.19 (d, 2H), 2.82-2.96 (m, 1H), 7.25 (d, 2H), 7.76 (d, 2H), 7.93 (d, 2H), 8.04 (d, 2H). MS (ES−): m/e 323.

Compound 279

3-[5-(4-Isopropyl-phenyl)-2-oxo-[1,3,4]oxadiazol-3-yl]-benzoic acid: m.p. 218-220° C. (decomp.). $^1$H NMR (300 MHz, CDCl$_3$): δ 1.31 (d, 2H), 2.93-3.08 (m, 1H), 7.37 (d, 2H), 7.60 (t, 1H), 7.89 (d, 2H), 8.00-8.05 (m, 1H), 8.27-8.31 (m, 1H), 8.66 (t, 1H). MS (ES−): m/e 323.

Compound 283

3-[5-(4-Isopropyl-phenyl)-2-thioxo-[1,3,4]oxadiazol-3-yl]-benzoic acid: m.p. 215-217° C. $^1$H NMR (300 MHz, CDCl$_3$): δ 1.31 (d, 2H), 2.95-3.05 (m, 1H), 7.40 (d, 2H), 7.66 (t, 1H), 7.97 (d, 2H), 8.14-8.19 (m, 1H), 8.55-8.60 (m, 1H), 8.90 (t, 1H). MS (ES−): m/e 339.

Compound 285

4-[5-(4-Isopropyl-phenyl)-2-thioxo-[1,3,4]oxadiazol-3-yl]-benzoic acid: m.p. 239-240° C. $^1$H NMR (300 MHz, CDCl$_3$): δ 1.30 (d, 2H), 2.96-3.05 (m, 1H), 7.41 (d, 2H), 7.96 (d, 2H), 8.28 (d, 2H), 8.46 (d, 2H). MS (ES−): m/e 339.

Preparation of 4-[5-(4-isopropylphenyl)-2-oxo-1,3,4-thiadiazol-3(2H)-yl]benzoic acid (Compound 281)

Part A.

To a toluene (25 mL) solution of methyl 4-[2-(4-isopropylbenzoyl)hydrazino]benzoate (0.94 g, 3.0 mmol), prepared from 4-methoxycarbonylphenylhydrazine and 4-isopropylbenzoic acid using the coupling technique described above, is added Lawesson's Reagent (1.82 g, 4.5 mmol). The mixture is stirred at 120° C. for 10 hr and cooled to room temperature. The precipitate is removed and the filtrate is concentrated, chromatographed (silica gel, 1:9 ethyl acetate-hexane) to give an intermediate compound, MS (ES+): m/e 496. The intermediate is then treated with NaOH (1.25N, 2.63 mL, 3.3 mmol) in THF (20 mL) at 65° C. for 1 h. The solvent is then replaced with ether (50 mL), and the mixture is washed with water, dried and chromatographed to provide the thiohydrazide, methyl 4-{2-[(4-isopropylphenyl)carbonothioyl]hydrazino}benzoate (0.82 g, 81%). MS (ES+): m/e 329.

Part B.

Methyl 4-{2-[(4-isopropylphenyl)carbonothioyl]hydrazino}benzoate (0.26 g, 0.8 mmol) and carbonyldiimidazole (0.19 g, 1.2 mmol) are stirred at 80° C. in dichloroethane (20 mL) overnight, and the mixture is subjected to chromatography directly (silica gel, 4:1 ethyl acetate-hexanes) to provide methyl 4-[5-(4-isopropylphenyl)-2-oxo-1,3,4-thiadiazol-3(2H)-yl]benzoate (0.21 g, 75%). MS (ES+): m/e 355.

Part C.

Methyl 4-[5-(4-isopropylphenyl)-2-oxo-1,3,4-thiadiazol-3(2H)-yl]benzoate (0.20 g, 0.56 mmol) in dichloromethane (10 mL) is then treated with boron tribromide (1M in dichloromethane, 1.7 mL, 1.7 mmol) at room temperature overnight. The volatiles are removed in vacuum and the residue is treated with water. The precipitate is collected and washed thoroughly with water to furnish the desired product, 4-[5-(4-isopropylphenyl)-2-oxo-1,3,4-thiadiazol-3(2H)-yl]benzoic acid (0.19 g, 100%), m.p. 205-208° C. $^1$H NMR (CDCl$_3$, 300 MHz) δ (ppm) 1.30 (d, 6H), 2.92-3.06 (m, 1H), 7.35 (d, 2H), 7.70 (d, 2H), 8.11-8.23 (m, 4H). (ES+) m/z: 341.

The following compounds may be prepared in the same fashion as described above. For thio-1,3,4-thiadiazolone analogues, thiocarbonyldiimidazole is used in stead of carbonyldiimidazole.

Compound 282

4-[5-(4-Isopropyl-phenyl)-2-thioxo-[1,3,4]thiadiazol-3-yl]-benzoic acid: m.p. 176-179° C. $^1$H NMR (300 MHz, CDCl$_3$): δ 1.19 (d, 2H), 2.83-2.92 (m, 1H), 7.24 (d, 2H), 7.55 (d, 2H), 7.87 (d, 2H), 8.01 (d, 2H), 12.35 (s, 1H). MS (ES−): m/e 355.

Compound 284

3-[5-(4-Isopropyl-phenyl)-2-oxo-[1,3,4]thiadiazol-3-yl]-benzoic acid: m.p. 220-221° C. $^1$H NMR (300 MHz, CDCl$_3$): δ 1.29 (d, 2H), 2.93-3.03 (m, 1H), 7.34 (d, 2H), 7.59 (t, 1H), 7.71 (d, 2H), 8.05-8.08 (m, 1H), 8.21-8.25 (m, 1H), 8.63 (t, 1H). MS (ES−): m/e 339.

Preparation of 4-{[5-(4-isopropylphenyl)-2-oxo-1,3,4-oxadiazol-3(2H)-yl]methyl}benzoic acid (Compound 278)

Part A.

At 0° C., to a solution of 4-isopropylbenzoic acid (3.28 g, 20.0 mmol), triethylamine (2.12 g, 2.93 mL, 21.0 mmol) in dichloromethane/THF (15 mL/5 mL), is added isobutylchloroformate (2.87 g, 2.72 mL, 21.0 mmol). The mixture is stirred at 0° C. for 20 min. with warming to room temperature over 2 hr., and then treated with ethyl hydrazinoacetate (2.18 g, 21.0 mmol) and stirred overnight. The mixture is then washed with water, brine and dried over Na$_2$SO$_4$. The crude product obtained after the removal of the solvent is chromatographed (silica gel, 5:1 dichloromethane-ethyl acetate) to provide ethyl[2-(4-isopropylbenzoyl)hydrazino]acetate (4.85 g, 97%). MS (ES+): m/e 251.

Part B.

Ethyl[2-(4-isopropylbenzoyl)hydrazino]acetate (4.85 g, 19.4 mmol) is treated with phosphorus oxychloride (50 mL), heated to reflux for 3 h, and then poured onto ice. The precipitate is collected and washed thoroughly with water and dried in the air to furnish 5-(4-isopropylphenyl)-1,3,4-oxadiazol-2(3H)-one (2.30 g, 58%) MS (ES+): m/e 205.

Part C.

5-(4-Isopropylphenyl)-1,3,4-oxadiazol-2(3H)-one (0.41 g, 2.0 mmol) is dissolved in dichloromethane (5 mL) and stirred vigorously with methyl 4-bromomethylbenoate (0.50 g, 2.2 mmol) in the presence of sodium hydroxide (1.25 N, 1.76 mL, 2.2 mmol) and tetra-n-butylammonium bromide (0.07 g, 0.022 mmol) at room temperature overnight. The solvent is removed in vacuum, and the residue is treated with water. The precipitate is collected by filtration, washed with hexanes thoroughly and dried in the air to provide methyl 4-{[5-(4-isopropylphenyl)-2-oxo-1,3,4-oxadiazol-3(2H)-yl]methyl}benzoate (0.65 g, 93%). (ES+): m/e 353.

Part D.

Methyl 4-{[5-(4-isopropylphenyl)-2-oxo-1,3,4-oxadiazol-3(2H)-yl]methyl}benzoate (50 mg, 0.14 mmol) is refluxed with lithium iodide (0.19 g, 1.4 mmol) in pyridine (5 mL) for 48 h and the mixture is diluted with water (30 mL) after cooling to room temperature. The precipitate is collected by filtration, washed with dichloromethane and dried in the air to furnish the desired product 4-{[5-(4-isopropylphenyl)-2-oxo-1,3,4-oxadiazol-3(2H)-yl]methyl}benzoic acid (31 mg, 66%), m.p. 217-219° C. $^1$H NMR (CDCl$_3$, 300 MHz) δ (ppm) 1.13 (d, 6H) 2.70-2.90 (m, 1H), 4.86 (s, 2H), 7.17 (d, 2H), 7.30 (d, 2H), 7.59 (d, 2H), 7.89 (d, 2H). MS (ES+): m/e 339.

Preparation of 3-[4-(2,4-Difluoro-phenyl)-5-oxo-4,5-dihydro-[1,3,4]oxadiazol-2-yl]-benzoic acid (Compound 286)

Part A.

A suspension of isophthalic acid monobenzyl ester (prepared according to the procedure published in *J. Med. Chem.* 2001, 44, 1491-1508) (1.72 g, 6.71 mmol) in diethyl ether (30 mL) is treated with pyridine (550 µL, 6.80 mmol), and then a solution of cyanuric fluoride (1 equiv.) in ether (10 mL) is delivered by cannula dropwise over 15 min. A gummy precipitate forms, and the resulting mixture is made homogeneous by partial evaporation of the ether and addition of dichloromethane (50 mL). After 3 hrs., the solution is diluted with dichloromethane and poured over ice. The organic layer is washed with brine. The aqueous layers are back-extracted with dichloromethane, and the organic extracts are combined, dried over MgSO4, filtered and evaporated to afford benzyl isophthaloyl fluoride (1.68 g, 97%), which is taken on diectly to the next step.

Part B.

A 16×100 mm screw-cap tube containing 2,4-difluorophenyihydrazine (41.5 mg, 0.29 mmol), polystyrene-NMM resin (0.303 g, 2 equiv.), and anhydrous dimethylformamide (5 mL) is treated with a solution of benzyl isophthaloyl fluoride (0.289 mmol) in dimethylformamide (1 mL). The tube is sealed, and mixed at ambient temperature for 5.5 d. The contents of the tube are filtered into another tube, and the resin is washed with additional dimethylformamide. The solution is heated to 80° C. and treated with portions of carbonyldiimidazole (100 mg each) until analysis by LC/MS showed complete consumption of starting material. The tube is allowed to cool and the solvent is evaporated. The residual material is eluted through a short column of silica gel with a gradient of 10:90 to 40:60 ethyl acetate-chloroform, and the fractions containing the product, benzyl 3-[4-(2,4-difluoro-phenyl)-5-oxo-4,5-dihydro-[1,3,4]oxadiazol-2-yl]-benzoate, are collected and evaporated.

Part C.

Benzyl 3-[4-(2,4-difluoro-phenyl)-5-oxo-4,5-dihydro-[1,3,4]oxadiazol-2-yl]-benzoate from Part B is treated with a 45% solution of hydrogen bromide in acetic acid. After 1 h, ether is added (5 mL), and the resulting solution is stirred for an additional 1 h. The solvents are evaporated, and analysis by LC/MS of the residual material shows the presence of unconverted starting material. The residue is taken up in chloroform (10 mL), cooled to 0° C., and treated with a solution of boron tribromide (1 mL, 1.0 M). After stirring for 17 h, the solution is evaporated, and the residue is suspended in 10 mL cold water. This mixture is sonicated to achieve a homogeneous suspension and filtered. The resulting solution is separated by HPLC to afford pure title product. MS (ES+): m/e 320 (20), 319.13 (100).

In summary, certain preferred compounds of the invention are prepared in a manner similar to those described above as follows:

TABLE 1

| Compound | Melting Point | Mass Spec Data |
| --- | --- | --- |
| 1 | 279-282 | 322 |
| 2 | 248-250 | 307 |
| 3 | 225-226 | 307 |
| 4 |  | 307 |
| 5 | 215-216 | 307 |
| 6 | 210-215 | 306 |

TABLE 1-continued

| Compound | Melting Point | Mass Spec Data |
| --- | --- | --- |
| 8 | 268-271 | 266 |
| 9 | 307-311 | 282 |
| 10 | 259-261 | 372 |
| 11 | 268-270 | 296 |
| 12 | 230-232 | 296 |
| 13 | >310 | 284 |
| 14 | 263-265 | 280 |
| 15 | 173-175 | 308 |
| 16 | 290-291 | 302 |
| 17 | 239-241 | 284 |
| 18 | 141-143 | 334 |
| 19 | 219-221 | 350 |
| 20 | 271-273 | 402 |
| 21 | 176-178 | 294 |
| 22 | >310 | 344 |
| 23 | 284-286 | 311 |
| 24 | 263-265 | 342 |
| 25 | 270-272 | 318 |
| 26 | 293-295 | 382 |
| 27 | 243-246 | 372 |
| 28 | 225-228 | 384 |
| 32 | 272-275 | 360 |
| 33 | 295-298 | 358 |
| 34 | 236-238 |  |
| 41 | >310 | 296 |
| 42 | >310 | 300 |
| 43 | 270-273 | 349 |
| 44 | 295-297 | 335 |
| 45 | 263-265 | 335 |
| 46 |  | 294 |
| 47 | 238-239 | 295- |
| 48 | 208-209 | 279 |
| 49 | 253-254 | 299 |
| 50 | 289-290 | 295 |
| 51 | 298-299 | 279 |
| 52 | 300-302 | 299 |
| 53 | 122-123 | 296 |
| 54 | 194-196 | 300 |
| 55 | 249-250 | 240 |
| 56 | 270-271 | 244 |
| 57 | 78-80 | 246 |
| 58 | 110-112 | 276 |
| 59 | 100-101 | 276 |
| 60 | 144-147 | 290 |
| 61 | 83-84 | 330 |
| 62 | 70-74 | 314 |
| 63 | 142-145 | 282 |
| 64 | 143-145 | 304 |
| 65 | 202-204 | 265 |
| 66 | 171-174 | 349 |
| 67 | 225-227 | 333 |
| 68 | 240-244 | 301 |
| 74 | 228-230 | 281 |
| 75 | 178-179 | 281 |
| 76 | 160-161 | 295 |
| 77 | 153-154 | 295 |
| 78 | 164-166 | 290 |
| 79 | 180-182 | 265 |
| 80 | 230-235 | 299 |
| 81 | 210-211 | 295 |
| 82 | 230-235 | 350 |
| 83 | 205-206 | 299 |
| 84 | 225-226 | 283 |
| 85 | 260-261 | 281 (ES−) |
| 86 | 157-158 | 283 |
| 87 | 210-215 | 309 |
| 88 | 177-178 | 343 |
| 89 | 247-248 | 343 |
| 90 | 181-182 | 279 |
| 91 | 251-252 | 279 |
| 92 | 237-240 | 283 |
| 93 | 173-174 | 283 |
| 94 | 225-227 | 333 |
| 95 | 191-194 | 349 |
| 96 | 245-246 | 283 |
| 97 | 223-225 | 295 |
| 98 | 225-226 | 265 |

TABLE 1-continued

| Compound | Melting Point | Mass Spec Data |
|---|---|---|
| 99 | 267-269 | 265 |
| 100 | 282-284 | 281 |
| 101 | 274-276 | 308 (ES−) |
| 102 | 276-277 | 308 (ES−) |
| 103 | 283-285 | 301 |
| 104 | 291-293 | 301 |
| 105 | 315-317 | 332 |
| 106 | 240-243 | 306 |
| 107 | 118-120 | 331 |
| 108 | 209-210 | 280 |
| 109 | 222-223 | 295 |
| 110 | 224-225 | 308 |
| 111 | 264-265 | 309 |
| 112 | 157-158 | 295 |
| 113 | 243-245 | 266 |
| 114 | 260-262 | 266 |
| 115 | 300-302 | 266 |
| 116 | >350 | 266 |
| 117 | 297-299 | 267 |
| 118 | >350 | 267 |
| 119 | 310-311 | 267 |
| 120 | 319-321 | 267 |
| 121 | 331-333 | 306 |
| 122 | 325-326 | 317 |
| 123 | 250-252 | 316 |
| 124 | 182-183 | 331 |
| 125 | 190-192 | 292 |
| 126 | 178-180 | 294 |
| 127 | 231-233 | 300 |
| 128 | 209-211 | 332 |
| 129 | 278-280 | 292 |
| 130 | 239-241 | 264 |
| 131 | 318-320 | 348 |
| 132 | 203-205 | 296 |
| 133 | 213-215 | 349 |
| 134 | 246-248 | 249 |
| 135 | 273-275 | 291 |
| 136 | 241-243 | 277 |
| 137 | 191-192 | 291 |
| 138 | 249-250 | 277 |
| 139 | 272-273 | 307 |
| 140 | 225-227 | 307 |
| 141 | 233-234 | 291 |
| 142 | 217-218 | 321 |
| 143 | 192-193 | 321 |
| 144 | 227-228 | 293 |
| 145 | 290-292 | 321 |
| 146 | 246-248 | 277 |
| 147 | 232-233 | 321 |
| 148 | 288-290 | 321 |
| 149 | 304-306 | 307 |
| 150 | 273-276 | 321 |
| 151 | 202-204 | 282 |
| 152 | 211-213 | 282 |
| 153 | 243-245 | 300 |
| 154 | 224-226 | 332 |
| 155 | 211-213 | 282 |
| 156 | 178-181 | 278 |
| 157 | 201-202 | 348 |
| 158 | | 348 |
| 159 | | 278 |
| 160 | 190-191 | 295 |
| 161 | 288-290 | 291 |
| 162 | 308-310 | 293 |
| 163 | 279-280 | 321 |
| 164 | 180-183 | 308 |
| 165 | 180-183 | 343 |
| 166 | 192-193 | 279 |
| 167 | 162-164 | 279 |
| 168 | 280-281 | 310 |
| 169 | 166-167 | 283 |
| 170 | 180-182 | 279 |
| 171 | 211-212 | 295 |
| 172 | 179-181 | 331 |
| 173 | 255-257 | 331 |
| 174 | 156-157 | 295 |
| 175 | 152-153 | 371 |
| 176 | 210-212 | 371 |
| 177 | 229-231 | 279 |
| 178 | 280-282 | 279 |
| 179 | 200-202 | 301 |
| 180 | 258-260 | 301 |
| 181 | 235-237 | 283 |
| 182 | 266-268 | 283 |
| 183 | 235-237 | 357 |
| 184 | 277-278 | 307 |
| 185 | 240-241 | 343 |
| 186 | 282-283 | 357 |
| 187 | 311-313 | 307 |
| 188 | 277-278 | 344 |
| 193 | 200-202 | 294 |
| 194 | 212-213 | 278 |
| 195 | 208-209 | 278 |
| 196 | >350 | 298 |
| 197 | 200-202 | 298 |
| 198 | 198-200 | 298 |
| 199 | 164-165 | 348 |
| 200 | >350 | 294 |
| 201 | 302-303 | 280 |
| 202 | 305-306 | 334 |
| 203 | 294-295 | 296 |
| 204 | 276-277 | 296 |
| 205 | 286-288 | 309 |
| 206 | 273-275 | 281 |
| 207 | 272-274 | 281 |
| 208 | 225-227 | 349 |
| 209 | 166-168 | 349 |
| 210 | 178-180 | 299 |
| 211 | 252-255 | 299 |
| 212 | 261-265 | 283 |
| 213 | 228-230 | 283 |
| 214 | 220-222 | 331 |
| 215 | 211-213 | 357 |
| 216 | 164-165 | 357 |
| 217 | 252-253 | 295 |
| 218 | 214-215 | 349 |
| 219 | 268-270 | 295 |
| 220 | 179-180 | 295 |
| 221 | 200-202 | 295 |
| 222 | 244-245 | 265 |
| 223 | 143-145 | 349 |
| 224 | 230-231 | 349 |
| 225 | 201-203 | 323 |
| 226 | 238-240 | 323 |
| 227 | 266-268 | 309 |
| 228 | 212-215 | 307 |
| 229 | 215-218 | 307 |
| 230 | 209-211 | 313 |
| 231 | 285-288 | 313 |
| 232 | 135-138 | 333 |
| 233 | 286-289 | 333 |
| 234 | 259-261 | 299 |
| 235 | 218-220 | 333 |
| 236 | 271-273 | 333 |
| 237 | 196-197 | 293 |
| 238 | 254-256 | 293 |
| 239 | 221-223 | 309 |
| 240 | 161-163 | 278 |
| 241 | 205-208 | 296 |
| 242 | 193-194 | 300 |
| 243 | 199-201 | 298 |
| 244 | 264-268 | 296 |
| 245 | 215-218 | 300 |
| 246 | 142-144 | 370 |
| 247 | 177-180 | 308 |
| 253 | 239-241 | 321 |
| 254 | 269-271 | 321 |
| 255 | 215-216 | 307 |
| 256 | 278-279 | 307 |
| 257 | 281-282 | 304 |
| 258 | 198-199 | 271 |
| 259 | 200-202 | 272 |
| 260 | 235-236 | 266 |
| 261 | 280-282 | 266 |

TABLE 1-continued

| Compound | Melting Point | Mass Spec Data |
|---|---|---|
| 262 | 277-279 | 263 |
| 263 | 263-265 | 263 |
| 264 | 292-294 | 284 |
| 265 | 327-328 | 284 |
| 266 | 321-323 | 284 |
| 267 | 327-328 | 364 |
| 268 | 312-313 | 302 |
| 269 | 313-314 | 300 |
| 270 | 261-262 | 346 |
| 271 | 265-266 | 316 |
| 272 | 253-254 | 326 |
| 273 | 310-311 | 310 |
| 274 | 244-245 | 310 |
| 275 | 311-312 | 308 |
| 276 | 263-267 | 323 |
| 277 | 252-254 | 323 |
| 278 | 217-219 | 339 |
| 279 | 218-220 | 323 |
| 280 | 294-295 | 307 |
| 281 | 205-208 | 341 |
| 282 | 176-179 | 355 (ES−) |
| 283 | 215-217 | 339 (ES−) |
| 284 | 220-221 | 339 (ES−) |
| 285 | 239-240 | 339 (ES−) |
| 286 | | 319-320 |
| 287 | 244-245 | 306.22 |
| 288 | | |
| 289 | | |
| 290 | | |
| 291 | | |
| 292 | 230-232 | |
| 293 | >310 | |
| 294 | 263-265 | |
| 295 | 173-175 | |
| 296 | 290-292 | |
| 297 | 239-241 | |
| 298 | 141-143 | |
| 299 | 219-221 | |
| 300 | 271-273 | |
| 301 | 176-178 | |
| 302 | >300 | |
| 303 | 284-286 | |
| 304 | 263-265 | |
| 305 | 270-272 | |
| 306 | 293-295 | |
| 307 | 243-246 | |
| 308 | 225-228 | |
| 309 | 266-268 | |
| 310 | 245-247 | |
| 311 | >330 | |
| 312 | 272-275 | |
| 313 | 295-298 | |
| 314 | 236-238 | |
| 315 | 253-255 | |
| 316 | 241-244 | |
| 317 | 257-259 | |
| 318 | 269-272 | |
| 319 | 223-225 | |
| 320 | 209-211 | |
| 321 | >310 | |
| 322 | >310 | |
| 323 | 270-273 | |
| 324 | 295-297 | |
| 325 | 263-265 | |
| 326 | | |
| 327 | 203-205 | |
| 328 | 223-225 | |
| 329 | 220-223 | |
| 330 | 221-223 | |
| 331 | 250-253 | |
| 332 | 169-170 | |
| 333 | 276-278 | |
| 334 | 203-206 | |
| 335 | 255-258 | |
| 336 | 165-168 | |
| 337 | 188-191 | |
| 338 | 209-211 | |
| 339 | 252-255 | |
| 340 | 225-227 | |
| 341 | 280-282 | |
| 342 | 296-298 | |
| 343 | 193-194 | |
| 344 | >320 | |
| 345 | 191-193 | |
| 346 | | 282.40 |
| 347 | 205-208 | |
| 348 | 195-199 | |
| 349 | 163-165 | |
| 350 | 184-187 | |
| 351 | 183-186 | |
| 352 | 188-189 | |
| 353 | 204-205 | |
| 354 | 200-204 | |
| 355 | 239-240 | |
| 356 | 249-250 | |
| 357 | 237-239 | |
| 358 | 212-214 | |
| 359 | 230-232 | |
| 360 | 173-178 | |
| 361 | 180-185 | |
| 362 | 193-195 | |
| 363 | 230-235 | |
| 364 | 169-170 | |
| 365 | 210-212 | |
| 366 | 246-247 | |
| 367 | 275-246 | |
| 368 | 215-216 | |
| 369 | 266-268 | |
| 370 | 274-276 | |
| 371 | 259-260 | |
| 372 | 251-252 | |
| 373 | 259-260 | |
| 374 | 205-207 | |
| 375 | 274-276 | |
| 376 | 171-172 | |
| 377 | 176-177 | |
| 378 | 330-332 | |
| 379 | 295-296 | |
| 380 | 305-307 | |
| 381 | 271-272 | |
| 382 | 291-292 | |
| 383 | 238-240 | |
| 384 | 251-252 | |
| 385 | 266.5-267.5 | |
| 386 | 277-278 | |
| 387 | 256-257 | |
| 388 | 225-226 | |
| 389 | 216-217 | |
| 390 | 276-277 | |
| 391 | 262-263 | |
| 392 | 235.5-237 | |
| 393 | 211-213 | |
| 394 | 275-277 | |
| 395 | 158-160 | |
| 396 | 162-164 | |
| 397 | 197-199 | |
| 398 | 241-243 | |
| 399 | 295-298 | |
| 400 | 247-249 | |
| 401 | >300 | |
| 402 | 187-189 | |
| 403 | 257-259 | |
| 404 | 233-235 | |
| 405 | 127-129 | |
| 406 | 142-144 | |
| 407 | 199-200 | |
| 408 | 175-177 | |
| 409 | 172-173 | |
| 410 | 202-204 | |
| 411 | 283-285 | |
| 412 | 284-285 | |
| 413 | 217-219 | |
| 414 | 155-157 | |
| 415 | 167-169 | |

TABLE 1-continued

| Compound | Melting Point | Mass Spec Data |
|---|---|---|
| 416 | 290-292 | |
| 417 | 292-293 | |
| 418 | 223-225 | |
| 419 | 283-285 | |
| 420 | 153-154 | |
| 421 | 156-158 | |
| 422 | 220-223 | |
| 423 | 208-210 | |
| 424 | 269-270 | |
| 425 | 247-249 | |
| 426 | 207-209 | |
| 427 | 273-275 | |
| 428 | 241-243 | |
| 429 | 297-299 | |
| 430 | 207-209 | |
| 431 | 257-259 | |
| 432 | 268-270 | |
| 433 | 174-176 | |
| 434 | 210-211 | |
| 435 | 251-252 | |
| 436 | 212-213 | |
| 437 | 227-228 | |
| 438 | 192-193 | |
| 439 | >320 | |
| 440 | 272-273 | |
| 441 | 212-213 | |
| 442 | 263-265 | |
| 443 | 226-227 | |
| 444 | 262-263 | |
| 445 | 247-248.5 | |
| 446 | 285-287 | |
| 447 | 291-292 | |
| 448 | 245-250 | |
| 449 | 203-205 | |
| 450 | 165-170 | |
| 451 | 280-283 | |
| 452 | 282-284 | |
| 453 | 286-287 | |
| 454 | | |
| 455 | 177-180 | |
| 456 | 171-174 | |
| 457 | 246-250 | |
| 458 | 183-186 | |
| 459 | 135-138 | |
| 460 | 209-211 | |
| 461 | 267-270 | |
| 462 | 286-289 | |
| 463 | 256-258 | |
| 464 | 260-262 | |
| 465 | 250-252 | |
| 466 | 283-285 | |
| 467 | 265-267 | |
| 468 | 253-255 | |
| 469 | 263-265 | |
| 470 | 267-269 | |
| 471 | 269-271 | |
| 472 | 271-273 | |
| 473 | 291-293 | |
| 474 | | 293.28 |

Example 2

Nonsense Suppression Activity

A functional, cell-based translation assay based on luciferase-mediated chemoluminescence (International Application PCT/US2003/023185, filed on Jul. 23, 2003, hereby incorporated by reference in its entirety) permits quantitative assessment of the level of nonsense suppression. Human embryonic kidney cells (293 cells) are grown in medium containing fetal bovine serum (FBS). These cells can be stably transfected with the luciferase gene containing a premature termination codon at amino acid position 190. In place of the threonine codon (ACA) normally present in the luciferase gene at this site, each of the 3 possible nonsense codons (TAA, TAG, or TGA) and each of the 4 possible nucleotides (adenine, thymine, cytosine, or guanine) at the contextually important downstream +1 position following the nonsense codon are introduced by site-directed mutagenesis. As such, amino acid 190 in the luciferase gene containing a premature termination codon is either TAA, TAG, or TGA. For each stop codon, the nucleotide following amino acid 190 of luciferase gene containing a premature termination codon can be replaced with an adenine, thymine, cytosine, or guanine (A, T, C, G) such that these mutations do not change the reading frame of the luciferase gene. Schematics of these constructs are depicted in FIG. 1.

The nonsense suppression activity from a cell-based luciferase reporter assay of the present invention as described above shown in the table below (Table 2). Human Embryonic Kidney 293 cells are stably transfected with a luciferase reporter construct comprising a UGA nonsense mutation at position 190, which is followed, in-frame by an adenine nucleotide (UGAA).

Activity measurements in Table 2 are determined in a cell-based luciferase reporter assay of the present invention construct containing a UGA premature termination codon which is followed, in-frame by an adenine nucleotide (UGAA).

Gentamicin, an aminoglycoside antibiotic known to allow readthrough of premature termination codons, is used as an internal standard. Activity measurements are based on the qualitative ratio between the minimum concentration of compound required to produce a given protein in a cell versus the amount of protein produced by the cell at that concentration. Compounds which are found to have either or both very high potency and very high efficacy of protein synthesis are classified as "***". Compounds which are found to have intermediate potency and/or efficacy of protein synthesis are classified as ""; "*"; or "**". Similarly, compounds which are found to have lower potency and/or efficacy of protein synthesis are classified as "*".

TABLE 2

| Compound | UGAA |
|---|---|
| 1 | * |
| 2 | ** |
| 3 | *** |
| 4 | **** |
| 5 | **** |
| 6 | **** |
| 8 | * |
| 9 | * |
| 10 | * |
| 11 | ** |
| 12 | *** |
| 13 | *** |
| 14 | **** |
| 15 | **** |
| 16 | ** |
| 17 | *** |
| 18 | **** |
| 19 | ***** |
| 20 | *** |
| 21 | *** |
| 22 | ***** |
| 23 | **** |
| 24 | **** |
| 25 | **** |
| 26 | **** |
| 27 | ** |
| 28 | ** |
| 29 | ***** |
| 30 | *** |

TABLE 2-continued

| Compound | UGAA |
|---|---|
| 31 | * |
| 32 | *** |
| 33 | * |
| 34 | * |
| 35 | **** |
| 36 | *** |
| 37 | *** |
| 38 | **** |
| 39 | ***** |
| 40 | *** |
| 41 | * |
| 42 | * |
| 43 | * |
| 44 | * |
| 45 | *** |
| 46 | **** |
| 47 | *** |
| 48 | *** |
| 49 | *** |
| 50 | *** |
| 51 | ***** |
| 52 | *** |
| 53 | ** |
| 54 | ** |
| 55 | * |
| 56 | * |
| 57 | ** |
| 58 | ** |
| 59 | ** |
| 60 | ** |
| 61 | ** |
| 62 | ** |
| 63 | * |
| 64 | * |
| 65 | **** |
| 66 | **** |
| 67 | **** |
| 68 | **** |
| 69 | * |
| 70 | ** |
| 71 | ** |
| 72 | ** |
| 73 | * |
| 74 | **** |
| 75 | **** |
| 76 | ***** |
| 77 | **** |
| 78 | *** |
| 79 | *** |
| 80 | *** |
| 81 | **** |
| 82 | *** |
| 83 | **** |
| 84 | **** |
| 85 | ***** |
| 86 | **** |
| 87 | **** |
| 88 | *** |
| 89 | ** |
| 90 | **** |
| 91 | *** |
| 92 | *** |
| 93 | *** |
| 94 | *** |
| 95 | *** |
| 96 | *** |
| 97 | **** |
| 98 | *** |
| 99 | ***** |
| 100 | *** |
| 101 | **** |
| 102 | *** |
| 103 | **** |
| 104 | **** |
| 105 | ***** |
| 106 | ***** |
| 107 | *** |
| 108 | *** |
| 109 | ***** |
| 110 | *** |
| 111 | *** |
| 112 | *** |
| 113 | *** |
| 114 | * |
| 115 | * |
| 116 | * |
| 117 | * |
| 118 | * |
| 119 | * |
| 120 | * |
| 121 | ** |
| 122 | *** |
| 123 | *** |
| 124 | **** |
| 125 | ***** |
| 126 | ***** |
| 127 | *** |
| 128 | *** |
| 129 | ***** |
| 130 | *** |
| 131 | **** |
| 132 | ***** |
| 133 | **** |
| 134 | ** |
| 135 | ** |
| 136 | * |
| 137 | *** |
| 138 | **** |
| 139 | **** |
| 140 | *** |
| 141 | *** |
| 142 | *** |
| 143 | * |
| 144 | ** |
| 145 | * |
| 146 | **** |
| 147 | *** |
| 148 | **** |
| 149 | * |
| 150 | ***** |
| 151 | ** |
| 152 | ** |
| 153 | ** |
| 154 | **** |
| 155 | ***** |
| 156 | **** |
| 157 | **** |
| 158 | *** |
| 159 | **** |
| 160 | *** |
| 161 | ** |
| 162 | ** |
| 163 | * |
| 164 | **** |
| 165 | **** |
| 166 | ***** |
| 167 | **** |
| 168 | *** |
| 169 | *** |
| 170 | **** |
| 171 | *** |
| 172 | *** |
| 173 | ** |
| 174 | **** |
| 175 | *** |
| 176 | **** |
| 177 | ***** |
| 178 | **** |
| 179 | ***** |
| 180 | ** |
| 181 | **** |
| 182 | ** |
| 183 | *** |
| 184 | *** |
| 185 | *** |
| 186 | *** |

TABLE 2-continued

| Compound | UGAA |
|---|---|
| 187 | **** |
| 188 | *** |
| 189 | * |
| 190 | ** |
| 191 | * |
| 192 | ** |
| 193 | *** |
| 194 | ***** |
| 195 | *** |
| 196 | ***** |
| 197 | **** |
| 198 | **** |
| 199 | *** |
| 200 | **** |
| 201 | **** |
| 202 | **** |
| 203 | *** |
| 204 | *** |
| 205 | **** |
| 206 | **** |
| 207 | *** |
| 208 | *** |
| 209 | *** |
| 210 | *** |
| 211 | **** |
| 212 | **** |
| 213 | **** |
| 214 | **** |
| 215 | * |
| 216 | ** |
| 217 | *** |
| 218 | **** |
| 219 | *** |
| 220 | **** |
| 221 | ** |
| 222 | * |
| 223 | *** |
| 224 | ** |
| 225 | **** |
| 226 | ***** |
| 227 | *** |
| 228 | **** |
| 229 | **** |
| 230 | **** |
| 231 | *** |
| 232 | **** |
| 233 | ** |
| 234 | *** |
| 235 | **** |
| 236 | *** |
| 237 | ***** |
| 238 | *** |
| 239 | ***** |
| 240 | **** |
| 241 | ***** |
| 242 | **** |
| 243 | ** |
| 244 | ***** |
| 245 | *** |
| 246 | **** |
| 247 | **** |
| 248 | ** |
| 249 | **** |
| 250 | **** |
| 251 | * |
| 252 | * |
| 253 | * |
| 254 | * |
| 255 | **** |
| 256 | *** |
| 257 | *** |
| 258 | ***** |
| 259 | * |
| 260 | **** |
| 261 | * |
| 262 | * |
| 263 | * |
| 264 | * |
| 265 | * |
| 266 | *** |
| 267 | *** |
| 268 | ** |
| 269 | *** |
| 270 | * |
| 271 | *** |
| 272 | *** |
| 273 | **** |
| 274 | *** |
| 275 | **** |
| 276 | *** |
| 277 | **** |
| 278 | * |
| 279 | *** |
| 280 | * |
| 281 | ** |
| 282 | ** |
| 283 | *** |
| 284 | **** |
| 285 | *** |
| 286 | * |
| 287 | * |
| 288 | * |
| 289 | * |
| 290 | * |
| 291 | * |
| 292 | **** |
| 293 | *** |
| 294 | **** |
| 295 | **** |
| 296 | ** |
| 297 | ** |
| 298 | **** |
| 299 | ***** |
| 300 | *** |
| 301 | *** |
| 302 | **** |
| 303 | *** |
| 304 | *** |
| 305 | *** |
| 306 | **** |
| 307 | * |
| 308 | ** |
| 309 | ***** |
| 310 | **** |
| 311 | * |
| 312 | *** |
| 313 | * |
| 314 | * |
| 315 | **** |
| 316 | ** |
| 317 | *** |
| 318 | **** |
| 319 | **** |
| 320 | *** |
| 321 | * |
| 322 | * |
| 323 | * |
| 324 | * |
| 325 | *** |
| 326 | **** |
| 327 | ***** |
| 328 | *** |
| 329 | ***** |
| 330 | * |
| 331 | **** |
| 332 | **** |
| 333 | * |
| 334 | *** |
| 335 | *** |
| 336 | **** |
| 337 | * |
| 338 | *** |
| 339 | * |
| 340 | **** |
| 341 | *** |
| 342 | ***** |

TABLE 2-continued

| Compound | UGAA |
|---|---|
| 343 | ** |
| 344 | * |
| 345 | ** |
| 346 | **** |
| 347 | **** |
| 348 | **** |
| 349 | *** |
| 350 | **** |
| 351 | ** |
| 352 | ***** |
| 353 | ***** |
| 354 | ***** |
| 355 | ***** |
| 356 | **** |
| 357 | **** |
| 358 | **** |
| 359 | ***** |
| 360 | **** |
| 361 | **** |
| 362 | **** |
| 363 | ** |
| 364 | *** |
| 365 | **** |
| 366 | ** |
| 367 | *** |
| 368 | ** |
| 369 | *** |
| 370 | *** |
| 371 | *** |
| 372 | *** |
| 373 | *** |
| 374 | ** |
| 375 | *** |
| 376 | **** |
| 377 | *** |
| 378 | * |
| 379 | * |
| 380 | ** |
| 381 | *** |
| 382 | ** |
| 383 | * |
| 384 | **** |
| 385 | *** |
| 386 | *** |
| 387 | *** |
| 388 | *** |
| 389 | ** |
| 390 | *** |
| 391 | ** |
| 392 | ** |
| 393 | ***** |
| 394 | ***** |
| 395 | * |
| 396 | * |
| 397 | ***** |
| 398 | ** |
| 399 | *** |
| 400 | ** |
| 401 |  |
| 402 | **** |
| 403 | * |
| 404 | **** |
| 405 | **** |
| 406 | **** |
| 407 | * |
| 408 | * |
| 409 | * |
| 410 | * |
| 411 | **** |
| 412 | * |
| 413 | * |
| 414 | *** |
| 415 | **** |
| 416 | * |
| 417 | *** |
| 418 | **** |
| 419 | * |
| 420 | * |
| 421 | *** |
| 422 | **** |
| 423 | ** |
| 424 | *** |
| 425 | ** |
| 426 | **** |
| 427 | ** |
| 428 | **** |
| 429 | **** |
| 430 | **** |
| 431 | ** |
| 432 | *** |
| 433 | ** |
| 434 | *** |
| 435 | **** |
| 436 | **** |
| 437 | **** |
| 438 | **** |
| 439 | * |
| 440 | *** |
| 441 | *** |
| 442 | **** |
| 443 | *** |
| 444 | *** |
| 445 | *** |
| 446 | ** |
| 447 | *** |
| 448 | *** |
| 449 | *** |
| 450 | *** |
| 451 | * |
| 452 | * |
| 453 | * |
| 454 | *** |
| 455 | *** |
| 456 | *** |
| 457 | *** |
| 458 | **** |
| 459 | *** |
| 460 | ** |
| 461 | **** |
| 462 | * |
| 463 | **** |
| 464 | * |
| 465 | *** |
| 466 | ***** |
| 467 | **** |
| 468 | **** |
| 469 | **** |
| 470 | **** |
| 471 | ***** |
| 472 | **** |
| 473 | **** |
| 474 | **** |

Nonsense suppression activity in an assay as described above is shown in the Table 3 below, for a construct with a UGA nonsense mutation at position 190, followed by a cytosine nucleotide in-frame, (UGAC); for a construct with UAG nonsense mutation at position 190, followed by an adenine nucleotide in-frame, (UAGA); for a construct with IAA nonsense mutation at position 190, followed by an adenine nucleotide in-frame, (UAAA); and a construct with a UAA nonsense mutation at position 190, followed by an cytosine nucleotide in-frame, (UAAC). Also included in Table 3 is a column ("western blot") indicating whether treatment of cells with the indicated compound suppresses the nonsense mutation in a specific codon context (UGAA, UGAC, UAAA or UAAC) in luciferase and results in production of luciferase protein as determined by a positive signal on a western blot. A positive result in the western blot assay is indicated by a "+" and the nonsense codon and context of the codon that is suppressed.

TABLE 3

| Compound No. | UGAC | UAAA | UAAC | UAGA | western blot |
|---|---|---|---|---|---|
| 47 | | * | | * | |
| 48 | | * | | * | |
| 65 | | ** | | *** | |
| 66 | | ** | | *** | +UGAC; UAAC |
| 67 | | **** | | **** | |
| 68 | | *** | | **** | |
| 76 | | **** | | **** | |
| 81 | | *** | | *** | |
| 83 | | *** | | * | |
| 84 | | * | | * | |
| 85 | | * | | * | +; UGAC |
| 86 | | * | | * | |
| 90 | | * | | * | |
| 91 | | * | | * | |
| 92 | | * | | * | |
| 93 | | * | | * | |
| 95 | | * | | * | |
| 96 | | *** | | ** | |
| 97 | | *** | | ** | |
| 98 | | | | *** | |
| 99 | | * | | * | |
| 100 | | | | * | |
| 101 | | | | * | |
| 102 | | | | * | |
| 103 | | * | | ** | |
| 104 | | * | | * | |
| 105 | | * | | *** | +; UGAA; UGAC; UAAA |
| 106 | ***** | *** | | **** | |
| 109 | ***** | * | | * | |
| 131 | | * | | * | |
| 133 | | * | | * | |
| 135 | * | | * | | |
| 136 | *** | | * | | |
| 137 | *** | | * | | |
| 138 | ***** | * | ** | * | |
| 139 | ***** | * | * | * | |
| 140 | ***** | ** | * | *** | |
| 141 | *** | | * | | |
| 142 | *** | * | *** | *** | |
| 143 | * | | * | | |
| 144 | ** | | * | | |
| 145 | * | | * | | |
| 146 | ***** | * | ** | * | |
| 147 | *** | | ** | | |
| 148 | *** | * | * | *** | |
| 149 | * | | * | | |
| 150 | | * | | * | |
| 154 | | * | | *** | |
| 155 | | ** | | *** | |
| 156 | | * | | * | |
| 157 | | ** | | * | |
| 159 | | * | | * | |
| 164 | | ** | | ** | |
| 177 | | ** | | ** | |
| 179 | | * | | ** | |
| 196 | | * | | * | |
| 198 | | * | | * | |
| 205 | | * | | * | |
| 214 | | * | | * | |
| 225 | | ** | | *** | |
| 228 | | ** | | ** | |
| 230 | | ** | | ** | |
| 232 | | * | | * | |
| 235 | | ** | | ** | |
| 237 | | *** | | ** | +; UGAC |
| 239 | | * | | * | |
| 241 | | *** | | ** | |
| 242 | | ** | | ** | |
| 249 | | * | | * | |
| 255 | | ** | | ** | |

Example 3

Readthrough Assay

A functional, cell-based translation assay based on luciferase-mediated chemoluminescence (International Application PCT/US2003/023185, filed on Jul. 23, 2003 and incorporated by reference in its entirety) permits assessment of translation-readthough of the normal stop codon in a mRNA. Human embryonic kidney cells (293 cells) are grown in medium containing fetal bovine serum (FBS). These cells are stably transfected with the luciferase gene containing a premature termination codon at amino acid position 190. In place of the threonine codon (ACA) normally present in the luciferase gene at this site, each of the 3 possible nonsense codons (TAA, TAG, or TGA) and each of the 4 possible nucleotides (adenine, thymine, cytosine, or guanine) at the contextually important downstream +1 position following the nonsense codon are introduced by site-directed mutagenesis. As such, amino acid 190 in the luciferase gene containing a premature termination codon is either TAA, TAG, or TGA. For each stop codon, the nucleotide following amino acid 190 of luciferase gene containing a premature termination codon are replaced with an adenine, thymine, cytosine, or guanine (A, T, C, G) such that these mutation do not change the reading frame of the luciferase gene. Schematics of these constructs are depicted above in FIG. 1.

Another assay of the present invention can evaluate compounds that promote nonsense mutation suppression. The luciferase constructs described above in FIG. 1 are engineered to harbor two epitope tags in the N-terminus of the luciferase protein. Based on luciferase protein production, these constructs qualitatively assess the level of translation-readthrough. The presence of the full-length luciferase protein produced by suppression of the premature termination codon is measured by immunoprecipitation of the suppressed luciferase protein (using an antibody against a His tag) followed by western blotting using an antibody against the second epitope (the Xpress™ epitope; Invitrogen®; Carlsbad, Calif.). These constructs are depicted in FIG. 2.

Cells that harbor the constructs of FIG. 2 show increased full-length protein production when treated with a compound of the present invention. After treatment for 20 hours, cells containing the constructs of FIG. 2 are collected and an antibody recognizing the His epitope is used to immunoprecipitate the luciferase protein. Following immunoprecipitation, western blotting is performed using the antibody to the Xpress™ epitope (Invitrogen®; Carlsbad, Calif.) to detect the truncated luciferase (produced when no nonsense suppression occurs) and to detect the full-length protein (produced by suppression of the nonsense codon). Treatment of cells with a test compound produces full-length protein and not a readthrough protein (See e.g., FIG. 3). The readthrough protein is produced if suppression of the normal termination codon occurs. Compounds of the present invention suppress the premature, i.e. nonsense mutation, but not the normal termination codon in the luciferase mRNA.

Compounds of the present invention selectively act on premature termination codons but not normal termination codons in mammals.

Rats and dogs are administered high doses of compound (up to 1800 mg/kg) by gavage (oral) once daily for 14 days. After the treatment, tissues are collected, lysates are prepared, and Western blot analysis is performed. Selection of the proteins for evaluation of normal termination codon readthrough is based primarily on the corresponding mRNA having a second stop codon in the 3'-UTR that is in-frame with the normal termination codon. Between these 2 stop codons, each selected protein has an intervening sequence of nucleotides that codes for an extension of the protein in the event of ribosomal readthrough of the first termination codon. If the compound has the capacity to induce nonspecific, ribosomal readthrough, an elongated protein is differentiated from the wild-type protein using Western blot. Tissues are collected from rats and are analyzed for suppression of the normal termination codon (UAA) in the vimentin mRNA. No evidence of suppression is apparent. Tissues are collected from dogs treated with compounds of the present invention. There is no evidence of suppression of the normal termination codon of beta actin, which harbors a UAG stop codon.

In healthy human volunteers, a single dose of a compound of the present invention (200 mg/kg) is administered orally. Blood samples are collected, plasma is prepared, and a Western blot is conducted using plasma samples from female and male subjects. C-reactive protein (CRP), which harbors a UGA termination codon, is used to determine if treatment of subjects with compounds of the present invention result in suppression of the normal termination codon in the CRP mRNA. A luciferase assay in combination with a premature termination assay demonstrates selective suppression of premature termination codons but not normal termination codons.

Example 4

Animal Models

Animal model systems can also be used to demonstrate the safety and efficacy of a compound of the present invention. The compounds of the present invention are tested for biological activity using animal models for a disease, condition, or syndrome of interest. These include animals engineered to contain the target RNA element coupled to a functional readout system, such as a transgenic mouse.

Cystic Fibrosis

Examples of animal models for cystic fibrosis include, but are not limited to, cftr(−/−) mice (see, e.g., Freedman et al., 2001, *Gastroenterology* 121(4):950-7), cftr(tm1HGU/tm1HGU) mice (see, e.g., Bernhard et al., 2001, *Exp Lung Res* 27(4):349-66), CFTR-deficient mice with defective cAMP-mediated Cl(−) conductance (see, e.g., Stotland et al., 2000, *Pediatr Pulmonol* 30(5):413-24), and C57BL/6-Cftr (m1UNC)/Cftr(m1UNC) knockout mice (see, e.g., Stotland et al., 2000, *Pediatr Pulmonol* 30(5):413-24).

Muscular Dystrophy

Examples of animal models for muscular dystrophy include, but are not limited to, mouse, hamster, cat, dog, and *C. elegans*. Examples of mouse models for muscular dystrophy include, but are not limited to, the dy−/− mouse (see, e.g., Connolly et al., 2002, *J Neuroimmunol* 127(1-2):80-7), a muscular dystrophy with myositis (mdm) mouse mutation (see, e.g., Garvey et al., 2002, *Genomics* 79(2):146-9), the mdx mouse (see, e.g., Nakamura et al., 2001, *Neuromuscul Disord* 11(3):251-9), the utrophin-dystrophin knockout (dko) mouse (see, e.g., Nakamura et al., 2001, *Neuromuscul Disord* 11(3):251-9), the dy/dy mouse (see, e.g., Dubowitz et al., 2000, *Neuromuscul Disord* 10(4-5):292-8), the mdx(Cv3) mouse model (see, e.g., Pillers et al., 1999, *Laryngoscope* 109(8):1310-2), and the myotonic ADR-MDX mutant mice (see, e.g., Kramer et al., 1998, *Neuromuscul Disord* 8(8):542-50). Examples of hamster models for muscular dystrophy include, but are not limited to, sarcoglycan-deficient hamsters (see, e.g., Nakamura et al., 2001, *Am J Physiol Cell Physiol* 281(2):C690-9) and the BIO 14.6 dystrophic hamster (see, e.g., Schlenker & Burbach, 1991, *J Appl Physiol* 71(5):1655-62). An example of a feline model for muscular dystrophy includes, but is not limited to, the hypertrophic feline muscular dystrophy model (see, e.g., Gasehen & Burgunder, 2001, *Acta Neuropathol* (Berl) 101(6):591-600). Canine models for muscular dystrophy include, but are not limited to, golden retriever muscular dystrophy (see, e.g., Fletcher et al., 2001, *Neuromuscul Disord* 11(3):239-43) and canine X-linked muscular dystrophy (see, e.g., Valentine et al., 1992, Am J Med Genet 42(3):352-6). Examples of *C. elegans* models for muscular dystrophy are described in Chamberlain & Benian, 2000, *Curr Biol* 10(21):R795-7 and Culette & Sattelle, 2000, *Hum Mol Genet* 9(6):869-77.

Familial Hypercholesterolemia

Examples of animal models for familial hypercholesterolemia include, but are not limited to, mice lacking functional LDL receptor genes (see, e.g., Aji et al., 1997, *Circulation* 95(2):430-7), Yoshida rats (see, e.g., Fantappie et al., 1992, *Lift Sci* 50(24):1913-24), the JCR:LA-cp rat (see, e.g., Richardson et al., 1998, *Atherosclerosis* 138(1):135-46), swine (see, e.g., Hasler-Rapacz et al., 1998, *Am J Med Genet* 76(5):379-86), and the Watanabe heritable hyperlipidaemic rabbit (see, e.g., Tsutsumi et al., 2000, *Arzneimittelforschung* 50(2):118-21; Harseh et al., 1998, *Br J Pharmacol* 124(2):227-82; and Tanaka et al., 1995, *Atherosclerosis* 114(1):73-82).

Human Cancer

An example of an animal model for human cancer, in general includes, but is not limited to, spontaneously occurring tumors of companion animals (see, e.g., Vail & MacEwen, 2000, *Cancer Invest* 18(8):781-92). Examples of animal models for lung cancer include, but are not limited to, lung cancer animal models described by Zhang & Roth (1994, *In Vivo* 8(5):755-69) and a transgenic mouse model with disrupted p53 function (see, e.g., Morris et al., 1998, *J La State Med Soc* 150(4):179-85). An example of an animal model for breast cancer includes, but is not limited to, a transgenic mouse that overexpresses cyclin D1 (see, e.g., Hosokawa et al., 2001, *Transgenic Res* 10(5):471-8). An example of an animal model for colon cancer includes, but is not limited to, a TCRbeta and p53 double knockout mouse (see, e.g., Kado et al., 2001, *Cancer Res* 61(6):2395-8). Examples of animal models for pancreatic cancer include, but are not limited to, a metastatic model of Panc02 murine pancreatic adenocarcinoma (see, e.g., Wang et al., 2001, *Int J Pancreatol* 29(1):37-46) and nu-nu mice generated in subcutaneous pancreatic tumours (see, e.g., Ghaneh et al., 2001, *Gene Ther* 8(3):199-208). Examples of animal models for non-Hodgkin's lymphoma include, but are not limited to, a severe combined immunodeficiency ("SCID") mouse (see, e.g., Bryant et al., 2000, *Lab Invest* 80(4):553-73) and an IgHmu-HOX11 transgenic mouse (see, e.g., Hough et al., 1998, *Proc Natl Acad Sci USA* 95(23):13853-8). An example of an animal model for esophageal cancer includes, but is not limited to, a mouse transgenic for the human papillomavirus type 16 E7 oncogene (see, e.g., Herber et al., 1996, *J Viral* 70(3):1873-81). Examples of animal models for colorectal carcinomas include, but are not limited to, Apc mouse models (see, e.g., Fodde & Smits, 2001, *Trends Mol Med* 7(8):369-73 and Kuraguchi et al., 2000, *Oncogene* 19(50):5755-63). An example of an animal model for neurofibromatosis includes, but is not limited to, mutant NF1 mice (see, e.g., Cichowski et al., 1996, *Semin Cancer Biol* 7(5):291-8). Examples of animal models for retinoblastoma include, but are not limited to, transgenic mice that expression the simian virus 40 T antigen in the retina (see, e.g., Howes et al., 1994, *Invest Ophthalmol Vis Sci* 35(2):342-51 and Windle et al, 1990, Nature 343(6259):665-9) and inbred rats (see, e.g., Nishida et al., 1981, *Curr Eye Res* 1(1):53-5 and Kobayashi et al., 1982, *Acta Neuropathol (Berl)* 57(2-3):203-8). Examples of animal models for Wilm's tumor include, but are not limited to, a WT1 knockout mice (see, e.g., Scharnhorst et al., 1997, *Cell Growth Differ* 8(2):133-43), a rat subline with a high incidence of neuphrobtastoma (see, e.g., Mesfin & Breech, 1996, *Lab Anim Sci* 46(3):321-6), and a Wistar/Furth rat with Wilms' tumor (see, e.g., Murphy et al., 1987, *Anticancer Res* 7(4B):717-9).

Retinitis Pigmentosa

Examples of animal models for retinitis pigmentosa include, but are not limited to, the Royal College of Surgeons ("RCS") rat (see, e.g., Vollrath et al., 2001, *Proc Natl Acad Sci USA* 98(22); 12584-9 and Hanitzsch et al., 1998, *Acta Anat (Basel)* 162(2-3):119-26), a rhodopsin knockout mouse (see, e.g., Jaissle et al., 2001, *Invest Ophthalmol Vis Sci* 42(2):506-13), and Wag/Rij rats (see, e.g., Lai et al., 1980, *Am J Pathol* 98(1):281-4).

Cirrhosis

Examples of animal models for cirrhosis include, but are not limited to, $CCl_4$-exposed rats (see, e.g., Kloehn et al., 2001, *Horm Metab Res* 33(7):394-401) and rodent models instigated by bacterial cell components or colitis (see, e.g., Vierling, 2001, *Best Pract Res Clin Gastroenterol* 15(4):591-610).

Hemophilia

Examples of animal models for hemophilia include, but are not limited to, rodent models for hemophilia A (see, e.g., Reipert et al., 2000, *Thromb Haemost* 84(5):826-32; Jarvis et al., 1996, *Thromb Haemost* 75(2):318-25; and Bi et al., 1995, *Nat Genet* 10(1):119-21), canine models for hemophilia A (see, e.g., Gallo-Penn et al., 1999, *Hum Gene Ther* 10(11): 1791-802 and Connelly et al, 1998, *Blood* 91(9); 3273-81), murine models for hemophilia B (see, e.g., Snyder et al., 1999, *Nat Med* 5(1):64-70; Wang et al., 1997, *Proc Natl Acad Sci USA* 94(21):11563-6; and Fang et al., 1996, *Gene Ther* 3(3):217-22), canine models for hemophilia B (see, e.g., Mount et al., 2002, *Blood* 99(8):2670-6; Snyder et al., 1999, *Nat Med* 5(1):64-70; Fang et al., 1996, *Gene Ther* 3(3):217-22; and Kay et al., 1994, *Proc Natl Acad Sci USA* 91(6): 2353-7), and a rhesus macaque model for hemophilia B (see, e.g., Lazier et al., 1999, *Blood* 93(6):1875-81).

Von Willebrand Disease

Examples of animal models for von Willebrand disease include, but are not limited to, an inbred mouse strain RIIIS/J (see, e.g., Nichols et al., 1994, 83(11):3225-31 and Sweeney et al., 1990, 76(11):2258-65), rats injected with botrocetin (see, e.g., Sanders et al., 1988, *Lab Invest* 59(4):443-52), and porcine models for von Willebrand disease (see, e.g., Nichols et al., 1995, *Proc Natl Acad Sci USA* 92(7):2455-9; Johnson & Bowie, 1992, *J Lab Clin Med* 120(4):553-8); and Brinkhous et al., 1991, *Mayo Clin Proc* 66(7):733-42).

β-Thalassemia

Examples of animal models for β-thalassemia include, but are not limited to, murine models with mutations in globin genes (see, e.g., Lewis et al., 1998, *Blood* 91(6):2152-6; Raja et al., 1994, *Br J Haematol* 86(1):156-62; Popp et al., 1985, 445:432-44; and Skow et al., 1983, *Cell* 34(3):1043-52).

Kidney Stones

Examples of animal models for kidney stones include, but are not limited to, genetic hypercalciuric rats (see, e.g., Bushinsky et al., 1999, *Kidney Int* 55(1):234-43 and Bushinsky et al., 1995, *Kidney Int* 48(6):1705-13), chemically treated rats (see, e.g., Grases et al., 1998, *Scand J Urol Nephrol* 32(4): 261-5; Burgess et al., 1995, *Urol Res* 23(4):239-42; Kumar et al., 1991, *J Urol* 146(5):1384-9; Okada et al., 1985, Hinyokika Kiyo 31(4):565-77; and Bluestone et al., 1975, *Lab Invest* 33(3):273-9), hyperoxaluric rats (see, e.g., Jones et al., 1991, *J Urol* 145(4):868-74), pigs with unilateral retrograde flexible nephroscopy (see, e.g., Seifmah et al., 2001, 57(4): 832-6), and rabbits with an obstructed upper urinary tract (see, e.g., Itatani et al., 1979, *Invest Urol* 17(3):234-40).

Ataxia-Telangiectasia

Examples of animal models for ataxia-telangiectasia include, but are not limited to, murine models of ataxia-telangiectasia (see, e.g., Barlow et al., 1999, *Proc Natl Acad Sci USA* 96(17):9915-9 and Inoue et al., 1986, *Cancer Res* 46(8):3979-82).

Lysosomal Storage Diseases

Examples of animal models for lysosomal storage diseases include, but are not limited to, mouse models for mucopolysaccharidosis type VII (see, e.g., Brooks et al., 2002, *Proc Natl Acad Sci USA.* 99(9):6216-21; Monroy et al., 2002, *Bone* 30(2):352-9; Vogler et al., 2001, *Pediatr Dev Pathol.* 4(5):421-33; Vogler et al., 2001, *Pediatr Res.* 49(3):342-8; and Wolfe et al., 2000, *Mol Ther.* 2(6):552-6), a mouse model for metachromatic leukodystrophy (see, e.g., Matzner et al., 2002, *Gene Ther.* 9(1):53-63), a mouse model of Sandhoff disease (see, e.g., Sango et al., 2002, *Neuropathol Appl Neurobiol.* 28(1):23-34), mouse models for mucopolysaccharidosis type III A (see, e.g., Bhattacharyya et al., 2001, *Glycobiology* 11(1):99-10 and Bhaumik et al., 1999, *Glycobiology* 9(12):1389-96.), arylsulfatase A (ASA)-deficient mice (see, e.g., D'Hooge et al., 1999, *Brain Res.* 847(2):352-6 and D'Hooge et al, 1999, *Neurosci Lett.* 273(2):93-6); mice with an aspartylglucosaminuria mutation (see, e.g., Jalanko et al., 1998, *Hum Mol Genet.* 7(2):265-72); feline models of mucopolysaccharidosis type VI (see, e.g., Crawley et al., 1998, *J Clin Invest.* 101(1):109-19 and Norrdin et al., 1995, *Bone* 17(5):485-9); a feline model of Niemann-Pick disease type C (see, e.g., March et al., 1997, *Acta Neuropathol (Berl).* 94(2): 164-72); acid sphingomyelinase-deficient mice (see, e.g., Otterbach & Stoffel, 1995, *Cell* 81(7):1053-6), and bovine mannosidosis (see, e.g., Jolly et al., 1975, *Birth Defects Orig Arctic Ser.* 11(6):273-8).

Tuberous Sclerosis

Examples of animal models for tuberous sclerosis ("TSC") include, but are not limited to, a mouse model of TSC1 (see, e.g., Kwiatkowski et al., 2002, *Hum Mol Genet.* 11(5):525-34), a Tsc1 (TSC1 homologue) knockout mouse (see, e.g., Kobayashi et al., 2001, *Proc Natl Acad Sci USA.* 2001 Jul. 17; 98(15):8762-7), a TSC2 gene mutant(Eker) rat model (see, e.g., Hino 2000, *Nippon Rinsho* 58(6):1255-61; Mizuguchi et al., 2000, *J Neuropathol Exp Neural.* 59(3):188-9; and Hino et al., 1999, *Prog Exp Tumor Res.* 35:95-108); and Tsc2(+/−) mice (see, e.g., Onda et al., 1999, *J Clin Invest.* 104(6):687-95).

Example 5 mdx Mouse, an Animal Model Stud

The mutation in the mdx mouse that causes premature translation termination of the 427 kDa dystrophin polypeptide has been shown to be a C to T transition at position 3185 in exon 23 (Sicinski et al., *Science* 244(4912):1578-1580 (1989)). Mouse primary skeletal muscle cultures derived from 1-day old mdx mice are prepared as described previously (Barton-Davis et al., *J. Clin. Invest.* 104(4):375-381 (1999)). Cells are cultured for 10 days in the presence of a compound of the invention. Culture medium is replaced every four days and the presence of dystrophin in myoblast cultures is detected by immunostaining as described previously (Barton-Davis et al., *J. Clin. Invest.* 104(4):375-381(1999), hereby incorporated by reference in its entirety). A primary monoclonal antibody to the C-terminus of the dystrophin protein is used undiluted and rhodamine conjugated anti-mouse IgG is used as the secondary antibody. The antibody detects the full-length protein produced by suppression of the nonsense codon. Staining is viewed using a Leica DMR microscope, digital camera, and associated imaging software.

As previously described (Barton-Davis et al., *J. Clin. Invest.* 104(4):375-381(1999), a compound is delivered by Alzet osmotic pumps implanted under the skin of anesthetized mice. Two doses of a compound of the invention are administered. Gentamicin serves as a positive control and pumps filled with solvent only serve as the negative control. Pumps are loaded with appropriate compound such that the calculated doses to which tissue is exposed are 10 mM and 20 mM. The gentamicin concentration is calculated to achieve tissue exposure of approximately 200 mM. In the initial experiment, mice are treated for 14 days, after which animals are anesthetized with ketamine and exsanguinated. The tibialis anterior (TA) muscle of the experimental animals is then excised, frozen, and used for immunofluorescence analysis of dystrophin incorporation into striated muscle. The presence of dystrophin in TA muscles is detected by immunostaining, as described previously (Barton-Davis et al., *J Clin. Invest.* 04(4):375-381(1999).

Western Blot Analysis

Quadricep muscles from an mdx mouse treated with a compound of the present invention for 4 weeks are analyzed by western blot using a commercially available antibody to dystrophin. Protein extracted from the quadriceps of a wild-type mouse serve as a positive control. Production of full-length dystrophin is observed in the treated animal. The amount of full-length dystrophin produced, as a result of nonsense suppression, but not limited by this theory, is approximately 10% of wild-type levels of expression.

Immunofluorescence

Male mdx mice (age 9-11 weeks) are treated with different compounds of the present inventin (n=2 at least for each compound). These compounds are injected SQ once per day for two weeks at 25 mg/kg. After 2 weeks of treatment, mice are sacrificed for the removal of muscles to determine dystrophin readthrough efficiency.

Immunofluorescence (IF) is performed on 10 μm cryosections using a dystrophin antibody. The antibody recognizes an epitope C-terminal to the premature stop mutation found in mdx mice. Image analysis is performed in an identical manner in all sections. Images from treated and untreated mice are analyzed and a signal greater than the signal on the untreated control is deemed positive and indicates that suppression of the premature termination codon in the dystrophin mRNA occurred.

Muscle Mechanics

Isolated whole muscle mechanics is performed on EDL muscles from animals. Optimum muscle length (Lo) is defined as the length that produced maximum twitch tension. Maximum tetanic force at Lo is measured using a 120 Hz, 500 msec pulse at supramaximal voltage. Protection against mechanical injury, induced by a series of 5 eccentric tetanic contractions, is monitored. These measurements are performed using a 700 msec stimulation period during which the muscle is held in an isometric contraction for the first 500 msec followed by a stretch of 8 or 10% La at a rate of 0.5 Lo/sec. Protection against mechanical injury is evaluated at 80 Hz stimulation frequency. Damage is determined as the loss in force between the first and last eccentric contraction. Treatment with compounds of the present invention result in protection from damage induced by eccentric contractions of the EDL muscle compared to the untreated control.

Example 6

Suppression of a Nonsense Mutation in the p53 Gene

For an animal model system, CAOV-3 cells ($1 \times 10^7$) are injected into the flanks of nude/nude mice. After 12 days, mice are randomized (10 mice per group) and treated subcutaneously (5 days per week) with 3 mg/kg of a compound of the present invention or intraperitonealy (1 day per week) with 30 mg/kg of a compound of the present invention. Tumor volumes are measured weekly. Suppression of nonsense mutations in the p53 gene by a compound of the present invention can inhibit cancer growth in vivo.

Example 7

Access to Specific Nucleotides of the 28S rRNA is Modified by Compounds of the Present Invention Previous studies have demonstrated that gentamicin and other members of the aminoglycoside family that decrease the fidelity of translation bind to the A site of the 16S rRNA. By chemical footprinting, UV cross-linking and NMR, gentamicin has been shown to bind at the A site (comprised of nucleotides 1400-1410 and 1490-1500, *E. coli* numbering) of the rRNA at nucleotides 1406, 1407, 1494, and 1496 (Moazed & Noller, *Nature* 327(6121):389-394 (1978); Woodcock et al., *EMBO J.* 10(10):3099-3103 (1991); and Schroeder et al., *EMBO J.* 19:1-9 (2000).

Ribosomes prepared from HeLa cells are incubated with the small molecules (at a concentration of 100 mM), followed by treatment with chemical modifying agents (dimethyl sulfate [DMS] and kethoxal [KE]). Following chemical modification, rRNA is phenol-chloroform extracted, ethanol pre cipitated, analyzed in primer extension reactions using end-labeled oligonucleotides hybridizing to different regions of the three rRNAs and resolved on 6% polyacrylamide gels. Probes for primer extension cover the entire 18S (7 oligonucleotide primers), 28S (24 oligonucleotide primers), and 5S (one primer) rRNAs. Controls in these experiments include DMSO (a control for changes in rRNA accessibility induced by DMSO), paromomycin (a marker for 18S rRNA binding), and anisomycin (a marker for 28S rRNA binding).

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

In a preferred embodiment of Formula 1-N, $Ar_4$ is a $C_1$-$C_4$ thioalkyl which is attached to $A_1$ to form a five to six membered heterocycle. In an embodiment of Formula 1-N, $R_1$ is preferably a carboxy group, and is preferably located in a meta or para position. In a preferred embodiment of Formula 1-N, $Ar_4$ is a thiomethyl group. In a further preferred embodiment of Formula 1-N, $Ar_2$ and $Ar_3$ are preferably absent.

In another preferred embodiment of Formula 1-N, $Ar_1$ is a phenyl group optionally substituted with one or more R groups. In another preferred embodiment of Formula 1-N, $Ar_1$ is a phenyl group optionally substituted with one R group. In another preferred embodiment of Formula 1-N, $Ar_1$ is a phenyl group substituted with a $C_1$-$C_4$ alkyl group. In another preferred embodiment of Formula 1-N, $Ar_1$ is a phenyl group substituted with a methyl group.

Preferred compounds of the invention include the compounds in Table X as follows:

As illustrated in Table X: As used herein, Compound 12 is the same structure as Compound 292. As used herein, Compound 13 is the same structure as Compound 293. As used herein, Compound 14 is the same structure as Compound 294. As used herein, Compound 15 is the same structure as Compound 295. As used herein, Compound 16 is the same structure as Compound 296. As used herein, Compound 17 is the same structure as Compound 297. As used herein, Compound 18 is the same structure as Compound 298. As used herein, Compound 19 is the same structure as Compound 299. As used herein, Compound 20 is the same structure as Compound 300. As used herein, Compound 21 is the same structure as Compound 301. As used herein, Compound 22 is the same structure as Compound 302. As used herein, Compound 23 is the same structure as Compound 303. As used herein, Compound 24 is the same structure as Compound 304. As used herein, Compound 25 is the same structure as Compound 305. As used herein, Compound 26 is the same structure as Compound 306. As used herein, Compound 27 is the same structure as Compound 307. As used herein, Compound 28 is the same structure as Compound 308. As used herein, Compound 29 is the same structure as Compound 309. As used herein, Compound 30 is the same structure as Compound 310. As used herein, Compound 31 is the same structure as Compound 311. As used herein, Compound 32 is the same structure as Compound 312. As used herein, Compound 33 is the same structure as Compound 313. As used herein, Compound 34 is the same structure as Compound 314. As used herein, Compound 35 is the same

What is claimed is:
1. A compound of Formula 1-A-10 or 1-A-11:

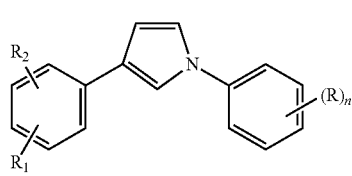

1-A-10

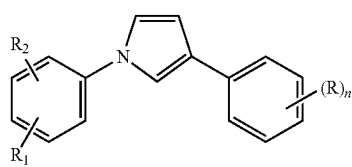

1-A-11 wherein:
n is 0, 1, or 2;
$R_1$ is carboxy, cyano, or a carbonyl group which is optionally substituted with a $C_1$-$C_4$ alkoxy group;
$R_2$ is absent or a nitro;
R is hydrogen; a —$R_a$ group; or two R groups, where R may also include an oxy group, together with the phenyl to which they are attached form a ring structure selected from RR;
wherein:
RR is a nine to ten membered bicyclic ring structure optionally substituted with one or more halogens, $C_1$-$C_4$ alkyl groups, $C_1$-$C_4$ haloalkyl groups, $C_1$-$C_4$ alkoxy groups, oxo groups, or $C_1$-$C_4$ haloalkoxy groups;
$R_a$ is selected from the group consisting of: a hydroxy group; a halogen; a $C_1$-$C_4$ alkyl which is substituted with one or more independently selected halogen or hydroxy groups; a $C_1$-$C_4$ alkoxy which is substituted with one or more independently selected halogen or phenyl groups; a $C_4$-$C_8$ cycloalkyl which is optionally substituted with one or more independently selected $C_1$-$C_4$ alkyl groups; an —$R_b$ group; a —O—$R_b$ group; a four to six-membered heterocycle which is optionally substituted with one or more independently selected $C_1$-$C_4$ alkyl, oxo, or —$R_b$ groups; a nine to ten membered heterocycle having two ring structures; a carbonyl which is optionally substituted with a hydroxy, a $C_1$-$C_4$ alkyl, or a $C_1$-$C_4$ alkoxy group; a carbamoyl which is optionally substituted with one or two $C_1$-$C_4$ alkyl groups; a nitro group; a thio which is optionally substituted with a hydroxy, a $C_1$-$C_4$ alkyl, or —$R_b$ group; a sulfonyl which is optionally substituted with a hydroxy, a $C_1$-$C_4$ alkyl, or —$R_b$ group; or an amino which is optionally substituted with one or two independently selected $C_1$-$C_4$ alkyl, sulfonyl, or carbonyl groups, wherein the aminosulfonyl group is optionally substituted with a hydroxy, a $C_1$-$C_4$ alkyl, or —$R_b$ group and wherein the aminocarbonyl group is optionally substituted with a $C_1$-$C_4$ alkyl, a $C_1$-$C_4$ haloalkyl, a benzoxy, or an amino group which is optionally substituted with an —$R_b$ group;
wherein —$R_b$ is a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups;
or a pharmaceutically acceptable salt thereof.

2. A compound selected from the group consisting of:

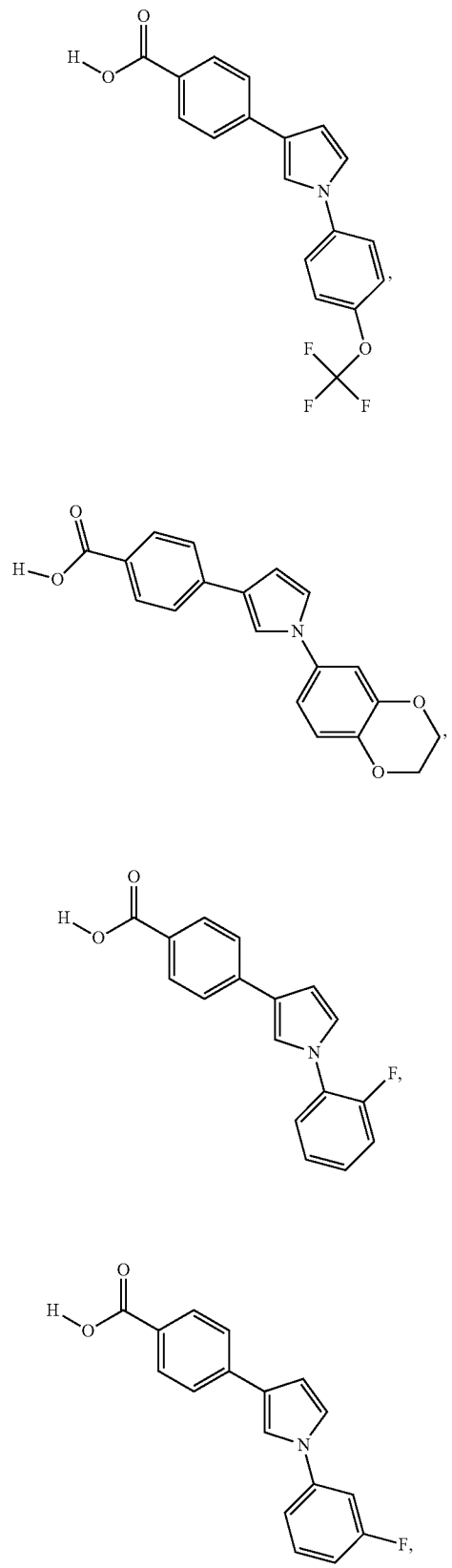
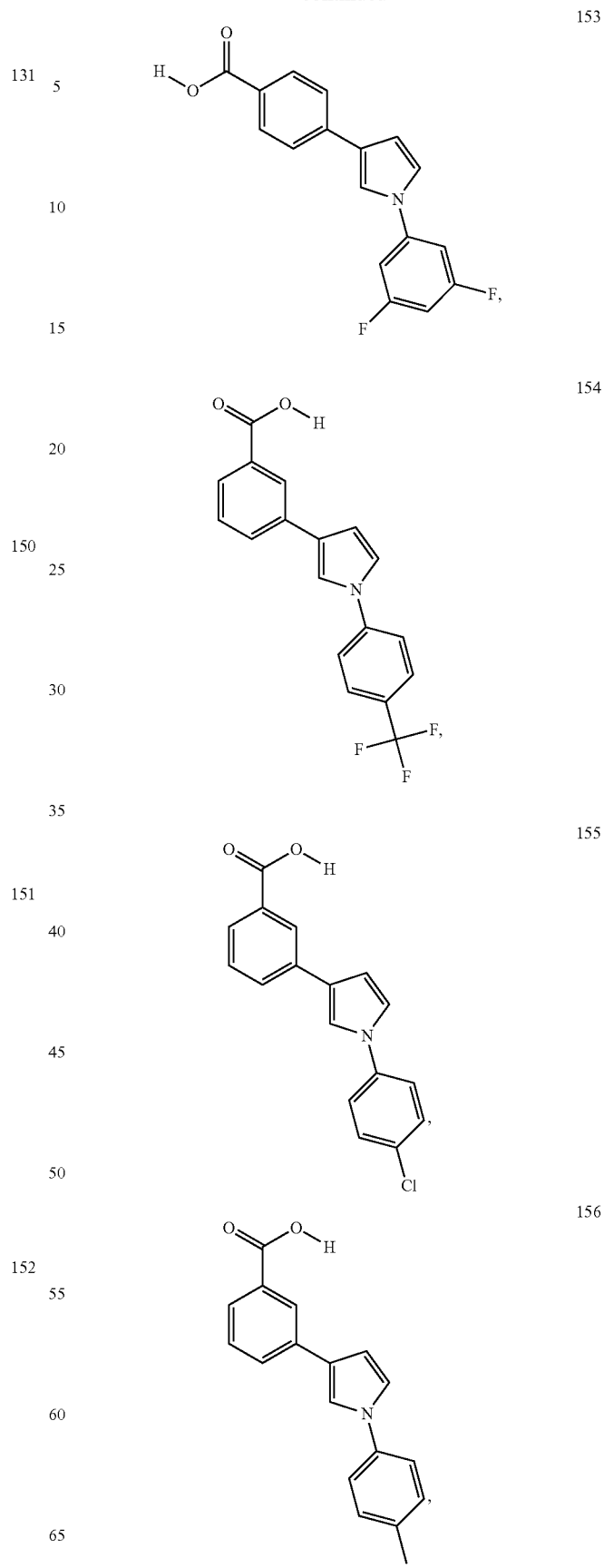

| 157 | 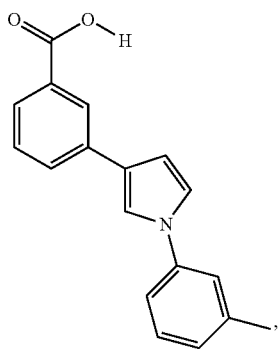 |
| 158 | 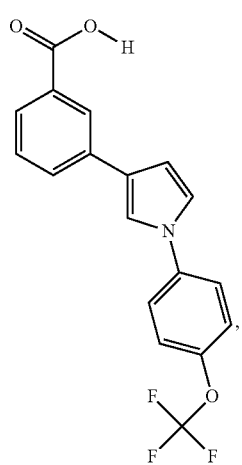 |
| 159 | 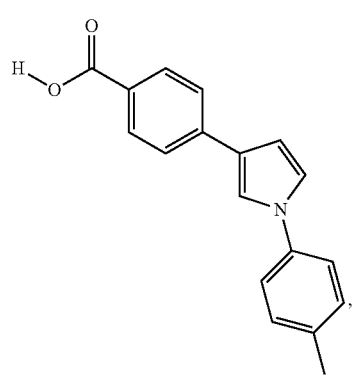 |
| 194 | 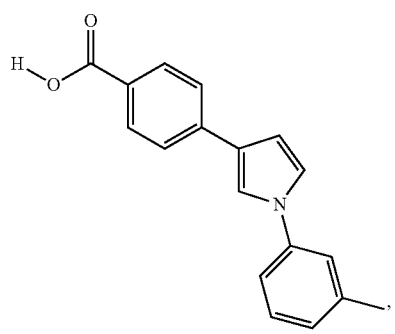 |
| 195 | 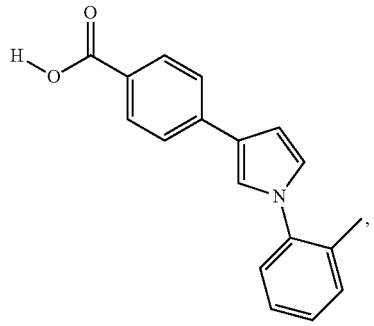 |
| 196 | 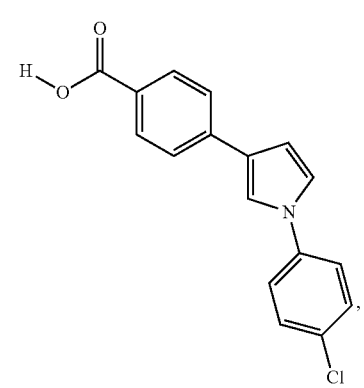 |
| 197 | 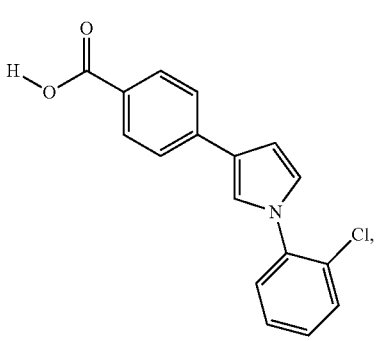 |
| 198 | 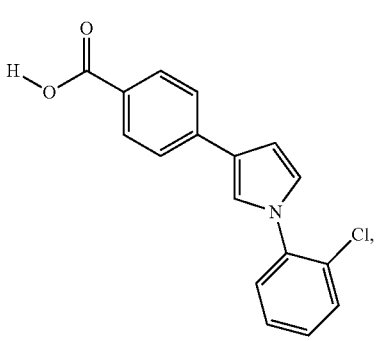 |
| 199 | 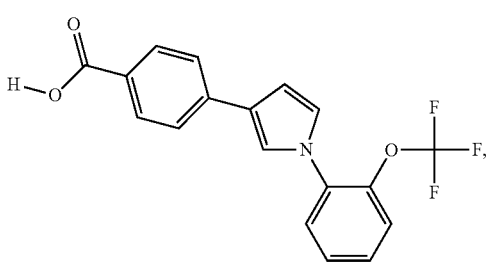 |

| 231 -continued | 232 -continued |
|---|---|
| 240 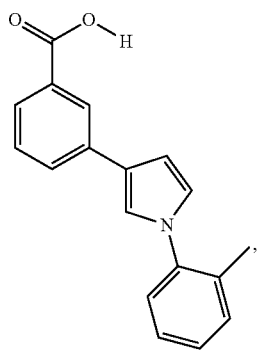 | 244 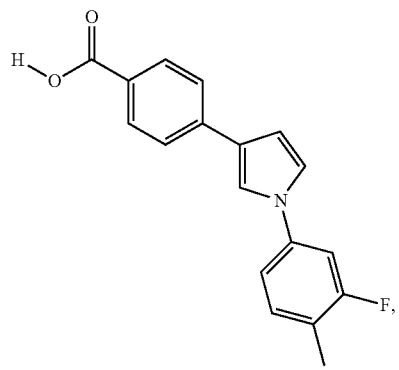 |
| 241 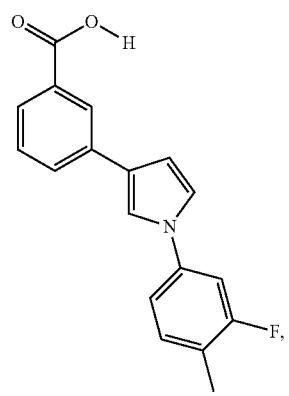 | 245 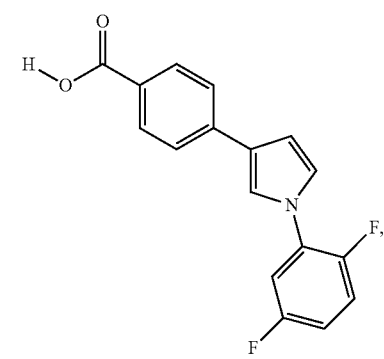 |
| 242 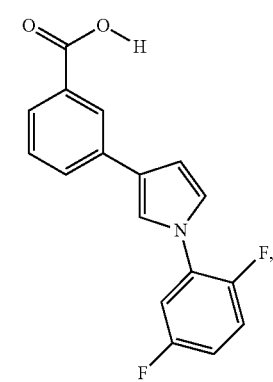 | 246 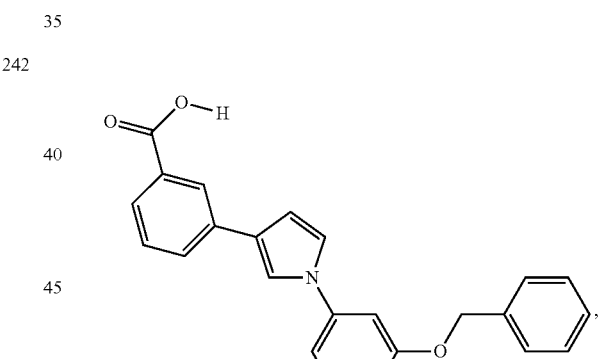 |
| 243 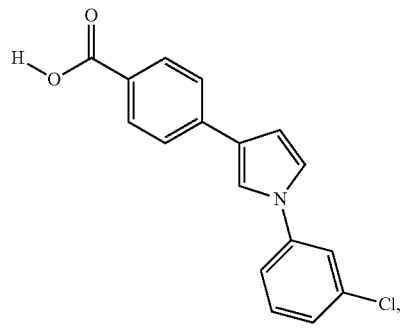 | 247 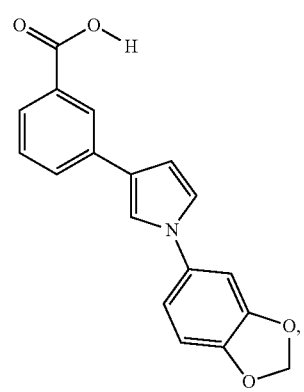 |

-continued
328 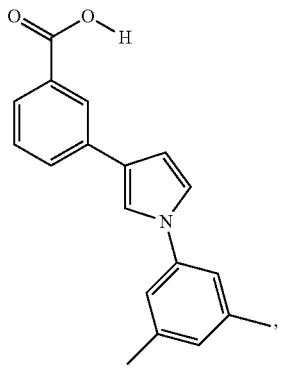
330 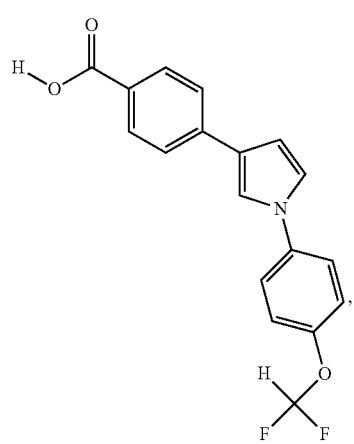
331 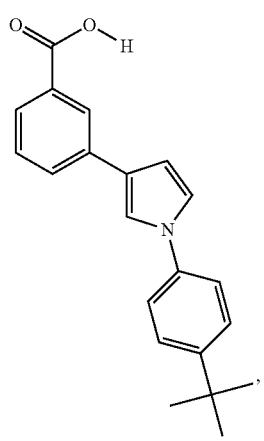
343 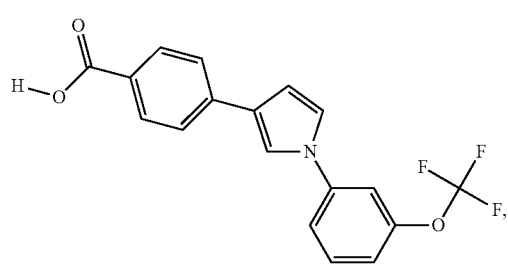
-continued
344 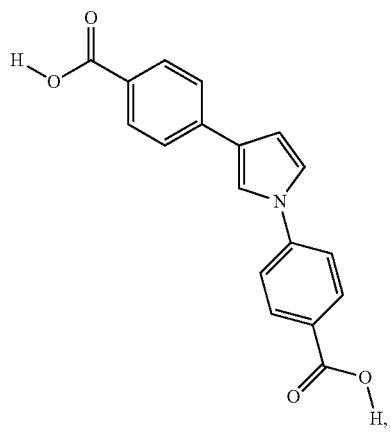
345 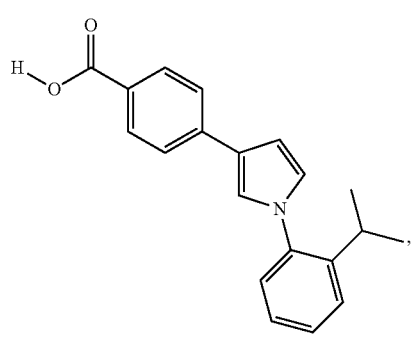
346 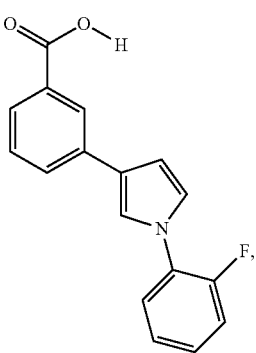
347 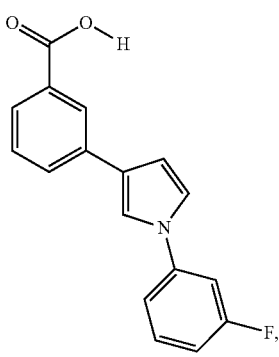

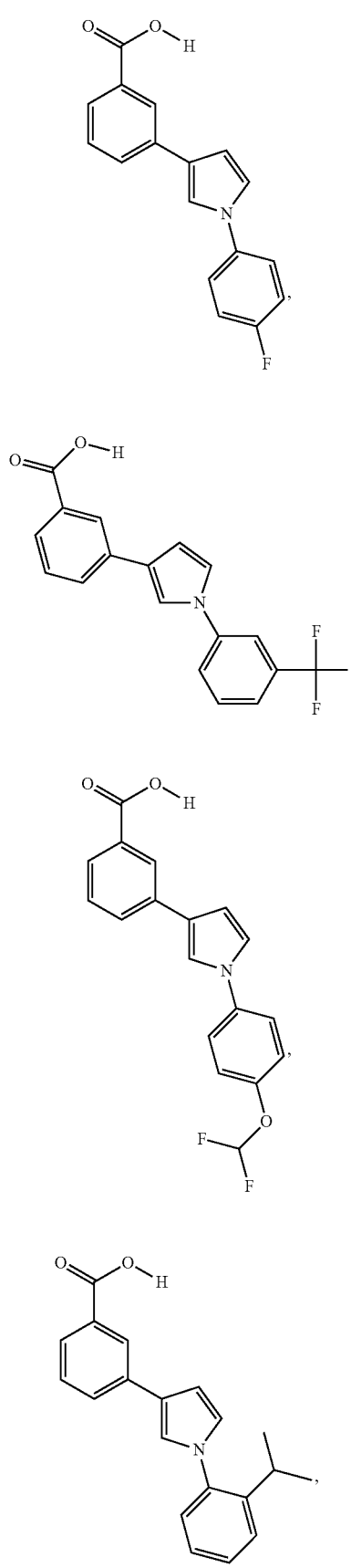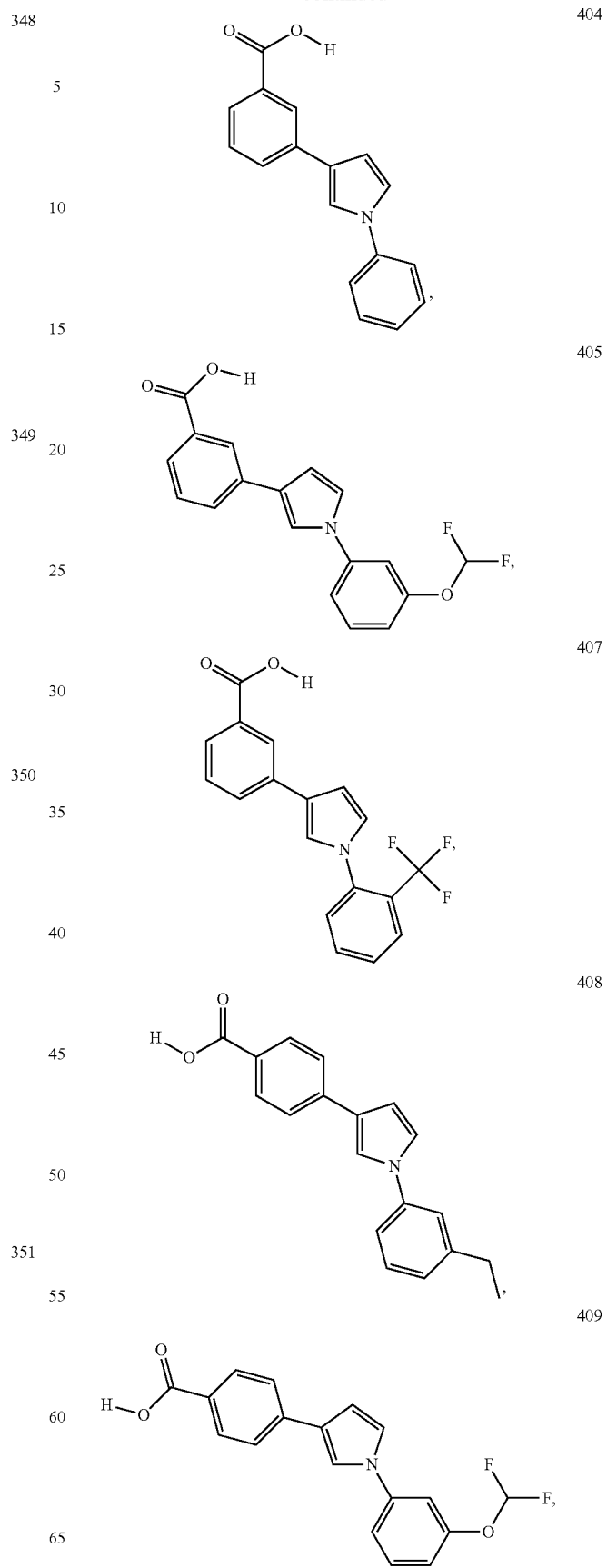

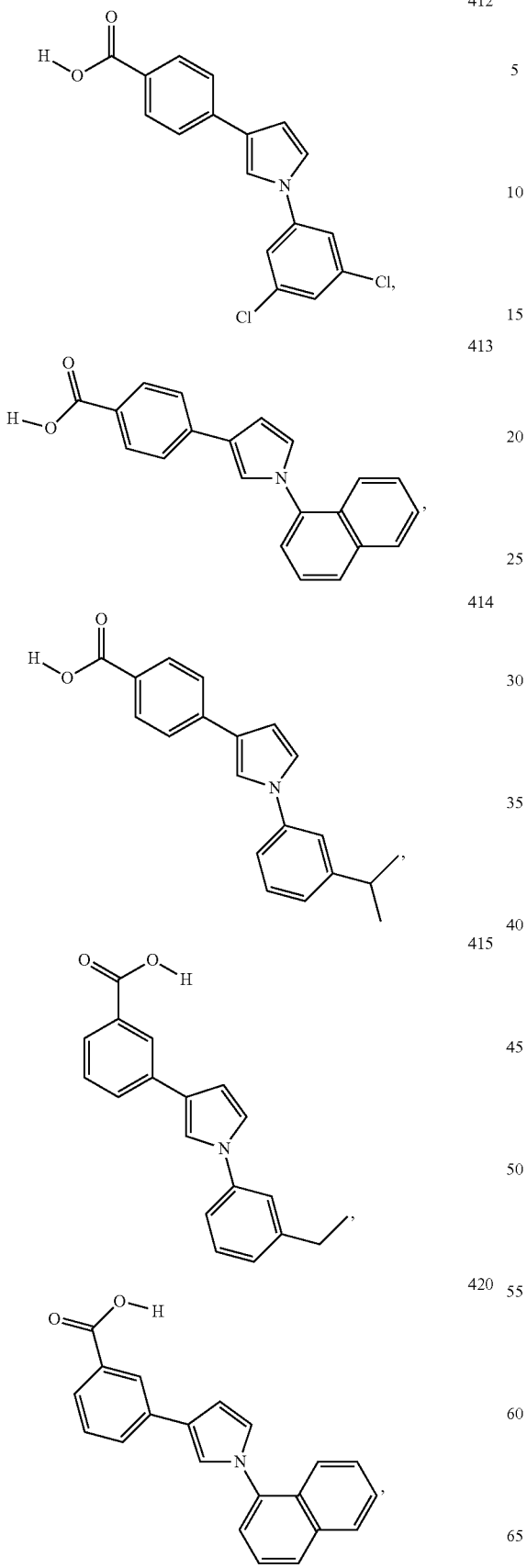
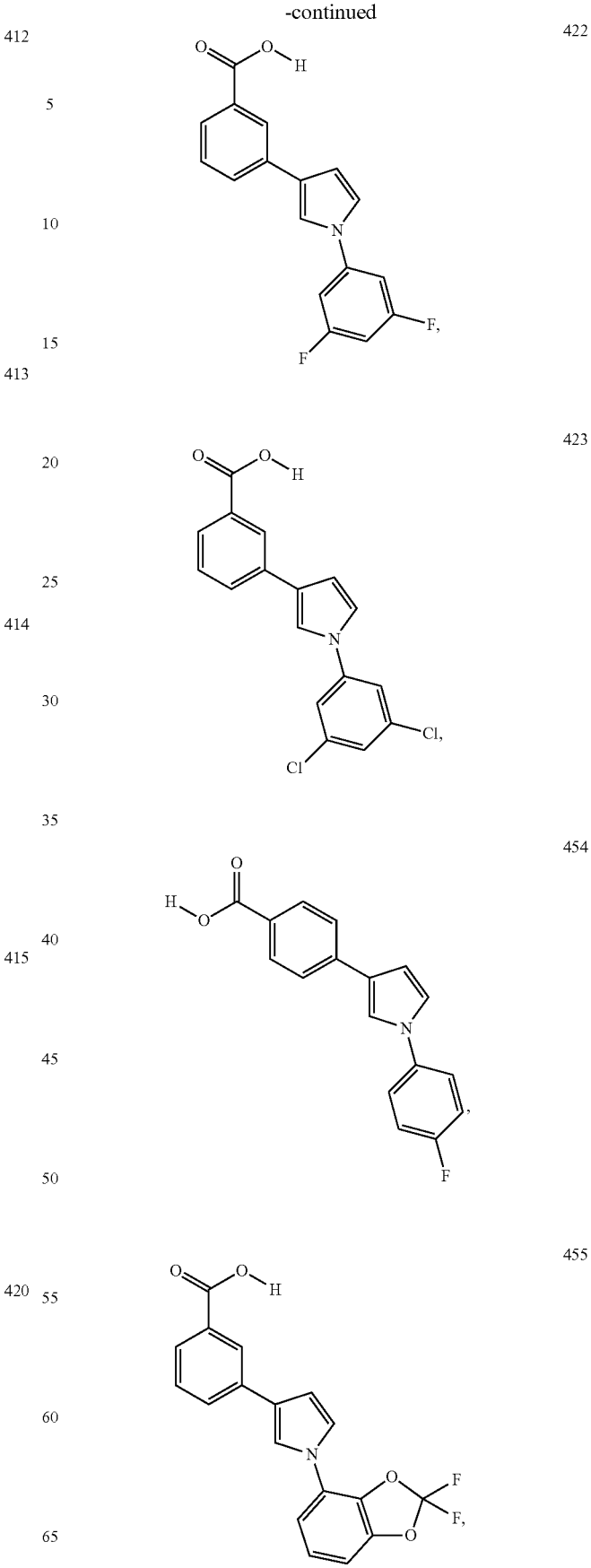

456
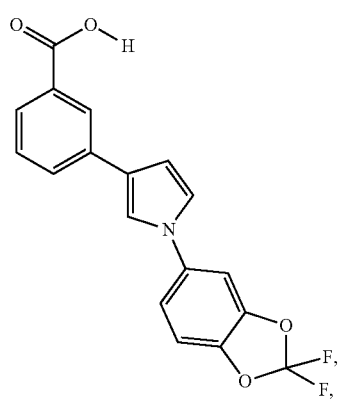
457
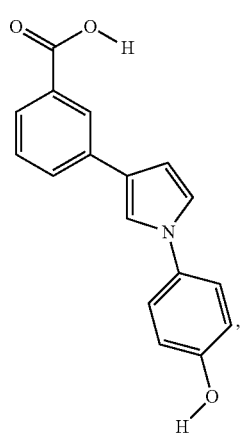
and pharmaceutically acceptable salts thereof.
3. The compound of claim 1, wherein RR is selected from:
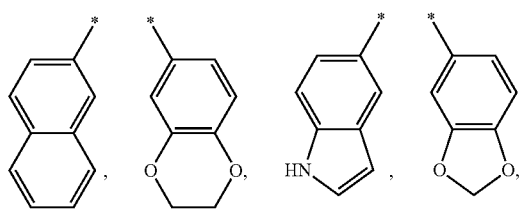
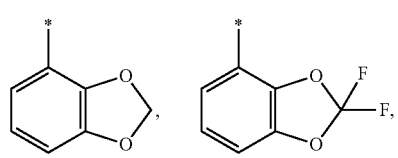
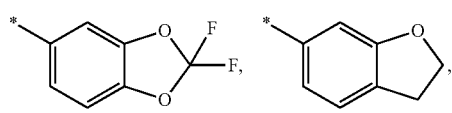
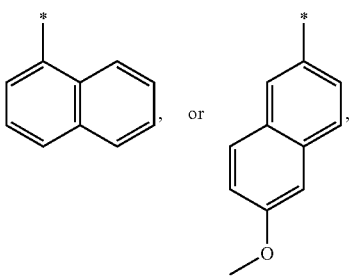
wherein the * indicates the bond of attachment of RR to the compound of Formula 1-A-10 or 1-A-11.
4. A compound selected from:
126
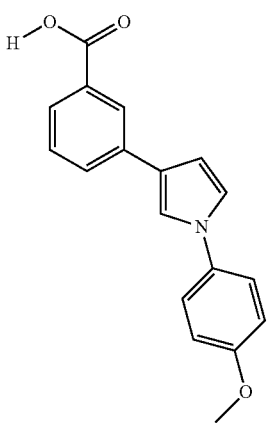
342
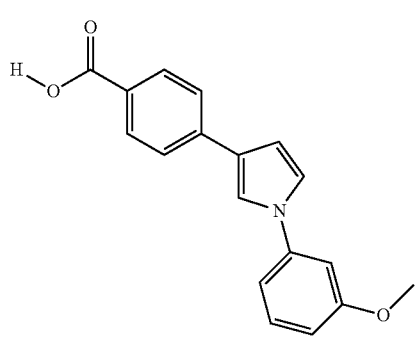
406
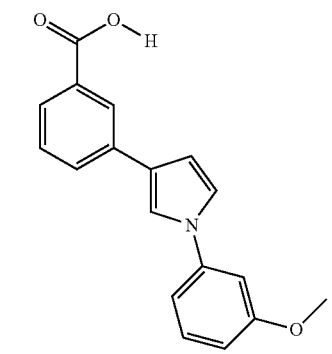

241
-continued
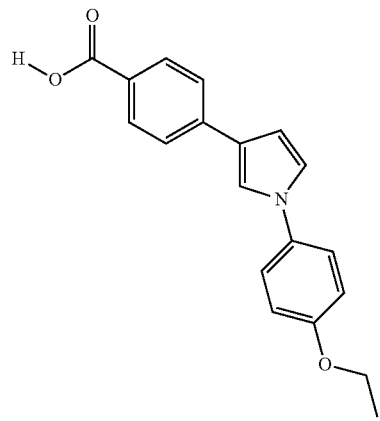
411
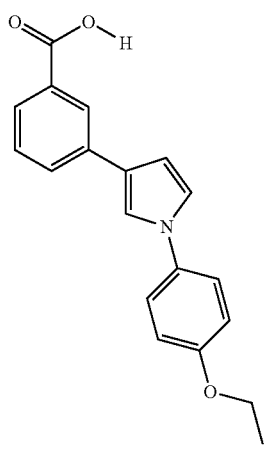
421
242
-continued
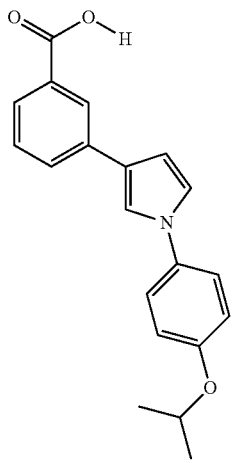
458
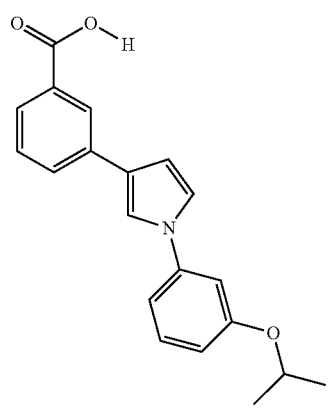
459
or a pharmaceutically acceptable salt thereof.
* * * * *